(12) United States Patent
Stull et al.

(10) Patent No.: US 9,534,058 B2
(45) Date of Patent: Jan. 3, 2017

(54) ANTI-CD324 MONOCLONAL ANTIBODIES AND USES THEREOF

(71) Applicant: STEM CENTRX, INC., South San Francisco, CA (US)

(72) Inventors: Robert A. Stull, Alameda, CA (US); Monette Aujay, San Francisco, CA (US); Orit Foord, Foster City, CA (US); Alex Bankovich, San Francisco, CA (US); Johannes Hampl, Santa Clara, CA (US); Scott J. Dylla, Emerald Hills, CA (US); David Liu, San Francisco, CA (US)

(73) Assignee: ABBVIE STEMCENTRX LLC, North Chicago, IL (US)

( * ) Notice: Subject to any disclaimer, the term of this patent is extended or adjusted under 35 U.S.C. 154(b) by 0 days.

(21) Appl. No.: 14/377,343

(22) PCT Filed: Feb. 8, 2013

(86) PCT No.: PCT/US2013/025356
§ 371 (c)(1),
(2) Date: Aug. 7, 2014

(87) PCT Pub. No.: WO2013/119960
PCT Pub. Date: Aug. 15, 2013

(65) Prior Publication Data
US 2015/0337048 A1    Nov. 26, 2015

Related U.S. Application Data

(63) Continuation-in-part of application No. 13/369,275, filed on Feb. 8, 2012, now abandoned.

(51) Int. Cl.
| | | |
|---|---|---|
| A61K 38/00 | (2006.01) | |
| A61K 39/00 | (2006.01) | |
| C07K 16/00 | (2006.01) | |
| C07K 16/28 | (2006.01) | |

(52) U.S. Cl.
CPC ....... *C07K 16/2896* (2013.01); *C07K 16/2803* (2013.01); *A61K 2039/505* (2013.01); *C07K 2317/24* (2013.01); *C07K 2317/31* (2013.01); *C07K 2317/33* (2013.01); *C07K 2317/56* (2013.01); *C07K 2317/73* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,597,725 A | 1/1997 | Suzuki |
| 5,610,281 A | 3/1997 | Brenner |
| 5,811,518 A | 9/1998 | Ranscht |
| 5,891,706 A | 4/1999 | Suzuki |
| 6,146,630 A | 11/2000 | Tsubota |
| 6,300,080 B1 | 10/2001 | Brenner |
| 6,406,870 B2 | 6/2002 | Brenner |
| 6,723,320 B2 | 4/2004 | Hofler |
| 7,029,676 B2 | 4/2006 | Brenner |
| 7,368,548 B2 | 5/2008 | Dahary |
| 7,517,662 B2 | 4/2009 | Ridder |
| 7,553,948 B2 | 6/2009 | Cojocaru |
| 7,608,413 B1 | 10/2009 | Joseloff |
| 7,695,963 B2 | 4/2010 | Agulnick |
| 8,062,859 B2 | 11/2011 | Roux |
| 8,093,011 B2 | 1/2012 | Haley |
| 8,226,943 B2 | 7/2012 | Gurney |
| 2002/0165188 A1 | 11/2002 | Herlyn |
| 2006/0281136 A1 | 12/2006 | Nishikawa |
| 2007/0059757 A1 | 3/2007 | Domon |
| 2008/0171047 A1 | 7/2008 | Hadley |
| 2008/0178305 A1 | 7/2008 | Clarke |
| 2009/0233324 A1 | 9/2009 | Kopf-Sill |
| 2009/0285883 A1 | 11/2009 | Houchen |
| 2010/0273160 A1 | 10/2010 | Donahoe |
| 2011/0165698 A1 | 7/2011 | Brouxhon |
| 2011/0191868 A1 | 8/2011 | Gupta |
| 2011/0201003 A1 | 8/2011 | Ono |
| 2011/0236904 A1 | 9/2011 | Hauch |
| 2011/0294186 A1 | 12/2011 | Fuchs |
| 2012/0039811 A1 | 2/2012 | Admon |
| 2013/0061340 A1 | 3/2013 | Dylla et al. |
| 2013/0061342 A1 | 3/2013 | Dylla et al. |
| 2013/0150386 A1 | 6/2013 | Goodenow |

(Continued)

FOREIGN PATENT DOCUMENTS

| | | |
|---|---|---|
| EP | 2325310 | 5/2011 |
| EP | 2385370 | 11/2011 |

(Continued)

OTHER PUBLICATIONS

Acloque et al., "The physiology and pathology of the EMT. Meeting on the epithelial-mesenchymal transition," *EMBO Rep*, vol. 9: a322-326 (2008).

Al-Shouli et al., "Lets connect: A novel role for CD46 in tight junction regulation," *Molecular Immunology* 47, 2252-2253 (Abstract #240) (2010).

Angst et al., "The cadherin superfamily," *J. Cell Sci.*, 114(4):625-626 (2001).

(Continued)

*Primary Examiner* — Maher Haddad
(74) *Attorney, Agent, or Firm* — Womble Carlyle Sandridge & Rice, LLP

(57) ABSTRACT

Novel modulators, including antibodies and derivatives thereof, and methods of using such modulators to treat proliferative disorders are provided.

10 Claims, 34 Drawing Sheets

(56) References Cited

U.S. PATENT DOCUMENTS

| | | |
|---|---|---|
| 2013/0260385 A1 | 10/2013 | Dylla et al. |
| 2013/0317201 A1 | 11/2013 | Ishii |
| 2015/0030636 A1 | 1/2015 | Dylla et al. |
| 2016/0176964 A1* | 6/2016 | Arathoon ............... C07K 16/28 424/133.1 |

FOREIGN PATENT DOCUMENTS

| | | |
|---|---|---|
| EP | 2444421 | 4/2012 |
| WO | WO 02/34880 | 5/2002 |
| WO | WO 2008/149803 | 12/2008 |
| WO | WO 2009/070767 | 6/2009 |
| WO | WO 2009/126310 | 10/2009 |
| WO | WO 2009/157623 | 12/2009 |
| WO | WO 2011/037643 | 3/2011 |
| WO | WO 2011/057034 | 5/2011 |
| WO | WO 2011/071541 | 6/2011 |
| WO | WO 2011/093927 | 8/2011 |
| WO | WO 2011/126264 | 10/2011 |
| WO | WO 2012/030854 | 3/2012 |
| WO | WO 2012/031280 | 3/2012 |
| WO | WO 2012/040226 | 3/2012 |
| WO | WO 2012/058418 | 5/2012 |
| WO | WO 2013/119964 | 8/2013 |
| WO | WO 2015/031698 | 3/2015 |
| WO | WO 2015/127407 | 8/2015 |

OTHER PUBLICATIONS

Angst et al., "The cadherin superfamily: diversity in form and function," *J. Cell Sci.*, 114(4):629-641 (2001).
Bae et al., "E-cadherin plasticity in prostate cancer stem cell invasion," *Am. J. Cancer Res*, 1(1): 71-84 (2011).
Berezhnaya et al., "Expression of E-cadherin in drug resistant human breast cancer cells and their sensitivity to lymphokinE-activated lymphocytes action," *Exp. Oncol.*, 31(4): 242-245 (2007).
Botchkina et al., "Phenotypic subpopulations of metastatic colon cancer stem cells: genomic analysis," *Cancer Genomics Proteomics*, 6(1): 19-29 (2009).
Bussemakers et al., "Molecular cloning and characterization of the human E-cadherin cDNA," *Mol. Biol. Reports*, 17:123-128 (1993).
Cavard et al., "Gene expression profiling provides insights into the pathways involved in solid pseudopapillary neoplasm of the pancreas," *J Pathol*, 218(2): 201-9 (2009).
Chen et al., "Specificity of cell-cell adhesion by classical canderins: Critical role for low-affinity dimerization through β-strand swapping," *Proc. Natl. Acad. Sci.* 102(24): 8531-8536 (2005).
Chen et al., "E-Cadherin-mediated cell-cell contact is critical for induced pluripotent stem cell generation," *Stem Cells*, 28: 1315-1325 (2010).
Day et al., "E-cadherin mediates aggregation-dependent survival of prostate and mammary epithelial cells through the retinoblastoma cell cycle control pathway." *The Journal of Biological Chemistry*, vol. 274, No. 14: 9656-9664, Issue of Apr. 2, 1999.
Devemy et al., "Identification of a novel dual E- and N-cadherin antagonist," *Peptides*, 30: 1539-1547 (2009).
Dietrich et al., "Rottlerin induces a transformed phenotype in human keratinocytes," *Biochemical and Biophysical Research Communications*, vol. 282, No. 2: 575-579 (2001).
Duguay et al., "Cadherin-mediated cell adhesion and tissue segregation: qualitative and quantitative determinants," *Dev. Biol.*, 253: 309-323 (2003).
Faull et al., "InsidE-out signaling through integrins," *J. Am. Soc. Nephrol.*, 7(8):1091-1097 (1996).
Frixen et al., "E-cadherin-mediated cell-cell adhesion prevents invasiveness of human carcinoma cells," *J. Cell Biol.*, 113: 173-85 (1991).
Green et al., "Antiadhesive antibodies targeting E-cadherin sensitize multicellular tumor spheroids to chemotherapy in vitro,"*Mol. Cancer Ther.*, 3:149-159 (2004).
Green et al., "Disruption of cell-cell adhesion enhances antibody-dependent cellular cytotoxicity: implications for antibody-based therapeutics of cancer." *Cancer Research*, 62:6891-6900 (2002).
Guillemard et al., "TaxanE-antibody conjugates afford potent cytotoxicity, enhanced solubility, and tumor target selectivity." *Cancer Research* 61, 694-699 (2001).
Gumbiner, "Cell Adhesion: The molecular basis of tissue architecture and Morphogenesis," *Cell*, 84:345-357 (1996).
Haegel et al., "Lack of β-catenin affects mouse development at gastrulation," *Development*, 121:3529-3537 (1995).
Harrison et al., "The extracellular architecture of adherens junctions revealed by crystal structures of type I cadherins," *Structure*, 19(2):244-256 (2011).
Hazan et al., "Cadherin switch in tumor progression," *Ann. N.Y. Acad. Sci.*, 1014:155-163 (2004).
Hong et al., "Cadherin exits the junction by switching its adhesive bond," *J. Cell Biol.*, 192(6): 1073-83 (2011).
Hordijk, "Inhibition of invasion of epithelial cells by tiam I-rac signaling", *Science*, vol. 278, No. 5342, 1464-1466 (1997).
Huntsman et al., "Assignment of the E-cadherin gene (CDH1) to chromosome 16q22.1 by radiation hybrid mapping," *Cytogenet. Cell Genet.* 83:82-83 (1998).
Jamora et al., "Links between signal transduction, transcription and adhesion in epithelial bud development," *Nature*, 422(6929):317-322 (2003).
Katayama et al., "Soluble E-cadherin fragments increased in circulation of cancer patients," *Br. J. Cancer*, 69:580-585 (1994).
Kobayashi et al., "Inhibition of E-cadherin-mediated homotypic adhesion of caco-2 cells: a novel evaluation assay for peptide activities in modulating cell-cell adhesion." *JPET* 317:309-316 (2006).
Kuefer et al., "Assessment of a fragment of E-cadherin as a serum biomarker with predictive value for prostate cancer," *Br. J. Cancer*, 92: 2018-23 (2005).
Le et al., "Recycling of E-cadherin: a potential mechanism for regulating cadherin dynamics," *J. Cell Biol*. 146(1):219-32 (1999).
Lecuit et al., "A single amino acid in E-cadherin responsible for host specificity towards the human pathogen *Listeria monocytogenes*," *EMBO J.*, 18(14): 3956-3963 (1999).
Lee et al., "Tumor specificity and in vivo targeting of an antibody against exon 9 deleted E-cadherin in gastric cancer," *J. Cancer Res. Clin. Oncol.*, 133: 987-994 (2007).
Li et al., "A mesenchymal-to-epithelial transition initiates and is required for the nuclear reprogramming of mouse fibroblasts," *Cell Stem Cell*, 7: 51-63 (2010).
Lowry, "E-cadherin, a new mixer in the Yamanaka cocktail," *EMBO Rep.*, 12(7):613-614 (2011).
Makagiansar et al., "Disulfide bond formation promotes the *cis*- and trans-dimerization of the E-cadherin-derived first repeat," *J. Biol. Chem.*, 277(18):16002-16010 (2002).
Mansouri et al., "Characterization and chromosomal localization of the gene encoding the human cell adhesion molecule uvomorulin," *Differentiation*, 38:67-71 (1988).
McIntosh et al., "Pharmacokinetics and tissue distribution of cisplatin and conjugates of cisplatin with carboxymethyldextran and A5B7 monoclonal antibody in CD1 mice," *Journal of Pharmaceutical Sciences*, vol. 86, No. 12, pp. 1478-1483 (2007).
Miederer et al., "Comparison of the radiotoxicity of two alpha-particle-emitting immunoconjugates, terbium-149 and bismuth-213, directed against a tumor-specific, exon 9 deleted (d9) E-cadherin adhesion protein," *Radiation Research*, 159, 612-620 (2003).
Milsom et al., "Tissue factor regulation by epidermal growth factor receptor and epithelial-to-mesenchymal transitions: effect on tumor initiation and angiogenesis," *Cancer Res.*, 68(24): 10068-10076 (2008).
Mohamet et al., "Loss of function of E-cadherin in embryonic stem cells and the relevance to models of tumorigenesis," *J. Oncol.*, 2011: Article ID 352616, pp. 1-19 (2011).
Munz et al., "The emerging role of EpCAM in cancer and stem cell signaling," *Cancer Res.*, 14(69):5627-5629 (2009).
Nagafuchi et al., "Cell binding function of E-cadherin is regulated by the cytoplasmic domain," *EMBO J.*, 7(12):3679-3684 (1988).

(56) References Cited

OTHER PUBLICATIONS

Niessen et al., "Molecular components of the adherens junction," *Biochimica et Biophysica Acta*, 1778:562-571 (2008).
Nollet et al., "Phylogenetic analysis of the cadherin superfamily allows identification of six major subfamilies besides several solitary members," *J. Mol. Biol.*, 299:551-572 (2000).
Nose et al., "Expressed recombinant cadherins mediate cell sorting in model systems," *Cell*, 54: 993-1001 (1988).
Ozawa, "Lateral dimerization of the E-cadherin extracellular domain is necessary but not sufficient for adhesive activity," *J. Biol. Chem.*, 277(22):19600-19608 (2002).
Patel et al., "Type II cadherin ectodomain structures: Implications for classical cadherin specificity," *Cell*, 124: 1255-1268 (2006).
Pećina-Šlaus, "Tumor suppressor gene E-cadherin and its role in normal and malignant cells," *Cancer Cell Int.*, 3(17), 1-7 (2003).
Perez-Moreno et al., "Sticky business: Orchestrating cellular signals at adherens junctions," *Cell*, 112: 535-548 (2003).
PlusCellect™ Catalog No. PLS748, package insert, pp. 2-11 (2009).
Pokutta et al., "Structure and mechanism of cadherins and catenins in cell-cell contacts," *Annu. Rev. Cell Dev. Biol.*, 23: 237-261 (2007).
Redmer et al., "E-cadherin is crucial for embryonic stem cell pluripotency and can replace OCT4 during somatic cell reprogramming," *EMBO Reports*, 12(7): 720-726 (2011).
Samavarchi-Tehrani et al., "Functional genomics reveals a BMP-driven mesenchymal-to-epithelial transition in the initiation of somatic cell reprogramming," *Cell Stem Cell*, 7:64-77 (2010).
Schrappe et al., "Long-term growth suppression of human glioma xenografts by chemoimmunoconjugates of 4-desacetylvinblastine-3-carboxyhydrazide and monoclonal antibody. 9.2.27," *Cancer Res.*, 52, 3838-3844 (1992).
Shapiro et al., "Structure and biochemistry of cadherins and catenins," *Cold Spring Harb. Perspect. Biol.*, 1:a003053; pp. 1-21 (2009).
Shimoyama et al., "Cadherin cell-adhesion molecules in human epithelial tissues and carcinomas," *Cancer Res.*, 49: 2128-2133 (1989).
Shiozaki et al., "Expression of immunoreactive E-cadherin adhesion molecules in human cancers," *Am. J. Path.*, 139(1):17-23 (1991).
Shiozaki et al., "E-Cadherin mediated adhesion system in cancer cells," *Cancer*, 77: 1605-1613 (1996).
Solanas et al., "Control of cell adhesion and compartmentalization in the intestinal epithelium," *Exp. Cell Res.*, 317(19):2695-2701 (2011).

Soyuer et al., "Prognostic significance of CD9 expression in locally advanced gastric cancer treated with surgery and adjuvant chemoradiotherapy," *Pathol Res. Pract.*, 206: 607-610 (2010).
Suzuki et al., "Protocadherins and diversity of the cadherin superfamily," *J. Cell. Sci.*, 109:2609-2611 (1996).
Takeichi, "Cadherin cell adhesion receptors as a morphogenetic regulator," *Science*, 251: 1451-1455 (1991).
Tang et al., "E-cadherin is the major mediator of human melanocyte adhesion to keratinocytes in vitro," *Journal of Cell Science*, vol. 107, No. 4, 983-992 (1994).
"Key molecule for stem cell pluripotency identified," from thenewKerala.com, 1 page (Jun. 3, 2011).
Todaro et al., "Colon cancer stem cells: promise of targeted therapy," Gastroenterology, 138(6): 2151-62 (2010).
Tomschy et al., "Homophilic adhesion of E-cadherin occurs by a co-operative two-step interaction of N-terminal domains," *EMBO J.*, 15(14): 3507-3514 (1996).
Van Roy et al., "The cell-cell adhesion molecule E-cadherin," *Cell Mol. Life Sci.*, 65: 3756-3788 (2008).
Vestweber et al., "Identification of a putative cell adhesion domain of uvomorulin", *EMBO J.*, vol. 4, No. 13A: 3393-3398 (1985).
Vleminckx et al., "Genetic manipulation of E-cadherin expression by epithelial tumor cells reveals an invasion suppressor role." *Cell*, 66:1:107-119 Abstract only (1991).
Von Schlippe et al., "Functional interaction between E-cadherin and αy-containing integrins in carcinoma cells," *J. Cell. Sci.*, (113): 425-437 (2000).
Wheelock et al., "Regulation of keratinocyte intercellular junction organization and epidermal morphogenesis by E-cadherin," *J. Cell. Biol.*, 117(2): 415-425 (1992).
Yamane et al., "Enforced Bcl-2 expression overrides serum and feeder cell requirements for mouse embryonic stem cell self-renewal," *Proc. Natl. Acad. Sci.*, 102(9): 3312-3317 (2005).
Yang et al., "Twist, a master regulator of morphogenesis, plays an essential role in tumor metastasis," *Cell*, 117: 927-939 (2004).
Zhang et al., "Anti-tumorigenic effect of a K-ras ribozyme against human lung cancer cell line heterotransplants in nude mice," *Gene Ther.*, 7: 2041-2050 (2000).
International Preliminary Report on Patentability (IPRP) issued in International Application No. PCT/US2013/025356.
Search Report issued in International Application No. PCT/US2013/025356.
Written Opinion issued in International Application No. PCT/US2013/025356.
Office Action dated Jul. 9, 2014 issued in U.S. Appl. No. 13/369,275.

\* cited by examiner

>gi|169790842|ref|NM_004360.3| Homo sapiens cadherin 1, type 1, E-cadherin (epithelial) (CDH1), CD324, mRNA
(SEQ ID NO: 1)

AGTGGCGTCGGAACTGCAAAGCACCTGTGAGCTTGCGGAAGTCAGTTCAGACTCCAGCCCGCTCCAGCCGGCGACCGCGACCGCCGACCCGGCCGCTGCCCTCG
CTCGGCGTCCCCGGCCAGCCATGGGCCCTTGGAGCCGCAGCCTCTGGGCGCTGCTGCTCTGCTGCTGCTGCAGGTCTCTCTCGGTCTGCCAGGAGCCGGAGCCCTGCC
ACCCTGGCTTGACGCCGAGAGCTACATGTTCCTCGACACCGATTCAAGTGCACAGATCCTCAAGAGGCCTCGACACCTCAAAAGGCCTCTACGGTTTCATAACCACAGATCCATTCT
CAAAGGACAGCCTATTTTCCTCGACACCGATTCAAAGTGGGCACAGATGGTGTGATTACAGTGGGCACTGGGAGACTGGTTTTCACGCATCAGCTGCCAGAGAAATGAAAAGG
TGGTCTACGCCTGGGACTCCACTCACAGAAAGTTTTCCACCAAGTGCCTGAATGGCAGACAAGAAGAAGGCAAGTTTTACACGAACGCATTGCCAACTGCCAGGAGCTGACACACCCCTGTTGGTGT
AATCAAGCAGAATTGCTTCATGCTTCTCCAACTCTCTCCTGGCCTGAAGTGACATCAGTCTACAGAAGAACAAAGACAAAGGCAAAGTTTCCATCAGCTGCCAAGAGATGGTGACACACCCCTGTTGGTGT
CCCATTCCTAAAAACCTGGTTCAGATCAAATCAACAAAGACAAAGAAGGACAAGTTTTCTACACAGAGGCTTGGATAAGAGAACGCATTGCCACATACACCTTCACCTCTCTCTCTCACGGTCTGTATGGAAG
CTTATTATTGAAAGAGAAACAGGATGCGTGAAGGTGACAGAGCCTGCTGGATAGACAGAGCTTGGATGAAGCAGACACTTCAAGGAGCTCTTACCACCATCTCACCAATATACCCTGG
GAATGCAGTTGAGGATTCCAGGAACCTCTGTGATGGAGGTCACAGCCACAGACTTAACGACCCGAATTGCAACACCTGCAACCTCGCATCAATGCGACCATGCGTTACACCATCTCAGCCAAGATC
GTGCTTCCGGAGTCTGATGGAGGTCACACACTTAACGGAACAGACCTGTTGAGCACCTCACACCAGTTGATGATCGATCAGCCACTGACCGCATCATGGCGACAATCAATGCGACATCATCGGATC
CTGAGCTCCCTGACAAAATATGTTCAAGGTGAGGGTTAAGCACAATCAGCAACTCAGTACAGCTGACTGGATGAAGGATGATCACATCGCTGCGATAATCTCATCATCCACCA
TGGTTCAAGCTGCTGACCTTCAAGGTGAGGGTTAAGCACAATCAGCAACTCAGTACAGCTGACTGGATGAAGGATGATCACATCGCTGCGATAATCTCATCATCCACCA
CGTACAAGGGTGCCTGAGAACGAGGCTAAGCTGTAATCACGTGAATCACCACCATCCAGTGAACAACGATGGCATTTGAAAACAGCAAGGGCTTGGATTTGAGCGCAAGCA
ACCATATTGAATGATGATGGTGGACAGTTGCTGTGACGAATGGTAACTGTGAGGTCTCTCACACAGCGGTCACGTCACTCACCACTCGTCCCAGGAGCCAGACACATTTATGG
GCAGTACATTCTACACGTAGCGAGTAGCAGTGCACAATGGTAACTGTGAAGTGTCCGAGGACTTTGCCTGAGGATTATACAATGCCGAGTCCAGGAGCCAGACACATTTATGG
CCCCATCTTGTCCTCTGAAATCGGATTGGAGAGACACTGCTGGATGCAACATCATCAGGATCATGCAACTGTAGAACAGGGACACTTCTGCTGATCGTCTGAT
AACAGAAAATAACGTGAAGAACAGCACGTACACACGTCCCTAATCATAGCTACACAGACCCTAATCATCAGCCTACAGACAATGGTTCCAGTTGCTACTGGAACAGGGACACTTCTGCTGATCGTCTGAT
TTTGAGCACGTGAAGAACAGCACGTACACACGTCCCTAATCATAGCTACACAGACCCTAATCATCAGCCTACAGACAATGGTTCCAGTTGCTACTGGAACAGGGACACTTCTGCTGATCGTCTGAT
GTGAATGACAACGCCCCATACCAGAACCTCGAACTATATTCTCTGTGAGGATCAACCTGAACATTCAGTGCCACTGGAGCCAACCAAGCAACAACGTAACCAAGCTCAGGTCATAAACATCATTGATGCAGACCTTCCTCCAATA
CATCTCCCTTCACAGCAGATACAAAATCAATCTCAAGCTCTGCTGAAGCTGATTCATGGAGGATCATGGAAGCTCATGATGGCAATAAGACCAAGTGACCACTTAGAGGTAACCTTAGAGGAATTCTGCTTGTTGTGACTGTGAAGGCCGCT
TAGAGGTGGGTGACTACAAATCAATCTCAAGCTCTGCTGAAGCTGATTCATGGAGGATCATGGAAGCTCATGATGGCAATAAGACCAAGTGACCACTTAGAGGTAACCTTAGAGGAATTCTGCTTGTTGTGACTGTGAAGGGCCGCT
GGCTGTGTAGGAAGGCACACTGCTGTGAAGCAAGCAGGATTGCAAATTCCTGCCCCAGAGGATGACACCGGGAACAGCGTTATTACTATGATGAAGAAGGAGGGAGA
TGCTGTTTCTTCGGAGGAGACTTTGACTTGAGCAGCGTGCACAGGGCCTGGCCTGCAGGGGACGTGCACGAAATGGATGACTGGGATGCAATGCTAGTACGACGTTGCACAACCCTCATGAGTGTCCCGGT
AGAGGACCAGGACTTTGACTTGAGCAGCGTGCACAGGGCCTGGCCTGCAGGGGACGTGCACGAAATGGATGACTGGGATGCAATGCTAGTACGACGTTGCACAACCCTCATGAGTGTCCCGGT
ATCTTCCCGCCCTGCCAATCCGATGAAATTGAAAATTTATTGATGAAATCTCCTCGAGCTCTGAGCTCCCTGAACTCCTCAGACAACAAAGACCAGGACTATGACTACTTGAACGAATGGGCAA
TTTGACTATGAAGGAAGCCGGTTCGACAATGTGGCTGACATGTACGGAGGCGGCCAGGAGACTGAGAGGCCGGGCCCCAGACTGTGGGAAATGCAGAAATCA
TCGCTTCAAGAAGCTGGCTGACATGTACGGAGGCGGCCAGGAGACTGAGAGGCCGGGCCCCAGACTGTGGGAAATGCAGAAATCA
CGTTGCTGCTGGTGGTTTTCAGCTCCCTCCTCCCTTCCTGAGATGAGTTTCTGGGAAAAAAAAGAGACTGGTTAGTCAGTTGATGATGCAGTAGTACTGGTTTATAGTTTATACTTCCACTTTA

FIG. 1A (SEQ ID NO: 1) Cont

TAGCTCTAATAAGTTTGTGTTAGAAAAGTTTCGACTTATTCTTAAAGCTTTTTTTTTCCCATCACTCTTTACATGGTGATGTCCAAAAGATACCCAAATTT
AATATTCCAGAAGAACAACTTAGCATCAGAAGGTTCACCCAGCACCTTGCAGATTTCTTAAGGAATTTGTCTCACTTTAAAAAGAAGGGGAGAAGTCAGCTA
CTCTAGTTCTGTTTGTTTGTGTATATAAATTTTAAAAAAAATTTGTGTGCTTCTGCTCATTACTACACTGGTGTCCCTGCCTTTTTTTTTTTAAGACAGGGT
CTCATTCTATCGGCCAGGCTGGAGTGCAGTGGTGCAGTGGCAATCACAGCTCACTGCTGCCTTGCACCTGAGGCTCAAGCTATCCTTGCACCTCAGCCTCCC
GGACCACAGGCATGCACCACTACGGATTGGGATTACAGACATGAGCACTGCACCTGCCCAGTCCCAACTCCTGCCATTTTTAAGAGACAGTTTCGTCCATCGCC
TCCCATCTTGGCCTCCCAGAGTGATGTGATCATAGCTCACTGTAACCTCAAACTCTGGGGCTCAAGCAGTTCTCCCACCAGCCTCTTTATTTTTTGTACAGATGGGG
CAGGCTGGGATGCAGTGGCTCTTGCCCAAGCTGGTCTTAAACTCCTGGCCTCAAGCAATCCTTGCCTCAGGAGGAGTTCTGATGCAGAAATTATTGGGCTCTTTAGGGTAAGAAGTTTGTG
TCCACATGTTTTAATATCAACTCTCACTCGTGGTAGTATTGTCTACTCTGAAGACCTTTAATTGGCTTCCCCTCTTTCATCTCCTGAGTATGTAACTTGCAATGGGCAGCTATCCAGTG
ACTTGTTCTGAGTAAGTGTGTTCATTAATGTTTATTTAGCTCGAAGCAAGAGTGATATACTCCAGGACTTAGAATACTCCAAAGTGCTGCAGCCAAAGACAGA
GCGAACTATGAAAAGTGGGCTTGGAGATGGCAGGAGAGCTTGTCATTGAGCCTGGCAATTTGTACTCAAAGCCCAGAATCCGTGGTTTGTACTCAAAGCCCAAGTGCCTGCTTTGATG
CTCTGAAAATTCTGAAGGAATGGCTGAGCTGAACACATTTGCCCAATTCCAGGTGTGCACAAGATCTTGATTGGATCTCTTTTATTTAAATGTGAATTCAACTTTGACAATCAA
ATGTCTACAGAAATGTGGCCCTAAAGGGGTTAGTGAGGGTTAGGGGGTAGGGGTAGGGCTAGGGGTAGGGGTTGAGGGTTGTTTGGAGAAAAAATCAACCCTGCAATCACTTTTGGAATTGTCTTGATTTTCGGCAGTTCAA
AGAAAAGACTTTGTTGAAATAGCTTTACTGTTTCTCAAGTGTTTGAGTGTTTGAGTTTTGAGTTTTGAGTTTGAGTTTTAGTTTGAGTGTATACATGTGGGTGCTGATAATGTGTATAATTGTGTATTTTCTTGGGGGTGGAAAGGAAA
GCTATATCGAATATAGTTCTGTGTAGAGAATGTCACTGTAGTTTGAGTGTATACATGTGGGTGCTGATAATGTGTATAATTGTGTATTTTCTTGGGGGTGGAAAGGAAA
ACAATTCAAGCTGAGAAAAGTATTCTCAAAGATGCATTTTTATAAATTTTATTAAACAATTTGTTAAACCAT

FIG. 1A(Cont.)

CD324 preproprotein [Homo sapiens]
>gi|4757960|ref|NP_004351.1|                              (SEQ ID NO: 2)

MGPWSRSLSALLLLQVSSWLCQEPEPCHPGFDAESYTFTVPRRHLERGRVLGRVNFEDCTGRQRTAYFS
LDTRFKVGTDGVITVKRPLRFHNPQIHFLVYAWDSTYRKFSTKVTLNTVGHHHRPPHQASVSGIQAELL
TFPNSSPGLRRQKRDWVIPPISCPENEKGPFPKNLVQIKSNKDKEGKVFYSITGQGADTPPVGVFIIERE
TGWLKVTEPLDRERIATYTLFSHAVSSNGNAVEDPMEILITVTDQNDNKPEFTQEVFKGSVMEGALPGTS
VMEVTATDADDDVNTYNAAIAYTILSQDPELPDKNMFTINRNTGVISVVTGLDRESFPTYTLVVQAADL
QGEGLSTTATAVITVTDTNDNPPIFNPTTYKGQVPENEANVVITLKVTDADAPNTPAWEAVYTILNDDG
GQFVVTTNPVNDGILKTAKGLDFEAKQQYILHVAVTNVVPFEVSLTTSTATVTVDVLDVNEAPIFVPPE
KRVEVSEDFGVGQEITSYTAQEPDTFMEQKITYRIWRDTANWLEINPDTGAISTRAELDREDFEHVKNST
YTALIIATDNGSPVATGTGTLLLILSDVNDNAPIPEPRTIFFCERNPKQVINIIDADLPPNTSPFTAEL
THGASANWTIQYNDPTQESIILKPKMALEVGDYKINLKLMDNQNKDQVTTLEVSVCDCEGAAGVCRKAQP
VEAGLQIPAILGILGGILALLILILLILFLRRRAVVKEPLLPPEDDTRDNVYYDEEGGGEDQDFDLS
QLHRGLDARPEVTRNDVAPTLMSVPRYLPRPANPDEIGNFIDENLKAADTDPTAPPYDSLLVFDYEGSGS
EAASLSSLNSSESDKDQDYDLNEWGNRFKKLADMYGGGEDD

FIG. 1B

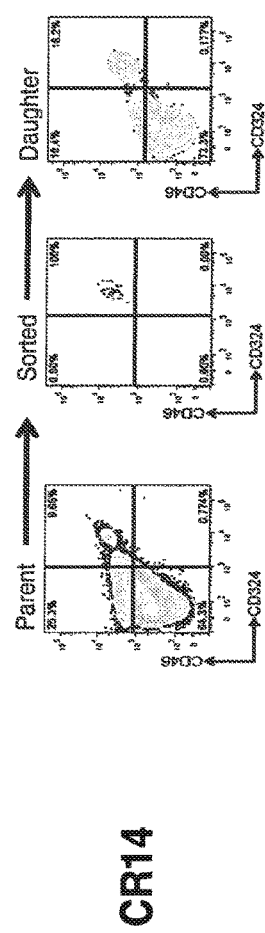
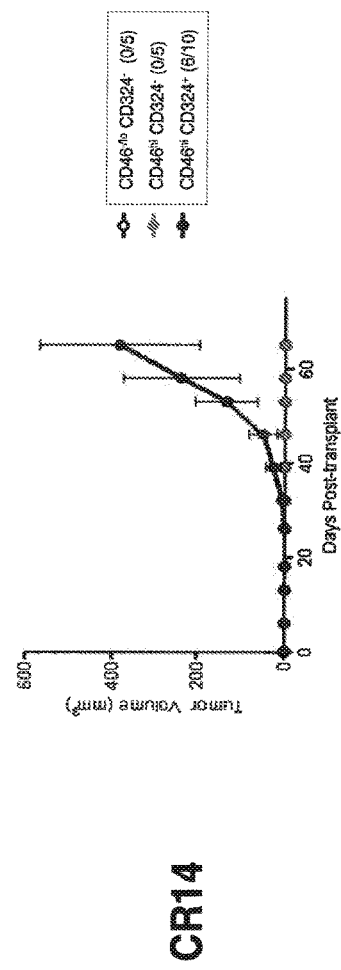
FIG. 3A
FIG. 3B

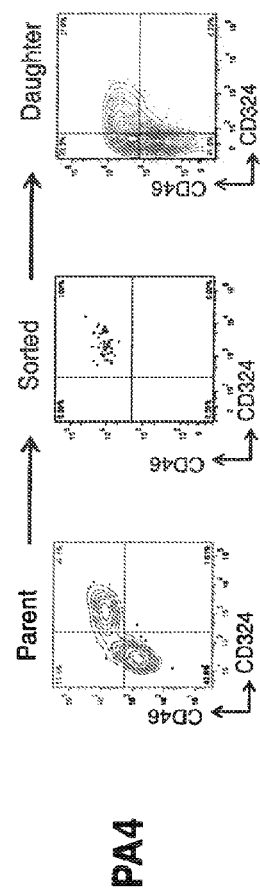
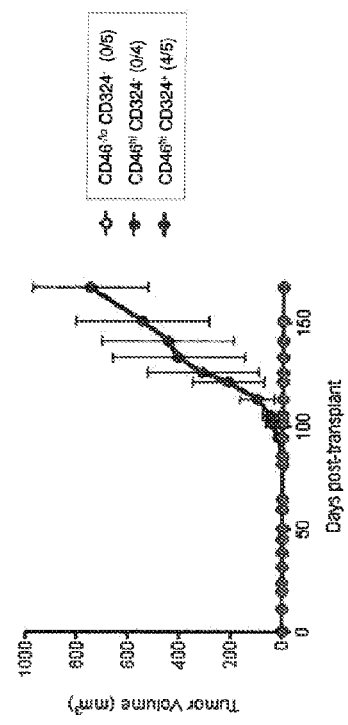
FIG. 4A
FIG. 4B

Non-Small Cell Lung Cancer Tumorigenicity is Associated with CD46hiCD324+ Tumor Cell Subpopulations

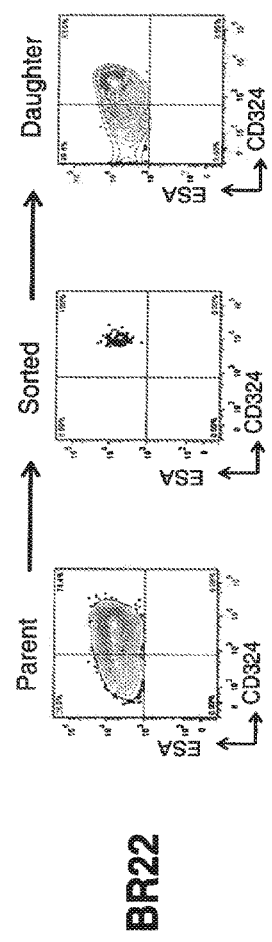
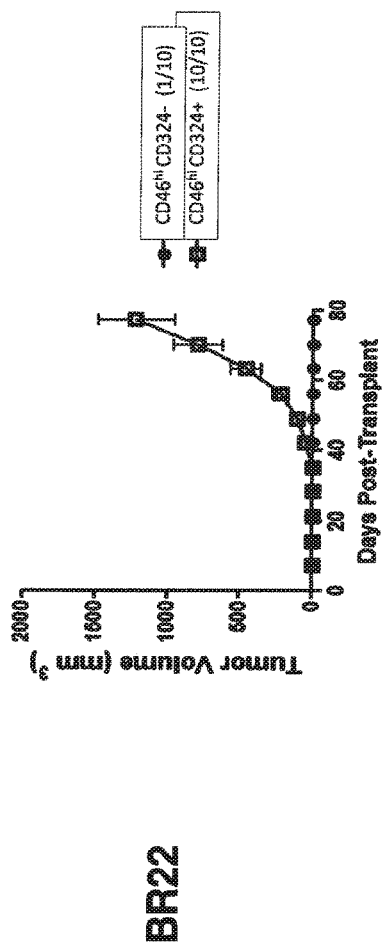
FIG. 6A
FIG. 6B

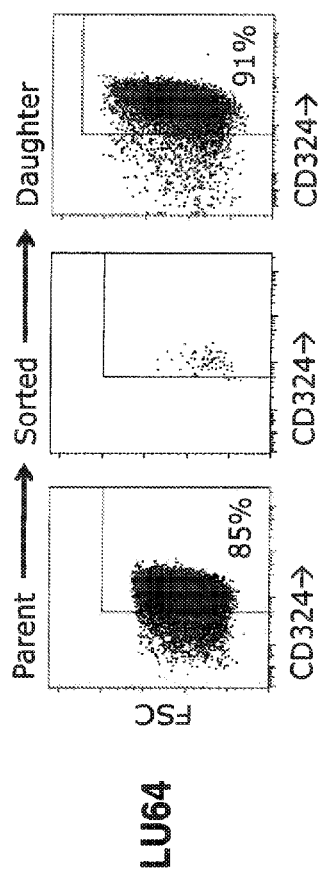
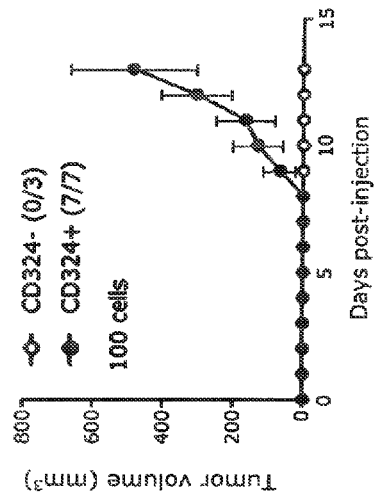
FIG. 8A
FIG. 8B

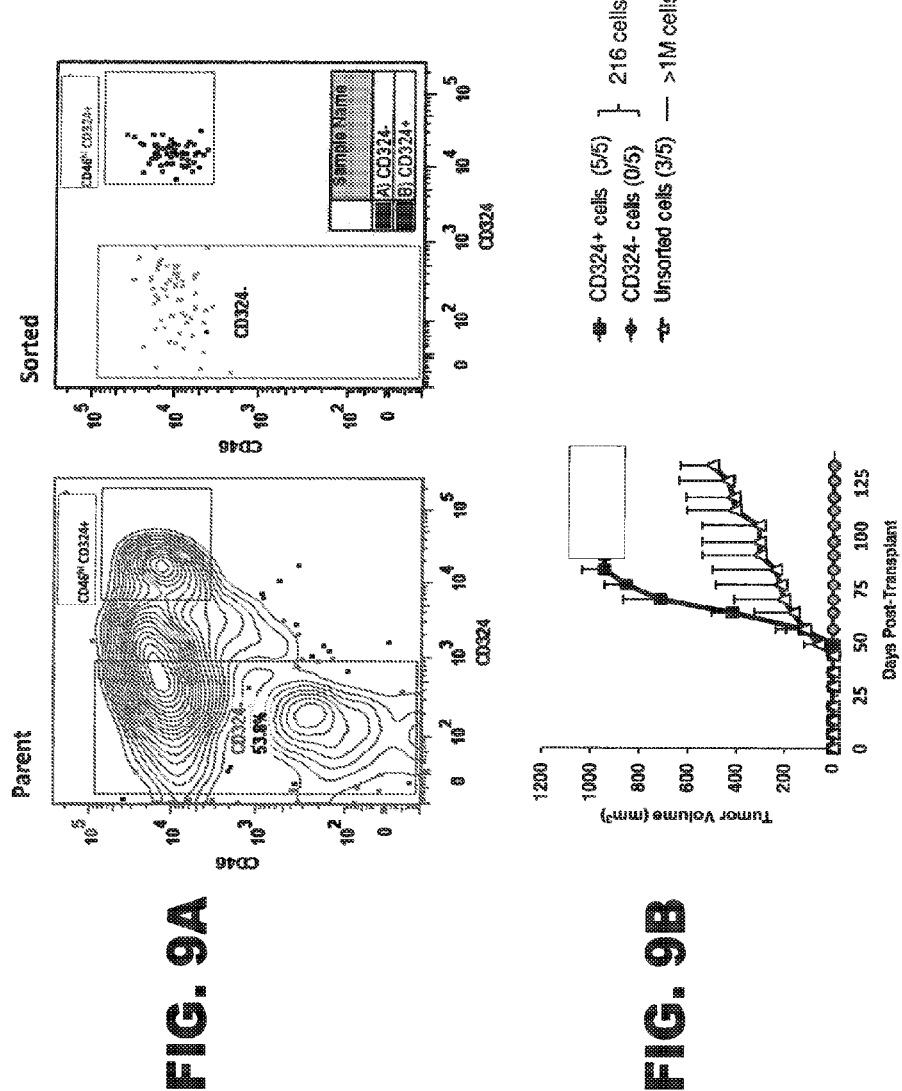

CD46hiCD324+ Cell Subpopulations Are Highly Tumorigenic With Regard to Various Cancers

| | | 500+ cells | | 200-499 cells | | 50-199 cells | | <50 cells | |
|---|---|---|---|---|---|---|---|---|---|
| SCRx-CR05 | CD46-/lo CD324- | | | 0/5 | 0% | 1/5 | 20% | 1/5 | 20% |
| | CD46hi CD324- | | | 5/5 | 100% | 7/9 | 78% | | |
| | CD46hi CD324+ | | | 5/5 | 100% | 14/14 | 100% | 18/25 | 72% |
| SCRx-CR10 | CD46-/lo CD324- | | | 0/5 | 0% | | | | |
| | CD46hi CD324- | | | 1/5 | 20% | | | | |
| | CD46hi CD324+ | | | 3/5 | 60% | | | | |
| SCRx-CR14 | CD46-/lo CD324- | 0/5 | 0% | 3/15 | 20% | 0/5 | 0% | 0/5 | 0% |
| | CD46hi CD324- | 0/5 | 0% | 8/15 | 53% | | | 0/5 | 0% |
| | CD46hi CD324+ | 10/10 | 100% | 20/20 | 100% | 4/5 | 80% | 6/10 | 60% |
| SCRx-CR16 | CD46-/lo CD324- | | | 0/5 | 0% | | | | |
| | CD46hi CD324- | | | 1/5 | 20% | | | | |
| | CD46hi CD324+ | | | 4/9 | 44% | | | | |
| SCRx-LU37 | CD46-/lo CD324- | 0/5 | 0% | | | | | | |
| | CD46hi CD324- | 0/5 | 0% | | | | | | |
| | CD46hi CD324+ | 6/10 | 60% | | | | | | |
| SCRx-LU49 | CD46-/lo CD324- | | | | | 0/5 | 0% | | |
| | CD46hi CD324- | | | | | | | | |
| | CD46hi CD324+ | | | | | 5/5 | 100% | | |
| SCRx-PA03 | CD46-/lo CD324- | | | 0/5 | 0% | | | | |
| | CD46hi CD324- | | | 3/5 | 60% | | | | |
| | CD46hi CD324+ | | | 5/5 | 100% | | | | |
| SCRx-PA04 | CD46-/lo CD324- | 0/5 | 0% | | | | | | |
| | CD46hi CD324- | 0/5 | 0% | | | | | | |
| | CD46hi CD324+ | 5/5 | 100% | | | | | | |

FIG. 10A

CD46hiCD324+ Cell Subpopulations Are Highly Tumorigenic With Regard to Various Cancers

| | | 500+ cells | | 200-499 cells | | 50-199 cells | | <50 cells | |
|---|---|---|---|---|---|---|---|---|---|
| SCRx-BR22 | CD46hi CD324- | | | 10/10 | 100% | | | 1/10 | 10% |
| | CD46hi CD324+ | | | 10/10 | 100% | | | 10/10 | 100% |
| SCRx-BR31 | CD46hi CD324- | | | | | | | 0/5 | 0% |
| | CD46hi CD324+ | | | | | | | 4/10 | 40% |
| SCRx-BR56 | CD46hi CD324- | | | | | | | 6/15 | 40% |
| | CD46hi CD324+ | | | | | | | 17/19 | 89% |
| SCRx-OV11 | CD46hi CD324- | | | 1/10 | 10% | | | | |
| | CD46hi CD324+ | | | 2/4 | 50% | | | | |
| SCRx-OV26 | CD46hi CD324- | 0/6 | 0% | | | | | | |
| | CD46hi CD324+ | 7/10 | 70% | | | | | | |
| SCRx-OV45 | CD46hi CD324- | 0/13 | 0% | 0/6 | 0% | | | | |
| | CD46hi CD324+ | 20/30 | 67% | 8/13 | 62% | | | | |
| SCRx-OV55 | CD46hi CD324- | | | | | 0/12 | 0% | | |
| | CD46hi CD324+ | | | | | 28/30 | 93% | | |

FIG. 10B

Protein Sequences of Exemplary Murine and Humanized CD324 Modulator Light Chain Variable Regions

| mAb | FR1 | CDR1 | FR2 | CDR2 | FR3 | CDR3 | SEQ ID NO. |
|---|---|---|---|---|---|---|---|
| SC10.6 | QIVLTQSPAIMSASPGEKVTMTC | SASSSVRY | MYWYQQKPRSSPKPWIH | LTSNLAS | GVPARFSGSGSGTSYSLTISSMEADAATYYC | QQWSSHPFTFGSGTKLEIK | 20 |
| SC10.15 | DIVMSQSPSSLAVSVGEKVTMSC | KSSQSLLYSNNQKNY | LAWYQQKPGQSPKLLIY | WASTRES | GVPDRFTGSGSGTDFTLTISSVKAEDLAVYYC | HQYYTSPYTFGGGTNLEIK | 22 |
| SC10.17 | DVLMTQTPLSLPVSLGDQASISC | RSSQSIVHSDGNTY | LEWYLRKPGQSPRLLIY | KVSNRFS | GVPDRFTGSGSGTDFTLKISRVEAEDLGVYYC | FQGSHAPWTFGGGTKLEIK | 24 |
| SC10.19 | DVVMSQSPSSLTVSVGEKGTMSC | KSSQSLLYSSNQKNY | LAWYQQKPGQGSPKLLIY | WASTRES | GVPDRFTGSGSGTDFSLTISSVLAEDLAVYFC | HQYSSPYTFGGGTKLEIK | 26 |
| SC10.35 | QIVLTQSPAIMSASPGERVTLTC | SASSSVSSF | LYWYQQKSGSSPRLWIY | STSTLAS | GVPARFSGSGSGTSYSLTISSMEAEDAASYFC | HQWSSYPWTFGGGTKLEIK | 28 |
| SC10.36 | DIVMTQSPSSLAMSVGQKVTMSC | KSSQSLLNSSTQKNY | LAWYQQKPGQSPKLLIY | FASTRGS | GVPDRFKGSGSGTDFTLTISSVQTEDLADYFC | QQHYSIPCTFGGGTKLEIK | 30 |
| SC10.38 | DIQMNQSPSSLSASLGDTITITC | HVSQNIINVW | LTWYQQKPGNIPKLLLY | KASMLQT | GVPSRFSGSGSGTGFTLTISSLQPEDIATYYC | QQGQSYPTFGSGGTK | 32 |
| SC10.75 | DIVMSQSPSSLAVSVGEKVTMSC | KSSQSLLYSNNQKNY | LAWYQQKPGQSPKLLIY | WASSRES | GVPDRFTGSGSGTDFTLTISSVKAEDLAVYYC | QQYYSSPYTFGGGTKLK | 34 |
| SC10.111 | DIVMTQSQKFMSTSVGDRVSVTC | KASQNVAIN | VAWYQQKPGQSPKALIY | SASYRYS | VVPDRFTGSGSGTDFTLPISNVQSEGLADYFC | LQYINYPYTFGGGTKLEIK | 36 |
| SC10.112 | QIVLSQSPAILSASPGEKVTMTC | RASSSVSY | IHWYQQKAGSSPTSWIY | ATSNLAS | GVPTRFSGSGSGTSYSLTVNRVEAEDAATYYC | QQWSTTPPTFGGGTRLEIK | 38 |
| SC10.115 | DIVMTQSPSSLTVTAGEKVTMSC | KSSQSLLKSGNQKNY | LTWYQQKPGQPPKLLIY | WASTRES | GVPDRFTGSGFGTDFTLTISSVQAEDLAVYFC | QSDYNYPTFGSGTKLK | 40 |
| SC10.118 | QIVLTQSPAIMSASPGERVTITC | SASSSVSY | MHWFQQKPGTSPKLWIY | STSNLAS | GVPARFSGSGSGTSYSLTISRMEAEDAATYYC | QQRSTYPTFGGGTKLEIK | 42 |
| SC10.123 | QIVLSQSPAILSASPGEKVTMTC | RASSSVSY | MHWYQQKPGSSPKPWIH | AASNLAS | GVPARFSATGSGSGTSYSLTISRVEAEDAATYC | CQQWSNNPPTFGGGTKLEIK | 44 |
| SC10.124 | DIVLTQSPASLAVSLGQRATISC | RANESVEYYGTSL | MQWYQQKPGQQPPKLLIY | AASVKS | GVPARFSGSGSGTDFSLNIHPVEEDDIAMYFC | QQSRKVPSTFGGGTKLEIK | 46 |
| SC10.125 | DIVLTQSPASLAVSLGQRATISC | RAHESVEYYGTSL | MQWYQQKPGQQPPKLLIY | AASVKS | GVPDRFSGSGSGTDFSLNIHPVEEDDIAMYFC | QQSRKVPSTFGGGTKLEIK | 48 |
| SC10.126 | DIVMSQSPSSLAVSVGEKVTMSC | KSSQSLLYSSNQKNY | LAWYQQKPGQSPKLLIY | WASTRES | GVPARFSGSGSGTDFSLNIHPVEEDDIAMYFC | QQYYNYPYTFGGGTKLEIK | 50 |
| SC10.127 | DIVLTQSPASLAVSLGQRATISC | RANENVEYYGTSL | MQWYQQKPGQPPKLLIY | AASNVKS | GVPARFSGSGSGTDFSLNIHPVEEDDIAMYFC | QQSRKVPSTFGGGTKLK | 52 |
| SC10.128 | DIVMSQSPSSLAVSVGEKVTMSC | KSSQSLLYSMQKNY | LAWYQQKPGQSPKLLIY | WASTRES | GVPDRFTGSGSGTDFTLTISTVKAEDLAVYYC | HQYYSYPTFGGGTKLEIK | 54 |
| SC10.129 | DIVMSQSPSSLAVSLGQRATISC | RASQSVSSSSYSY | MHWYQQKPGQPPKLLIK | FASNLES | GVPARFSGSGSGTDFTLNIHPVEEDTATYYC | QHSWEIPLTFGAGTKLEIK | 56 |
| SC10.130 | DVQITQSPYLAASPGETISINC | RASKNISKY | LAWYQEKPGKTNKLLIY | SGSTLQS | GIPSGFSGSGSGTSYSLTISSLEPEDFAMYYC | QQHFEYPYTFGGGTKLEIK | 58 |
| SC10.132 | QIVLTQSPSPAIMSASLGEEITLTC | SATSSVGY | IHWYQQTSGTSPRLLIY | TTSNLAS | GVPSRFSGSGSGTFYSLTISSVEAEDAADYYC | HQWSRYPTFGGGTKLEIK | 60 |
| SC10.133 | DIKMTQSPSSTYASLGERVTITC | KASQDINTYLY | WFQQKPGRPPKTLIY | RANRLID | GVPSRFSGSGSGQDYSLTISSLEYEDLGIHYC | LQYDEFPYTFGGGTKLEIK | 62 |
| SC10.134 | DIVLTQSPASLAVSLGQRATISC | RADESVEYYGTSL | MQWYQQKPGQPPKLLIY | AASNVKS | GVPARFSGSGSGTDFSLNIHPVEEDDIAVFC | QQSREVPSTFGGGTKLEIK | 64 |
| SC10.163 | DIVMTQAAFSNPVTLGTSASISC | RSSKSLLHSNGITY | LYWYLQKPGQSPQLLIY | QMSNLAS | GVPDRFSNSGSGTDFTLRISRVEAEDVGVYYC | AQNLELPWTFGGGTKLEIK | 66 |
| SC10.168 | DIVMTQSHKLMSASVGDRVSITC | KASQDVGTAVA | WYQQKPGRSPKLLIY | WASNRHT | GVPDPFTGSGSGTDFTLTISNVQSEDLADYFC | QQFGSYPYTFGGGTKLEIKR | 68 |
| SC10.178 | DIVLTQSPLSLVSLGDQASISC | RSSQSLVHSNGNTY | LHWYLQKPGQSPNLLIF | KVSNRFS | GVPDRFSGSGSGTDFTLRISRVEAEDLGVYFC | SQTTHVWTFGGGTKVEIK | 70 |
| hSC10.17 | DVVMTQSPLSLPVTLGQPASISC | RSSQSIVHSDGNTY | LEWYLQKPGQSPRRLIY | KVSNRFS | GVPDRFSGSGSGTDFTLKISRVEAEDVGVYYC | FQGSHAPWTFGGGTKVEIK | 72 |

FIG. 11A

Protein Sequences of Exemplary Murine and
Humanized CD324 Modulator Heavy Chain Variable Regions

| mAb | FR1 | CDR1 | FR2 | CDR2 | FR3 | CDR3 | SEQ ID NO. |
|---|---|---|---|---|---|---|---|
| SC10.6 | DVQLQESGPGLVKPSQSLSLTCTVT | GFSITSDYS | WNWIRQRPGNKLEWMGY | ISYSGHT | SYNPSLESRISITRDTSKNQFFLQLNSVTTEDTATYYC | TRGNWDVYWGQGTLVTVSA | 21 |
| SC10.15 | QVQLKESGGPFLVAPSQSLSITCTVS | GFSLSRYS | VQWVRQPPGKGLEWLGM | IWGGGST | DVNSGLKSRLTISKONSKSQVFLKMNSLQTDDTAMYFC | ARTQFYYGHDGGYAMDFWGQGTSVTVSS | 23 |
| SC10.17 | DVQLVESGGGLVQPGGSRKLSCAAS | GFTFSSYG | MHWVRQAPETGLEWVAY | ITTRSSTI | YYAATVKGRFTISRDNAKNRNTLFLQMTSLRSEDTAMYYC | TREPLTGYYAMDYWGQGTSVTVSS | 25 |
| SC10.19 | QVQLKESGPGILVKPGSQSLSITCTVS | GFSLSRYS | VHVWVRQPPGKGLEWLGM | IWGGGSI | DVNSGLKSRLSISKDNSKSQVFLKMNSLQSDDTAMYHC | VRAQFYYGVDGGYAMDYWGQGTAMDFWGQGTSVTVSS | 27 |
| SC10.35 | SDVQLQESGPGLVKPDQSLSLTCTVT | DYSITSDYA | WNWIRQFPGNMLEWMGN | IGYSGDT | SYNPSLKSRISITRDTSKNQFFLQLNSVTTEDSATYYC | ARSSLGPFDYWGQGTALTVSS | 29 |
| SC10.36 | QVQLQQSGSGNELVRPGSAVKISCKAS | GYAFSSYW | MNWVKQRPGQGLEWIGQ | IYPGDDS | NYNGKFKGKATLTADKSSSSAYMHLSSLTSEDSAVYFC | ARGFATPTMDYWGQGTSVTVSS | 31 |
| SC10.38 | QVQLQQSGAELMKTGASVKISCKAT | GYTFSSY | WIEWVKQRPGHGLEWIGE | ILPGSGKT | NYNENFKGKATFTADTSSNTAYMQLSSLTSEDSVVYYC | ARRGAYYGNFDYWGQGTTLTVSS | 33 |
| SC10.75 | QVQLKESGPGLVAPSQSLSITCTVT | GFSLSRYS | VHWIRQPPGKGLEWLG | MIWGGGST | DVNSALKSRLSINKDNSKSQVFLKMNSLQDTAMYYC | ARTQFYYGHDGGYAMDYWGQGTSVTVSS | 35 |
| SC10.111 | EVQLQQSGPELLKPGASVKISCKAS | GYTFTDYN | MHWVKQSHGKSLEWIG | NIVPYNGGT | GYNQKFKTKATLTVDNSSTAYMELRSLTSEDSAVYYC | AIGNYWFAFWGQGTLVTVSA | 37 |
| SC10.112 | EVQLQQSGPDVKPGTSVKISCKAS | GYSFTACY | IHWVKQSHGKSLEWIG | RFSPNNDRT | TYNQKFKDKAALTVDKSSTAYMDLRSLTSEDSAVYYC | ARGEESWDAWFTYWGQGTLVTVSA | 39 |
| SC10.115 | QVTLKESGPGILQPSQTLSLTCSFS | GFSLSTSG | MGVGWIRQPSGKGLEWLA | HIWWDDVK | RYNPALKSRLTISKRDTSSSQVFLKIASVDTADTATYHC | ARIAIGQPFAYWGQGTLVTVSA | 41 |
| SC10.118 | QVQLQQPGAELVKPGASVKLSCKRTS | GYSFTSY | WIHWVKQRPGRGLEWIG | RIVPNSGGT | KYNENFKNKATLTVDKSSNTAYMQLSLTSEDSAVYYC | TREDSYGPFDLDYWGQGTSVTVSS | 43 |
| SC10.123 | EVQLQQSGPELVKPGASVKISCKAS | GYSFTGYF | MNWVKQSHGKSLEWIG | RINPYNGDN | FYNQKFKGKATLTVDKSSSTAHMELLSLTSEDSAVYYC | GRDYGSSYGWFDVWGAGTTVTVSS | 45 |
| SC10.124 | EVQLQQSGPELVKPGASMKISCKAS | GYTFTDHT | MHWVKQSHGKNLEWIG | RINPYNGDT | SHNQNFKGKATLTVDKSSNTAYMELLSLTSEDSAVYYC | ARYGGDYTSSYYTMDYWGQGTSSTVSS | 47 |
| SC10.125 | EVQLQQSGPELVKPGASMKISCKAS | GYTFTDYT | MHWVRQSHGKNLEWIG | RINPYNADT | SHNQNFKGKATLTVDKSFNTAYMELLSLTSEDSAVYYC | ARYGGDFTSSYYTMDYWGQGTSVTVSS | 49 |
| SC10.126 | QVQLKESGPGLVAPSQSLSITCTVS | GFSLTSYT | ISWVRQPPGKGLEWLG | IIWTAGAT | NYNSALKSRLSISKDNSKSQVFLKMMNSLQTDDTARYYC | ARYSKDYYAVDYWGQGTSVTVSS | 51 |
| SC10.127 | EVQLQQSGPELVKPGASMKISCKA | SGYTFTDYT | MHVWVKQSHGKNLEWIG | RINPYNDDI | SHNQNFKDKATLTVDKSSNTAYMELLSLTSEDSAVYYC | ARYGGDYTSSYYTMDYWGQGTSVTVSS | 53 |
| SC10.128 | QVQLKESGPGLVAPSQSLSITCTVS | GFSLSRYS | VHVWVRQPSGKGLEWIG | MIWGGGST | DVNSALKSRLISKONSIGSQVFLKMNSLQTDDTAMYYC | ARTQFYYGHDGGYAMDYWGQGTSVTVSS | 55 |
| SC10.129 | QVTLKESGPGILQPSQTLSLTCSFS | GFSLSTSGMG | VGWIRQPSGKGLEWLA | HIWWDDVK | RYNPALKSRLNISKDTSSSQVFLKIASVDTADTATYYC | GRKSNSGYFDYWGQGTTLTVSS | 57 |
| SC10.130 | EVQLQQSGPDLVKPGASVKISCKAS | GYSFTGYF | MNWVKQRQTPDKRLEWNG | RINPYNGDT | FYNQKFKGKATLTVDKSSSTAHMELLSLTSEDSAVYYC | GRGNYYFDYWGQGTLVTVSA | 59 |
| SC10.132 | QVQLQEQSGGDLVKPGGSLKLSCAAS | GFTFSSYG | MSWVRQTPDKRLEWVA | TISSGGSY | SYYPDSVKGRFTISRDNAKNTLYLQMSSLKSEDTAMYFC | RPSFFPSWGQGTLVTVSA | 61 |
| SC10.133 | EVQLQQSGAELVRPGASVKLSCTAS | GPNINDDY | FHWVKQRPEQGLEWIG | RIDPANGNT | KYGPKFQDKATITADTSSNTAYLQFSLTSEDTAVYYC | ASGWAFACWGQGT | 63 |
| SC10.134 | EVQLQQSGPELVKPGTSMKISCKAS | GYTFTDYT | MHVWVKQSHGKNLEWIG | RINPYTGST | SHNQNFKCKASLTVDKSSNTAYMDLLSLTSEDSAVYYC | ARFGGDYTSSYYTLDYWGQGTSVSVSS | 65 |
| SC10.163 | EVQLQLQSGPGLVKPGDSVKMSCKAS | GNTVTNYY | MDVWVKQRPGNKLEWMA | YNANNGGT | SYNQKFKGKATLTVDKSSTAYMEIHSLTSEDSAVYYC | AIVYRYEFAYWGQGTLVTVSA | 67 |
| SC10.168 | SDVQLQESGPGLVKPGSQSLSYTCVT | DYSLTSGYY | WNWIRQFPGNKLEWMA | YHSGST | HYNPSLKSRISVTRDTSKNQFFLQLNSVTTEDTATYYC | ARDGAYYSSWFPYWGQGTLVTVSA | 69 |
| SC10.178 | QILLVQSGPELKKPGETVKISCKA | NYTFTDYG | MHWVKQAPGKGLKWMG | WINPKTGVA | SYADDFKGRFAFSLETSASTAYLQINNNLENEDTSYFC | ARFDYWGQGTTLTVSS | 71 |
| hSC10.17 | EVQLVESGGGLVQPGGSLRLSCAAS | GFTFSSYG | MHWVRQAPGKGLEWVAY | ITTRSSTI | YYADSVKGRFTISRDNAKNSLYLQMMNSLRAEDTAVYYC | TREPLTGYYAMDYWGQGTSVTVSS | 73 |

FIG. 11B

Properties of Selected CD324 Modulators

| Clone | Reduced Epitope Recognition | Mouse Reactivity | Percent live cells remaining at 10pM | Bin |
|---|---|---|---|---|
| SC10.9 | + | - | ND | N.D. |
| SC10.17 | + | - | 32 | E |
| SC10.27 | - | - | 97 | U |
| SC10.43 | - | - | 110 | A |
| SC10.60 | + | + | 35 | N.D. |
| SC10.65 | + | + | 41 | D |
| SC10.70 | + | - | 81 | C |
| SC10.75 | - | - | 101 | B |
| SC10.164 | + | - | 55 | U |
| SC10.165 | + | - | 52 | C |
| SC10.178 | + | + | 68 | C |
| SC10.180 | + | - | 82 | U |

FIG. 12

Selected Modulators Mediate Killing of Cells Expressing CD324

| Antibody | Dose 100pM Normalized RLU | Dose 10pM Normalized RLU | Antibody | Dose 100pM Normalized RLU | Dose 10pM Normalized RLU | Antibody | Dose 100pM Normalized RLU | Dose 10pM Normalized RLU | Antibody | Dose 100pM Normalized RLU | Dose 10pM Normalized RLU |
|---|---|---|---|---|---|---|---|---|---|---|---|
| SC10.25 | 98.9 | 104.4 | SC10.50 | 85.4 | 108.7 | SC10.75 | 98.8 | 101.3 | SC10.160 | 69.8 | 83.6 |
| SC10.26 | 97.6 | 108.7 | SC10.51 | 59.9 | 94.8 | SC10.76 | 71.4 | 96.2 | SC10.161 | 45.7 | 82.4 |
| SC10.27 | 67.8 | 97.3 | SC10.52 | 68 | 86.8 | SC10.77 | 66.6 | 93.2 | SC10.162 | 100.4 | 95.4 |
| SC10.28 | 38 | 87.9 | SC10.53 | 36.5 | 71.1 | SC10.78 | 46.9 | 94.6 | SC10.163 | 90.3 | 91.5 |
| SC10.29 | 20 | 60.7 | SC10.54 | 43.2 | 77.6 | SC10.79 | 99.7 | 97.8 | SC10.164 | 31.2 | 54.7 |
| SC10.30 | 48.7 | 92.3 | SC10.55 | 57.9 | 87.4 | SC10.80 | 20.1 | 49.1 | SC10.165 | 24.2 | 52 |
| SC10.31 | 25.5 | 63.5 | SC10.56 | 99.4 | 103.1 | SC10.81 | 33.6 | 72 | SC10.166 | 93.7 | 87.4 |
| SC10.32 | 41 | 81.2 | SC10.57 | 89.2 | 100.1 | SC10.82 | 57.2 | 90.8 | SC10.167 | 100.4 | 89.4 |
| SC10.33 | 58.2 | 91.8 | SC10.58 | 66 | 97.8 | SC10.83 | 86.1 | 100.3 | SC10.168 | 34 | 64.8 |
| SC10.34 | 18.9 | 56.8 | SC10.59 | 80.3 | 102.1 | SC10.84 | 93.3 | 101.2 | SC10.169 | 36.6 | 63.5 |
| SC10.35 | 19.4 | 37.2 | SC10.60 | 21.7 | 35.2 | SC10.85 | 23.1 | 52.7 | SC10.170 | 21.1 | 48.9 |
| SC10.36 | 21.2 | 40.7 | SC10.61 | 95 | 95.9 | SC10.86 | 53.3 | 87.1 | SC10.171 | 26.5 | 60.1 |
| SC10.37 | 58.9 | 90.6 | SC10.62 | 90.2 | 100.6 | SC10.87 | 92.8 | 97.2 | SC10.172 | 44.3 | 77.5 |
| SC10.38 | 106 | 101.5 | SC10.63 | 73.5 | 78.4 | SC10.88 | 66.6 | 83.8 | SC10.173 | 63.6 | 91.4 |
| SC10.39 | 100.4 | 104.8 | SC10.64 | 58.3 | 83.9 | SC10.89 | 41.8 | 76.7 | SC10.174 | 23.9 | 51.3 |
| SC10.40 | 33.1 | 74.1 | SC10.65 | 19.4 | 40.5 | SC10.90 | 43.5 | 79.7 | SC10.175 | 22.1 | 48 |
| SC10.41 | 43 | 86.8 | SC10.66 | 68.3 | 84.3 | SC10.91 | 30.1 | 56.3 | SC10.176 | 20.6 | 48.5 |
| SC10.42 | 84.4 | 99.1 | SC10.67 | 49.2 | 77.9 | SC10.92 | 64.9 | 89.6 | SC10.177 | 46.5 | 79.9 |
| SC10.43 | 111.8 | 109.2 | SC10.68 | 48.4 | 68.1 | SC10.93 | 53.6 | 85 | SC10.178 | 38.1 | 68 |
| SC10.44 | 52.9 | 92.9 | SC10.69 | 33.3 | 55.5 | SC10.94 | 52.8 | 79.8 | SC10.179 | 58.3 | 81.7 |
| SC10.45 | 62.3 | 97.1 | SC10.70 | 74.9 | 81 | SC10.95 | 95.2 | 93.2 | SC10.180 | 84 | 89.9 |
| SC10.46 | 95.6 | 110.7 | SC10.71 | 30.5 | 59.4 | SC10.96 | 57.4 | 74.3 | | | |
| SC10.47 | 55.7 | 94.5 | SC10.72 | 25.5 | 51.8 | SC10.157 | 42.1 | 69.6 | | | |
| SC10.48 | 22.2 | 45.1 | SC10.73 | 20.6 | 46.8 | SC10.158 | 45.5 | 85.4 | | | |
| SC10.49 | 70.6 | 94 | SC10.74 | 35.1 | 77.6 | SC10.159 | 62.1 | 82.3 | | | |

FIG. 14B

CD324 Modulators Mediate Cytotoxicity in Several Human Tumor Xenografts

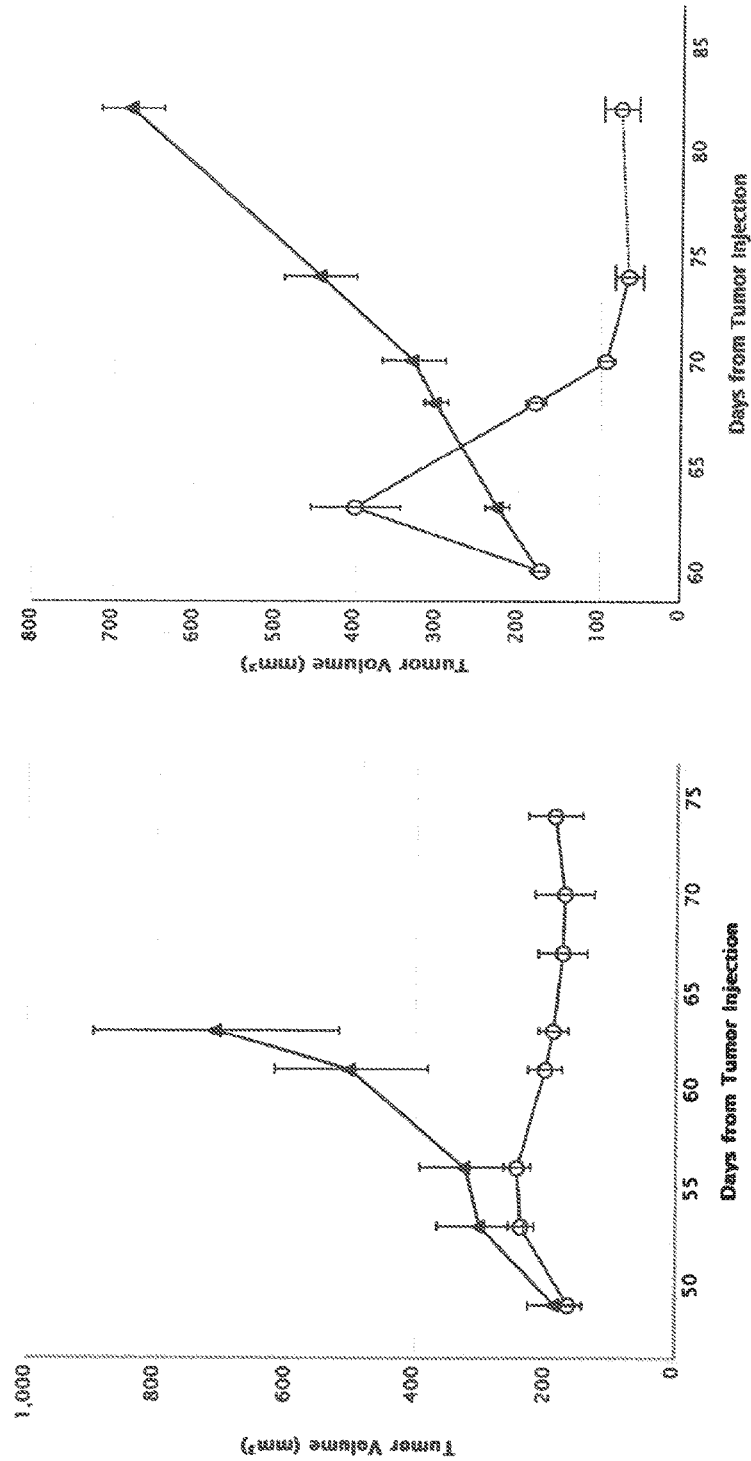

SEQ ID NO: 120          SC10.6 Light chain
CAAATTGTTCTCACCCAGTCTCCAGCACTCATGTCTGCATCTCCAGGGGAGAAGGTCACCATGACCTGCAGTGCCA
GCTCAAGTGTACGTTACATGTACTGGTACCAGCAGAAGCCAAGATCCTCCCCCAAACCCTGGATTCATCTCACATCC
AACCTGGCTTCTGGAGTCCCTGCTCGCTTCAGTGGCAGTGGGTCTGGGACCTCTTACTCTCTCACAATCAGCAGCAT
GGAGGCTGAAGATGCTGCCACCTATTACTGCCAGCAGTGGAGTAGTCACCCATTCACGTTCGGCTCGGGGACAAA
GTTGGAAATAAAAC SEQ ID NO: 121.          SC10.6 Heavy chain
TCTGATGTGCAGCTTCAGGAGTCGGGACCTGGCCTGGTGAAACCTTCTCAGTCTCTGTCCCTCACCTGCACTGTCAC
TGGCTTCTCAATCACCAGTGATTATTCCTGGAACTGGATCCGGCAGTTTCCAGGAAACAAACTGGAGTGGATGGG
CTACATAAGCTACAGTGGTCACACTAGCTACAACCCATCTCTCGAAAGTCGAATCTCTATCACTCGAGACACATCCA
AGAACCAGTTCTTCCTGCAGTTGAATTCTGTGACTACTGAGGACACAGCCACATATTACTGTACAAGAGGGAACTG
GGACGTTGTTTACTGGGGCCAAGGGACTCTGGTCACTGTCTCTGCA SEQ ID NO: 122          SC10.15 Light chain
GACATTGTGATGTCACAGTCTCCATCCTCCCTAGCTGTGTCAGTTGGAGAGAAGGTTACTATGAGCTGCAAGTCCA
GTCAGAGCCTTTTATATAGTAACAATCAAAAGAACTACTTGGCCTGGTACCAGCAGAAACCAGGGCAGTCTCCTAA
ACTGCTGATTTACTGGGCATCCACTAGGGAATCTGGGGTCCCTGATCGCTTCACAGGCAGTGGATCTGGGACAGA
TTTCACTCTCACCATCAGCAGTGTGAAGGCTGAAGACCTGGCAGTTTATTACTGTCACCAATATTATACCTCTCCGT
ACACGTTCGGAGGGGGGACCAACCTGGAAATAAAACG SEQ ID NO: 123          SC10.15 Heavy chain
CAGGTGCAGCTGAAGGAGTCAGGACCTGGCCTGGTGGCACCCTCACAGAGCCTGTCCATCACATGCACTGTCTCT
GGGTTCTCATTATCTAGATATAGTGTACAGTGGGTTCGCCAGCCTCCAGGAAAGGGTCTGGAGTGGCTGGGAATG
ATATGGGGTGGTGGAAGCACAGACTATAATTCAGGTCTCAAATCCAGACTGACCATCAGCAAGGACAACTCCAAG
AGCCAAGTTTTCTTAAAAATGAACAGTCTGCAAACTGATGACACAGCCATGTACTTCTGTGCCAGAACCCAGTTCTA
CTATGGCCACGACGGGGGTTATGCTATGGACTTCTGGGGTCAAGGAACCTCAGTCACCGTCTCCTCA SEQ ID NO: 124          SC10.17 Light chain
GATGTTTTGATGACCCAAACTCCACTCTCCCTGCCTGTCAGTCTTGGAGATCAAGCCTCCATCTCTTGCAGATCTAG
TCAGAGCATTGTACATAGTGATGGAAACACCTATTTAGAATGGTACCTGCGGAAACCAGGCCAGTCTCCAAGACTC
CTGATCTACAAAGTTTCCAACCGATTTTCTGGGGTCCCAGACAGGTTCAGTGGCAGTGGATCAGGGACAGATTTCA
CACTCAAGATCAGCAGAGTGGAGGCTGAGGATCTGGGAGTTTATTACTGCTTTCAAGGTTCACATGCTCCGTGGA
CGTTCGGTGGAGGCACCAAGCTGGAAATCAAAC SEQ ID NO: 125          SC10.17 Heavy chain
GATGTGCAGCTGGTGGAGTCTGGGGGAGGCTTAGTGCAGCCTGGAGGGTCCCGGAAACTCTCCTGTGCAGCCTCT
GGATTCACTTTCAGTAGCTACGGAATGCACTGGGTTCGTCAGGCTCCAGAGACGGGGCTGGAGTGGGTCGCATAC
ATTACTACTCGCAGTAGTACCATCTACTATGCAGCCACAGTGAAGGGCCGATTCACCATCTCCAGAGACAATGCCA
GGAACACCCTGTTCCTGCAAATGACCAGTCTAAGGTCTGAGGACACGGCCATGTATTACTGTACTAGAGAACCCCT
AACTGGATACTATGCTATGGACTACTGGGGTCAAGGAACCTCAGTCACCGTCTCCTCA

FIG. 19

SEQ ID NO: 126             SC10.19 Light chain
GACATTGTGATGTCGCAGTCTCCCTCCTCCCTAACTGTGTCAGTTGGAGAGAAGGTTACTATGAGCTGCAAGTCCA
GTCAGAGCCTTTTATATAGTAGCAATCAAAAGAACTACTTGGCCTGGTACCAGCAGAAACCAGGGCAGTCTCCTAA
ACTGCTGATTTACTGGGCATCCACTAGGGAATCTGGGGTCCCTGATCGCTTCACAGGCAGTGGATCTGGGACAGA
TTTCTCTCTCACCATCAGCAGTGTGCTGGCTGAAGACCTGGCAGTTTATTTCTGTCATCAATATTATAGCTCTCCGTA
CACGTTCGGAGGGGGGACCAAGCTGGAAATAAAACG SEQ ID NO: 127             SC10.19 Heavy chain
CAGGTGCAGCTGAAGGAGTCAGGACCTGGCCTGGTGGCACCCTCACAGAGCCTGTCCATCACATGCACTGTCTCT
GGGTTCTCATTATCCAGATATAGTGTACACTGGGTTCGCCAGCCTCCAGGAAAGGGTCTGGAGTGGCTGGGAATG
ATATGGGGTGGTGGAAGTATAGACTATAATTCAGGTCTCAAATCCAGACTGAGCATCAGTAAGGACAACTCCAAG
AGCCAAGTTTTCTTAAAAATGAACAGTCTGCAATCTGATGACACTGCCATGTACCACTGTGTCAGAGCCCAGTTTTA
CTATGGTTACGACGGGGGATACGCTATGGACTACTGGGGTCAAGGAACCTCAGTCACCGTCTCCTCA SEQ ID NO: 128             SC10.35 Light chain
CAAATTGTTCTCACCCAGTCTCCAGCAATCATGTCTGCATCTCCTGGGGAGAGGGTCACCTTGACCTGCAGTGCCA
GCTCAAGTGTAAGTTCCAGCTTCTTGTACTGGTACCAGCAGAAGTCAGGATCCTCCCCCAAACTCTGGATTTATAGC
ACATCCACCCTGGCTTCTGGAGTCCCTGCTCGCTTCAGTGGCAGTGGGTCTGGGACCTCTTACTCTCTCACAATCAG
CAGCATGGAGGCTGAAGATGCTGCCTCTTATTTCTGCCATCAGTGGAGTAGTTACCCATGGACGTTCGGTGGAGG
CACCAAGCTGGAAATCAAAC SEQ ID NO: 129             SC10.35 Heavy chain
TCTGATGTGCAGCTTCAGGAGTCGGGACCTGGCCTGGTGAAACCTTCTCAGTCTCTGTCCCTCACCTGCACTGTCAC
TGACTACTCAATTACCAGTGATTATGCCTGGAACTGGATCCGGCAGTTTCCAGGAAACAATCTGGAGTGGATGGG
CAACATAGGCTACAGTGGTGACACTAGCTACAACCCTTCTCTCAAAAGTCGAATCTCTATCACTCGAGACACATCCA
AGAACCAGTTCTTCCTGCAGTTGAATTCTGTGACTACTGAGGACTCAGCCACATATTACTGTGCAAGAAGTAGTCT
GGGGCCCTTTGACTACTGGGGCCAAGGCACCGCTCTCACAGTCTCCTCA SEQ ID NO: 130             SC10.36 Light chain
GACATTGTGATGACACAGTCTCCATCCTCCCTGGCTATGTCAGTAGGACAGAAGGTCACTATGAGCTGCAAGTCCA
GTCAGAGCCTTTTAAATAGTAGCACTCAAAAGAACTATTGGCCTGGTACCAGCAGAAACCAGGACAGTCTCCTAA
ACTTCTGATATACTTTGCATCCACTAGGGGATCTGGGGTCCCTGATCGCTTCATAGGCAGTGGATCTGGGACAGAT
TTCACTCTTACCATCAGCAGTGTGCAGACTGAAGACCTGGCAGATTACTTCTGTCAACAACATTATAGCATTCCGTG
CACGTTCGGAGGGGGGACCAAGCTGGAAATAAAACG SEQ ID NO: 131             SC10.36 Heavy chain
CAGGTTCAGCTGCAGCAGTCTGGGAATGAGCTGGTGAGGCCTGGGTCCGCAGTGAAGATTTCCTGCAAGGCGTCT
GGCTATGCATTCAGTAGTTACTGGATGAACTGGGTGAAGCAGAGGCCTGGACAGGGTCTTGAGTGGATTGGACA
GATTTATCCTGGAGATGATGATTCTAACTACAATGGAAAATTCAAGGGTAAAGCCACACTGACTGCAGACAAATCC
TCCAGCTCAGCCTACATGCACCTCAGCAGCCTAACATCTGAGGACTCTGCGGTCTATTTCTGTGCCAGAGGGTTTG
CTACACCTACCATGGACTACTGGGGTCAAGGAACCTCAGTCACCGTCTCCTCA

FIG. 19(Cont.)

SEQ ID NO: 132                SC10.38 Light chain
GACATCCAGATGAACCAGTCTCCATCCAGTCTGTCTGCATCCCTTGGAGACACAATTACCATCACTTGCCATGTCAG
TCAGAACATTAATGTTTGGTTAACCTGGTACCAGCAGAAACCAGGAAATATTCCTAAGCTATTGCTCTATAAGGCTT
CCAACTTGCAGACAGGCGTCCCATCAAGGTTTAGTGGCAGTGGATCTGGAACAGGTTTCACATTAACCATCAGCA
GCCTGCAGCCTGAAGACATTGCCACTTACTACTGTCAACAGGGTCAAAGTTATCCATTCACGTTCGGCTCGGGGAC
AAAGT SEQ ID NO: 133                SC10.38 Heavy chain
CAGGTTCAGCTGCAGCAGTCTGGAGCTGAGTTGATGAAGACTGGGGCCTCAGTAAAGATATCCTGCAAGGCTACT
GGCTACACATTCAGTAGCTACTGGATAGAGTGGGTAAAGCAGAGGCCTGGACATGGCCTTGAGTGGATTGGAGA
GATTTTACCTGGAAGTGGAAAAACTAATTATAATGAGAACTTTAAGGGCAAGGCCACATTCACTGCAGATACATCC
TCCAACACAGCCTACATGCAACTCAGCAGCCTGACATCTGAGGACTCTGTCGTCTATTACTGTGCAAGAAGGGGG
GCCTACTATGGTAACTTTGACTACTGGGGCCAAGGCACCACTCTCACAGTCTCCTCA SEQ ID NO: 134                SC10.75 Light chain
GACATTGTGATGTCACAGTCTCCATCCTCCCTAGCTGTGTCAGTTGGAGAGAAGGTTACTATGAGCTGCAAGTCCA
GTCAGAGCCTTTTATATAGTAACAATCAAAAGAATTACTTGGCCTGGTACCAGCAGAAACCAGGGCAGTCGCCTAA
ACTGCTGATTTACTGGGCATCCAGTAGGGAATCTGGGGTCCCTGAGCGCTTCACAGGCAGTGGATCTGGGACAGA
TTTCACTCTCACCATCAGCAGTGTGAAGGCTGAAGACCTGGCAGTTTATTACTGTCAGCAATATTATAGCTCTCCGT
ACACGTTCGGAGGGGGGACCAAGCTGAAA SEQ ID NO: 135                SC10.75 Heavy chain
CAGGTGCAGCTGAAGGAGTCAGGACCTGGCCTGGTGGCACCCTCACAGAGCCTGTCCATCACATGCACTGTCACT
GGGTTCTCATTATCCAGATATAGTGTACACTGGATTCGCCAGCCTCCAGGAAAGGGTCTGGAGTGGCTGGGAATG
ATATGGGGTGGTGGAAGCACAGACTATAATTCAGCTCTCAAATCCAGACTGAGTATCAACAAGGACAACTCCAAG
AGCCAAGTTTTCTTAAAAATGAACAGTCTGCAAACTGTTGACACAGCCATGTACTACTGTGCCAGAACCCAGTTCTA
CTATGGTCACGACGGGGGGTACGCTATGGACTACTGGGGTCAAGGAACCTCAGTCACCGTCTCCTCA SEQ ID NO: 136                SC10.111 Light chain
GACATTGTGATGACCCAGTCTCAAAAATTCATGTCCACATCAGTAGGAGACAGGGTCAGCGTCACCTGCAAGGCC
AGTCAGAATGTGGCTATTAATGTAGCCTGGTATCAACAGAAACCAGGCCAATCTCCTAAAGCTCTGATTTACTCGG
CATCCTACCGGTACAGTGTAGTCCCTGATCGCTTCACAGGCAGTGGATCTGGGACAGATTTCACTCTCCCCATCAG
CAATGTGCAGTCTGAAGGCTTGGCAGATTATTTCTGTCTACAATATATCAACTATCCGTACACGTTCGGAGGGGGG
ACCAAGCTGGAAATAAAACG SEQ ID NO: 137                SC10.111 Heavy chain
GAGGTCCAGCTTCAGCAGTCAGGACCTGAGCTGCTGAAACCTGGGGCCTCAGTGAAGATATCCTGCAAGGCTTCT
GGATACACATTCACTGACTACAACATGCACTGGGTGAAGCAGAGCCATGGAAAGAGCCTTGAGTGGATTGGAAAT
ATTTATCCTTACAATGGTGGTACTGGCTACAATCAGAAGTTCAAGACCAAGGCCACATTGACTGTAGACAATTCCT
CCAGCACAGCCTACATGGAGCTCCGCAGCCTGACATCTGAGGACTCTGCAGTCTATTACTGTCAATTGGTAACTA
CTGGTTTGCTTTCTGGGGCCAAGGGACTCTGGTCACTGTCTCTGCA SEQ ID NO: 138          SC10.112 Light chain
CAAATTGTTCTCTCCCAGTCTCCAGCAATCCTGTCTGCATCTCCAGGGGAGAAGGTCACAATGACTTGCAGGGCCA
GCTCAAGTGTTAGTTACATTCACTGGTACCAGCAGAAGGCAGGATCCTCCCCCACATCCTGGATTTATGCCACATCC
AACCTGGCTTCTGGAGTCCCTACTCGCTTCAGTGGCAGTGGGTCTGGGACCTCTTACTCTCTCACAGTCAACAGAG
TGGAGGCTGAAGATGCTGCCACTTATTACTGCCAGCAGTGGAGTACTACCCCACCCACGTTCGGAGGGGGGACCA
GGCTGGAAATAAAACG SEQ ID NO: 139          SC10.112 Heavy chain
GAGGTCCAGCTGCAGCAGTCTGGACCTGACCTGGTGAAGCCTGGGACTTCAGTGAAGATATCCTGCAAGGCTTCT
GGTTACTCCTTCACTGCCTGCTACATACACTGGGTGAAGCAGAGCCATGGAAAGAGCCTTGAGTGGATTGGACGT
TTTAGTCCTAACAATGATAGAACTACCTACAACCAGAAGTTCAAGGACAAGGCCATATTAACTGTAGACAAGTCAT
CCAGTACAGCCTACATGGACCTCCGCAGTCTGACATCTGAGGACTCTGCGGTCTATTACTGTGCAAGAGGGGAAG
AAAGCTGGGACGCCTGGTTTACTTACTGGGGCCAAGGGACTCTGGTCACTGTCTCTGCA SEQ ID NO: 140          SC10.115 Light chain
GACATTGTGATGACACAGTCTCCATCCTCCCTGACTGTGACAGCAGGAGAGAAGGTCACTATGAGTTGCAAGTCC
AGTCAGAGTCTGTTAAAGAGTGGAAATCAAAAGAACTACTTGACCTGGTACCAGCAGAAACCTGGGCAGCCTCCT
AAACTGTTGATCTACTGGGCATCCACTAGGGAATCTGGGGTCCCTGATCGCTTCACAGGCAGTGGATTTGGAACA
GATTTCACTCTCACCATCAGCAGTGTGCAGGCTGAAGACCTGGCAGTTTATTACTGTCAGAGTGATTATAATTATCC
TACGTTCGGCTCGGGGACAAAGTTG SEQ ID NO: 141          SC10.115 Heavy chain
CAGGTTACTCTGAAAGAGTCTGGCCCTGGGATATTGCAGCCCTCCCAGACCCTCAGTCTGACTTGTTCTTTCTCTGG
GTTTTCACTGAGCACTTCTGGTATGGGTGTAGGCTGGATTCGTCAGCCTTCAGGGAAGGGTCTGGAGTGGCTGGC
ACACATTTGGTGGGATGATGTCAAGCGCTATAACCCAGCCCTGAAGAGCCGACTGACTATCTCCAAGGATACCTCC
AGCAGCCAGGTATTCCTCAAGATCGCCAGTGTGGACACTGCAGATACTGCCACATATCACTGTGCTCGAATAGCAA
TCGGGCAACCGTTTGCTTACTGGGGCCAAGGGACTCTGGTCACTGTCTCTGCA SEQ ID NO: 142          SC10.118 Light chain
CAAATTGTTCTCACCCAGTCTCCAGCAATCATGTCTGCATCTCCAGGGGAGAAGGTCACCATAACCTGCAGTGCCA
GCTCAAGTGTGAGTTACATGCACTGGTTCCAGCAGAAGCCAGGCACTTCTCCCAAACTCTGGATTTATAGCACATC
CAACCTGGCTTCTGGAGTCCCTGCTCGCTTCAGTGGCAGTGGATCTGGGACCTCTTACTCTCTCACAATCAGCCGAA
TGGAGGCTGAAGATGCTGCCACTTATTACTGCCAGCAAAGGAGTACTTACCCGTACACGTTCGGAGGGGGGACCA
AGCTGGAAATAAAACG SEQ ID NO: 143          SC10.118 Heavy chain
CAGGTCCAACTACAACAGCCTGGGGCTGAGCTTGTGAAGCCTGGGGCTTCAGTGAAGCTGTCCTGCAGGACTTCT
GGCTACTCCTTCACCAGCTACTGGATACACTGGGTGAAGCAGAGGCCTGGACGAGGCCTTGAGTGGATTGGAAG
GATTGTTCCTAATAGTGGTGGTACTAAGTACAATGAGAACTTCAAGAACAAGGCCACACTGACTGTAGACAAATCC
TCCAACACAGCCTACATGCAGCTCAGCAGTCTGACATCTGAGGACTCTGCGGTCTATTACTGTACACGAGAGGATT
CCTACGGCCCGTTTGATTTGGACTACTGGGGTCAAGGAACCTCAGTCACCGTCTCCTCA

FIG. 19(Cont.)

SEQ ID NO: 144            10.123 Light chain
CAAATTGTTCTCTCCCAGTCTCCAGCAATCCTGTCTGCCTCTCCAGGGGAGAAGGTCACAATGACTTGCAGGGCCA
GCTCAAGTGTAAGTTACATGCACTGGTACCAGCAGAAGCCAGGATCCTCCCCCAAACCCTGGATTTATGCCGCATC
CAACCTGGCTTCTGGAGTCCCTGCTCGCTTCAGTGCCACTGGGTCTGGGACCTCTTACTCTCTCACAATCAGCAGAG
TGGAGGCTGAAGATGCTGCCACTTATTGCTGCCAGCAGTGGAGTAATAACCCACCAACGTTCGGCGGGGGGACCA
AGCTGGAAATAAAACG SEQ ID NO: 145            10.123 Heavy chain
GAGGTTCAGCTGCAGCAGTCTGGACCTGAACTGGTGAAGCCTGGGGCTTCAGTGAAGATATCCTGCAAGGCTTCT
GGTTACTCATTTACTGGGTACTTTATGAACTGGGTGAAGCAGAGCCATGGAAAGAGCCTTGAGTGGATTGGACGT
ATTAATCCTTACAATGGTGATAATTTCTACAACCAGAAGTTCAAGGGCAAGGCCACATTGACTGTAGACAAATCCT
CTAGCACAGCCCACATGGAGCTCCTGAGCCTGACATCTGAGGACTCTGCAGTCTATTATTGTGGAAGGGACTACG
GTAGTAGCTACGGATGGTTCTTCGATGTCTGGGGCGCAGGGACCACGGTCACCGTCTCCTCA SEQ ID NO: 146            10.124 Light chain
GACATTGTACTCACCCAATCTCCAGCTTCTTTGGCTGTGTCTCTAGGGCAGAGAGCCACCATCTCCTGCAGAGCCAA
TGAAAGTGTTGAATATTATGGCACAAGTTTAATGCAGTGGTACCAACAGAAACCAGGACAGCCACCCAAACTCCTC
ATCTATGCTGCATCCAGCGTAAAGTCTGGGGTCCCTGCCAGGTTTAGTGGCAGTGGGTCTGGGACAGACTTCAGC
CTCAATATCCATCCTGTGGAGGAGGATGATATTGCAATGTATTTCTGTCAGCAAAGTAGGAAGGTTCCTTCGACGT
TCGGTGGAGGCACCAAGCTGGAAATCAAAC SEQ ID NO: 147            10.124 Heavy chain
GAGGTCCAGCTGCAACAGTCTGGACCCGAGCTGGTGAAGCCTGGAGCTTCAATGAAGATATCCTGCAAGGCTTCT
GGTTATACATTCACTGACCACACCATGCACTGGGTGAAGCAGAGCCATGGAAAGAACCTTGAGTGGATTGGACGT
ATTAATCCTTACAATGGTGATACTAGTCACAACCAGAACTTCAAGGGCAAGGCCACATTAACTGTAGACAAGTCAT
CCAACACAGCCTACATGGAGCTCCTCAGTCTGACATCTGAGGACTCTGCAGTCTATTACTGTGCAAGATATGGTGG
TGATTATACGTCTTCTTACTATACTATGGACTACTGGGGTCAAGGAACCTCCTCCACCGTCTCCTCA SEQ ID NO: 148            10.125 Light chain
GACATTGTTCTCACCCAATCTCCAGCTTCTTTGGCTGTGTCTCTAGGGCAGAGAGCCACCATCTCCTGCAGAGCCCA
TGAAAGTGTTGAATATTATGGCACAAGTTTAATGCAGTGGTACCAACAGAAACCAGGACAGCCACCCAAACTCCTC
ATCTATGCTGCATCCAGCGTAAAGTCTGGGGTCCCTGCCAGGTTTAGTGGCAGTGGGTCTGGGACAGACTTCAGC
CTCAATATCCATCCTGTGGAGGAGGATGATATTGCAATGTATTTCTGTCAGCAAAGTAGGAAGGTTCCTTCGACGT
TCGGTGGAGGCACCAAGCTGGAAATCAAAC SEQ ID NO: 149            10.125 Heavy chain
GAGGTCCAGCTGCAACAGTCTGGACCCGAGCTGGTGAAGCCTGGAGCTTCAATGAAGATATCCTGCAAGGCTTCT
GGTTATACTTTCACTGACTACACCATGCACTGGGTGAGGCAGAGCCATGGAAAGAACCTTGAGTGGATTGGACGT
ATTAATCCTTACAATGCTGATACTAGTCACAACCAGAACTTCAAGGGCAGGGCCACATTAACTGTAGACAAGTCAT
TCAACACAGCCTACATGGAGCTCCTCAGTCTGACATCTGAGGACTCTGCAGTCTATTACTGTGCAAGATATGGTGG
TGATTTTACGTCTTCTTACTATACTATGGACTACTGGGGTCAAGGAACCTCAGTCACCGTCTCCTCA

FIG. 19(Cont.)

SEQ ID NO: 150                    10.126 Light chain
GACATTGTGATGACCCAGTCTCCATCCTCCCTAGCTGTGTCAGTTGGAGAGAAGGTTACTATGAGCTGCAAGTCCA
GTCAGAGCCTTTTATATAGTAGCAATCAAAAGAACTACTTGGCCTGGTACCAGCAGAAACCAGGGCAGTCTCCTAA
ACTGCTGATTTACTGGGCATCCACTAGGGAATCTGGGGTCCCTGATCGCTTCACAGGCAGTGGATCTGGGACAGA
TTTCACTCTCACCATCAGCAGTGTGAAGGCTGAAGACCTGGCAGTTTATTACTGTCAGCAATATTATAACTATCCCT
ACACGTTCGGAGGGGGGACCAAGCTGGAAATAAAACG SEQ ID NO: 151                    10.126 Heavy chain
CAGGTGCAGCTGAAGGAGTCAGGACCTGGCCTGGTGGCGCCCTCACAGAGCCTGTCCATCACATGCACTGTCTCT
GGTTTCTCATTAACCAGCTATACTATAAGCTGGGTTCGCCAGCCACCAGGAAAGGGTCTGGAGTGGCTTGGAATA
ATATGGACTGCTGGAGCCACAAATTATAATTCAGCTCTCAAATCCAGACTGAGCATCAGCAAAGACAACTCCAAGA
GTCAAGTTTTCTTAAAAATGAACAGTCTGCAAACTGATGACACAGCCAGGTACTACTGTGCCAGATATAGTAAGGA
TTACTATGCTGTGGACTACTGGGGTCAAGGAACCTCAGTCACCGTCTCCTCA SEQ ID NO: 152                    10.127 Light chain
GACATTGTACTCACCCAATCTCCAGCTTCTTTGGCTGTGTCTCTAGGACAGAGAGCCACCATCTCCTGCAGAGCCAA
TGAAAATGTTGAATATTATGGCACAAGTTTAATGCAGTGGTACCAACAGAAACCAGGACAGCCACCCAAACTCCTC
ATCTATGCTGCATCCAACGTAAAGTCTGGGGTCCCTGCCAGGTTTAGTGGCAGTGGGTCTGGGACAGACTTCAGC
CTCAATATCCATCCTGTGGAGGAGGATGATATTGCAATGTATTTCTGTCAGCAAAGTAGGAAGGTTCCTTCGACGT
TCGGTGGAGGCACCAAGCTGAAA SEQ ID NO: 153                    10.127 Heavy chain
GAGGTCCAGCTGCAACAGTCTGGACCCGAGCTGGTGAAGCCTGGAGCTTCAATGAAGATATCCTGCAAGGCTTCT
GGTTATACATTCACTGACTACACCATGCACTGGGTGAAGCAGAGCCATGGAAAGAACCTTGAGTGGATTGGACGT
ATTAATCCTTACAATGATGATATTAGTCACAACCAGAACTTCAAGGACAAGGCCACATTAACTGTAGACAAGTCAT
CCAACACAGCCTACATGGAGCTCCTCAGTCTGACATCTGAGGACTCTGCAGTCTATTACTGTGCAAGATATGGTGG
TGATTATACGTCTTCTTACTATACTATGGACTACTGGGGTCAAGGAACCTCAGTCACCGTCTCCTCA SEQ ID NO: 154                    10.128 Light chain
GACATTGTGATGTCACAGTCTCCATCCTCCCTAGCTGTGTCAGTTGGAGAGAAGGTTACTATGAGCTGCAAGTCCA
GTCAGAGCCTTTTATATAGTAGCAATCAAAAGAACTACTTGGCCTGGTACCAGCAGAAACCAGGGCAGTCTCCTAA
ACTGCTGATTTACTGGGCATCCACTAGGGAATCTGGGGTCCCTGATCGCTTCACAGGCAGTGGATCTGGGACAGA
TTTCACTCTCACCATCAGCACTGTGAAGGCTGAAGACCTGGCAGTTTATTACTGTCACCAATATTATAGCTATCCGT
ACACGTTCGGAGGGGGGACCAAGCTGGAAATAAAACG SEQ ID NO: 155                    10.128 Heavy chain
CAGGTGCAGCTGAAGGAGTCAGGACCTGGCCTGGTGGCACCCTCACAGAGCCTGTCCATCACATGCACTGTCTCT
GGGTTCTCATTATCCAGATATAGTGTACACTGGGTTCGCCAGCCTTCAGGAAAGGGTCTGGAGTGGCTGGGAATG
ATATGGGGTGGTGGAAGCACAGACTATAATTCAGCTCTCAAATCCAGACTGATCATCAGCAAGGACAACTCCAAG
AGCCAAGTTTTCTTAAAAATGAACAGTCTGCAAACTGATGACACAGCCATGTACTACTGTGCCAGAACCCAGTTCT
ACTATGGTCACGACGGGGGGTATGCTATGGACTACTGGGGTCAAGGAACCTCAGTCACCGTCTCCTCA

FIG. 19(Cont.)

SEQ ID NO: 156          10.129 Light chain
GACATTGTGCTGACACAGTCTCCTGGTTCCTTAGCTGTATCTCTGGGGCAGAGGGCCACCATCTCATGCAGGGCCA
GCCAAAGTGTCAGTTCATCTAGCTATAGTTATATGCACTGGTACCAACAGAAACCAGGACAGCCACCCAAACTCCT
CATCAAGTTTGCATCCAACCTAGAATCTGGGGTCCCTGCCAGGTTCAGTGGCAGTGGGTCTGGGACAGACTTCACC
CTCAACATCCATCCTGTGGAGGAGGAGGATACTGCAACATATTACTGTCAGCACAGTTGGGAGATTCCGCTCACAT
TCGGTGCTGGGACCAAGCTGGAGCTGAAAC SEQ ID NO: 157          10.129 Heavy chain
CAGGTTACTCTGAAAGAGTCTGGCCCTGGGATATTGCAGCCCTCCCAGACCCTCAGTCTGACTTGTTCTTTCTCTGG
GTTTTCACTGAGTACTTCTGGTATGGGTGTAGGCTGGATTCGCCAGCCATCAGGAAAGGGTCTGGAGTGGCTGGC
ACACATTTGGTGGGATGATGTCAAGCGCTATAATCCAGCCCTGAAGAGCCGACTGAATATCTCCAAGGACACCTCC
AGCAGCCAGGTCTTCCTCAAGATCGCCAGTGTGGACACTGCAGATACTGCCACATACTACTGTGGTCGAAAAAGT
AACTCAGGCTACTTTGACTACTGGGGCCAAGGCACCACTCTCACAGTCTCCTCA SEQ ID NO: 158          10.130 Light chain
GATGTCCAGATAACCCAGTCTCCATCTTATCTTGCTGCATCTCCTGGAGAAACCATTTCTATTAATTGCAGGGCAAG
TAAGAACATTAGCAAATATTTAGCCTGGTATCAAGAGAAACCTGGGAAAACTAATAAGCTTCTTATCTACTCTGGA
TCCACTTTGCAATCTGGAATTCCATCAGGGTTCAGTGGCAGTGGATCTGGTACAGATTTCACTCTCACCATCAGTAG
CCTGGAGCCTGAAGATTTTGCAATGTATTACTGTCAACAGCATTTTGAATACCCGTACACGTTCGGAGGGGGGACC
AAGCTGGAAATAAAACG SEQ ID NO: 159          10.130 Heavy chain
GAGGTTCAGCTGCAGCAGTCTGGACCTGACCTGGTGAAGCCTGGGGCTTCAGTGAAGATATCCTGCAAGGCTTCT
GGTTACTCATTTACTGGCTACTTTATGAACTGGGTGAAGCAGAGCCATGGAAAGAGCCTTGAGTGGATTGGACGT
ATTAATCCTTACAATGGTGATACTTTCTACAACCAGAAATTCAAGGGCAAGGCCACATTGACTGTAGACAAATCCTC
TAGCACAGCCCACATGGAGCTCCTGAGCCTGACATCTGAAGACTCTGCAGTCTATTATTGTGGAAGAGGGAATTAC
TACTTTGACTACTGGGGCCAAGGCACCACTCTCACAGTCTCCTCA SEQ ID NO: 160          10.132 Light chain
CAAATTGTTCTCACCCAGTCTCCAGCAATCATGTCTGCATCTCTGGGGGAGGAGATCACCCTAACCTGCAGTGCCA
CCTCGAGTGTTGGTTACATTCACTGGTACCAGCAGACGTCAGGCACTTCTCCCAGACTCTTGATTTATACCACATCC
AACCTGGCTTCTGGAGTCCCTTCTCGCTTCAGTGGCAGTGGGTCTGGGACCTTTTATTCTCTCACAATCAGCAGTGT
CGAGGCTGAAGATGCTGCCGATTATTACTGCCATCAGTGGAGTCGTTATCCCACGTTCGGAGGGGGGACCAAGCT
GGAAATAAAACG SEQ ID NO: 161          10.132 Heavy chain
GAGGTGCAGCTGGAGCAGTCAGGGGGAGACTTAGTGAAGCCTGGAGGGTCCCTGAAACTCTCCTGTGCAGCCTC
TGGATTCACTTTCAGTTCCTATGGCATGTCTTGGGTTCGCCAGACTCCAGACAAGAGGCTGGAGTGGGTCGCAACC
ATTAGTAGTGGTGGTTCTTACAGCTACTATCCAGACAGTGTGAAGGGGCGATTCACCATCTCCAGAGACAATGCCA
AGAACACCCTGTACCTGCAAATGAGCAGTCTGAAGTCTGAGGACACAGCCATGTATTTCTGTAGGCCCTCCTTCTTT
CCTTCCTGGGGCCAAGGGACTCTGGTCACTGTCTCTGCA

FIG. 19(Cont.)

SEQ ID NO: 162             10.133 Light chain
GACATCAAGATGACCCAGTCTCCATCTTCCACGTATGCATCTCTAGGAGAGAGAGTCACTATCACTTGCAAGGCGA
GTCAGGACATTAATACCTATTTATACTGGTTCCAACAGAAACCAGGGAAACCTCCTAAGACCCTGATCTATCGTGC
AAACAGATTGATAGATGGGGTCCCATCAAGGTTCAGTGGCAGTGGATCTGGGCAAGATTATTCTCTCACCATCAG
CAGCCTGGAGTATGAAGATTTGGGAATTTATTATTGTCTACAGTATGATGAGTTTCCGTATACGTTCGGTGGAGGC
ACCAAGCTGGAAATCAAAC SEQ ID NO: 163             10.133 Heavy chain
GAGGTTCAGCTGCAGCAGTCTGGGGCTGAGCTTGTGAGGCCAGGGGCCTCAGTCAAGTTGTCCTGCACAGCTTCT
GGCTTTAACATTAATGACGACTATTTTCACTGGGTGAAGCAGAGGCCTGAACAGGGCCTGGAGTGGATTGGAAGG
ATTGATCCTGCGAATGGTAATACTAAATATGGCCCGAAGTTCCAGGACAAGGCCACTATAACTGCAGACACATCAT
CCAACACAGCCTACCTGCAGTTCACCAGCCTGACATCTGAGGACACTGCCGTCTATTACTGTGCTAGCGGATGGGC
GTTTGCTTGCTGGGGCCAAGGGACT SEQ ID NO: 164             10.134 Light chain
GACATTGTACTCACCCAATCTCCAGCTTCTTTGGCTGTGTCTCTAGGGCAGAGAGCCACCATCTCCTGCAGAGCCG
ATGAAAGTGTTGAATATTATGGCACAAGTTTAATGCAGTGGTACCAACAGAAACCAGGACAGCCACCCAAACTCCT
CATCTATGCTGCATCCAACGTAAAGTCTGGGGTCCCTGCCAGGTTTAGTGGCAGTGGGTCTGGGACAGACTTCAG
CCTCAATATCCATCCTGTGGAGGAGGATGATATTGCAATTTATTTCTGTCAGCAAAGTAGGGAGGTTCCTTCGACG
TTCGGTGGAGGCACCAAGCTGGAAATCAAAC SEQ ID NO: 165             10.134 Heavy chain
GAGGTCCAGCTGCAACAGTCTGGACCCGAGCTGGTGAAGCCTGGAACTTCAATGAAGATATCCTGCAAGGCTTCT
GGTTATACATTCACTGACTACACCATGCACTGGGTGAAGCAGAGCCATGGAAAGAACCTTGAGTGGATTGGACGT
ATTAATCCTTACACTGGTTCTACTAGTCACAACCAGAACTTCAAGGACAAGGCCTCATTAACTGTAGACAAGTCATC
CAACACAGCCTACATGGACCTCCTCAGTCTGACATCTGAGGACTCTGCAGTCTATTACTGTGCAAGATTTGGTGGT
GATTATACGTCTTCTTACTATACTTTGGACTACTGGGGTCAAGGAACCTCAGTCAGCGTCTCCTCA SEQ ID NO: 166             SC10.163 Light chain
GATATTGTGATGACGCAGGCTGCATTCTCCAATCCAGTCACTCTTGGAACATCAGCTTCCATCTCCTGCAGGTCTAG
TAAGAGTCTCCTACATAGTAATGGCATCACTTATTTGTATTGGTATCTGCAGAAGCCAGGCCAGTCTCCTCAGCTCC
TGATTTATCAGATGTCCAACCTTGCCTCAGGAGTCCCAGACAGGTTCAGTAACAGTGGGTCAGGAACTGATTTCAC
ACTGAGAATCAGCAGAGTGGAGGCTGAGGATGTGGGTGTTTATTACTGTGCTCAAAATCTAGAACTTCCGTGGAC
GTTCGGTGGAGGCACCAAGCTGGAAATCAAAC SEQ ID NO: 167             SC10.163 Heavy chain
GAGGTCCAGCTGCAACAGTCTGGACCTGAGCTGGTGAAGCCTGGGGATTCAGTGAAGATGTCCTGCAAGGCTTCT
GGCAACACAGTCACTAACTACTACATGGACTGGGTGAAACAGAGCCATGGAAAGAGCCTTGAGTGGATTGGATAT
ATTTATGCTAACAATGGTGGAACTAGCTATAATCAGAAGTTCAAGGGCAAGGCTACATTGACTGTAGACAAGTCCT
CCAGCACAGCCTACATGGAGATCCACAGCCTGACATCTGAGGACTCTGCAGTCTATTACTGTGCAATCTACTATAG
GTACGAGTTTGCTTACTGGGGCCAAGGGACTCTGGTCACTGTCTCTGCA

FIG. 19(Cont.)

SEQ ID NO: 168          SC10.168 Light chain
GACATTGTGATGACCCAGTCTCACAAACTCATGTCCGCATCAGTAGGAGACAGGGTCAGCATCACCTGCAAGGCC
AGTCAGGATGTGGGTACTGCTGTAGCCTGGTATCAACAGAAACCAGGGCGATCTCCTAAACTACTGATTTACTGG
GCATCCAACCGGCACACTGGAGTCCCTGATCGCTTCACAGGCAGTGGATCTGGGACAGATTTCACTCTCACCATTA
GCAATGTGCAGTCTGAAGACTTGGCAGATTATTTCTGTCAGCAGTTTGGCAGCTATCCGTACACGTTCGGAGGGG
GGACCAAGCTGGAAATAAAACG SEQ ID NO: 169          SC10.168 Heavy chain
TCTGATGTGCAGCTTCAGGAGTCAGGACCTGGCCTGGTGAAACCTTCTCAGTCTCTGTCCGTCACCTGCACTGTCAC
TGACTACTCCCTCACCAGTGGTTATTACTGGAACTGGATCCGGCAGTTTCCAGGAAACAAACTGGAGTGGATGGCC
TACATACACAGCAGTGGTAGCACTCACTACAACCCATCTCTCAAAAGTCGAATCTCTGTCACTCGAGACACATCCAA
GAACCAGTTCTTCCTGCAGTTGAATTCTGTGACTACTGAGGACACAGCCACATATTACTGTGCAAGAGATGGGGCC
TACTATAGTTCCTGGTTTCCTTACTGGGGCCAAGGGACTCTGGTCACTGTCTCTGCA SEQ ID NO: 170          SC10.178 Light chain
GATATTGTGCTGACACAGTCTCCACTCTCCCTGCTTGTCAGTCTTGGAGATCAAGCCTCCATCTCTTGCAGATCTAG
TCAGAGCCTTGTACACAGTAATGGAAACACCTATTTACATTGGTATCTGCAGAAGCCAGGCCAGTCTCCAAACCTC
CTGATCTTCAAAGTTTCCAACCGATTTTCTGGGGTCCCAGACAGGTTCAGTGGCAGTGGATCAGGGACAGATTTCA
CACTCAGGATCAGCAGAGTGGAGGCTGAGGATCTGGGAGTTTATTTCTGCTCTCAAACTACACATGTGTGGACGTT
CGGTGGAGGCACCAAGCTGGAAATCAAAC SEQ ID NO: 171          SC10.178 Heavy chain
CAGATCCTGTTGGTGCAGTCTGGACCTGAGCTGAAGAAGCCTGGAGAGACAGTCAAGATCTCCTGCAAGGCTTCT
AATTTATACCTTCACAGACTATGGAATGCACTGGGTGAAGCAGGCTCCAGGAAAGGGTTTAAAGTGGATGGGCTG
GATAAACCCCAAGACTGGTGTGGCATCATATGCAGATGACTTCAAGGGAAGATTTGCCTTCTCTTTGGAAACCTCT
GCCAGCACTGCCTATTTGCAGATCAACAACCTCGAAAATGAGGACACGTCTATATATTTCTGTGCTAGATTTTTTGA
CTACTGGGGCCAAGGCACCACTCTCACAGTCTCCTCA SEQ ID NO: 172          hSC10.17 Light chain
GATGTTGTGATGACTCAGTCTCCACTCTCCCTGCCCGTCACCCTTGGACAGCCGGCCTCCATCTCCTGCAGGTCTAG
TCAAAGCATCGTACACAGTGATGGAAACACCTACTTGGAATGGTATCAGCAGAGGCCAGGCCAATCTCCAAGGCG
CCTAATTTATAAGGTTTCTAACCGGTTCTCTGGGGTCCCAGACAGATTCAGCGGCAGTGGGTCAGGCACTGATTTC
ACACTGAAAATCAGCAGGGTGGAGGCTGAGGATGTTGGGGTTTATTACTGCTTTCAAGGTTCACATGCTCCGTGG
ACGTTCGGTGGAGGCACCAAGGTGGAAATCAAAC SEQ ID NO: 173          hSC10.17 Heavy chain
GAGGTGCAGCTGGTGGAGTCTGGGGGAGGCTTGGTACAGCCTGGGGGGTCCCTGAGACTCTCCTGTGCAGCCTC
TGGATTCACCTTCAGTAGCTATGGCATGCACTGGGTCCGCCAGGCTCCAGGGAAGGGGCTGGAGTGGGTTGCATA
CATTACTACTAGAAGTAGTACCATATACTACGCAGACTCTGTGAAGGGCCGATTCACCATCTCCAGAGACAATGCC
AAGAACTCACTGTATCTGCAAATGAACAGCCTGAGAGCCGAGGACACGGCTGTGTATTACTGTACTAGAGAACCC
CTAACTGGATACTATGCTATGGACTACTGGGGTCAAGGAACCTCAGTCACCGTCTCCTCAG

FIG. 19(Cont.)

```
                        SEQUENCE LISTING

<160> NUMBER OF SEQ ID NOS: 173

<210> SEQ ID NO 1
<211> LENGTH: 4815
<212> TYPE: DNA
<213> ORGANISM: Homo sapiens

<400> SEQUENCE: 1
agtggcgtcg gaactgcaaa gcacctgtga gcttgcggaa gtcagttcag actccagccc      60
gctccagccc ggcccgaccc gaccgcaccc ggcgcctgcc ctcgctcggc gtccccggcc     120
agccatgggc ccttggagcc gcagcctctc ggcgctgctg ctgctgctgc aggtctcctc     180
ttggctctgc caggagccgg agccctgcca ccctggcttt gacgccgaga gctacacgtt     240
cacggtgccc cggcgccacc tggagagagg ccgcgtcctg ggcagagtga attttgaaga     300
ttgcaccggt cgacaaagga cagcctattt ttccctcgac acccgattca aagtgggcac     360
agatggtgtg attacagtca aaaggcctct acggtttcat aacccacaga tccatttctt     420
ggtctacgcc tgggactcca cctacagaaa gttttccacc aaagtcacgc tgaatacagt     480
ggggcaccac caccgccccc cgccccatca ggcctccgtt tctggaatcc aagcagaatt     540
gctcacattt cccaactcct ctcctggcct cagaagacag aagagagact gggttattcc     600
tcccatcagc tgcccagaaa atgaaaaagg cccatttcct aaaaacctgg ttcagatcaa     660
atccaacaaa gacaaagaag gcaaggtttt ctacagcatc actggccaag gagctgacac     720 acccctgtt ggtgtcttta ttattgaaag agaaacagga tggctgaagg tgacagagcc     780
tctggataga gaacgcattg ccacatacac tctcttctct cacgctgtgt catccaacgg     840
gaatgcagtt gaggatccaa tggagatttt gatcacggta accgatcaga atgacaacaa     900
gcccgaattc acccaggagg tctttaaggg gtctgtcatg gaaggtgctc ttccaggaac     960
ctctgtgatg gaggtcacag ccacagacgc ggacgatgat gtgaacacct acaatgccgc    1020
catcgcttac accatcctca gccaagatcc tgagctccct gacaaaaata tgttcaccat    1080
taacaggaac acaggagtca tcagtgtggt caccactggg ctggaccgag agagtttccc    1140
tacgtatacc ctggtggttc aagctgctga ccttcaaggt gaggggttaa gcacaacagc    1200
aacagctgtg atcacagtca ctgacaccaa cgataatcct ccgatcttca atcccaccac    1260
gtacaagggt caggtgcctg agaacgaggc taacgtcgta atcaccacac tgaaagtgac    1320
tgatgctgat gccccaata ccccagcgtg ggaggctgta tacaccatat tgaatgatga    1380
tggtggacaa tttgtcgtca ccacaaatcc agtgaacaac gatggcattt tgaaaacagc    1440
aaagggcttg gattttgagg ccaagcagca gtacattcta cacgtagcag tgacgaatgt    1500
ggtacctttt gaggtctctc tcaccacctc cacagccacc gtcaccgtgg atgtgctgga    1560
tgtgaatgaa gcccccatct ttgtgcctcc tgaaaagaga gtggaagtgt ccgaggactt    1620
```

```
tggcgtgggc caggaaatca catcctacac tgcccaggag ccagacacat ttatggaaca    1680
gaaaataaca tatcggattt ggagagacac tgccaactgg ctggagatta atccggacac    1740
tggtgccatt tccactcggg ctgagctgga cagggaggat tttgagcacg tgaagaacag    1800
cacgtacaca gccctaatca tagctacaga caatggttct ccagttgcta ctggaacagg    1860
gacacttctg ctgatcctgt ctgatgtgaa tgacaacgcc cccataccag aacctcgaac    1920
tatattcttc tgtgagagga atccaaagcc tcaggtcata aacatcattg atgcagacct    1980
tcctcccaat acatctccct tcacagcaga actaacacac ggggcgagtg ccaactggac    2040
cattcagtac aacgacccaa cccaagaatc tatcattttg aagccaaaga tggccttaga    2100
ggtgggtgac tacaaaatca atctcaagct catggataac cagaataaag accaagtgac    2160
caccttagag gtcagcgtgt gtgactgtga agggggccgct ggcgtctgta ggaaggcaca    2220
gcctgtcgaa gcaggattgc aaattcctgc cattctgggg attcttggag gaattcttgc    2280
tttgctaatt ctgattctgc tgctcttgct gtttcttcgg aggagagcgg tggtcaaaga    2340
gcccttactg cccccagagg atgacacccg ggacaacgtt tattactatg atgaagaagg    2400
aggcggagaa gaggaccagg actttgactt gagccagctg cacaggggcc tggacgctcg    2460
gcctgaagtg actcgtaacg acgttgcacc aaccctcatg agtgtccccc ggtatcttcc    2520
ccgccctgcc aatcccgatg aaattggaaa ttttattgat gaaatctga aagcggctga    2580
tactgacccc acagcccgc cttatgattc tctgctcgtg tttgactatg aaggaagcgg    2640
ttccgaagct gctagtctga gctccctgaa ctcctcagag tcagacaaag accaggacta    2700
tgactacttg aacgaatggg gcaatcgctt caagaagctg gctgacatgt acggaggcgg    2760
cgaggacgac taggggactc gagagaggcg ggccccagac ccatgtgctg ggaaatgcag    2820
aaatcacgtt gctggtggtt tttcagctcc cttcccttga gatgagtttc tggggaaaaa    2880
aaagagactg gttagtgatg cagttagtat agctttatac tctctccact ttatagctct    2940
aataagtttg tgttagaaaa gtttcgactt atttcttaaa gcttttttt ttttcccatc    3000
actctttaca tggtggtgat gtccaaaaga tacccaaatt ttaatattcc agaagaacaa    3060
ctttagcatc agaaggttca cccagcacct tgcagatttt cttaaggaat tttgtctcac    3120
tttaaaaag aagggggagaa gtcagctact ctagttctgt tgttttgtgt atataatttt    3180
ttaaaaaaaa tttgtgtgct tctgctcatt actacactgg tgtgtccctc tgccttttt    3240
ttttttttaa gacagggtct cattctatcg gccaggctgg agtgcagtgg tgcaatcaca    3300
gctcactgca gccttgtcct cccaggctca agctatcctt gcacctcagc ctcccaagta    3360
gctgggacca caggcatgca ccactacgca tgactaattt tttaaatatt tgagacgggg    3420
tctccctgtg ttacccaggc tggtctcaaa ctcctgggct caagtgatcc tcccatcttg    3480
gcctcccaga gtattgggat tacagacatg agccactgca cctgcccagc tccccaactc    3540
cctgccattt tttaagagac agtttcgctc catcgcccag gctgggatg cagtgatgtg    3600
atcatagctc actgtaacct caaactctgg ggctcaagca gttctcccac cagcctcctt    3660
tttatttttt tgtacagatg gggtcttgct atgttgccca agctggtctt aaactcctgg    3720
cctcaagcaa tccttctgcc ttggccccc aaagtgctgg gattgtgggc atgagctgct    3780
gtgcccagcc tccatgtttt aatatcaact ctcactcctg aattcagttg ctttgcccaa    3840
gataggagtt ctctgatgca gaaattattg ggctctttta gggtaagaag tttgtgtctt    3900
tgtctggcca catcttgact aggtattgtc tactctgaag accttttaatg gcttccctct    3960
```

-continued

```
ttcatctcct gagtatgtaa cttgcaatgg gcagctatcc agtgacttgt tctgagtaag    4020
tgtgttcatt aatgtttatt tagctctgaa gcaagagtga tatactccag gacttagaat    4080
agtgcctaaa gtgctgcagc caaagacaga gcggaactat gaaaagtggg cttggagatg    4140
gcaggagagc ttgtcattga gcctggcaat ttagcaaact gatgctgagg atgattgagg    4200
tgggtctacc tcatctctga aaattctgga aggaatggag gagtctcaac atgtgtttct    4260
gacacaagat ccgtggtttg tactcaaagc ccagaatccc caagtgcctg cttttgatga    4320
tgtctacaga aaatgctggc tgagctgaac acatttgccc aattccaggt gtgcacagaa    4380
aaccgagaat attcaaaatt ccaaattttt ttcttaggag caagaagaaa atgtggccct    4440 aaaggggggtt agttgagggg taggggggtag tgaggatctt gatttggatc tcttttttatt    4500 taaatgtgaa tttcaacttt tgacaatcaa agaaaagact tttgttgaaa tagctttact    4560
gtttctcaag tgttttggag aaaaaaatca accctgcaat cacttttttgg aattgtcttg    4620 atttttcggc agttcaagct atatcgaata tagttctgtg tagagaatgt cactgtagtt    4680
ttgagtgtat acatgtgtgg gtgctgataa ttgtgtattt tctttggggg tggaaaagga    4740
aaacaattca agctgagaaa agtattctca aagatgcatt tttataaatt ttattaaaca    4800
attttgttaa accat                                                    4815
```

<210> SEQ ID NO 2
<211> LENGTH: 882
<212> TYPE: PRT
<213> ORGANISM: Homo sapiens

<400> SEQUENCE: 2

```
Met Gly Pro Trp Ser Arg Ser Leu Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His Arg Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220
```

```
Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
            245                 250                 255

Asp Asn Lys Pro Glu Phe Thr Gln Glu Val Phe Lys Gly Ser Val Met
        260                 265                 270

Glu Gly Ala Leu Pro Gly Thr Ser Val Met Glu Val Thr Ala Thr Asp
    275                 280                 285

Ala Asp Asp Asp Val Asn Thr Tyr Asn Ala Ala Ile Ala Tyr Thr Ile
290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
                355                 360                 365

Asn Asp Asn Pro Pro Ile Phe Asn Pro Thr Thr Tyr Lys Gly Gln Val
370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
                420                 425                 430

Asp Gly Ile Leu Lys Thr Ala Lys Gly Leu Asp Phe Glu Ala Lys Gln
            435                 440                 445

Gln Tyr Ile Leu His Val Ala Val Thr Asn Val Val Pro Phe Glu Val
    450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
        515                 520                 525

Thr Ala Asn Trp Leu Glu Ile Asn Pro Asp Thr Gly Ala Ile Ser Thr
    530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
        595                 600                 605

Pro Gln Val Ile Asn Ile Ile Asp Ala Asp Leu Pro Pro Asn Thr Ser
    610                 615                 620

Pro Phe Thr Ala Glu Leu Thr His Gly Ala Ser Ala Asn Trp Thr Ile
625                 630                 635                 640
```

```
Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
    690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Glu Glu Asp Gln Asp Phe Asp
        755                 760                 765

Leu Ser Gln Leu His Arg Gly Leu Asp Ala Arg Pro Glu Val Thr Arg
    770                 775                 780

Asn Asp Val Ala Pro Thr Leu Met Ser Val Pro Arg Tyr Leu Pro Arg
785                 790                 795                 800

Pro Ala Asn Pro Asp Glu Ile Gly Asn Phe Ile Asp Glu Asn Leu Lys
                805                 810                 815

Ala Ala Asp Thr Asp Pro Thr Ala Pro Pro Tyr Asp Ser Leu Leu Val
            820                 825                 830

Phe Asp Tyr Glu Gly Ser Gly Ser Glu Ala Ala Ser Leu Ser Ser Leu
        835                 840                 845

Asn Ser Ser Glu Ser Asp Lys Asp Gln Asp Tyr Asp Tyr Leu Asn Glu
    850                 855                 860

Trp Gly Asn Arg Phe Lys Lys Leu Ala Asp Met Tyr Gly Gly Gly Glu
865                 870                 875                 880

Asp Asp

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7
```

000

<210> SEQ ID NO 8

<400> SEQUENCE: 8

000

<210> SEQ ID NO 9

<400> SEQUENCE: 9

000

<210> SEQ ID NO 10

<400> SEQUENCE: 10

000

<210> SEQ ID NO 11

<400> SEQUENCE: 11

000

<210> SEQ ID NO 12

<400> SEQUENCE: 12

000

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000

<210> SEQ ID NO 20
<211> LENGTH: 106
<212> TYPE: PRT
<213> ORGANISM: Mus sp.

<400> SEQUENCE: 20

Gln Ile Val Leu Thr Gln Ser Pro Ala Leu Met Ser Ala Ser Pro Gly
1               5                   10                  15

Glu Lys Val Thr Met Thr Cys Ser Ala Ser Ser Val Arg Tyr Met
            20                  25                  30

Tyr Trp Tyr Gln Gln Lys Pro Arg Ser Ser Pro Lys Pro Trp Ile His
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser His Pro Phe Thr
                85                  90                  95

Phe Gly Ser Gly Thr Lys Leu Glu Ile Lys
            100                 105

<210> SEQ ID NO 21
<211> LENGTH: 116
<212> TYPE: PRT
<213> ORGANISM: Mus sp.

<400> SEQUENCE: 21

Asp Val Gln Leu Gln Glu Ser Gly Pro Gly Leu Val Lys Pro Ser Gln
1               5                   10                  15

Ser Leu Ser Leu Thr Cys Thr Val Thr Gly Phe Ser Ile Thr Ser Asp
            20                  25                  30

Tyr Ser Trp Asn Trp Ile Arg Gln Phe Pro Gly Asn Lys Leu Glu Trp
        35                  40                  45

Met Gly Tyr Ile Ser Tyr Ser Gly His Thr Ser Tyr Asn Pro Ser Leu
    50                  55                  60

Glu Ser Arg Ile Ser Ile Thr Arg Asp Thr Ser Lys Asn Gln Phe Phe
65                  70                  75                  80

Leu Gln Leu Asn Ser Val Thr Thr Glu Asp Thr Ala Thr Tyr Tyr Cys
                85                  90                  95

Thr Arg Gly Asn Trp Asp Val Val Tyr Trp Gly Gln Gly Thr Leu Val
            100                 105                 110

Thr Val Ser Ala
        115

<210> SEQ ID NO 22
<211> LENGTH: 113
<212> TYPE: PRT
<213> ORGANISM: Mus sp.

<400> SEQUENCE: 22

Asp Ile Val Met Ser Gln Ser Pro Ser Ser Leu Ala Val Ser Val Gly
1               5                   10                  15

```
Glu Lys Val Thr Met Ser Cys Lys Ser Ser Gln Ser Leu Leu Tyr Ser
                20                  25                  30

Asn Asn Gln Lys Asn Tyr Leu Ala Trp Tyr Gln Gln Lys Pro Gly Gln
            35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys His Gln
                85                  90                  95

Tyr Tyr Thr Ser Pro Tyr Thr Phe Gly Gly Gly Thr Asn Leu Glu Ile
            100                 105                 110

Lys

<210> SEQ ID NO 23
<211> LENGTH: 123
<212> TYPE: PRT
<213> ORGANISM: Mus sp.

<400> SEQUENCE: 23

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
                20                  25                  30

Ser Val Gln Trp Val Arg Gln Pro Pro Gly Lys Gly Leu Glu Trp Leu
            35                  40                  45

Gly Met Ile Trp Gly Gly Ser Thr Asp Tyr Asn Ser Gly Leu Lys
    50                  55                  60

Ser Arg Leu Thr Ile Ser Lys Asp Asn Ser Lys Ser Gln Val Phe Leu
65                  70                  75                  80

Lys Met Asn Ser Leu Gln Thr Asp Asp Thr Ala Met Tyr Phe Cys Ala
                85                  90                  95

Arg Thr Gln Phe Tyr Tyr Gly His Asp Gly Gly Tyr Ala Met Asp Phe
            100                 105                 110

Trp Gly Gln Gly Thr Ser Val Thr Val Ser Ser
        115                 120

<210> SEQ ID NO 24
<211> LENGTH: 112
<212> TYPE: PRT
<213> ORGANISM: Mus sp.

<400> SEQUENCE: 24

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asp Gly Asn Thr Tyr Leu Glu Trp Tyr Leu Arg Lys Pro Gly Gln Ser
            35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95
```

-continued

```
Ser His Ala Pro Trp Thr Phe Gly Gly Gly Thr Lys Leu Glu Ile Lys
            100                 105                 110

<210> SEQ ID NO 25
<211> LENGTH: 120
<212> TYPE: PRT
<213> ORGANISM: Mus sp.

<400> SEQUENCE: 25

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Tyr
            20                  25                  30

Gly Met His Trp Val Arg Gln Ala Pro Glu Thr Gly Leu Glu Trp Val
        35                  40                  45

Ala Tyr Ile Thr Thr Arg Ser Ser Thr Ile Tyr Tyr Ala Ala Thr Val
    50                  55                  60

Lys Gly Arg Phe Thr Ile Ser Arg Asp Asn Ala Arg Asn Thr Leu Phe
65                  70                  75                  80

Leu Gln Met Thr Ser Leu Arg Ser Glu Asp Thr Ala Met Tyr Tyr Cys
                85                  90                  95

Thr Arg Glu Pro Leu Thr Gly Tyr Tyr Ala Met Asp Tyr Trp Gly Gln
            100                 105                 110

Gly Thr Ser Val Thr Val Ser Ser
        115                 120

<210> SEQ ID NO 26
<211> LENGTH: 113
<212> TYPE: PRT
<213> ORGANISM: Mus sp.

<400> SEQUENCE: 26

Asp Ile Val Met Ser Gln Ser Pro Ser Ser Leu Thr Val Ser Val Gly
1               5                   10                  15

Glu Lys Gly Thr Met Ser Cys Lys Ser Ser Gln Ser Leu Leu Tyr Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Ser Leu Thr
65                  70                  75                  80

Ile Ser Ser Val Leu Ala Glu Asp Leu Ala Val Tyr Phe Cys His Gln
                85                  90                  95

Tyr Tyr Ser Ser Pro Tyr Thr Phe Gly Gly Gly Thr Lys Leu Glu Ile
            100                 105                 110

Lys

<210> SEQ ID NO 27
<211> LENGTH: 123
<212> TYPE: PRT
<213> ORGANISM: Mus sp.

<400> SEQUENCE: 27

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30
```

Ser Val His Trp Val Arg Gln Pro Pro Gly Lys Gly Leu Glu Trp Leu
            35                  40                  45

Gly Met Ile Trp Gly Gly Ser Ile Asp Tyr Asn Ser Gly Leu Lys
        50                  55                  60

Ser Arg Leu Ser Ile Ser Lys Asp Asn Ser Lys Ser Gln Val Phe Leu
65                  70                  75                  80

Lys Met Asn Ser Leu Gln Ser Asp Asp Thr Ala Met Tyr His Cys Val
                85                  90                  95

Arg Ala Gln Phe Tyr Tyr Gly Tyr Asp Gly Gly Tyr Ala Met Asp Tyr
                100                 105                 110

Trp Gly Gln Gly Thr Ser Val Thr Val Ser Ser
            115                 120

<210> SEQ ID NO 28
<211> LENGTH: 108
<212> TYPE: PRT
<213> ORGANISM: Mus sp.

<400> SEQUENCE: 28

Gln Ile Val Leu Thr Gln Ser Pro Ala Ile Met Ser Ala Ser Pro Gly
1               5                   10                  15

Glu Arg Val Thr Leu Thr Cys Ser Ala Ser Ser Ser Val Ser Ser Ser
                20                  25                  30

Phe Leu Tyr Trp Tyr Gln Gln Lys Ser Gly Ser Ser Pro Lys Leu Trp
            35                  40                  45

Ile Tyr Ser Thr Ser Thr Leu Ala Ser Gly Val Pro Ala Arg Phe Ser
        50                  55                  60

Gly Ser Gly Ser Gly Thr Ser Tyr Ser Leu Thr Ile Ser Ser Met Glu
65                  70                  75                  80

Ala Glu Asp Ala Ala Ser Tyr Phe Cys His Gln Trp Ser Ser Tyr Pro
                85                  90                  95

Trp Thr Phe Gly Gly Gly Thr Lys Leu Glu Ile Lys
            100                 105

<210> SEQ ID NO 29
<211> LENGTH: 118
<212> TYPE: PRT
<213> ORGANISM: Mus sp.

<400> SEQUENCE: 29

Ser Asp Val Gln Leu Gln Glu Ser Gly Pro Gly Leu Val Lys Pro Ser
1               5                   10                  15

Gln Ser Leu Ser Leu Thr Cys Thr Val Thr Asp Tyr Ser Ile Thr Ser
                20                  25                  30

Asp Tyr Ala Trp Asn Trp Ile Arg Gln Phe Pro Gly Asn Asn Leu Glu
            35                  40                  45

Trp Met Gly Asn Ile Gly Tyr Ser Gly Asp Thr Ser Tyr Asn Pro Ser
        50                  55                  60

Leu Lys Ser Arg Ile Ser Ile Thr Arg Asp Thr Ser Lys Asn Gln Phe
65                  70                  75                  80

Phe Leu Gln Leu Asn Ser Val Thr Thr Glu Asp Ser Ala Thr Tyr Tyr
                85                  90                  95

Cys Ala Arg Ser Ser Leu Gly Pro Phe Asp Tyr Trp Gly Gln Gly Thr
                100                 105                 110

Ala Leu Thr Val Ser Ser
            115

<210> SEQ ID NO 30
<211> LENGTH: 113
<212> TYPE: PRT
<213> ORGANISM: Mus sp.

<400> SEQUENCE: 30

Asp Ile Val Met Thr Gln Ser Pro Ser Ser Leu Ala Met Ser Val Gly
1               5                   10                  15

Gln Lys Val Thr Met Ser Cys Lys Ser Ser Gln Ser Leu Leu Asn Ser
            20                  25                  30

Ser Thr Gln Lys Asn Tyr Leu Ala Trp Tyr Gln Gln Lys Pro Gly Gln
        35                  40                  45

Ser Pro Lys Leu Leu Ile Tyr Phe Ala Ser Thr Arg Gly Ser Gly Val
    50                  55                  60

Pro Asp Arg Phe Ile Gly Ser Gly Ser Gly Thr Asp Phe Thr Leu Thr
65                  70                  75                  80

Ile Ser Ser Val Gln Thr Glu Asp Leu Ala Asp Tyr Phe Cys Gln Gln
                85                  90                  95

His Tyr Ser Ile Pro Cys Thr Phe Gly Gly Gly Thr Lys Leu Glu Ile
            100                 105                 110

Lys

<210> SEQ ID NO 31
<211> LENGTH: 118
<212> TYPE: PRT
<213> ORGANISM: Mus sp.

<400> SEQUENCE: 31

Gln Val Gln Leu Gln Gln Ser Gly Asn Glu Leu Val Arg Pro Gly Ser
1               5                   10                  15

Ala Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Tyr Pro Gly Asp Asp Ser Asn Tyr Asn Gly Lys Phe
    50                  55                  60

Lys Gly Lys Ala Thr Leu Thr Ala Asp Lys Ser Ser Ser Ser Ala Tyr
65                  70                  75                  80

Met His Leu Ser Ser Leu Thr Ser Glu Asp Ser Ala Val Tyr Phe Cys
                85                  90                  95

Ala Arg Gly Phe Ala Thr Pro Thr Met Asp Tyr Trp Gly Gln Gly Thr
            100                 105                 110

Ser Val Thr Val Ser Ser
        115

<210> SEQ ID NO 32
<211> LENGTH: 103
<212> TYPE: PRT
<213> ORGANISM: Mus sp.

<400> SEQUENCE: 32

Asp Ile Gln Met Asn Gln Ser Pro Ser Ser Leu Ser Ala Ser Leu Gly
1               5                   10                  15

Asp Thr Ile Thr Ile Thr Cys His Val Ser Gln Asn Ile Asn Val Trp
            20                  25                  30

Leu Thr Trp Tyr Gln Gln Lys Pro Gly Asn Ile Pro Lys Leu Leu Leu

```
              35                  40                  45
Tyr Lys Ala Ser Asn Leu Gln Thr Gly Val Pro Ser Arg Phe Ser Gly
         50                  55                  60

Ser Gly Ser Gly Thr Gly Phe Thr Leu Thr Ile Ser Ser Leu Gln Pro
 65                  70                  75                  80

Glu Asp Ile Ala Thr Tyr Tyr Cys Gln Gln Gly Gln Ser Tyr Pro Phe
                 85                  90                  95

Thr Phe Gly Ser Gly Thr Lys
            100

<210> SEQ ID NO 33
<211> LENGTH: 119
<212> TYPE: PRT
<213> ORGANISM: Mus sp.

<400> SEQUENCE: 33

Gln Val Gln Leu Gln Gln Ser Gly Ala Glu Leu Met Lys Thr Gly Ala
 1               5                  10                  15

Ser Val Lys Ile Ser Cys Lys Ala Thr Gly Tyr Thr Phe Ser Ser Tyr
                20                  25                  30

Trp Ile Glu Trp Val Lys Gln Arg Pro Gly His Gly Leu Glu Trp Ile
            35                  40                  45

Gly Glu Ile Leu Pro Gly Ser Gly Lys Thr Asn Tyr Asn Glu Asn Phe
         50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Ser Glu Asp Ser Val Val Tyr Tyr Cys
                 85                  90                  95

Ala Arg Arg Gly Ala Tyr Tyr Gly Asn Phe Asp Tyr Trp Gly Gln Gly
            100                 105                 110

Thr Thr Leu Thr Val Ser Ser
        115

<210> SEQ ID NO 34
<211> LENGTH: 111
<212> TYPE: PRT
<213> ORGANISM: Mus sp.

<400> SEQUENCE: 34

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
                20                  25                  30

Asn Asn Gln Lys Asn Tyr Leu Ala Trp Tyr Gln Gln Lys Pro Gly Gln
            35                  40                  45

Ser Pro Lys Leu Leu Ile Tyr Trp Ala Ser Ser Arg Glu Ser Gly Val
         50                  55                  60

Pro Glu Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Ser Ser Pro Tyr Thr Phe Gly Gly Gly Thr Lys Leu Lys
            100                 105                 110

<210> SEQ ID NO 35
<211> LENGTH: 123
<212> TYPE: PRT
```

<213> ORGANISM: Mus sp.

<400> SEQUENCE: 35

```
Gln Val Gln Leu Lys Glu Ser Gly Pro Gly Leu Val Ala Pro Ser Gln
1               5                   10                  15

Ser Leu Ser Ile Thr Cys Thr Val Thr Gly Phe Ser Leu Ser Arg Tyr
            20                  25                  30

Ser Val His Trp Ile Arg Gln Pro Pro Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ser Ile Asn Lys Asp Asn Ser Lys Ser Gln Val Phe Leu
65                  70                  75                  80

Lys Met Asn Ser Leu Gln Thr Val Asp Thr Ala Met Tyr Tyr Cys Ala
                85                  90                  95

Arg Thr Gln Phe Tyr Tyr Gly His Asp Gly Gly Tyr Ala Met Asp Tyr
            100                 105                 110

Trp Gly Gln Gly Thr Ser Val Thr Val Ser Ser
        115                 120
```

<210> SEQ ID NO 36
<211> LENGTH: 107
<212> TYPE: PRT
<213> ORGANISM: Mus sp.

<400> SEQUENCE: 36

```
Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Ala Ile Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Val Val Pro Asp Arg Phe Thr Gly
    50                  55                  60

Ser Gly Ser Gly Thr Asp Phe Thr Leu Pro Ile Ser Asn Val Gln Ser
65                  70                  75                  80

Glu Gly Leu Ala Asp Tyr Phe Cys Leu Gln Tyr Ile Asn Tyr Pro Tyr
                85                  90                  95

Thr Phe Gly Gly Gly Thr Lys Leu Glu Ile Lys
            100                 105
```

<210> SEQ ID NO 37
<211> LENGTH: 116
<212> TYPE: PRT
<213> ORGANISM: Mus sp.

<400> SEQUENCE: 37

```
Glu Val Gln Leu Gln Gln Ser Gly Pro Glu Leu Leu Lys Pro Gly Ala
1               5                   10                  15

Ser Val Lys Ile Ser Cys Lys Ala Ser Gly Tyr Thr Phe Thr Asp Tyr
            20                  25                  30

Asn Met His Trp Val Lys Gln Ser His Gly Lys Ser Leu Glu Trp Ile
        35                  40                  45

Gly Asn Ile Tyr Pro Tyr Asn Gly Gly Thr Gly Tyr Asn Gln Lys Phe
    50                  55                  60

Lys Thr Lys Ala Thr Leu Thr Val Asp Asn Ser Ser Ser Thr Ala Tyr
65                  70                  75                  80
```

```
Met Glu Leu Arg Ser Leu Thr Ser Glu Asp Ser Ala Val Tyr Tyr Cys
                85                  90                  95

Ala Ile Gly Asn Tyr Trp Phe Ala Phe Trp Gly Gln Gly Thr Leu Val
            100                 105                 110

Thr Val Ser Ala
        115

<210> SEQ ID NO 38
<211> LENGTH: 106
<212> TYPE: PRT
<213> ORGANISM: Mus sp.

<400> SEQUENCE: 38

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Tyr Gln Gln Lys Ala Gly Ser Ser Pro Thr Ser Trp Ile Tyr
            35                  40                  45

Ala Thr Ser Asn Leu Ala Ser Gly Val Pro Thr Arg Phe Ser Gly Ser
        50                  55                  60

Gly Ser Gly Thr Ser Tyr Ser Leu Thr Val Asn Arg Val Glu Ala Glu
65                  70                  75                  80

Asp Ala Ala Thr Tyr Tyr Cys Gln Gln Trp Ser Thr Pro Pro Thr
                85                  90                  95

Phe Gly Gly Gly Thr Arg Leu Glu Ile Lys
            100                 105

<210> SEQ ID NO 39
<211> LENGTH: 120
<212> TYPE: PRT
<213> ORGANISM: Mus sp.

<400> SEQUENCE: 39

Glu Val Gln Leu Gln Gln Ser Gly Pro Asp Leu Val Lys Pro Gly Thr
1               5                   10                  15

Ser Val Lys Ile Ser Cys Lys Ala Ser Gly Tyr Ser Phe Thr Ala Cys
                20                  25                  30

Tyr Ile His Trp Val Lys Gln Ser His Gly Lys Ser Leu Glu Trp Ile
            35                  40                  45

Gly Arg Phe Ser Pro Asn Asn Asp Arg Thr Thr Tyr Asn Gln Lys Phe
        50                  55                  60

Lys Asp Lys Ala Ile Leu Thr Val Asp Lys Ser Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Gly Glu Glu Ser Trp Asp Ala Trp Phe Thr Tyr Trp Gly Gln
            100                 105                 110

Gly Thr Leu Val Thr Val Ser Ala
        115                 120

<210> SEQ ID NO 40
<211> LENGTH: 110
<212> TYPE: PRT
<213> ORGANISM: Mus sp.

<400> SEQUENCE: 40
```

```
Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Lys Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Phe Gly Thr Asp Phe Thr Leu Thr
65                  70                  75                  80

Ile Ser Ser Val Gln Ala Glu Asp Leu Ala Val Tyr Tyr Cys Gln Ser
                85                  90                  95

Asp Tyr Asn Tyr Pro Thr Phe Gly Ser Gly Thr Lys Leu Lys
            100                 105                 110
```

<210> SEQ ID NO 41
<211> LENGTH: 119
<212> TYPE: PRT
<213> ORGANISM: Mus sp.

<400> SEQUENCE: 41

```
Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Ser Ser Gln Val
65                  70                  75                  80

Phe Leu Lys Ile Ala Ser Val Asp Thr Ala Asp Thr Ala Thr Tyr His
                85                  90                  95

Cys Ala Arg Ile Ala Ile Gly Gln Pro Phe Ala Tyr Trp Gly Gln Gly
            100                 105                 110

Thr Leu Val Thr Val Ser Ala
        115
```

<210> SEQ ID NO 42
<211> LENGTH: 106
<212> TYPE: PRT
<213> ORGANISM: Mus sp.

<400> SEQUENCE: 42

```
Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Thr Tyr Pro Tyr Thr
                85                  90                  95
```

```
Phe Gly Gly Gly Thr Lys Leu Glu Ile Lys
            100                 105
```

<210> SEQ ID NO 43
<211> LENGTH: 120
<212> TYPE: PRT
<213> ORGANISM: Mus sp.

<400> SEQUENCE: 43

```
Gln Val Gln Leu Gln Gln Pro Gly Ala Glu Leu Val Lys Pro Gly Ala
1               5                   10                  15

Ser Val Lys Leu Ser Cys Arg Thr Ser Gly Tyr Ser Phe Thr Ser Tyr
            20                  25                  30

Trp Ile His Trp Val Lys Gln Arg Pro Gly Arg Gly Leu Glu Trp Ile
        35                  40                  45

Gly Arg Ile Val Pro Asn Ser Gly Gly Thr Lys Tyr Asn Glu Asn Phe
    50                  55                  60

Lys Asn Lys Ala Thr Leu Thr Val Asp Lys Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Thr Arg Glu Asp Ser Tyr Gly Pro Phe Asp Leu Asp Tyr Trp Gly Gln
            100                 105                 110

Gly Thr Ser Val Thr Val Ser Ser
        115                 120
```

<210> SEQ ID NO 44
<211> LENGTH: 106
<212> TYPE: PRT
<213> ORGANISM: Mus sp.

<400> SEQUENCE: 44

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Met
            20                  25                  30

His Trp Tyr Gln Gln Lys Pro Gly Ser Ser Pro Lys Pro Trp Ile Tyr
        35                  40                  45

Ala Ala Ser Asn Leu Ala Ser Gly Val Pro Ala Arg Phe Ser Ala Thr
    50                  55                  60

Gly Ser Gly Thr Ser Tyr Ser Leu Thr Ile Ser Arg Val Glu Ala Glu
65                  70                  75                  80

Asp Ala Ala Thr Tyr Cys Cys Gln Gln Trp Ser Asn Asn Pro Pro Thr
                85                  90                  95

Phe Gly Gly Gly Thr Lys Leu Glu Ile Lys
            100                 105
```

<210> SEQ ID NO 45
<211> LENGTH: 121
<212> TYPE: PRT
<213> ORGANISM: Mus sp.

<400> SEQUENCE: 45

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
```

```
                35                  40                  45

Gly Arg Ile Asn Pro Tyr Asn Gly Asp Asn Phe Tyr Asn Gln Lys Phe
     50                  55                  60

Lys Gly Lys Ala Thr Leu Thr Val Asp Lys Ser Ser Thr Ala His
65                   70                  75                  80

Met Glu Leu Leu Ser Leu Thr Ser Glu Asp Ser Ala Val Tyr Tyr Cys
                 85                  90                  95

Gly Arg Asp Tyr Gly Ser Ser Tyr Gly Trp Phe Phe Asp Val Trp Gly
                100                 105                 110

Ala Gly Thr Thr Val Thr Val Ser Ser
            115                 120

<210> SEQ ID NO 46
<211> LENGTH: 111
<212> TYPE: PRT
<213> ORGANISM: Mus sp.

<400> SEQUENCE: 46

Asp Ile Val Leu Thr Gln Ser Pro Ala Ser Leu Ala Val Ser Leu Gly
1               5                   10                  15

Gln Arg Ala Thr Ile Ser Cys Arg Ala Asn Glu Ser Val Glu Tyr Tyr
             20                  25                  30

Gly Thr Ser Leu Met Gln Trp Tyr Gln Gln Lys Pro Gly Gln Pro Pro
         35                  40                  45

Lys Leu Leu Ile Tyr Ala Ala Ser Val Lys Ser Gly Val Pro Ala
 50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                 85                  90                  95

Lys Val Pro Ser Thr Phe Gly Gly Gly Thr Lys Leu Glu Ile Lys
             100                 105                 110

<210> SEQ ID NO 47
<211> LENGTH: 123
<212> TYPE: PRT
<213> ORGANISM: Mus sp.

<400> SEQUENCE: 47

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Thr Phe Thr Asp His
             20                  25                  30

Thr Met His Trp Val Lys Gln Ser His Gly Lys Asn Leu Glu Trp Ile
         35                  40                  45

Gly Arg Ile Asn Pro Tyr Asn Gly Asp Thr Ser His Asn Gln Asn Phe
     50                  55                  60

Lys Gly Lys Ala Thr Leu Thr Val Asp Lys Ser Ser Asn Thr Ala Tyr
65                  70                  75                  80

Met Glu Leu Leu Ser Leu Thr Ser Glu Asp Ser Ala Val Tyr Tyr Cys
                 85                  90                  95

Ala Arg Tyr Gly Gly Asp Tyr Thr Ser Ser Tyr Tyr Thr Met Asp Tyr
                100                 105                 110

Trp Gly Gln Gly Thr Ser Ser Thr Val Ser Ser
            115                 120
```

<210> SEQ ID NO 48
<211> LENGTH: 111
<212> TYPE: PRT
<213> ORGANISM: Mus sp.

<400> SEQUENCE: 48

Asp Ile Val Leu Thr Gln Ser Pro Ala Ser Leu Ala Val Ser Leu Gly
1               5                   10                  15

Gln Arg Ala Thr Ile Ser Cys Arg Ala His Glu Ser Val Glu Tyr Tyr
            20                  25                  30

Gly Thr Ser Leu Met Gln Trp Tyr Gln Gln Lys Pro Gly Gln Pro Pro
        35                  40                  45

Lys Leu Leu Ile Tyr Ala Ala Ser Ser Val Lys Ser Gly Val Pro Ala
    50                  55                  60

Arg Phe Ser Gly Ser Gly Ser Gly Thr Asp Phe Ser Leu Asn Ile His
65                  70                  75                  80

Pro Val Glu Glu Asp Asp Ile Ala Met Tyr Phe Cys Gln Gln Ser Arg
                85                  90                  95

Lys Val Pro Ser Thr Phe Gly Gly Gly Thr Lys Leu Glu Ile Lys
            100                 105                 110

<210> SEQ ID NO 49
<211> LENGTH: 123
<212> TYPE: PRT
<213> ORGANISM: Mus sp.

<400> SEQUENCE: 49

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Thr Phe Thr Asp Tyr
            20                  25                  30

Thr Met His Trp Val Arg Gln Ser His Gly Lys Asn Leu Glu Trp Ile
        35                  40                  45

Gly Arg Ile Asn Pro Tyr Asn Ala Asp Thr Ser His Asn Gln Asn Phe
    50                  55                  60

Lys Gly Arg Ala Thr Leu Thr Val Asp Lys Ser Phe Asn Thr Ala Tyr
65                  70                  75                  80

Met Glu Leu Leu Ser Leu Thr Ser Glu Asp Ser Ala Val Tyr Tyr Cys
                85                  90                  95

Ala Arg Tyr Gly Gly Asp Phe Thr Ser Ser Tyr Tyr Thr Met Asp Tyr
            100                 105                 110

Trp Gly Gln Gly Thr Ser Val Thr Val Ser Ser
        115                 120

<210> SEQ ID NO 50
<211> LENGTH: 113
<212> TYPE: PRT
<213> ORGANISM: Mus sp.

<400> SEQUENCE: 50

Asp Ile Val Met Thr Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

```
Pro Asp Arg Phe Thr Gly Ser Gly Ser Gly Thr Asp Phe Thr Leu Thr
 65                  70                  75                  80

Ile Ser Ser Val Lys Ala Glu Asp Leu Ala Val Tyr Tyr Cys Gln Gln
                 85                  90                  95

Tyr Tyr Asn Tyr Pro Tyr Thr Phe Gly Gly Gly Thr Lys Leu Glu Ile
            100                 105                 110

Lys

<210> SEQ ID NO 51
<211> LENGTH: 118
<212> TYPE: PRT
<213> ORGANISM: Mus sp.

<400> SEQUENCE: 51

Gln Val Gln Leu Lys Glu Ser Gly Pro Gly Leu Val Ala Pro Ser Gln
 1               5                  10                  15

Ser Leu Ser Ile Thr Cys Thr Val Ser Gly Phe Ser Leu Thr Ser Tyr
                 20                  25                  30

Thr Ile Ser Trp Val Arg Gln Pro Pro Gly Lys Gly Leu Glu Trp Leu
             35                  40                  45

Gly Ile Ile Trp Thr Ala Gly Ala Thr Asn Tyr Asn Ser Ala Leu Lys
         50                  55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Arg Tyr Tyr Cys Ala
                 85                  90                  95

Arg Tyr Ser Lys Asp Tyr Tyr Ala Val Asp Tyr Trp Gly Gln Gly Thr
            100                 105                 110

Ser Val Thr Val Ser Ser
        115

<210> SEQ ID NO 52
<211> LENGTH: 109
<212> TYPE: PRT
<213> ORGANISM: Mus sp.

<400> SEQUENCE: 52

Asp Ile Val Leu Thr Gln Ser Pro Ala Ser Leu Ala Val Ser Leu Gly
 1               5                  10                  15

Gln Arg Ala Thr Ile Ser Cys Arg Ala Asn Glu Asn Val Glu Tyr Tyr
                 20                  25                  30

Gly Thr Ser Leu Met Gln Trp Tyr Gln Gln Lys Pro Gly Gln Pro Pro
             35                  40                  45

Lys Leu Leu Ile Tyr Ala Ala Ser Asn Val Lys Ser Gly Val Pro Ala
         50                  55                  60

Arg Phe Ser Gly Ser Gly Ser Gly Thr Asp Phe Ser Leu Asn Ile His
 65                  70                  75                  80

Pro Val Glu Glu Asp Asp Ile Ala Met Tyr Phe Cys Gln Gln Ser Arg
                 85                  90                  95

Lys Val Pro Ser Thr Phe Gly Gly Gly Thr Lys Leu Lys
            100                 105

<210> SEQ ID NO 53
<211> LENGTH: 123
<212> TYPE: PRT
<213> ORGANISM: Mus sp.
```

<400> SEQUENCE: 53

Glu Val Gln Leu Gln Gln Ser Gly Pro Glu Leu Val Lys Pro Gly Ala
1               5                   10                  15

Ser Met Lys Ile Ser Cys Lys Ala Ser Gly Tyr Thr Phe Thr Asp Tyr
            20                  25                  30

Thr Met His Trp Val Lys Gln Ser His Gly Lys Asn Leu Glu Trp Ile
        35                  40                  45

Gly Arg Ile Asn Pro Tyr Asn Asp Ile Ser His Asn Gln Asn Phe
    50                  55                  60

Lys Asp Lys Ala Thr Leu Thr Val Asp Lys Ser Ser Asn Thr Ala Tyr
65                  70                  75                  80

Met Glu Leu Leu Ser Leu Thr Ser Glu Asp Ser Ala Val Tyr Tyr Cys
                85                  90                  95

Ala Arg Tyr Gly Gly Asp Tyr Thr Ser Ser Tyr Tyr Thr Met Asp Tyr
            100                 105                 110

Trp Gly Gln Gly Thr Ser Val Thr Val Ser Ser
            115                 120

<210> SEQ ID NO 54
<211> LENGTH: 113
<212> TYPE: PRT
<213> ORGANISM: Mus sp.

<400> SEQUENCE: 54

Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Thr Val Lys Ala Glu Asp Leu Ala Val Tyr Tyr Cys His Gln
                85                  90                  95

Tyr Tyr Ser Tyr Pro Tyr Thr Phe Gly Gly Gly Thr Lys Leu Glu Ile
            100                 105                 110

Lys

<210> SEQ ID NO 55
<211> LENGTH: 123
<212> TYPE: PRT
<213> ORGANISM: Mus sp.

<400> SEQUENCE: 55

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Ser Arg Tyr
            20                  25                  30

Ser Val His Trp Val Arg Gln Pro Ser Gly Lys Gly Leu Glu Trp Leu
        35                  40                  45

Gly Met Ile Trp Gly Gly Gly Ser Thr Asp Tyr Asn Ser Ala Leu Lys
    50                  55                  60

Ser Arg Leu Ile Ile Ser Lys Asp Asn Ser Lys Ser Gln Val Phe Leu
65                  70                  75                  80

-continued

```
Lys Met Asn Ser Leu Gln Thr Asp Asp Thr Ala Met Tyr Tyr Cys Ala
                85                  90                  95

Arg Thr Gln Phe Tyr Tyr Gly His Asp Gly Gly Tyr Ala Met Asp Tyr
            100                 105                 110

Trp Gly Gln Gly Thr Ser Val Thr Val Ser Ser
        115                 120

<210> SEQ ID NO 56
<211> LENGTH: 111
<212> TYPE: PRT
<213> ORGANISM: Mus sp.

<400> SEQUENCE: 56

Asp Ile Val Leu Thr Gln Ser Pro Gly Ser Leu Ala Val Ser Leu Gly
1               5                   10                  15

Gln Arg Ala Thr Ile Ser Cys Arg Ala Ser Gln Ser Val Ser Ser Ser
            20                  25                  30

Ser Tyr Ser Tyr Met His Trp Tyr Gln Gln Lys Pro Gly Gln Pro Pro
        35                  40                  45

Lys Leu Leu Ile Lys Phe Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Thr Ala Thr Tyr Tyr Cys Gln His Ser Trp
                85                  90                  95

Glu Ile Pro Leu Thr Phe Gly Ala Gly Thr Lys Leu Glu Leu Lys
            100                 105                 110

<210> SEQ ID NO 57
<211> LENGTH: 119
<212> TYPE: PRT
<213> ORGANISM: Mus sp.

<400> SEQUENCE: 57

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Val Lys Arg Tyr Asn Pro Ala
    50                  55                  60

Leu Lys Ser Arg Leu Asn Ile Ser Lys Asp Thr Ser Ser Ser Gln Val
65                  70                  75                  80

Phe Leu Lys Ile Ala Ser Val Asp Thr Ala Asp Thr Ala Thr Tyr Tyr
                85                  90                  95

Cys Gly Arg Lys Ser Asn Ser Gly Tyr Phe Asp Tyr Trp Gly Gln Gly
            100                 105                 110

Thr Thr Leu Thr Val Ser Ser
        115

<210> SEQ ID NO 58
<211> LENGTH: 107
<212> TYPE: PRT
<213> ORGANISM: Mus sp.

<400> SEQUENCE: 58
```

```
Asp Val Gln Ile Thr Gln Ser Pro Ser Tyr Leu Ala Ala Ser Pro Gly
1               5                   10                  15

Glu Thr Ile Ser Ile Asn Cys Arg Ala Ser Lys Asn Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Gly Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Tyr Cys Gln Gln His Phe Glu Tyr Pro Tyr
                85                  90                  95

Thr Phe Gly Gly Gly Thr Lys Leu Glu Ile Lys
            100                 105
```

<210> SEQ ID NO 59
<211> LENGTH: 116
<212> TYPE: PRT
<213> ORGANISM: Mus sp.

<400> SEQUENCE: 59

```
Glu Val Gln Leu Gln Gln Ser Gly Pro Asp Leu Val Lys Pro Gly Ala
1               5                   10                  15

Ser Val Lys Ile Ser Cys Lys Ala Ser Gly Tyr Ser Phe Thr Gly Tyr
            20                  25                  30

Phe Met Asn Trp Val Lys Gln Ser His Gly Lys Ser Leu Glu Trp Ile
        35                  40                  45

Gly Arg Ile Asn Pro Tyr Asn Gly Asp Thr Phe Tyr Asn Gln Lys Phe
    50                  55                  60

Lys Gly Lys Ala Thr Leu Thr Val Asp Lys Ser Ser Ser Thr Ala His
65                  70                  75                  80

Met Glu Leu Leu Ser Leu Thr Ser Glu Asp Ser Ala Val Tyr Tyr Cys
                85                  90                  95

Gly Arg Gly Asn Tyr Tyr Phe Asp Tyr Trp Gly Gln Gly Thr Thr Leu
            100                 105                 110

Thr Val Ser Ser
        115
```

<210> SEQ ID NO 60
<211> LENGTH: 105
<212> TYPE: PRT
<213> ORGANISM: Mus sp.

<400> SEQUENCE: 60

```
Gln Ile Val Leu Thr Gln Ser Pro Ala Ile Met Ser Ala Ser Leu Gly
1               5                   10                  15

Glu Glu Ile Thr Leu Thr Cys Ser Ala Thr Ser Ser Val Gly Tyr Ile
            20                  25                  30

His Trp Tyr Gln Gln Thr Ser Gly Thr Ser Pro Arg Leu Leu Ile Tyr
        35                  40                  45

Thr Thr Ser Asn Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Ser Arg Tyr Pro Thr Phe
                85                  90                  95
```

```
Gly Gly Gly Thr Lys Leu Glu Ile Lys
            100             105
```

<210> SEQ ID NO 61
<211> LENGTH: 114
<212> TYPE: PRT
<213> ORGANISM: Mus sp.

<400> SEQUENCE: 61

```
Gln Val Gln Leu Glu Gln Ser Gly Gly Asp Leu Val Lys Pro Gly Gly
1               5                   10                  15

Ser Leu Lys Leu Ser Cys Ala Ala Ser Gly Phe Thr Phe Ser Ser Tyr
            20                  25                  30

Gly Met Ser Trp Val Arg Gln Thr Pro Asp Lys Arg Leu Glu Trp Val
        35                  40                  45

Ala Thr Ile Ser Ser Gly Gly Ser Tyr Ser Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Phe Cys
                85                  90                  95

Arg Pro Ser Phe Phe Pro Ser Trp Gly Gln Gly Thr Leu Val Thr Val
            100                 105                 110

Ser Ala
```

<210> SEQ ID NO 62
<211> LENGTH: 107
<212> TYPE: PRT
<213> ORGANISM: Mus sp.

<400> SEQUENCE: 62

```
Asp Ile Lys Met Thr Gln Ser Pro Ser Ser Thr Tyr Ala Ser Leu Gly
1               5                   10                  15

Glu Arg Val Thr Ile Thr Cys Lys Ala Ser Gln Asp Ile Asn Thr Tyr
            20                  25                  30

Leu Tyr Trp Phe Gln Gln Lys Pro Gly Lys Pro Pro Lys Thr Leu Ile
        35                  40                  45

Tyr Arg Ala Asn Arg Leu Ile Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Leu Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105
```

<210> SEQ ID NO 63
<211> LENGTH: 109
<212> TYPE: PRT
<213> ORGANISM: Mus sp.

<400> SEQUENCE: 63

```
Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Asn Asp Asp
            20                  25                  30

Tyr Phe His Trp Val Lys Gln Arg Pro Glu Gln Gly Leu Glu Trp Ile
        35                  40                  45
```

-continued

Gly Arg Ile Asp Pro Ala Asn Gly Asn Thr Lys Tyr Gly Pro Lys Phe
         50                  55                  60

Gln Asp Lys Ala Thr Ile Thr Ala Asp Thr Ser Ser Asn Thr Ala Tyr
 65                  70                  75                  80

Leu Gln Phe Thr Ser Leu Thr Ser Glu Asp Thr Ala Val Tyr Tyr Cys
                 85                  90                  95

Ala Ser Gly Trp Ala Phe Ala Cys Trp Gly Gln Gly Thr
                100                 105

<210> SEQ ID NO 64
<211> LENGTH: 111
<212> TYPE: PRT
<213> ORGANISM: Mus sp.

<400> SEQUENCE: 64

Asp Ile Val Leu Thr Gln Ser Pro Ala Ser Leu Ala Val Ser Leu Gly
  1               5                  10                  15

Gln Arg Ala Thr Ile Ser Cys Arg Ala Asp Glu Ser Val Glu Tyr Tyr
                 20                  25                  30

Gly Thr Ser Leu Met Gln Trp Tyr Gln Gln Lys Pro Gly Gln Pro Pro
             35                  40                  45

Lys Leu Leu Ile Tyr Ala Ala Ser Asn Val Lys Ser Gly Val Pro Ala
 50                  55                  60

Arg Phe Ser Gly Ser Gly Ser Gly Thr Asp Phe Ser Leu Asn Ile His
 65                  70                  75                  80

Pro Val Glu Glu Asp Asp Ile Ala Ile Tyr Phe Cys Gln Gln Ser Arg
                 85                  90                  95

Glu Val Pro Ser Thr Phe Gly Gly Gly Thr Lys Leu Glu Ile Lys
                100                 105                 110

<210> SEQ ID NO 65
<211> LENGTH: 123
<212> TYPE: PRT
<213> ORGANISM: Mus sp.

<400> SEQUENCE: 65

Glu Val Gln Leu Gln Gln Ser Gly Pro Glu Leu Val Lys Pro Gly Thr
  1               5                  10                  15

Ser Met Lys Ile Ser Cys Lys Ala Ser Gly Tyr Thr Phe Thr Asp Tyr
                 20                  25                  30

Thr Met His Trp Val Lys Gln Ser His Gly Lys Asn Leu Glu Trp Ile
             35                  40                  45

Gly Arg Ile Asn Pro Tyr Thr Gly Ser Thr Ser His Asn Gln Asn Phe
 50                  55                  60

Lys Asp Lys Ala Ser Leu Thr Val Asp Lys Ser Ser Asn Thr Ala Tyr
 65                  70                  75                  80

Met Asp Leu Leu Ser Leu Thr Ser Glu Asp Ser Ala Val Tyr Tyr Cys
                 85                  90                  95

Ala Arg Phe Gly Gly Asp Tyr Thr Ser Ser Tyr Tyr Thr Leu Asp Tyr
                100                 105                 110

Trp Gly Gln Gly Thr Ser Val Ser Val Ser Ser
            115                 120

<210> SEQ ID NO 66
<211> LENGTH: 112
<212> TYPE: PRT
<213> ORGANISM: Mus sp.

<400> SEQUENCE: 66

Asp Ile Val Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Asn Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Trp Thr Phe Gly Gly Gly Thr Lys Leu Glu Ile Lys
            100                 105                 110

<210> SEQ ID NO 67
<211> LENGTH: 117
<212> TYPE: PRT
<213> ORGANISM: Mus sp.

<400> SEQUENCE: 67

Glu Val Gln Leu Gln Gln Ser Gly Pro Glu Leu Val Lys Pro Gly Asp
1               5                   10                  15

Ser Val Lys Met Ser Cys Lys Ala Ser Gly Asn Thr Val Thr Asn Tyr
            20                  25                  30

Tyr Met Asp Trp Val Lys Gln Ser His Gly Lys Ser Leu Glu Trp Ile
        35                  40                  45

Gly Tyr Ile Tyr Ala Asn Asn Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Ile His Ser Leu Thr Ser Glu Asp Ser Ala Val Tyr Tyr Cys
                85                  90                  95

Ala Ile Tyr Tyr Arg Tyr Glu Phe Ala Tyr Trp Gly Gln Gly Thr Leu
            100                 105                 110

Val Thr Val Ser Ala
        115

<210> SEQ ID NO 68
<211> LENGTH: 108
<212> TYPE: PRT
<213> ORGANISM: Mus sp.

<400> SEQUENCE: 68

Asp Ile Val Met Thr Gln Ser His Lys Leu Met Ser Ala Ser Val Gly
1               5                   10                  15

Asp Arg Val Ser Ile Thr Cys Lys Ala Ser Gln Asp Val Gly Thr Ala
            20                  25                  30

Val Ala Trp Tyr Gln Gln Lys Pro Gly Arg Ser Pro Lys Leu Leu Ile
        35                  40                  45

Tyr Trp Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

```
Glu Asp Leu Ala Asp Tyr Phe Cys Gln Gln Phe Gly Ser Tyr Pro Tyr
            85                  90                  95

Thr Phe Gly Gly Gly Thr Lys Leu Glu Ile Lys Arg
            100                 105

<210> SEQ ID NO 69
<211> LENGTH: 121
<212> TYPE: PRT
<213> ORGANISM: Mus sp.

<400> SEQUENCE: 69

Ser Asp Val Gln Leu Gln Glu Ser Gly Pro Gly Leu Val Lys Pro Ser
1               5                   10                  15

Gln Ser Leu Ser Val Thr Cys Thr Val Thr Asp Tyr Ser Leu Thr Ser
            20                  25                  30

Gly Tyr Tyr Trp Asn Trp Ile Arg Gln Phe Pro Gly Asn Lys Leu Glu
            35                  40                  45

Trp Met Ala Tyr Ile His Ser Ser Gly Ser Thr His Tyr Asn Pro Ser
        50                  55                  60

Leu Lys Ser Arg Ile Ser Val Thr Arg Asp Thr Ser Lys Asn Gln Phe
65                  70                  75                  80

Phe Leu Gln Leu Asn Ser Val Thr Thr Glu Asp Thr Ala Thr Tyr Tyr
                85                  90                  95

Cys Ala Arg Asp Gly Ala Tyr Tyr Ser Ser Trp Phe Pro Tyr Trp Gly
            100                 105                 110

Gln Gly Thr Leu Val Thr Val Ser Ala
        115                 120

<210> SEQ ID NO 70
<211> LENGTH: 111
<212> TYPE: PRT
<213> ORGANISM: Mus sp.

<400> SEQUENCE: 70

Asp Ile Val Leu Thr Gln Ser Pro Leu Ser Leu Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
            35                  40                  45

Pro Asn Leu Leu Ile Phe Lys Val Ser Asn Arg Phe Ser Gly Val Pro
        50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Phe Cys Ser Gln Thr
                85                  90                  95

Thr His Val Trp Thr Phe Gly Gly Gly Thr Lys Leu Glu Ile Lys
            100                 105                 110

<210> SEQ ID NO 71
<211> LENGTH: 112
<212> TYPE: PRT
<213> ORGANISM: Mus sp.

<400> SEQUENCE: 71

Gln Ile Leu Leu Val Gln Ser Gly Pro Glu Leu Lys Lys Pro Gly Glu
1               5                   10                  15

Thr Val Lys Ile Ser Cys Lys Ala Asn Tyr Thr Phe Thr Asp Tyr Gly
```

```
            20                  25                  30
Met His Trp Val Lys Gln Ala Pro Gly Lys Gly Leu Lys Trp Met Gly
                35                  40                  45

Trp Ile Asn Pro Lys Thr Gly Val Ala Ser Tyr Ala Asp Asp Phe Lys
         50                  55                  60

Gly Arg Phe Ala Phe Ser Leu Glu Thr Ser Ala Ser Thr Ala Tyr Leu
 65                  70                  75                  80

Gln Ile Asn Asn Leu Glu Asn Glu Asp Thr Ser Ile Tyr Phe Cys Ala
                 85                  90                  95

Arg Phe Phe Asp Tyr Trp Gly Gln Gly Thr Thr Leu Thr Val Ser Ser
            100                 105                 110
```

<210> SEQ ID NO 72
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

```
Asp Val Val Met Thr Gln Ser Pro Leu Ser Leu Pro Val Thr Leu Gly
  1               5                  10                  15

Gln Pro Ala Ser Ile Ser Cys Arg Ser Ser Gln Ser Ile Val His Ser
                 20                  25                  30

Asp Gly Asn Thr Tyr Leu Glu Trp Tyr Gln Gln Arg Pro Gly Gln Ser
             35                  40                  45

Pro Arg Arg Leu Ile Tyr Lys Val Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser His Ala Pro Trp Thr Phe Gly Gly Gly Thr Lys Val Glu Ile Lys
            100                 105                 110
```

<210> SEQ ID NO 73
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Tyr Ile Thr Thr Arg Ser Ser Thr Ile Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Thr Arg Glu Pro Leu Thr Gly Tyr Tyr Ala Met Asp Tyr Trp Gly Gln
```

100                 105                 110
Gly Thr Ser Val Thr Val Ser Ser
        115                 120

<210> SEQ ID NO 74

<400> SEQUENCE: 74

000

<210> SEQ ID NO 75

<400> SEQUENCE: 75

000

<210> SEQ ID NO 76

<400> SEQUENCE: 76

000

<210> SEQ ID NO 77

<400> SEQUENCE: 77

000

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81

000

<210> SEQ ID NO 82

<400> SEQUENCE: 82

000

<210> SEQ ID NO 83

<400> SEQUENCE: 83

000

<210> SEQ ID NO 84

<400> SEQUENCE: 84

000

<210> SEQ ID NO 85
<400> SEQUENCE: 85
000

<210> SEQ ID NO 86
<400> SEQUENCE: 86
000

<210> SEQ ID NO 87
<400> SEQUENCE: 87
000

<210> SEQ ID NO 88
<400> SEQUENCE: 88
000

<210> SEQ ID NO 89
<400> SEQUENCE: 89
000

<210> SEQ ID NO 90
<400> SEQUENCE: 90
000

<210> SEQ ID NO 91
<400> SEQUENCE: 91
000

<210> SEQ ID NO 92
<400> SEQUENCE: 92
000

<210> SEQ ID NO 93
<400> SEQUENCE: 93
000

<210> SEQ ID NO 94
<400> SEQUENCE: 94
000

<210> SEQ ID NO 95
<400> SEQUENCE: 95
000

```
<210> SEQ ID NO 96
<400> SEQUENCE: 96
000

<210> SEQ ID NO 97
<400> SEQUENCE: 97
000

<210> SEQ ID NO 98
<400> SEQUENCE: 98
000

<210> SEQ ID NO 99
<400> SEQUENCE: 99
000

<210> SEQ ID NO 100
<400> SEQUENCE: 100
000

<210> SEQ ID NO 101
<400> SEQUENCE: 101
000

<210> SEQ ID NO 102
<400> SEQUENCE: 102
000

<210> SEQ ID NO 103
<400> SEQUENCE: 103
000

<210> SEQ ID NO 104
<400> SEQUENCE: 104
000

<210> SEQ ID NO 105
<400> SEQUENCE: 105
000

<210> SEQ ID NO 106
<400> SEQUENCE: 106
000
```

-continued

<210> SEQ ID NO 107
<400> SEQUENCE: 107
000

<210> SEQ ID NO 108
<400> SEQUENCE: 108
000

<210> SEQ ID NO 109
<400> SEQUENCE: 109
000

<210> SEQ ID NO 110
<400> SEQUENCE: 110
000

<210> SEQ ID NO 111
<400> SEQUENCE: 111
000

<210> SEQ ID NO 112
<400> SEQUENCE: 112
000

<210> SEQ ID NO 113
<400> SEQUENCE: 113
000

<210> SEQ ID NO 114
<400> SEQUENCE: 114
000

<210> SEQ ID NO 115
<400> SEQUENCE: 115
000

<210> SEQ ID NO 116
<400> SEQUENCE: 116
000

<210> SEQ ID NO 117
<400> SEQUENCE: 117
000

<210> SEQ ID NO 118

<400> SEQUENCE: 118

000

<210> SEQ ID NO 119

<400> SEQUENCE: 119

000

<210> SEQ ID NO 120
<211> LENGTH: 319
<212> TYPE: DNA
<213> ORGANISM: Mus sp.

<400> SEQUENCE: 120

```
caaattgttc tcacccagtc tccagcactc atgtctgcat ctccagggga gaaggtcacc        60
atgacctgca gtgccagctc aagtgtacgt tacatgtact ggtaccagca gaagccaaga       120
tcctccccca aaccctggat tcatctcaca tccaacctgg cttctggagt ccctgctcgc       180
ttcagtggca gtgggtctgg gacctcttac tctctcacaa tcagcagcat ggaggctgaa       240
gatgctgcca cctattactg ccagcagtgg agtagtcacc cattcacgtt cggctcgggg       300
acaaagttgg aaataaaac                                                    319
```

<210> SEQ ID NO 121
<211> LENGTH: 351
<212> TYPE: DNA
<213> ORGANISM: Mus sp.

<400> SEQUENCE: 121

```
tctgatgtgc agcttcagga gtcgggacct ggcctggtga aaccttctca gtctctgtcc        60
ctcacctgca ctgtcactgg cttctcaatc accagtgatt attcctggaa ctggatccgg       120
cagtttccag gaaacaaact ggagtggatg ggctacataa gctacagtgg tcacactagc       180
tacaacccat ctctcgaaag tcgaatctct atcactcgag acacatccaa gaaccagttc       240
ttcctgcagt tgaattctgt gactactgag gacacagcca catattactg tacaagaggg       300
aactgggacg ttgtttactg gggccaaggg actctggtca ctgtctctgc a                351
```

<210> SEQ ID NO 122
<211> LENGTH: 341
<212> TYPE: DNA
<213> ORGANISM: Mus sp.

<400> SEQUENCE: 122

```
gacattgtga tgtcacagtc tccatcctcc ctagctgtgt cagttggaga gaaggttact        60
atgagctgca gtccagtca gagcctttta tatagtaaca atcaaaagaa ctacttggcc       120
tggtaccagc agaaaccagg gcagtctcct aaactgctga tttactgggc atccactagg       180
gaatctgggg tccctgatcg cttcacaggc agtggatctg gacagatttc actctcacc        240
atcagcagtg tgaaggctga agacctggca gtttattact gtcaccaata ttatacctct       300
ccgtacacgt tcggagggggg gaccaacctg gaaataaaac g                          341
```

<210> SEQ ID NO 123
<211> LENGTH: 369
<212> TYPE: DNA
<213> ORGANISM: Mus sp.

<400> SEQUENCE: 123

```
caggtgcagc tgaaggagtc aggacctggc ctggtggcac cctcacagag cctgtccatc    60
acatgcactg tctctgggtt ctcattatct agatatagtg tacagtgggt tcgccagcct   120
ccaggaaagg gtctggagtg gctgggaatg atatggggtg gtggaagcac agactataat   180
tcaggtctca aatccagact gaccatcagc aaggacaact ccaagagcca agttttctta   240
aaaatgaaca gtctgcaaac tgatgacaca gccatgtact tctgtgccag aacccagttc   300
tactatggcc acgacggggg ttatgctatg gacttctggg gtcaaggaac ctcagtcacc   360
gtctcctca                                                          369

<210> SEQ ID NO 124
<211> LENGTH: 337
<212> TYPE: DNA
<213> ORGANISM: Mus sp.

<400> SEQUENCE: 124
gatgttttga tgacccaaac tccactctcc ctgcctgtca gtcttggaga tcaagcctcc    60
atctcttgca gatctagtca gagcattgta catagtgatg gaaacaccta tttagaatgg   120
tacctgcgga aaccaggcca gtctccaaga ctcctgatct acaaagtttc caaccgattt   180
tctggggtcc cagacaggtt cagtggcagt ggatcaggga cagatttcac actcaagatc   240
agcagagtgg aggctgagga tctgggagtt tattactgct ttcaaggttc acatgctccg   300
tggacgttcg gtggaggcac caagctggaa atcaaac                            337

<210> SEQ ID NO 125
<211> LENGTH: 360
<212> TYPE: DNA
<213> ORGANISM: Mus sp.

<400> SEQUENCE: 125
gatgtgcagc tggtggagtc tgggggaggc ttagtgcagc ctggagggtc ccggaaactc    60
tcctgtgcag cctctggatt cactttcagt agctacggaa tgcactgggt tcgtcaggct   120
ccagagacgg ggctggagtg ggtcgcatac attactactc gcagtagtac catctactat   180
gcagccacag tgaagggccg attcaccatc tccagagaca atgccaggaa caccctgttc   240
ctgcaaatga ccagtctaag gtctgaggac acggccatgt attactgtac tagagaaccc   300
ctaactggat actatgctat ggactactgg ggtcaaggaa cctcagtcac cgtctcctca   360

<210> SEQ ID NO 126
<211> LENGTH: 341
<212> TYPE: DNA
<213> ORGANISM: Mus sp.

<400> SEQUENCE: 126
gacattgtga tgtcgcagtc tccctcctcc ctaactgtgt cagttggaga aaggttact    60 atgagctgca agtccagtca gagcctttta tatagtagca atcaaaagaa ctacttggcc   120
tggtaccagc agaaaccagg gcagtctcct aaactgctga tttactgggc atccactagg   180
gaatctgggg tccctgatcg cttcacaggc agtggatctg ggacagattt ctctctcacc   240
atcagcagtg tgctgctga agacctggca gtttatttct gtcatcaata ttatagctct   300
ccgtacacgt tcggagggg gaccaagctg gaaataaaac g                        341

<210> SEQ ID NO 127
<211> LENGTH: 369
<212> TYPE: DNA
<213> ORGANISM: Mus sp.
```

<400> SEQUENCE: 127

```
caggtgcagc tgaaggagtc aggacctggc ctggtggcac cctcacagag cctgtccatc      60
acatgcactg tctctgggtt ctcattatcc agatatagtg tacactgggt tcgccagcct     120
ccaggaaagg gtctggagtg gctgggaatg atatggggtg tggaagtat  agactataat     180
tcaggtctca aatccagact gagcatcagt aaggacaact ccaagagcca agttttctta     240
aaaatgaaca gtctgcaatc tgatgacact gccatgtacc actgtgtcag agcccagttt     300
tactatggtt acgacggggg atacgctatg gactactggg gtcaaggaac ctcagtcacc     360
gtctcctca                                                             369
```

<210> SEQ ID NO 128
<211> LENGTH: 325
<212> TYPE: DNA
<213> ORGANISM: Mus sp.

<400> SEQUENCE: 128

```
caaattgttc tcacccagtc tccagcaatc atgtctgcat ctcctgggga gagggtcacc      60
ttgacctgca gtgccagctc aagtgtaagt tccagcttct tgtactggta ccagcagaag     120
tcaggatcct ccccccaaact ctggatttat agcacatcca ccctggcttc tggagtccct     180
gctcgcttca gtggcagtgg gtctgggacc tcttactctc tcacaatcag cagcatggag     240
gctgaagatg ctgcctctta tttctgccat cagtggagta gttacccatg gacgttcggt     300
ggaggcacca agctggaaat caaac                                            325
```

<210> SEQ ID NO 129
<211> LENGTH: 354
<212> TYPE: DNA
<213> ORGANISM: Mus sp.

<400> SEQUENCE: 129

```
tctgatgtgc agcttcagga gtcgggacct ggcctggtga aaccttctca gtctctgtcc      60
ctcacctgca ctgtcactga ctactcaatt accagtgatt atgcctggaa ctggatccgg     120
cagtttccag gaaacaatct ggagtggatg ggcaacatag gctacagtgg tgacactagc     180
tacaaccctt ctctcaaaag tcgaatctct atcactcgag acacatccaa gaaccagttc     240
ttcctgcagt tgaattctgt gactactgag gactcagcca catattactg tgcaagaagt     300
agtctggggc cctttgacta ctggggccaa ggcaccgctc tcacagtctc ctca           354
```

<210> SEQ ID NO 130
<211> LENGTH: 341
<212> TYPE: DNA
<213> ORGANISM: Mus sp.

<400> SEQUENCE: 130

```
gacattgtga tgacacagtc tccatcctcc ctggctatgt cagtaggaca gaaggtcact      60
atgagctgca gtccagtca  gagcctttta aatagtagca ctcaaaagaa ctatttggcc     120
tggtaccagc agaaaccagg acagtctcct aaacttctga tatactttgc atccactagg     180
ggatctgggg tccctgatcg cttcataggc agtggatctg gacagattt  cactcttacc     240
atcagcagtg tgcagactga agacctggca gattacttct gtcaacaaca ttatagcatt     300
ccgtgcacgt tcggaggggg gaccaagctg gaaataaaac g                         341
```

<210> SEQ ID NO 131

```
<211> LENGTH: 354
<212> TYPE: DNA
<213> ORGANISM: Mus sp.

<400> SEQUENCE: 131
caggttcagc tgcagcagtc tgggaatgag ctggtgaggc ctgggtccgc agtgaagatt      60
tcctgcaagg cgtctggcta tgcattcagt agttactgga tgaactgggt gaagcagagg     120
cctggacagg gtcttgagtg gattggacag atttatcctg agatgatga ttctaactac      180 aatggaaaat tcaagggtaa agccacactg actgcagaca atcctccag ctcagcctac      240 atgcacctca gcagcctaac atctgaggac tctgcggtct atttctgtgc cagagggttt     300
gctacaccta ccatggacta ctggggtcaa ggaacctcag tcaccgtctc ctca           354

<210> SEQ ID NO 132
<211> LENGTH: 310
<212> TYPE: DNA
<213> ORGANISM: Mus sp.

<400> SEQUENCE: 132
gacatccaga tgaaccagtc tccatccagt ctgtctgcat cccttggaga cacaattacc      60
atcacttgcc atgtcagtca gaacattaat gtttggttaa cctggtacca gcagaaacca     120
ggaaatattc ctaagctatt gctctataag gcttccaact gcagacagg cgtcccatca      180 aggtttagtg gcagtggatc tggaacaggt ttcacattaa ccatcagcag cctgcagcct     240
gaagacattg ccacttacta ctgtcaacag ggtcaaagtt atccattcac gttcggctcg     300
gggacaaagt                                                           310

<210> SEQ ID NO 133
<211> LENGTH: 357
<212> TYPE: DNA
<213> ORGANISM: Mus sp.

<400> SEQUENCE: 133
caggttcagc tgcagcagtc tggagctgag ttgatgaaga ctggggcctc agtaaagata      60
tcctgcaagg ctactggcta cacattcagt agctactgga tagagtgggt aaagcagagg     120
cctggacatg gccttgagtg gattggagag attttacctg gaagtggaaa aactaattat     180
aatgagaact ttaagggcaa ggccacattc actgcagata catcctccaa cacagcctac     240
atgcaactca gcagcctgac atctgaggac tctgtcgtct attactgtgc aagaagggg     300 gcctactatg gtaactttga ctactggggc caaggcacca ctctcacagt ctcctca       357

<210> SEQ ID NO 134
<211> LENGTH: 333
<212> TYPE: DNA
<213> ORGANISM: Mus sp.

<400> SEQUENCE: 134
gacattgtga tgtcacagtc tccatcctcc ctagctgtgt cagttggaga aaggttact       60 atgagctgca agtccagtca gagcctttta tatagtaaca atcaaaagaa ttacttggcc     120
tggtaccagc agaaaccagg gcagtcgcct aaactgctga tttactgggc atccagtagg     180
gaatctgggg tccctgagcg cttcacaggc agtggatctg gacagattt cactctcacc      240 atcagcagtg tgaaggctga agacctggca gtttattact gtcagcaata ttatagctct     300
ccgtacacgt tcggagggg gaccaagctg aaa                                  333
```

```
<210> SEQ ID NO 135
<211> LENGTH: 369
<212> TYPE: DNA
<213> ORGANISM: Mus sp.

<400> SEQUENCE: 135
caggtgcagc tgaaggagtc aggacctggc ctggtggcac cctcacagag cctgtccatc      60
acatgcactg tcactgggtt ctcattatcc agatatagtg tacactggat tcgccagcct     120
ccaggaaagg gtctggagtg gctgggaatg atatggggtg tggaagcac agactataat      180 tcagctctca aatccagact gagtatcaac aaggacaact ccaagagcca gttttcttta     240
aaaatgaaca gtctgcaaac tgttgacaca gccatgtact actgtgccag aacccagttc     300
tactatggtc acgacggggg gtacgctatg gactactggg gtcaaggaac ctcagtcacc     360
gtctcctca                                                              369

<210> SEQ ID NO 136
<211> LENGTH: 323
<212> TYPE: DNA
<213> ORGANISM: Mus sp.

<400> SEQUENCE: 136
gacattgtga tgacccagtc tcaaaaattc atgtccacat cagtaggaga cagggtcagc      60
gtcacctgca aggccagtca gaatgtgggct attaatgtag cctggtatca acagaaacca    120
ggccaatctc ctaaagctct gatttactcg gcatcctacc ggtacagtgt agtccctgat     180
cgcttcacag gcagtggatc tgggacagat ttcactctcc ccatcagcaa tgtgcagtct    240
gaaggcttgg cagattattt ctgtctacaa tatatcaact atccgtacac gttcggaggg     300
gggaccaagc tggaaataaa acg                                              323

<210> SEQ ID NO 137
<211> LENGTH: 348
<212> TYPE: DNA
<213> ORGANISM: Mus sp.

<400> SEQUENCE: 137
gaggtccagc ttcagcagtc aggacctgag ctgctgaaac tggggcctc agtgaagata       60 tcctgcaagg cttctggata cacattcact gactacaaca tgcactgggt gaagcagagc    120
catggaaaga gccttgagtg gattggaaat atttatcctt acaatggtgg tactggctac     180
aatcagaagt tcaagaccaa ggccacattg actgtagaca attcctccag cacagcctac    240
atggagctcc gcagcctgac atctgaggac tctgcagtct attactgtgc aattggtaac    300
tactggtttg ctttctgggg ccaagggact ctggtcactg tctctgca                  348

<210> SEQ ID NO 138
<211> LENGTH: 320
<212> TYPE: DNA
<213> ORGANISM: Mus sp.

<400> SEQUENCE: 138
caaattgttc tctcccagtc tccagcaatc ctgtctgcat ctccagggga gaaggtcaca      60
atgacttgca gggccagctc aagtgttagt tacattcact ggtaccagca gaaggcagga    120
tcctccccca catcctggat ttatgccaca tccaacctgg cttctggagt ccctactcgc    180
ttcagtggca gtgggtctgg gacctcttac tctctcacag tcaacagagt ggaggctgaa    240
gatgctgcca cttattactg ccagcagtgg agtactaccc cacccacgtt cggagggggg    300
```
accaggctgg aaataaaacg    320

<210> SEQ ID NO 139
<211> LENGTH: 360
<212> TYPE: DNA
<213> ORGANISM: Mus sp.

<400> SEQUENCE: 139
gaggtccagc tgcagcagtc tggacctgac ctggtgaagc ctgggacttc agtgaagata    60
tcctgcaagg cttctggtta ctccttcact gcctgctaca tacactgggt gaagcagagc    120
catggaaaga gccttgagtg gattggacgt tttagtccta acaatgatag aactacctac    180
aaccagaagt tcaaggacaa ggccatatta actgtagaca agtcatccag tacagcctac    240
atggacctcc gcagtctgac atctgaggac tctgcggtct attactgtgc aagaggggaa    300
gaaagctggg acgcctggtt tacttactgg ggccaaggga ctctggtcac tgtctctgca    360

<210> SEQ ID NO 140
<211> LENGTH: 327
<212> TYPE: DNA
<213> ORGANISM: Mus sp.

<400> SEQUENCE: 140
gacattgtga tgacacagtc tccatcctcc ctgactgtga cagcaggaga gaaggtcact    60
atgagttgca gtccagtca gagtctgtta aagagtggaa tcaaaagaa ctacttgacc    120
tggtaccagc agaaacctgg gcagcctcct aaactgttga tctactgggc atccactagg    180
gaatctgggg tccctgatcg cttcacaggc agtggatttg gaacagattt cactctcacc    240
atcagcagtg tgcaggctga agacctggca gtttattact gtcagagtga ttataattat    300
cctacgttcg gctcggggac aaagttg    327

<210> SEQ ID NO 141
<211> LENGTH: 357
<212> TYPE: DNA
<213> ORGANISM: Mus sp.

<400> SEQUENCE: 141
caggttactc tgaaagagtc tggccctggg atattgcagc cctcccagac cctcagtctg    60
acttgttctt tctctgggtt ttcactgagc acttctggta tgggtgtagg ctggattcgt    120
cagccttcag ggaagggtct ggagtggctg gcacacattt ggtgggatga tgtcaagcgc    180
tataacccag ccctgaagag ccgactgact atctccaagg atacctccag cagccaggta    240
ttcctcaaga tcgccagtgt ggacactgca gatactgcca catatcactg tgctcgaata    300
gcaatcgggc aaccgtttgc ttactggggc caagggactc tggtcactgt ctctgca    357

<210> SEQ ID NO 142
<211> LENGTH: 320
<212> TYPE: DNA
<213> ORGANISM: Mus sp.

<400> SEQUENCE: 142
caaattgttc tcacccagtc tccagcaatc atgtctgcat ctccagggga gaaggtcacc    60
ataacctgca gtgccagctc aagtgtgagt tacatgcact ggttccagca gaagccaggc    120
acttctccca aactctggat ttatagcaca tccaacctgg cttctggagt ccctgctcgc    180
ttcagtggca gtggatctgg gacctcttac tctctcacaa tcagccgaat ggaggctgaa    240
gatgctgcca cttattactg ccagcaaagg agtacttacc cgtacacgtt cggaggggg    300

```
accaagctgg aaataaaacg                                                    320
```

<210> SEQ ID NO 143
<211> LENGTH: 360
<212> TYPE: DNA
<213> ORGANISM: Mus sp.

<400> SEQUENCE: 143

```
caggtccaac tacaacagcc tggggctgag cttgtgaagc ctggggcttc agtgaagctg         60
tcctgcagga cttctggcta ctccttcacc agctactgga tacactgggt gaagcagagg        120
cctggacgag gccttgagtg gattggaagg attgttccta atagtggtgg tactaagtac        180
aatgagaact tcaagaacaa ggccacactg actgtagaca atcctccaa cacagcctac         240 atgcagctca gcagtctgac atctgaggac tctgcggtct attactgtac acgagaggat        300
tcctacggcc cgtttgattt ggactactgg ggtcaaggaa cctcagtcac cgtctcctca        360
```

<210> SEQ ID NO 144
<211> LENGTH: 320
<212> TYPE: DNA
<213> ORGANISM: Mus sp.

<400> SEQUENCE: 144

```
caaattgttc tctcccagtc tccagcaatc ctgtctgcct ctccagggga gaaggtcaca         60
atgacttgca gggccagctc aagtgtaagt tacatgcact ggtaccagca gaagccagga        120
tcctccccca aaccctggat ttatgccgca tccaacctgg cttctggagt ccctgctcgc        180
ttcagtgcca ctgggtctgg gacctcttac tctctcacaa tcagcagagt ggaggctgaa        240
gatgctgcca cttattgctg ccagcagtgg agtaataacc caccaacgtt cggcgggggg        300
accaagctgg aaataaaacg                                                    320
```

<210> SEQ ID NO 145
<211> LENGTH: 363
<212> TYPE: DNA
<213> ORGANISM: Mus sp.

<400> SEQUENCE: 145

```
gaggttcagc tgcagcagtc tggacctgaa ctggtgaagc ctggggcttc agtgaagata         60
tcctgcaagg cttctggtta ctcatttact gggtacttta tgaactgggt gaagcagagc        120
catggaaaga gccttgagtg gattggacgt attaatcctt acaatggtga taatttctac        180
aaccagaagt tcaagggcaa ggccacattg actgtagaca atcctctag cacagcccac         240 atggagctcc tgagcctgac atctgaggac tctgcagtct attattgtgg aagggactac        300
ggtagtagct acggatggtt cttcgatgtc tggggcgcag ggaccacggt caccgtctcc        360
tca                                                                      363
```

<210> SEQ ID NO 146
<211> LENGTH: 334
<212> TYPE: DNA
<213> ORGANISM: Mus sp.

<400> SEQUENCE: 146

```
gacattgtac tcacccaatc tccagcttct ttggctgtgt ctctagggca gagagccacc         60
atctcctgca gagccaatga aagtgttgaa tattatggca caagtttaat gcagtggtac        120
caacagaaac caggacagcc acccaaactc ctcatctatg ctgcatccag cgtaaagtct        180
```

```
ggggtccctg ccaggtttag tggcagtggg tctgggacag acttcagcct caatatccat    240
cctgtggagg aggatgatat tgcaatgtat ttctgtcagc aaagtaggaa ggttccttcg    300
acgttcggtg gaggcaccaa gctggaaatc aaac                                334
```

<210> SEQ ID NO 147
<211> LENGTH: 369
<212> TYPE: DNA
<213> ORGANISM: Mus sp.

<400> SEQUENCE: 147

```
gaggtccagc tgcaacagtc tggacccgag ctggtgaagc ctggagcttc aatgaagata     60
tcctgcaagg cttctggtta tacattcact gaccacacca tgcactgggt gaagcagagc    120
catggaaaga accttgagtg gattggacgt attaatcctt acaatggtga tactagtcac    180
aaccagaact tcaagggcaa ggccacatta actgtagaca agtcatccaa cacagcctac    240
atggagctcc tcagtctgac atctgaggac tctgcagtct attactgtgc aagatatggt    300
ggtgattata cgtcttctta ctatactatg gactactggg gtcaaggaac ctcctccacc    360
gtctcctca                                                           369
```

<210> SEQ ID NO 148
<211> LENGTH: 334
<212> TYPE: DNA
<213> ORGANISM: Mus sp.

<400> SEQUENCE: 148

```
gacattgttc tcacccaatc tccagcttct ttggctgtgt ctctagggca gagagccacc     60
atctcctgca gagcccatga agtgttgaa tattatggca caagtttaat gcagtggtac    120
caacagaaac caggacagcc acccaaactc ctcatctatg ctgcatccag cgtaaagtct    180
ggggtccctg ccaggtttag tggcagtggg tctgggacag acttcagcct caatatccat    240
cctgtggagg aggatgatat tgcaatgtat ttctgtcagc aaagtaggaa ggttccttcg    300
acgttcggtg gaggcaccaa gctggaaatc aaac                                334
```

<210> SEQ ID NO 149
<211> LENGTH: 369
<212> TYPE: DNA
<213> ORGANISM: Mus sp.

<400> SEQUENCE: 149

```
gaggtccagc tgcaacagtc tggacccgag ctggtgaagc ctggagcttc aatgaagata     60
tcctgcaagg cttctggtta tactttcact gactacacca tgcactgggt gaggcagagc    120
catggaaaga accttgagtg gattggacgt attaatcctt acaatgctga tactagtcac    180
aaccagaact tcaagggcag gccacatta actgtagaca agtcattcaa cacagcctac    240
atggagctcc tcagtctgac atctgaggac tctgcagtct attactgtgc aagatatggt    300
ggtgatttta cgtcttctta ctatactatg gactactggg gtcaaggaac ctcagtcacc    360
gtctcctca                                                           369
```

<210> SEQ ID NO 150
<211> LENGTH: 341
<212> TYPE: DNA
<213> ORGANISM: Mus sp.

<400> SEQUENCE: 150

```
gacattgtga tgacccagtc tccatcctcc ctagctgtgt cagttggaga aaggttact     60
```

```
atgagctgca agtccagtca gagccttta tatagtagca atcaaaagaa ctacttggcc    120
tggtaccagc agaaaccagg gcagtctcct aaactgctga tttactgggc atccactagg    180
gaatctgggg tccctgatcg cttcacaggc agtggatctg ggacagattt cactctcacc    240
atcagcagtg tgaaggctga agacctggca gtttattact gtcagcaata ttataactat    300
ccctacacgt tcggagggg gaccaagctg gaaataaaac g                         341

<210> SEQ ID NO 151
<211> LENGTH: 354
<212> TYPE: DNA
<213> ORGANISM: Mus sp.

<400> SEQUENCE: 151
caggtgcagc tgaaggagtc aggacctggc ctggtggcgc cctcacagag cctgtccatc    60
acatgcactg tctctggttt ctcattaacc agctatacta aagctgggt cgccagcca     120 ccaggaaagg gtctggagtg gcttggaata atatggactg ctggagccac aaattataat    180
tcagctctca atccagact gagcatcagc aaagacaact ccaagagtca gttttctta    240 aaaatgaaca gtctgcaaac tgatgacaca gccaggtact actgtgccag atatagtaag    300
gattactatg ctgtggacta ctggggtcaa ggaacctcag tcaccgtctc ctca         354

<210> SEQ ID NO 152
<211> LENGTH: 327
<212> TYPE: DNA
<213> ORGANISM: Mus sp.

<400> SEQUENCE: 152
gacattgtac tcacccaatc tccagcttct ttggctgtgt ctctaggaca gagagccacc    60
atctcctgca gagccaatga aaatgttgaa tattatggca caagtttaat gcagtggtac    120
caacagaaac caggacagcc acccaaactc ctcatctatg ctgcatccaa cgtaaagtct    180
ggggtccctg ccaggtttag tggcagtggg tctgggacag acttcagcct caatatccat    240
cctgtggagg aggatgatat tgcaatgtat ttctgtcagc aaagtaggaa ggttccttcg    300
acgttcggtg gaggcaccaa gctgaaa                                        327

<210> SEQ ID NO 153
<211> LENGTH: 369
<212> TYPE: DNA
<213> ORGANISM: Mus sp.

<400> SEQUENCE: 153
gaggtccagc tgcaacagtc tggacccgag ctggtgaagc ctggagcttc aatgaagata    60
tcctgcaagg cttctggtta tacattcact gactacacca tgcactgggt gaagcagagc    120
catggaaaga accttgagtg gattggacgt attaatcctt acaatgatga tattagtcac    180
aaccagaact tcaaggacaa ggccacatta actgtagaca gtcatccaa cacagcctac    240 atggagctcc tcagtctgac atctgaggac tctgcagtct attactgtgc aagatatggt    300
ggtgattata cgtcttctta ctatactatg gactactggg gtcaaggaac ctcagtcacc    360
gtctcctca                                                            369

<210> SEQ ID NO 154
<211> LENGTH: 341
<212> TYPE: DNA
<213> ORGANISM: Mus sp.
```

<400> SEQUENCE: 154

```
gacattgtga tgtcacagtc tccatcctcc ctagctgtgt cagttggaga gaaggttact    60
atgagctgca agtccagtca gagccttttta tatagtagca atcaaaagaa ctacttggcc   120
tggtaccagc agaaaccagg gcagtctcct aaactgctga tttactgggc atccactagg   180
gaatctgggg tccctgatcg cttcacaggc agtggatctg gacagatttt cactctcacc   240
atcagcactg tgaaggctga agacctggca gtttattact gtcaccaata ttatagctat   300
ccgtacacgt tcggaggggg gaccaagctg gaaataaaac g                       341
```

<210> SEQ ID NO 155
<211> LENGTH: 369
<212> TYPE: DNA
<213> ORGANISM: Mus sp.

<400> SEQUENCE: 155

```
caggtgcagc tgaaggagtc aggacctggc ctggtggcac cctcacagag cctgtccatc    60
acatgcactg tctctgggtt ctcattatcc agatatagtg tacactgggt tcgccagcct   120
tcaggaaagg gtctggagtg gctgggaatg atatggggtg gtggaagcac agactataat   180
tcagctctca aatccagact gatcatcagc aaggacaact ccaagagcca gttttcttta   240
aaaatgaaca gtctgcaaac tgatgacaca gccatgtact actgtgccag aacccagttc   300
tactatggtc acgacggggg gtatgctatg gactactggg gtcaaggaac ctcagtcacc   360
gtctcctca                                                            369
```

<210> SEQ ID NO 156
<211> LENGTH: 334
<212> TYPE: DNA
<213> ORGANISM: Mus sp.

<400> SEQUENCE: 156

```
gacattgtgc tgacacagtc tcctggttcc ttagctgtat ctctggggca gagggccacc    60
atctcatgca gggccagcca agtgtcagt tcatctagct atagttatat gcactggtac   120
caacagaaac caggacagcc acccaaactc ctcatcaagt ttgcatccaa cctagaatct   180
ggggtccctg ccaggttcag tggcagtggg tctgggacag acttcaccct caacatccat   240
cctgtggagg aggaggatac tgcaacatat tactgtcagc acagttggga gattccgctc   300
acattcggtg ctgggaccaa gctggagctg aaac                                334
```

<210> SEQ ID NO 157
<211> LENGTH: 357
<212> TYPE: DNA
<213> ORGANISM: Mus sp.

<400> SEQUENCE: 157

```
caggttactc tgaaagagtc tggccctggg atattgcagc cctcccagac cctcagtctg    60
acttgttctt tctctgggtt ttcactgagt acttctggta tgggtgtagg ctggattcgc   120
cagccatcag gaaagggtct ggagtggctg gcacacattt ggtgggatga tgtcaagcgc   180
tataatccag ccctgaagag ccgactgaat atctccaagg acacctccag cagccaggtc   240
ttcctcaaga tcgccagtgt ggacactgca gatactgcca catactactg tggtcgaaaa   300
agtaactcag gctactttga ctactggggc caaggcacca ctctcacagt ctcctca      357
```

<210> SEQ ID NO 158
<211> LENGTH: 323

<212> TYPE: DNA
<213> ORGANISM: Mus sp.

<400> SEQUENCE: 158

| | | | | | |
|---|---|---|---|---|---|
| gatgtccaga | taacccagtc | tccatcttat | cttgctgcat | ctcctggaga | aaccatttct | 60 |
| attaattgca | gggcaagtaa | gaacattagc | aaatatttag | cctggtatca | agagaaacct | 120 |
| gggaaaacta | ataagcttct | tatctactct | ggatccactt | tgcaatctgg | aattccatca | 180 |
| gggttcagtg | gcagtggatc | tggtacagat | ttcactctca | ccatcagtag | cctgagcct | 240 |
| gaagattttg | caatgtatta | ctgtcaacag | catttgaat | acccgtacac | gttcggaggg | 300 |
| gggaccaagc | tggaaataaa | acg | | | 323 |

<210> SEQ ID NO 159
<211> LENGTH: 348
<212> TYPE: DNA
<213> ORGANISM: Mus sp.

<400> SEQUENCE: 159

| | | | | | |
|---|---|---|---|---|---|
| gaggttcagc | tgcagcagtc | tggacctgac | ctggtgaagc | ctggggcttc | agtgaagata | 60 |
| tcctgcaagg | cttctggtta | ctcatttact | ggctacttta | tgaactgggt | gaagcagagc | 120 |
| catggaaaga | gccttgagtg | gattggacgt | attaatcctt | acaatggtga | tactttctac | 180 |
| aaccagaaat | tcaagggcaa | ggccacattg | actgtagaca | aatcctctag | cacagcccac | 240 |
| atggagctcc | tgagcctgac | atctgaagac | tctgcagtct | attattgtgg | aagagggaat | 300 |
| tactactttg | actactgggg | ccaaggcacc | actctcacag | tctcctca | 348 |

<210> SEQ ID NO 160
<211> LENGTH: 317
<212> TYPE: DNA
<213> ORGANISM: Mus sp.

<400> SEQUENCE: 160

| | | | | | |
|---|---|---|---|---|---|
| caaattgttc | tcacccagtc | tccagcaatc | atgtctgcat | ctctggggga | ggagatcacc | 60 |
| ctaacctgca | gtgccacctc | gagtgttggt | tacattcact | ggtaccagca | gacgtcaggc | 120 |
| acttctccca | gactcttgat | ttataccaca | tccaacctgg | cttctggagt | cccttctcgc | 180 |
| ttcagtggca | gtgggtctgg | gacctttat | tctctcacaa | tcagcagtgt | cgaggctgaa | 240 |
| gatgctgccg | attattactg | ccatcagtgg | agtcgttatc | ccacgttcgg | aggggggacc | 300 |
| aagctggaaa | taaaacg | | | | 317 |

<210> SEQ ID NO 161
<211> LENGTH: 342
<212> TYPE: DNA
<213> ORGANISM: Mus sp.

<400> SEQUENCE: 161

| | | | | | |
|---|---|---|---|---|---|
| gaggtgcagc | tggagcagtc | aggggagac | ttagtgaagc | ctggagggtc | cctgaaactc | 60 |
| tcctgtgcag | cctctggatt | cactttcagt | tcctatggca | tgtcttgggt | tcgccagact | 120 |
| ccagacaaga | ggctggagtg | ggtcgcaacc | attagtagtg | gtggttctta | cagctactat | 180 |
| ccagacagtg | tgaaggggcg | attcaccatc | tccagagaca | atgccaagaa | cacctgtac | 240 |
| ctgcaaatga | gcagtctgaa | gtctgaggac | acagccatgt | atttctgtag | gccctccttc | 300 |
| tttccttcct | ggggccaagg | gactctggtc | actgtctctg | ca | 342 |

<210> SEQ ID NO 162

```
<211> LENGTH: 322
<212> TYPE: DNA
<213> ORGANISM: Mus sp.

<400> SEQUENCE: 162
gacatcaaga tgacccagtc tccatcttcc acgtatgcat ctctaggaga gagagtcact      60
atcacttgca aggcgagtca ggacattaat acctatttat actggttcca acagaaacca     120
gggaaacctc ctaagaccct gatctatcgt gcaaacagat tgatagatgg ggtcccatca     180
aggttcagtg gcagtggatc tgggcaagat tattctctca ccatcagcag cctggagtat     240
gaagatttgg gaatttatta ttgtctacag tatgatgagt ttccgtatac gttcggtgga     300
ggcaccaagc tggaaatcaa ac                                              322

<210> SEQ ID NO 163
<211> LENGTH: 327
<212> TYPE: DNA
<213> ORGANISM: Mus sp.

<400> SEQUENCE: 163
gaggttcagc tgcagcagtc tggggctgag cttgtgaggc caggggcctc agtcaagttg      60
tcctgcacag cttctggctt taacattaat gacgactatt tcactgggt gaagcagagg      120 cctgaacagg gcctggagtg gattggaagg attgatcctg cgaatggtaa tactaaatat     180
ggcccgaagt tccaggacaa ggccactata actgcagaca catcatccaa cacagcctac     240
ctgcagttca ccagcctgac atctgaggac actgccgtct attactgtgc tagcggatgg     300
gcgtttgctt gctggggcca aggact                                         327

<210> SEQ ID NO 164
<211> LENGTH: 334
<212> TYPE: DNA
<213> ORGANISM: Mus sp.

<400> SEQUENCE: 164
gacattgtac tcacccaatc tccagcttct ttggctgtgt ctctagggca gagagccacc      60
atctcctgca gagccgatga aagtgttgaa tattatggca aagtttaat gcagtggtac      120 caacagaaac caggacagcc acccaaactc ctcatctatg ctgcatccaa cgtaaagtct     180
ggggtccctg ccaggtttag tggcagtggg tctgggacag acttcagcct caatatccat     240
cctgtggagg aggatgatat tgcaatttat ttctgtcagc aaagtaggga ggttccttcg     300
acgttcggtg gaggcaccaa gctggaaatc aaac                                334

<210> SEQ ID NO 165
<211> LENGTH: 369
<212> TYPE: DNA
<213> ORGANISM: Mus sp.

<400> SEQUENCE: 165
gaggtccagc tgcaacagtc tggacccgag ctggtgaagc ctggaacttc aatgaagata      60
tcctgcaagg cttctggtta tacattcact gactacacca tgcactgggt gaagcagagc     120
catggaaaga accttgagtg gattggacgt attaatcctt acactggttc tactagtcac     180
aaccagaact tcaaggacaa ggcctcatta actgtagaca gtcatccaa cacagcctac      240 atggacctcc tcagtctgac atctgaggac tctgcagtct attactgtgc aagatttggt     300
ggtgattata cgtcttctta ctatactttg gactactggg gtcaaggaac ctcagtcagc     360
gtctcctca                                                            369
```

<210> SEQ ID NO 166
<211> LENGTH: 337
<212> TYPE: DNA
<213> ORGANISM: Mus sp.

<400> SEQUENCE: 166

```
gatattgtga tgacgcaggc tgcattctcc aatccagtca ctcttggaac atcagcttcc      60
atctcctgca ggtctagtaa gagtctccta catagtaatg catcactta tttgtattgg     120
tatctgcaga agccaggcca gtctcctcag ctcctgattt atcagatgtc caaccttgcc    180
tcaggagtcc cagacaggtt cagtaacagt gggtcaggaa ctgatttcac actgagaatc    240
agcagagtgg aggctgagga tgtgggtgtt tattactgtg ctcaaaatct agaacttccg    300
tggacgttcg gtggaggcac caagctggaa atcaaac                             337
```

<210> SEQ ID NO 167
<211> LENGTH: 351
<212> TYPE: DNA
<213> ORGANISM: Mus sp.

<400> SEQUENCE: 167

```
gaggtccagc tgcaacagtc tggacctgag ctggtgaagc ctggggattc agtgaagatg      60
tcctgcaagg cttctggcaa cacagtcact aactactaca tggactgggt gaaacagagc     120
catggaaaga gccttgagtg gattggatat atttatgcta caatggtgg aactagctat     180
aatcagaagt tcaagggcaa ggctacattg actgtagaca gtcctccag cacagcctac     240
atggagatcc acagcctgac atctgaggac tctgcagtct attactgtgc aatctactat    300
aggtacgagt ttgcttactg gggccaaggg actctggtca ctgtctctgc a              351
```

<210> SEQ ID NO 168
<211> LENGTH: 323
<212> TYPE: DNA
<213> ORGANISM: Mus sp.

<400> SEQUENCE: 168

```
gacattgtga tgacccagtc tcacaaactc atgtccgcat cagtaggaga cagggtcagc      60
atcacctgca aggccagtca ggatgtgggt actgctgtag cctggtatca acagaaacca     120
gggcgatctc ctaaaactact gatttactgg gcatccaacc ggcacactgg agtccctgat    180
cgcttcacag gcagtggatc tgggacagat ttcactctca ccattagcaa tgtgcagtct    240
gaagacttgg cagattattt ctgtcagcag tttggcagct atccgtacac gttcggaggg    300
gggaccaagc tggaaataaa acg                                             323
```

<210> SEQ ID NO 169
<211> LENGTH: 363
<212> TYPE: DNA
<213> ORGANISM: Mus sp.

<400> SEQUENCE: 169

```
tctgatgtgc agcttcagga gtcaggacct ggcctggtga accttctca gtctctgtcc      60
gtcacctgca ctgtcactga ctactccctc accagtggtt attactggaa ctggatccgg    120
cagtttccag gaaacaaact ggagtggatg cctacatac acagcagtgg tagcactcac    180
tacaacccat ctctcaaaag tcgaatctct gtcactcgag acacatccaa gaaccagttc    240
ttcctgcagt tgaattctgt gactactgag gacacagcca catattactg tgcaagagat    300
```

```
ggggcctact atagttcctg gtttccttac tggggccaag ggactctggt cactgtctct      360
gca                                                                    363

<210> SEQ ID NO 170
<211> LENGTH: 334
<212> TYPE: DNA
<213> ORGANISM: Mus sp.

<400> SEQUENCE: 170
gatattgtgc tgacacagtc tccactctcc ctgcttgtca gtcttggaga tcaagcctcc       60
atctcttgca gatctagtca gagccttgta cacagtaatg aaacaccta tttacattgg      120 tatctgcaga agccaggcca gtctccaaac ctcctgatct caaagtttc caaccgattt      180 tctggggtcc cagacaggtt cagtggcagt ggatcaggga cagatttcac actcaggatc      240
agcagagtgg aggctgagga tctgggagtt tatttctgct ctcaaactac acatgtgtgg      300
acgttcggtg gaggcaccaa gctggaaatc aaac                                  334

<210> SEQ ID NO 171
<211> LENGTH: 339
<212> TYPE: DNA
<213> ORGANISM: Mus sp.

<400> SEQUENCE: 171
cagatcctgt tggtgcagtc tggacctgag ctgaagaagc ctggagagac agtcaagatc       60
tcctgcaagg cttctaatta taccttcaca gactatggaa tgcactgggt gaagcaggct      120
ccaggaaagg gtttaaagtg gatgggctgg ataaaccca agactggtgt ggcatcatat       180
gcagatgact tcaagggaag atttgccttc tctttggaaa cctctgccag cactgcctat      240
ttgcagatca caaacctcga aaatgaggac acgtctatat atttctgtgc tagattttt      300 gactactggg gccaaggcac cactctcaca gtctcctca                             339

<210> SEQ ID NO 172
<211> LENGTH: 337
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 172
gatgttgtga tgactcagtc tccactctcc ctgcccgtca cccttggaca gccggcctcc       60
atctcctgca ggtctagtca aagcatcgta cacagtgatg aaacaccta cttggaatgg      120 tatcagcaga ggccaggcca atctccaagg cgcctaattt ataaggtttc taaccggttc      180
tctggggtcc cagacagatt cagcggcagt gggtcaggca ctgatttcac actgaaaatc      240
agcagggtgg aggctgagga tgttggggtt tattactgct ttcaaggttc acatgctccg      300
tggacgttcg gtggaggcac caaggtggaa atcaaac                               337

<210> SEQ ID NO 173
<211> LENGTH: 361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 173
gaggtgcagc tggtggagtc tgggggaggc ttggtacagc ctgggggtgtc cctgagactc       60
```

-continued

```
tcctgtgcag cctctggatt caccttcagt agctatggca tgcactgggt ccgccaggct    120
ccagggaagg ggctggagtg ggttgcatac attactacta gaagtagtac catatactac    180
gcagactctg tgaagggccg attcaccatc tccagagaca atgccaagaa ctcactgtat    240
ctgcaaatga acagcctgag agccgaggac acggctgtgt attactgtac tagagaaccc    300
ctaactggat actatgctat ggactactgg ggtcaaggaa cctcagtcac cgtctcctca    360
g                                                                   361
```

ANTI-CD324 MONOCLONAL ANTIBODIES AND USES THEREOF

CROSS REFERENCED APPLICATIONS

This application is a 371 national phase of International Application NO. PCT/U.S.2013/025356 filed on Feb. 8,2013, which is a continuation-in-part under 35 U.S.C. §120 of U.S. application Ser. No. 13/369,275 filed on Feb. 8, 2012 (now abandoned) which is incorporated herein by reference in its entirety.

FIELD OF THE INVENTION

This application generally relates to novel compounds, compositions and methods of their use in diagnosing, preventing, treating or ameliorating proliferative disorders and any expansion, recurrence, relapse or metastasis thereof. In a broad aspect, the present invention relates to the use of CD324 (i.e., E-cadherin, CDH1) modulators, including anti-CD324 antibodies and fusion constructs, for the treatment, diagnosis or prophylaxis of neoplastic disorders. Selected embodiments of the present invention provide for the use of such CD324 modulators, including antibody drug conjugates, for the immunotherapeutic treatment of malignancies preferably comprising a reduction in tumor initiating cell frequency. In particularly preferred embodiments the disclosed modulators will comprise bispecific or multispecific constructs comprising a CD324 binding site.

BACKGROUND OF THE INVENTION

Stem and progenitor cell differentiation and cell proliferation are normal ongoing processes that act in concert to support tissue growth during organogenesis and cell replacement and repair of most tissues during the lifetime of all living organisms. In the normal course of events cellular differentiation and proliferation is controlled by numerous factors and signals that are generally balanced to maintain cell fate decisions and tissue architecture. Thus, to a large extent is it this controlled microenvironment that regulates cell division and tissue maturation where signals are properly generated based on the needs of the organism. In this regard cell proliferation and differentiation normally occurs only as necessary for the replacement of damaged or dying cells or for growth. Unfortunately, disruption of cell proliferation and/or differentiation can result from a myriad of factors including, for example, the under- or overabundance of various signaling chemicals, the presence of altered microenvironments, genetic mutations or some combination thereof. When normal cellular proliferation and/or differentiation is disturbed or somehow disrupted it can lead to various diseases or disorders including proliferative disorders such as cancer.

Conventional treatments for cancer include chemotherapy, radiotherapy, surgery, immunotherapy (e.g., biological response modifiers, vaccines or targeted therapeutics) or combinations thereof. Unfortunately, certain cancers are non-responsive or minimally responsive to such treatments. For example, in some patients tumors exhibit gene mutations that render them non-responsive despite the general effectiveness of selected therapies. Moreover, depending on the type of cancer and what form it takes some available treatments, such as surgery, may not be viable alternatives. Limitations inherent in current standard of care therapeutics are particularly evident when attempting to treat patients who have undergone previous treatments and have subsequently relapsed. In such cases the failed therapeutic regimens and resulting patient deterioration may contribute to refractory tumors which often manifest themselves as a relatively aggressive disease that ultimately proves to be incurable. Although there have been great improvements in the diagnosis and treatment of cancer over the years, overall survival rates for many solid tumors have remained largely unchanged due to the failure of existing therapies to prevent relapse, tumor recurrence and metastases. Thus, it remains a challenge to develop more targeted and potent therapies for proliferative disorders.

SUMMARY OF THE INVENTION

These and other objectives are provided for by the present invention which, in a broad sense, is directed to methods, compounds, compositions and articles of manufacture that may be used in the treatment of CD324 associated disorders (e.g., proliferative disorders or neoplastic disorders). To that end, the present invention provides novel CD324 (i.e., E-cadherin or CDH1) modulators that effectively target tumor cells and/or cancer stem cells and may be used to treat patients suffering from a wide variety of malignancies. Compatible modulators may comprise any compound that recognizes, competes, agonizes, antagonizes, interacts, binds or associates with a CD324 genotypic or phenotypic determinant (or fragment thereof) and modulates, adjusts, alters, regulates, changes or modifies the impact of the CD324 protein on one or more physiological pathways and/or eliminates CD324 associated cells. Thus, in a broad sense the present invention is generally directed to isolated CD324 modulators and use thereof. In preferred embodiments the invention is more particularly directed to isolated CD324 modulators comprising antibodies (i.e., antibodies or multispecific antibodies that immunopreferentially bind, recognize, react with or associate with CD324 or an immunoreactive fragment thereof) that, in particularly preferred embodiments, are associated or conjugated to one or more cytotoxic agents. Moreover, as discussed extensively below, such modulators may be used to provide pharmaceutical compositions useful for the prophylaxis, diagnosis or treatment of proliferative disorders including cancer.

In selected embodiments of the invention, CD324 modulators may comprise a CD324 polypeptide or fragments thereof, either in an isolated form or fused or associated with other moieties (e.g., Fc-CD324, PEG-CD324 or CD324 associated with a targeting moiety). In other selected embodiments CD324 modulators may comprise CD324 antagonists which, for the purposes of the instant application, shall be held to mean any construct or compound that recognizes, competes, interacts, binds or associates with CD324 and neutralizes, eliminates, reduces, sensitizes, reprograms, inhibits or controls the growth of neoplastic cells including tumor initiating cells. In preferred embodiments the CD324 modulators of the instant invention comprise anti-CD324 antibodies (including bispecific or multispecific constructs), or fragments or derivatives thereof, that have unexpectedly been found to silence, neutralize, reduce, decrease, deplete, moderate, diminish, reprogram, eliminate, or otherwise inhibit the ability of tumor initiating cells to propagate, maintain, expand, proliferate or otherwise facilitate the survival, recurrence, regeneration and/or metastasis of neoplastic cells. In particularly preferred embodiments the antibodies or immunoreactive fragments may be associated with or conjugated to one or more anti-proliferative or anti-cancer agents (e.g., a cytotoxic agent).

With regard to such modulators it will be appreciated that compatible antibodies may take on any one of a number of forms including, for example, bispecific or multispecific antibodies, polyclonal or monoclonal antibodies, chimeric, CDR grafted, humanized or human antibodies and immunoreactive fragments and/or variants of each of the foregoing. In selected embodiments modulators compatible with the instant invention may comprise bispecific or multispecific constructs comprising a first binding site or component that recognizes, associates or binds to a first phenotypic determinant of CD324 (e.g., an epitope) and a second binding site or component that recognizes, associates or binds with a phenotypic component that is not the same as the first (i.e., a "second epitope"). In any event particularly [referred embodiments will comprise antibodies (including bispecific antibodies) that are relatively non-immunogenic such as humanized or fully human constructs.

Accordingly, in one aspect of the invention the modulators will comprise a multispecific or bispecific antibody comprising a first binding site recognizing a first epitope on CD324 and a second binding site recognizing a second epitope wherein said first and second epitopes are not equivalent. As will be discussed in more detail below, two epitopes that are "not equivalent" shall be held to mean any two epitopes that are immunologically distinct and where there is no competition between the binding sites of the multispecific constructs. With this in mind it will be appreciated that the second epitope may be an non-competing epitope on CD324 (i.e., the binding sites are in different CD324 bins) or an epitope presented by an antigen that is not CD324.

Of course, in view of the instant disclosure those skilled in the art could readily identify one or more complementarity determining regions (CDRs) associated with heavy and light chain variable regions of CD324 antibody modulators and use those CDRs to engineer or fabricate multispecific, chimeric, humanized or CDR grafted antibodies without undue experimentation. Accordingly, in certain preferred embodiments CD324 modulators comprise an antibody that incorporates one or more complementarity determining regions (CDRs) as defined in FIGS. 11A and 11B and derived from the light (FIG. 11A) or heavy (FIG. 11B) contiguous chain murine variable regions (SEQ ID NOS: 20-71) set forth therein. In preferred embodiments such antibodies will comprise monoclonal antibodies and, in even more preferred embodiments, will comprise bispecific, chimeric, CDR grafted or humanized antibodies.

Exemplary nucleic acid sequences encoding each of the amino acid sequences set forth in FIGS. 11A and 11B are shown in FIG. 19 and comprise SEQ ID NOS: 120 to 173. In this respect it will be appreciated that the invention further comprises nucleic acid molecules (and associated constructs, vectors and host cells) encoding disclosed antibody variable region amino acid sequences including those set forth in FIG. 19.

In selected embodiments compatible CD324 modulators may comprise an antibody having a light chain variable region and a heavy chain variable region wherein said light chain variable region comprises an amino acid sequence having at least 60% identity to an amino acid sequence selected from the group consisting of amino acid sequences as set forth in SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68 and SEQ ID NO: 70 and wherein said heavy chain variable region comprises an amino acid sequence having at least 60% identity to an amino acid sequence selected from the group consisting of amino acid sequences as set forth in SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69 and SEQ ID NO: 71. In this respect preferred embodiments will comprise humanized antibodies incorporating such heavy and light chain variable regions. In still other embodiments the modulators of the instant invention will comprise any antibody or immunoreactive fragment thereof that competes for binding with any of the foregoing modulators.

Other preferred embodiments will comprise a CD324 modulator selected or derived from the group consisting of SC10.6, SC10.15, SC10.17, SC10.19, SC10.35, SC10.36, SC10.38, SC10.75, SC10.111, SC10.112, SC10.115, SC10.118, SC10.123, SC10.124, SC10.125, SC10.126, SC10.127, SC10.128, SC10.129, SC10.130, SC10.132, SC10.133, SC10.134, SC10.163, SC10.168, and SC10.178.

Of course, in view of the instant disclosure those skilled in the art could readily identify CDRs associated with each of the aforementioned heavy and light chain variable regions and use those CDRs to engineer or fabricate chimeric, humanized or CDR grafted antibodies without undue experimentation. As such, in selected embodiments the present invention is directed to anti-CD324 antibodies comprising one or more CDRs from a variable region sequence set forth in FIG. 11A or FIG. 11B. In preferred embodiments such antibodies will comprise monoclonal antibodies and, in even more preferred embodiments will comprise bispecific, chimeric, CDR grafted or humanized antibodies. As discussed in more detail below still other embodiments will comprise such antibodies conjugated or associated with one or more cytotoxic agents.

Accordingly, in other embodiments the instant invention will comprise a humanized CD324 modulator termed hSC10.17. Still other embodiments are directed to a CD324 modulator comprising a humanized antibody wherein said humanized antibody comprises a light chain variable region and a heavy chain variable region wherein said light chain variable region comprises an amino acid sequence having at least 60% identity to the amino acid sequence set forth in SEQ ID NO: 72 and wherein said heavy chain variable region comprises an amino acid sequence having at least 60% identity to the amino acid sequence set forth in SEQ ID NO: 73.

Besides the aforementioned aspects, other preferred embodiments of the instant invention will comprise CD324 modulators associated or conjugated to one or more drugs to provide modulator conjugates that may be particularly effective in treating proliferative disorders (alone or in combination with other pharmaceutically active agents). More generally, once the modulators of the invention have been fabricated and selected they may be linked with, fused to, conjugated to (e.g., covalently or non-covalently) or otherwise associated with pharmaceutically active or diagnostic moieties or biocompatible modifiers. As used herein the term "conjugate" or "modulator conjugate" or "antibody conjugate" will be used broadly and held to mean any biologically active or detectable molecule or drug associated with the disclosed modulators regardless of the method of association. In this respect it will be understood that such conjugates may, in addition to the disclosed modulators, comprise peptides, polypeptides, proteins, prodrugs which are metabolized to an active agent in vivo, polymers, nucleic acid molecules, small molecules, binding agents, mimetic agents, synthetic drugs, inorganic molecules, organic molecules and radioisotopes. Moreover, as indicated above the selected conjugate may be covalently or non-covalently associated with, or linked to, the modulator and exhibit various stoichiometric molar ratios depending, at least in part, on the method used to effect the conjugation.

Particularly preferred aspects of the instant invention will comprise antibody modulator conjugates or antibody-drug conjugates that may be used for the diagnosis and/or treatment of proliferative disorders. Such conjugates may be represented by the formula M-[L-D]n where M stands for a disclosed modulator or target binding moiety, L is an optional linker or linker unit, D is a compatible drug or prodrug and n is an integer from about 1 to about 20. It will be appreciated that, unless otherwise dictated by context, the terms "antibody-drug conjugate" or "ADC" or the formula M-[L-D]n shall be held to encompass conjugates comprising both therapeutic and diagnostic moieties. In such embodiments antibody-drug conjugate compounds will typically comprise anti-CD324 as the modulator unit (M), a therapeutic or diagnostic moiety (D), and optionally a linker (L) that joins the drug and the antigen binding agent. In a preferred embodiment, the antibody is a CD324 mAb comprising at least one CDR from the heavy and light chain variable regions as described above.

As previously alluded to, certain embodiments of the invention are directed to CD324 modulators comprising bispecific or multispecific constructs (e.g., bispecific or multispecific antibodies). Consistent with these art-recognized terms, and as discussed in more detail below, bispecific constructs (i.e., bispecific antibodies) shall be held to comprise any compound or molecule that specifically associates or binds to two discrete immunogenic determinants or epitopes. Similarly, multispecific constructs shall be held to comprise any compound or molecule that specifically associates or binds to two or more discrete determinants. For the purposes of the instant disclosure the terms "multispecific construct" or multispecific antibody" shall be held to include bispecific constructs or bispecific antibodies unless otherwise dictated by contextual constraints. In particularly preferred embodiments the determinants recognized by the binding sites of a multispecific construct will comprise epitopes present on a phenotypic determinant (e.g., a glycoprotein). It will be appreciated that such epitopes may comprise proteins, carbohydrates lipids, etc. or some combination thereof. Moreover, the binding sites or components of the multispecific modulators may recognize epitopes on a single protein or molecule, epitopes on two or more protein subunits, epitopes on two or more discrete molecules or proteins or, in selected embodiments, epitopes on proteins expressed on two discrete cells.

Another significant aspect of the invention comprises the therapeutic association of CD324 polypeptides with various cancer stem cells. Thus, in certain embodiments the invention will comprise a CD324 modulator that reduces the frequency of tumor initiating cells upon administration to a subject. Preferably the reduction in frequency will be determined using in vitro or in vivo limiting dilution analysis. In particularly preferred embodiments such analysis may be conducted using in vivo limiting dilution analysis comprising transplant of live human tumor cells into immunocompromised mice. Alternatively, the limiting dilution analysis may be conducted using in vitro limiting dilution analysis comprising limiting dilution deposition of live human tumor cells into in vitro colony supporting conditions. In either case, the analysis, calculation or quantification of the reduction in frequency will preferably comprise the use of Poisson distribution statistics to provide an accurate accounting. It will be appreciated that, while such quantification methods are preferred, other, less labor intensive methodology such as flow cytometry or immunohistochemistry may also be used to provide the desired values and, accordingly, are expressly contemplated as being within the scope of the instant invention. In such cases the reduction in frequency may be determined using flow cytometric analysis or immunohistochemical detection of tumor cell surface markers known to enrich for tumor initiating cells.

As such, in another preferred embodiment of the instant invention comprises a method of treating a CD324 associated disorder comprising administering a therapeutically effective amount of a CD324 modulator to a subject in need thereof whereby the frequency of tumor initiating cells is reduced. Preferably the CD324 associated disorder comprises a neoplastic disorder. Again, the reduction in the tumor initiating cell frequency will preferably be determined using in vitro or in vivo limiting dilution analysis.

In this regard it will be appreciated that the present invention is based, at least in part, upon the discovery that CD324 immunogens are associated with tumor perpetuating cells (i.e., cancer stem cells) that are involved in the etiology of various proliferative disorders including neoplasia. More specifically, the instant application unexpectedly demonstrates that the administration of various exemplary CD324 modulators can mediate, reduce, deplete, inhibit or eliminate tumorigenic signaling by tumor initiating cells (i.e., reduce the frequency of tumor initiating cells). This reduced signaling, whether by depletion, neutralization, reduction, elimination, reprogramming or silencing of the tumor initiating cells or by modifying tumor cell morphology (e.g., induced differentiation, niche disruption), in turn allows for the more effective treatment of CD324 associated disorders by inhibiting tumorigenesis, tumor maintenance, expansion and/or metastasis and recurrence.

Besides the aforementioned association with cancer stem cells, there is evidence that disregulated CD324 on abnormal cells may be involved in homotypic and heterotypic binding that promotes unnatural cellular association that may contribute to tumor growth or maintenance. Intervention in the proliferation of such tumorigenic cells using the novel CD324 modulators described herein, may thereby ameliorate or treat a disorder by more than one mechanism (i.e., tumor initiating cell reduction and disruption of oncogenic pathway signaling) to provide additive or synergistic effects. Still other preferred embodiments may take advantage of the cellular internalization of disregulated cell surface CD324 to deliver a modulator mediated anti-cancer agent. In this regard it will be appreciated that the present invention is not limited by any particular mechanism of action but rather encompasses the broad use of the disclosed modulators to treat CD324 associated disorders (including various neoplasia).

Thus, in other embodiments the present invention will comprise the use of the disclosed modulators that inhibit or interfere with CD324 homotypic interactions and the use thereof to treat proliferative disorders. In still other preferred embodiments the present invention is directed to modulators that inhibit or interfere with CD324 heterotypic interactions and the use thereof to treat proliferative disorders.

With respect to this aspect (i.e., homotypic or heterotypic inhibition) of the invention those of skill in the art will appreciate that modulators may readily be generated and selected for that selectively inhibit homotypic binding or heterotypic binding or that inhibit or block both types of association. That is, through the selection of particular immunization reagents and the use of common screening techniques (e.g., ELISA assays) modulators may be produced that preferentially reduce either homotypic or heterotypic associations. Moreover, in particularly preferred embodiments modulators may be provided that can selectively inhibit specific types of heterotypic interactions such as, for example, those involving CD324 and EGFR or CD324 and αEβ7. Accordingly, such modulators and their use in treating proliferative disorders are expressly contemplated as being within the scope of the instant invention.

Other facets of the instant invention may exploit the ability of the disclosed modulators to potentially disrupt oncogenic pathways while simultaneously silencing tumor initiating cells. Such multi-active CD324 modulators (e.g., CD324 antagonists) may prove to be particularly effective when used in combination with standard of care anti-cancer agents or debulking agents. Accordingly preferred embodiments of the instant invention comprise using the disclosed modulators as anti-metastatic agents for maintenance therapy following initial treatments. In addition, two or more CD324 antagonists (e.g. antibodies that specifically bind to two discrete epitopes on CD324) may be used in combination in accordance with the present teachings. In selected embodiments the present invention will comprise the first administration of a CD324 modulator to reduce or eliminate an antigen sink (e.g., expression of a determinant on non-targeted cells) and the subsequent administration of a therapeutically effective amount of a CD324 modulator. In such embodiments the first administered modulator may be the same or different than the subsequently administered modulator. In certain preferred embodiments the first administered CD324 modulator will be non-internalizing. In other preferred embodiments the first administered CD324 modulator will be followed by administration of an internalizing CD324 antibody which, in selected embodiments is conjugated to a cytotoxic agent. As discussed in some detail below, the CD324 modulators of the present invention may generally be used in a conjugated or unconjugated state and, optionally, as a sensitizing agent in combination with a variety of chemical or biological anti-cancer agents.

Accordingly another preferred embodiment of the instant invention comprises a method of sensitizing a tumor in a subject for treatment with an anti-cancer agent comprising the step of administering a CD324 modulator to said subject. Other embodiments comprise a method of reducing metastasis or tumor recurrence following treatment comprising administering a CD324 modulator to a subject in need thereof. In a particularly preferred aspect of the invention the CD324 modulator will specifically result in a reduction of tumor initiating cell frequency as determined using in vitro or in vivo limiting dilution analysis.

More generally preferred embodiments of the invention comprise a method of treating a CD324 associated disorder in a subject in need thereof comprising the step of administering a CD324 modulator to the subject. In particularly preferred embodiments the CD324 modulator will be associated (e.g., conjugated) with an anti-cancer agent. In yet other embodiments the CD324 modulator will internalize following association or binding with the CD324 on or near the surface of the cell. Moreover the beneficial aspects of the instant invention, including any disruption of signaling pathways and collateral benefits, may be achieved whether the subject tumor tissue exhibits elevated levels of CD324 or reduced or depressed levels of CD324 as compared with normal adjacent tissue. Particularly preferred embodiments will comprise the treatment of disorders exhibiting elevated levels of CD324 on tumorigenic cells as compared to normal tissue or non-tumorigenic cells.

In yet another aspect the present invention will comprise a method of treating a subject suffering from a neoplastic disorder comprising the step of administering a therapeutically effective amount of at least one internalizing CD324 modulator. Preferred embodiments will comprise the administration of internalizing antibody modulators wherein, in other selected embodiments, the internalizing antibody modulators are conjugated or associated with a cytotoxic agent.

Other embodiments are directed to a method of treating a subject suffering from a CD324 associated disorder comprising the step of administering a therapeutically effective amount of at least one depleting CD324 modulator.

In yet another embodiment the present invention provides methods of maintenance therapy wherein the disclosed effectors or modulators are administered over a period of time following an initial procedure (e.g., chemotherapeutic, radiation or surgery) designed to remove at least a portion of the tumor mass. Such therapeutic regimens may be administered over a period of weeks, a period of months or even a period of years wherein the CD324 modulators may act prophylactically to inhibit metastasis and/or tumor recurrence. In yet other embodiments the disclosed modulators may be administered in concert with known debulking regimens to prevent or retard metastasis, tumor maintenance or recurrence.

In yet other preferred embodiments the modulators will associate or bind to a specific epitope, portion, motif or domain of CD324. The CD324 protein is composed of four extracellular cadherin repeats (EC1-EC4) of approximately 110 amino acids, a membrane proximal extracellular domain (EC5) that is less closely related to the other cadherin repeats, a transmembrane domain, and a highly conserved intracellular domain that can be further subdivided into the juxtamembrane domain (JMD) and a highly-phosphorylated β-catenin binding domain (CBD). Accordingly, in certain embodiments the modulators will bind or associate with one of the extracellular domains: EC1, EC2, EC3, EC4 or EC5. Other aspects of the instant invention comprise modulators that associate or bind to a specific epitope located in an extracellular domain of CD324. Of course it will be appreciated that each of the aforementioned domains may comprise more than one epitope and may be associated with more than one bin.

With regard to modulator or antibody "bins" it will be appreciated that the CD324 antigen may be analyzed or mapped through competitive antibody binding using art recognized techniques to define specific bins located on or along the protein. While discussed in more detail herein and shown in Example 7 below, two antibodies (one of which may be termed a "reference antibody," "bin delineating antibody" or "delineating antibody") may be considered to be in the same bin if they compete with each other for binding to the target antigen. In such cases the subject antibody epitopes may be identical, substantially identical or close enough (either in a linear sense where they are separated by a few amino acids or conformationally) so that both antibodies are sterically or electrostatically inhibited or precluded from binding to the antigen. Such defined bins may be generally associated with certain CD324 domains (e.g. the reference antibody will bind with an epitope contained in a specific domain) though the correlation is not always precise (e.g., there may be more than one bin in a domain or the bin may be defined conformationally and comprise more than one domain). In any event it will be appreciated that those skilled in the art can readily determine the relationship between CD324 domains and empirically determined bins.

With regard to the present invention competitive binding analysis using art recognized techniques (e.g., ELISA, surface plasmon resonance or bio-layer interferometry) defined at least six distinct bins, each of which was found to contain a number of antibody modulators. For the purposes of the instant disclosure five of the bins were termed bin A to bin E and the sixth bin (not as well defined) was termed bin U. More particularly bins A-E comprise unique defined bins and the antibodies contained in each of these bins compete with each other for binding to the SEZ6 protein. Bin U contains antibodies that do not compete with antibodies in Bins A-E, but may compete for binding with each other. Thus, in selected embodiments the present invention will comprise a modulator residing in a bin selected from the group consisting of bin A, bin B, bin C, bin D, bin E, and bin U.

In other selected embodiments the present invention will comprise a modulator residing in a bin selected from the group consisting of bin A, bin B, bin C, bin D, and bin E. In yet other embodiments the present invention comprise a modulator residing in a bin defined by a reference antibody selected from the group consisting of SC10.6, SC10.15, SC10.17, SC10.19, SC10.35, SC10.36, SC10.38, SC10.75, SC10.111, SC10.112, SC10.115, SC10.118, SC10.123, SC10.124, SC10.125, SC10.126, SC10.127, SC10.128, SC10.129, SC10.130, SC10.132, SC10.133, SC10.134, SC10.163, SC10.168, and SC10.178. In still other embodiments the invention will comprise modulators from bin A, modulators from bin B, modulators from bin C, modulators from bin D or modulators from bin E. Yet other preferred embodiments will comprise a reference antibody modulator and any antibody that competes with the reference antibody.

The term "compete" or "competing antibody" when used in the context of the disclosed modulators means binding competition between antibodies as determined by an assay in which a reference antibody or immunologically functional fragment prevents or inhibits or reduces (e.g., greater than 40%) specific binding of a test antibody to a common antigen. Compatible methods for determining such competition comprise art known techniques such as, for example, bio-layer interferometry, surface plasmon resonance, flow cytometry, competitive ELISA, etc.

Beyond the therapeutic uses discussed above it will also be appreciated that the modulators of the instant invention may be used to diagnose CD324 related disorders and, in particular, proliferative disorders. In some embodiments the modulator may be administered to the subject and detected or monitored in vivo. Those of skill in the art will appreciate that such modulators may be labeled or associated with markers or reporters as disclosed below and detected using any one of a number of standard techniques (e.g., MRI, CAT scan PET scan, etc.).

Thus, in some embodiments the invention will comprise a method of diagnosing, detecting or monitoring a CD324 associated disorder in vivo in a subject in need thereof comprising the step of administering a CD324 modulator.

In other instances the modulators may be used in an in vitro diagnostic setting using art-recognized procedures (e.g., immunohistochemistry or IHC). As such, a preferred embodiment comprises a method of diagnosing a hyperproliferative disorder in a subject in need thereof comprising the steps of:
  a. obtaining a tissue sample from said subject;
  b. contacting the tissue sample with at least one CD324 modulator; and
  c. detecting or quantifying the CD324 modulator associated with the sample.

Such methods may be easily discerned in conjunction with the teachings of the instant application and may be readily performed using generally available commercial technology such as automatic plate readers, dedicated reporter systems, etc. In selected embodiments the CD324 modulator will be associated with tumor perpetuating cells present in the sample. In other preferred embodiments the detecting or quantifying step will comprise a reduction of tumor initiating cell frequency and detection thereof. Moreover, limiting dilution analysis may be conducted as previously alluded to above and will preferably employ the use of Poisson distribution statistics to provide an accurate accounting as to the reduction of frequency.

In a similar vein the present invention also provides kits or devices and associated methods that are useful in the diagnosis and monitoring of CD324 associated disorders such as cancer. To this end the present invention preferably provides an article of manufacture useful for diagnosing or treating CD324 associated disorders comprising a receptacle comprising a CD324 modulator and instructional materials for using said CD324 modulator to treat or diagnose the CD324 associated disorder. In selected embodiments the devices and associated methods will comprise contacting at least one circulating tumor cell.

Other preferred embodiments of the invention also exploit the properties of the disclosed modulators as an instrument useful for identifying, characterizing, isolating, sectioning or enriching populations or subpopulations of tumor initiating cells through methods such as flow cytometric analysis, fluorescence activated cell sorting (FACS) or laser mediated sectioning.

As such, another preferred embodiment of the instant invention is directed to a method of identifying, isolating, sectioning or enriching a population of tumor initiating cells comprising the step of contacting said tumor initiating cells with a CD324 modulator.

The foregoing is a summary and thus contains, by necessity, simplifications, generalizations, and omissions of detail; consequently, those skilled in the art will appreciate that the summary is illustrative only and is not intended to be in any way limiting. Other aspects, features, and advantages of the methods, compositions and/or devices and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter. scope of the claimed subject matter.

BRIEF DESCRIPTION OF THE FIGURES

FIGS. 1A and 1B depict, respectively, the mRNA transcript that contains the open reading frame (underlined nucleotides) encoding prepro human CD324 (SEQ ID NO: 1), the corresponding amino acid sequence of prepro human CD324 (SEQ ID NO: 2), with the final mature protein in underlined amino acid residues, and the corresponding amino acid sequence of human CD324 signal peptide bolded;

FIGS. 3A and 3B depict, respectively, a scatter plot demonstrating the CD46 CD324 phenotype of the parental tumor, an enriched $CD46^{hi}CD324^+$ subpopulation transplanted into a recipient animal, and the CD46 CD324 phenotype of the resultant daughter tumor (FIG. 3A) and the tumorigenicity of the various sorted subpopulations (FIG. 3B) from a representative colorectal tumor (CR14);

FIGS. 4A and 4B depict, respectively, a scatter plot demonstrating the CD46 CD324 phenotype of the parental tumor, an enriched $CD46^{hi}CD324^+$ subpopulation transplanted into a recipient animal, and the CD46 CD324 phenotype of the resultant daughter tumor (FIG. 4A) and a graphical representation of the tumorigenicity of the various sorted subpopulations (FIG. 4B) from a representative pancreatic tumor (PA4);

FIGS. 6A and 6B depict, respectively, a scatter plot demonstrating the ESA CD324 phenotype of the parental tumor, an enriched $ESA^+CD46^{hi}CD324^+$ subpopulation transplanted into a recipient animal, and the ESA CD324 phenotype of the resultant daughter tumor (FIG. 6A) and a graphical representation of the tumorigenicity of the various sorted subpopulations (FIG. 6B) from a representative breast tumor (BR22);

FIGS. 8A and 8B depict, respectively, scatter plots demonstrating the CD324 phenotype of the parental tumor, an enriched $CD324^+$ subpopulation transplanted into a recipient animal, and the CD324 phenotype of the resultant daughter tumor (FIG. 8A) and a graphical representation of the tumorigenicity of the various sorted subpopulations (FIG. 8B) from a representative small-cell lung cancer tumor (LU64);

FIGS. 9A and 9B depict, respectively, scatter plots demonstrating the CD46 CD324 phenotype of a parental tumor, and enriched $CD46^{hi}CD324^+CD46^{hi}CD324^-$ subpopulations that are then transplanted into a recipient animal (FIG. 9A), and a graphical representation of the tumorigenicity of the various sorted subpopulations (FIG. 9B) from a representative primary melanoma tumor;

FIGS. 10A and 10B comprise tabular summaries of representative colorectal, lung, pancreatic, breast and ovarian tumor cell subpopulations enriched and transplanted into immunocompromised mice whereby the tumorigenicity of various CD46 and CD324 phenotypes are demonstrated;

FIGS. 11A and 11B provide, in a tabular form, the contiguous amino acid sequences (SEQ ID NOS: 20-73) of heavy and light chain variable regions of a number of exemplary murine CD324 modulators along with a humanized construct isolated, cloned and engineered as described in the Examples herein;

FIG. 12 provides, in a tabular representation, selected biochemical and immunological characteristics of exemplary CD324 modulators;

FIGS. 14A-14D are graphical and tabular representations illustrating that CD324 modulators may effectively be used as targeting moieties to direct cytotoxic payloads to cells expressing CD324, wherein the decrease in normalized RLU value is indicative of cell killing through internalized toxin, and the EC50 (e.g., half-maximal effective concentration) was determined for selected modulators;

FIGS. 18A and 18B illustrate the in vivo efficacy of an exemplary antagonistic CD324 modulator in reducing the tumor size of two individual patient-derived NTX cells from pancreatic tumors; and FIG. 19 depicts nucleic acid sequences (SEQ ID NOS: 120-173) encoding each of the heavy and light chain variable region amino acid sequences of CD324 modulators set forth in FIGS. 11A and 11B.

DETAILED DESCRIPTION OF THE INVENTION

I. Introduction

Figure 2A:
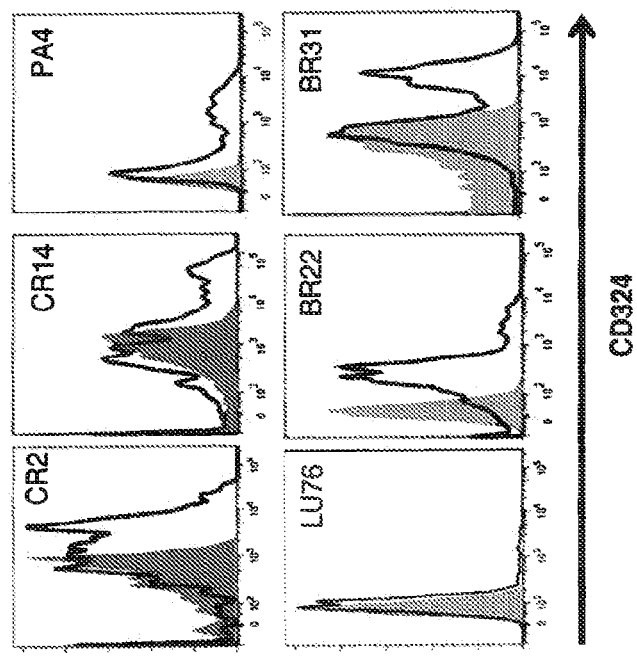
FIGS. 2A and 2B are graphical representations of flow cytometry-based determination of CD324 protein expression on the surface of individual human tumor cell populations derived from NTX colorectal (CR), pancreatic (PA), breast (BR), lung ("LU") and ovarian ("OV") tumors (FIGS. 2A and 2B), or a primary human ovarian tumor (FIG. 2B), displayed as histogram plots (black line) referenced to fluorescence minus one (FMO) isotype-control stained populations (solid gray)

While the present invention may be embodied in many different forms, disclosed herein are specific illustrative embodiments thereof that exemplify the principles of the invention. It should be emphasized that the present invention is not limited to the specific embodiments illustrated. Moreover, any section headings used herein are for organizational purposes only and are not to be construed as limiting the subject matter described. Finally, for the purposes of the instant disclosure all identifying sequence Accession numbers may be found in the NCBI Reference Sequence (RefSeq) database and/or the NCBI GenBank® archival sequence database unless otherwise noted.

As discussed above it has surprisingly been found that CD325 genotypic and/or phenotypic determinants are associated with various proliferative disorders, including neoplasia, and that CD324 and variants thereof provide useful tumor markers which may be exploited in the treatment of related diseases. Moreover, as shown in the instant application it has unexpectedly been found that CD324 markers or determinants such as cell surface CD324 protein are therapeutically associated with cancer stem cells (also known as tumor perpetuating cells) and may be effectively exploited to eliminate or silence the same. The ability to selectively reduce or eliminate cancer stem cells (e.g., through the use of conjugated CD324 modulators) is particularly surprising in that such cells are known to generally be resistant to many conventional treatments. That is, the effectiveness of traditional, as well as more recent targeted treatment methods, is often limited by the existence and/or emergence of resistant cancer stem cells that are capable of perpetuating tumor growth even in face of these diverse treatment methods. Further, determinants associated with cancer stem cells often make poor therapeutic targets due to low or inconsistent expression, failure to remain associated with the tumorigenic cell or failure to present at the cell surface. In sharp contrast to the teachings of the prior art, the instantly disclosed compounds and methods effectively overcome this inherent resistance and to specifically eliminate, deplete, silence or promote the differentiation of such cancer stem cells thereby negating their ability to sustain or re-induce the underlying tumor growth.

Thus, it is particularly remarkable that CD324 modulators such as those disclosed herein may advantageously be used in the prognosis, diagnosis, theragnosis, treatment and/or prevention of selected proliferative (e.g., neoplastic) disorders in subjects in need thereof. It will be appreciated that, while preferred embodiments of the invention will be discussed extensively below, particularly in terms of particular multispecific constructs, antigen regions or epitopes or in the context of cancer stem cells or tumor cell populations and their interactions with the disclosed modulators, those skilled in the art will appreciate that the scope of the instant invention is not limited by such exemplary embodiments. Rather, the most expansive embodiments of the present invention and the appended claims are broadly and expressly directed to CD324 modulators (including conjugated and multispecific modulators) and their use in the prognosis, diagnosis, theragnosis, treatment and/or prevention of a variety of CD324 associated or mediated disorders, including neoplastic or cell proliferative disorders, regardless of any particular mechanism of action or specifically targeted tumor, cellular or molecular component.

With regard to the instant invention CD324 protein is known to bind other CD324 proteins, otherwise known as homotypic binding, in a calcium dependent manner. However CD324 present on normal tissues may be sequestered in tight junctions where homotypic binding domains are inaccessible. Conversely, in tumors CD324 is often disregulated and these homotypic binding domains may be accessible to the modulators disclosed herein. Using such modulators in accordance with the instant teachings that disrupt this function may target cancer cells with disregulated CD324 while sparing the normal cells where the binding domain is masked. By inhibiting or disrupting such homotypic interactions the neutralizing or antagonistic modulators of the instant invention may compromise, silence or otherwise retard the growth or maintenance of tumorigenic cells. Similarly, as will be discussed in more detail below, the disregulated and exposed CD324 may promote heterotypic interactions (i.e., where CD324 interacts with different ligands) that may disrupt normal cell-cell interactions and promote tumor growth. Again, interfering with such heterotypic interactions using the disclosed modulators may disrupt abnormal cell associations and retard tumor maintenance or growth. In other embodiments the disclosed modulators conjugated to cytotoxic agents may be used to target such disregulated CD324 and immunospecifically deliver cytotoxic payloads to tumorigenic cells.

To that end, and as demonstrated in the instant application, it has unexpectedly been found that the disclosed CD324 modulators can effectively be used to target and eliminate or otherwise incapacitate proliferative or tumorigenic cells and treat CD324 associated disorders (e.g., neoplasia). As used herein a "CD324 associated disorder" shall be held to mean any disorder or disease (including proliferative disorders) that is marked, diagnosed, detected or identified by a phenotypic or genotypic aberration of CD324 genetic components or expression ("CD324 determinant") during the course or etiology of the disease or disorder. In this regard a CD324 phenotypic aberration or determinant may, for example, comprise elevated or depressed levels of CD324 protein expression, abnormal CD324 protein expression on certain definable cell populations or abnormal CD324 protein expression at an inappropriate phase or stage of a cell lifecycle. Of course, it will be appreciated that similar expression patterns of genotypic determinants (e.g., mRNA transcription levels) of CD324 may also be used to classify, detect or treat CD324 disorders.

As used herein the term "determinant" or "CD324 determinant" shall mean any detectable trait, property, marker or factor that is identifiably associated with, or specifically found in or on a particular cell, cell population or tissue including those identified in or on a tissue, cell or cell population affected by a CD324 associated disease or disorder. In selected preferred embodiments the CD324 modulators may associate, bind or react directly with the CD324 determinant (e.g., cell surface CD324 protein or CD324 mRNA) and thereby ameliorate the disorder. More generally determinants may be morphological, functional or biochemical in nature and may be genotypic or phenotypic. In other preferred embodiments the determinant is a cell surface antigen or genetic component that is differentially or preferentially expressed (or is not) by specific cell types (e.g., cancer stem cells) or by cells under certain conditions (e.g., during specific points of the cell cycle or cells in a particular niche). In still other preferred embodiments the determinant may comprise a gene or genetic entity that is differently regulated (up or down) in a specific cell or discrete cell population, a gene that is differentially modified with regard to its physical structure and chemical composition or a protein or collection of proteins physically associated with a gene that show differential chemical modifications. Determinants contemplated herein are specifically held to be positive or negative and may denote a cell, cell subpopulation or tissue (e.g., tumors) by its presence (positive) or absence (negative).

In a similar vein "CD324 modulators" of the invention broadly comprise any compound that recognizes, reacts, competes, antagonizes, interacts, binds, agonizes, or associates with a CD324 or a variant thereof (or specific domains, regions or epitopes thereof) or its genetic component. By these interactions, the CD324 modulators may advantageously eliminate, reduce or moderate the frequency, activity, recurrence, metastasis or mobility of tumorigenic cells (e.g., tumor perpetuating cells or cancer stem cells). Exemplary modulators disclosed herein comprise nucleotides, oligonucleotides, polynucleotides, peptides or polypeptides. In certain preferred embodiments the selected modulators will comprise antibodies to a CD324 protein isoform or immunoreactive fragments or derivatives thereof. Such antibodies may be antagonistic or agonistic in nature and may optionally be conjugated or associated with a therapeutic or diagnostic agent. Moreover, such antibodies or antibody fragments may comprise depleting, neutralizing or internalizing antibodies. In other embodiments, modulators within the instant invention will constitute a CD324 construct comprising a CD324 isoform or a reactive fragment thereof. It will be appreciated that such constructs may comprise fusion proteins and can include reactive domains from other polypeptides such as immunoglobulins or biological response modifiers. In still other aspects, the CD324 modulator will comprise a nucleic acid moiety (e.g. miRNA, siRNA, shRNA, antisense constructs, etc.) that exerts the desired effects at a genomic level. Still other modulators compatible with the instant teachings will be discussed in detail below.

More generally CD324 modulators of the present invention broadly comprise any compound that recognizes, reacts, competes, antagonizes, interacts, binds, agonizes, or associates with a CD324 determinant (genotypic or phenotypic) including cell surface CD324 protein. Whichever form of modulator is ultimately selected it will preferably be in an isolated and purified state prior to introduction into a subject. In this regard the term "isolated CD324 modulator" or "isolated CD324 antibody" shall be construed in a broad sense and in accordance with standard pharmaceutical practice to mean any preparation or composition comprising the modulator in a state substantially free of unwanted contaminants (biological or otherwise). Moreover these preparations may be purified and formulated as desired using various art recognized techniques. Of course, it will be appreciated that such "isolated" preparations may be intentionally formulated or combined with inert or active ingredients as desired to improve the commercial, manufacturing or therapeutic aspects of the finished product and provide pharmaceutical compositions. In a broader sense the same general considerations may be applied to an "isolated" CD324 protein or variant thereof or an "isolated" nucleic acid encoding the same.

Besides the association with tumors generally discussed above, there are also indications of phenotypic or genotypic association between selected tumor initiating cells (TIC) and CD324 determinants. In this regard selected TICs (e.g., cancer stem cells) may express elevated levels of CD324 proteins when compared to normal tissue and non-tumorigenic cells (NTG), which together typically comprise much of a solid tumor. Thus, CD324 determinants may comprise a tumor associated marker (or antigen or immunogen) and the disclosed modulators may provide effective agents for the detection and suppression of TIC and associated neoplasia due to altered levels of the proteins on cell surfaces or in the tumor microenvironment. Accordingly, CD324 modulators, including immunoreactive antagonists and antibodies that associate, bind or react with the proteins, may effectively reduce the frequency of tumor initiating cells and could be useful in eliminating, depleting, incapacitating, reducing, promoting the differentiation of, or otherwise precluding or limiting the ability of these tumor-initiating cells to lie dormant and/or continue to fuel tumor growth, metastasis or recurrence in a patient. In this regard those skilled in the art will appreciate that the present invention further provides CD324 modulators and their use in reducing the frequency of tumor initiating cells II. CD324 Physiology Cadherins (Ca2+-dependent adhesion receptors) are a class of type-1 transmembrane proteins involved in selective cell-cell recognition. They play important roles in tissue morphogenesis, cell recognition, cell adhesion and maintenance of tissue integrity in biological and pathological processes as diverse as early embryogenesis, synapse formation and tumor invasion (Takeichi, 1990, 1991; Gumbiner, 1996; Nollet, 2000). Classical cadherins, a subfamily of more than 16 cadherin molecules encoded by different genes and defined by the presence of five extracellular cadherin (EC) domains and a conserved intracellular domain that mediates interactions with catenins, make up a distinct group of phylogenetically and structurally related proteins with molecular weights of approximately 120 kDa. The classic cadherins are differentially expressed during normal embryonic development, suggesting they have distinct functions related and unrelated to their adhesive capacity.

CD324 (also known as E-cadherin or epithelial cadherin; gene symbol, CDH1) is a member of the classical subfamily of cadherins, and as such is a calcium-dependent cell-cell adhesion glycoprotein that mediates homotypic (i.e., epithelial-epithelial) cell-cell adhesion. As used herein the term "CD324" or cluster of differentiation 324 (also known as CDH1, E-cadherin, E-cad, Cadherin-1, L-CAM, uvomorulin, Arc-1 and cell-CAM 120/80) refers to naturally occurring human CD324 or immunoreactive fragments or derivatives thereof unless contextually dictated otherwise. Representative CD324 protein orthologs include, but are not limited to, human (i.e. hCD324, NP_004351.1, AAI41839.1 and AAI46663.1), mouse (NP_033994.1), chimpanzee (XM_001168150) and rat (NP_112624, BAA84920.1).

In humans the CD324 protein is encoded by the CDH1 gene (Shiozaki et al., 1996; Huntsman and Caldas, 1998) consisting of 16 exons spanning 98.3 kb located on chromosome 16q22. The CDH1 gene is transcribed and spliced into a 4815 bp mature mRNA transcript (FIG. 1A; SEQ ID NO. 1), which has an open reading frame encoding a preproprotein of 882 amino acids (FIG. 1B; SEQ ID NO: 2). Further, human CD324 preproproteins include a predicted signal or leader sequence comprising amino acids 1-22 (bolded in FIG. 1B), which is clipped off to provide the proprotein (i.e., 860 aa, amino acids 23-882, FIG. 1B). Those skilled in the art will appreciate that this signal peptide targets the polypeptide to the cell surface/secretory pathway. During its trafficking to the cell surface, the proprotein is glycosylated and proteolytically cleaved by a furin-like protease into the mature 728 amino acid CD324 protein (FIG. 1B). Comparison of the human CD324 to the other well characterized members of the cadherin family, shows a homology to human P-cadherin of 56% at the DNA (ORF) level and of 60% at the (mature) protein level when compared to the mature CD324 protein. Similarly, with regard to human N-cadherin a homology of 59% at the DNA (ORF) level and 49% at the (mature) CD324 protein level was found. Accordingly, CD324 appears well conserved between the different species and the sequence homology among the various members of the cadherin family is generally high.

Epithelial cells are characterized by strong cell-cell adhesion interfaces. CD324 is a major protein component of the adherens junction, a specialized cell-cell adhesive site where a variety of transmembrane glycoproteins interface with one another and with the cytoskeleton (Niessen and Gottardi, 2008). The CD324 protein is composed of four extracellular cadherin repeats (EC1 EC4) of approximately 110 amino acids, a membrane-proximal extracellular domain (EC5) that is less closely related to the other cadherin repeats, a transmembrane domain, and a highly conserved intracellular domain that can be further subdivided into the juxtamembrane domain (JMD) and a highly-phosphorylated β-catenin binding domain (CBD). Solution of the structure of an EC repeat domain revealed it to bear striking similarity to an immunoglobulin fold, although there is little sequence homology between these two types of protein modules. Calcium ions bind at sites between the EC repeats of cadherins, conferring a rigid rod-like structure to the extracellular portion of these proteins.

When cadherins were initially cloned and described, mixing experiments revealed that cells expressing similar cadherins associated with one another, whereas cells expressing different cadherins segregated from one another, suggesting that cadherins mediated homotypic associations via homophilic (i.e., CD324-CD324) interactions (Nose et al. 1988). Mutagenesis and domain swapping experiments have demonstrated that the extracellular domain of cadherins mediates these interactions. Type I classical cadherins, like CD324 contain a conserved tryptophan residue at position 2 of the mature protein. An early model of homophilic interactions suggested that this tryptophan inserted into a hydrophobic pocket on an adjacent CD324 molecule on a cis (same) or trans (apposing) cell surface (Nose et al. 1988; Chen et al. 2005; Patel et al. 2006). This model implies that the cadherin molecule acquires competence for homophilic interactions, with prerequisites including processing of the prodomain and conformational changes in the protein during the formation of homophilic interactions. The specific details of the nature of molecular interactions mediating the homotypic binding remain debated, for instance if cis-dimer formation is a prerequisite to trans-dimer formation, although the requirement for the conserved tryptophan in the homotypic process is clear (Mohamet, 2011).

Besides the aforementioned homophilic adhesion mode of CD324, the ectodomain of CD324 binds in a heterophilic way (i.e., the binding of different types of cadherin to one another) or with other specific molecules, such as EGFR or integrin $\alpha E\beta 7$. Various studies have suggested that the overall homo- or heterotypic cell association and sorting may be determined by the expression levels of the particular cadherins on each cell, as well as the shear forces the cells are subjected to during the mixing and segregation processes (Duguay et al., 2003). Certain pairs of heterotypic interactions were permitted at low shear forces, whereas high shear forces tended to favor homotypic interactions. Therefore the kinetics of the cadherin homo- or heterophilic interactions may be more relevant than the thermodynamics of the interaction with respect to the ultimate homo- or heterotypic cell association.

The intracellular portions of CD324 interact with various proteins inside the cell, including $\alpha$-catenin, $\beta$-catenin and p120, which themselves interact with the actin filaments of the cytoskeleton (Perez-Moreno et al, 2003). Therefore, CD324 is thought to act as a bridge between the cell-adhesion machinery and the cytoskeleton, and provide cells with a compass that orients them in tissues such as stratified epithelia. Cells expressing cytoplasmic deletion mutants of CD324, in which the binding to catenins is disturbed, fail to form stable cell-cell contacts, indicating that proper interactions with the cytoskeleton are required to mediate proper interactions between CD324 on adjacent cells.

The critical importance of CD324 to normal development and tissue function is demonstrated by the lethality of CDH1 gene knockouts in mice at a very early stage in embryogenesis (Haegel et al., 1996). Cells are morphologically defined in vivo by their epithelial or mesenchymal nature. During development, some cells undergo epithelial-to-mesenchymal transitions (EMTs) or mesenchymal-to-epithelial transitions (METs) as a natural step in the adoption of particular cell fates. CD324 is commonly used as marker of the epithelial state, and is known to be down regulated during an EMT. But recent evidence suggests that CD324 and other cell-adhesion molecules also have functional roles in these cell fate decisions. Samavarchi-Tehrani (2010) have shown that during reprogramming to induced pluripotent stem cells, induction of MET by BMP (bone morphogenetic proteins) signaling was marked by CD324 upregulation and adherens junction formation and occurred at the earliest stages of reprogramming. Li and co-workers (2010) have shown that specifically ablating CD324 expression dramatically inhibited reprogramming, while a new study by Redmer and colleagues (2011) takes this work a step further and shows that the loss of CD324 expression drives pluripotent stem cells to differentiate. Additionally, in *Drosophila* male germline cells, fly CD324 homolog expression is required for proper orientation of the centrosome and spindles within the germline stem cell during asymmetric stem cell division. Together these studies suggest that CD324 is not just a marker of fate change, but that the spatial and mechanical input provided by CD324 has an important role in altering cell fate and is linked to fundamental stem cell biology.

With respect to the development of cancer, disturbance of the expression of CD324 is one of the main events in the early and late steps of tumorigenesis and metastasis. Inactivating germline mutations of CDH1 that result in structurally altered CD324 proteins or complete loss of CD324 expression have been correlated with gastric, breast, colorectal, thyroid, and ovarian cancers. To date, 69 somatic mutations have been reported comprising, in addition to mis-sense mutations, splice site mutations and truncation mutations caused by insertions, deletions, and nonsense mutations. More generally, well-differentiated tumors have long been known to exhibit a strong staining pattern of CD324/catenin compared to poorly differentiated ones. Accordingly CD324 has been used by pathologists as a significant prognostic marker to diagnose different kinds of cancer by immunohistochemistry.

A characteristic of epithelial cancers is an apparent activation of an EMT program leading to subsequent invasion of the underlying mesenchyme. In these malignancy-associated EMTs, CD324 and/or its adhesion partners are degraded, allowing for the physical separation of cells from their epithelial sheet into the underlying mesenchyme (Acloque et al, 2009). Furthermore, blocking the degradation of proteins like CD324 prevents invasion. Specific downregulation of CD324 function has been shown to occur via several mechanisms: transcriptional repression of CD324 expression by E-box binding proteins such as Snail and Slug, cleavage of CD324 protein from the cell surface by metallomatrix proteases (e.g., MMP7, MMP13) overexpressed by tumors, and internalization of CD324 via HGF-induced c-met receptor activation. Together these reports about the functional role of CD324 in providing mechanical support for cells, regulating cell localization and motility phenotypes, and its links to differentiation status of the cell make CD324 a very intriguing target for the development of anti-cancer therapeutics.

In addition to the aforementioned characteristics the present disclosure demonstrates that the expression of CD324 is elevated in various cancer stem cell populations. While not wishing to be bound by any particular theory it is believed that the CD324 modulators of the present invention (particularly those that are antagonistic or neutralizing with regard to homotypic and/or heterotypic interactions) act, at least in part, by either reducing or eliminating tumor initiating cell frequency thereby interfering with tumor propagation or survival in a different manner than traditional standard of care therapeutic regimens (e.g. irinotecan), or through immunotherapeutic signaling or delivering a payload able to kill CD324 expressing cells. For example, elimination of TPC by antagonizing CD324 may include simply promoting cell proliferation in the face of chemotherapeutic regimens that eliminate proliferating cells, or promote differentiation of TPC such that their self-renewal (i.e. unlimited proliferation and maintenance of multipotency) capacity is lost. Alternatively, in preferred embodiments the recruitment of cytotoxic T-cells to attack CDH1 expressing cells, or delivery of a potent toxin conjugated to an anti-CDH1 antibody that is able to internalize, may selectively kill or otherwise incapacitate TPC. Additionally, the CD324 conformational changes that underlie formation of homotypic interactions in normal adherens junctions may be reversed or disregulated during the disorganization of epithelium associated with cancer progression, and therefore offer opportunities for development of modulators specifically recognizing CD324 on cancerous tissues.

III Cancer Stem Cells

As alluded to above it has surprisingly been discovered that CD324 expression (genotypic and/or phenotypic) is therapeutically associated with various tumorigenic cell subpopulations. In this respect the present invention provides CD324 modulators that may be particularly useful for targeting such tumor initiating cells, and especially tumor perpetuating cells, thereby facilitating the treatment, management or prevention of neoplastic disorders. More specifically, as previously indicated it has surprisingly been found that specific tumor cell subpopulations aberrantly express CD324 and may modify cellular adhesion or cytoskeleton interactions important to cancer stem cell self-renewal and/or tumor cell survival. Thus, in preferred embodiments modulators of CD324 determinants (phenotypic or genotypic) may be advantageously be used to reduce tumor initiating cell frequency in accordance with the present teachings and thereby facilitate the treatment or management of proliferative disorders.

For the purposes of the instant application the term "tumor initiating cell" (TIC) encompasses both "tumor perpetuating cells" (TPC; i.e., cancer stem cells or CSC) and highly proliferative "tumor progenitor cells" (termed TProg), which together generally comprise a unique subpopulation (i.e. 0.1-40%) of a bulk tumor or mass. For the purposes of the instant disclosure the Willis "tumor perpetuating cells" and "cancer stem cells" or "neoplastic stem cells" are equivalent and may be used interchangeably herein. TPC differ from TProg in that TPC can completely recapitulate the composition of tumor cells existing within a tumor and have unlimited self-renewal capacity as demonstrated by serial transplantation (two or more passages through mice) of low numbers of isolated cells, whereas TProg will not display unlimited self-renewal capacity.

Those skilled in the art will appreciate that fluorescence-activated cell sorting (FACS) using appropriate cell surface markers is a reliable method to isolate highly enriched cancer stem cell subpopulations (e.g., >99.5% purity) due, at least in part, to its ability to discriminate between single cells and clumps of cells (i.e. doublets, etc.). Using such techniques it has been shown that when low cell numbers of highly purified TProg cells are transplanted into immuno-compromised mice they can fuel tumor growth in a primary transplant. However, unlike purified TPC subpopulations the TProg generated tumors do not completely reflect the parental tumor in phenotypic cell heterogeneity and are demonstrably inefficient at reinitiating serial tumorigenesis in subsequent transplants. In contrast, TPC subpopulations completely reconstitute the cellular heterogeneity of parental tumors and can efficiently initiate tumors when serially isolated and transplanted. Thus, those skilled in the art will recognize that a definitive difference between TPC and TProg, though both may be tumor generating in primary transplants, is the unique ability of TPC to perpetually fuel heterogeneous tumor growth upon serial transplantation at low cell numbers. Other common approaches to characterize TPC involve morphology and examination of cell surface markers, transcriptional profile, and drug response although marker expression may change with culture conditions and with cell line passage in vitro.

Accordingly, for the purposes of the instant invention tumor perpetuating cells, like normal stem cells that support cellular hierarchies in normal tissue, are preferably defined by their ability to self-renew indefinitely while maintaining the capacity for multilineage differentiation. Tumor perpetuating cells are thus capable of generating both tumorigenic progeny (i.e., tumor initiating cells: TPC and TProg) and non-tumorigenic (NTG) progeny. As used herein a "non-tumorigenic cell" (NTG) refers to a tumor cell that arises from tumor initiating cells, but does not itself have the capacity to self-renew or generate the heterogeneous lineages of tumor cells that comprise a tumor. Experimentally, NTG cells are incapable of reproducibly forming tumors in mice, even when transplanted in excess cell numbers.

As indicated, TProg are also categorized as tumor initiating cells (or TIC) due to their limited ability to generate tumors in mice. TProg are progeny of TPC and are typically capable of a finite number of non-self-renewing cell divisions. Moreover, TProg cells may further be divided into early tumor progenitor cells (ETP) and late tumor progenitor cells (LTP), each of which may be distinguished by phenotype (e.g., cell surface markers) and different capacities to recapitulate tumor cell architecture. In spite of such technical differences, both ETP and LTP differ functionally from TPC in that they are generally less capable of serially reconstituting tumors when transplanted at low cell numbers and typically do not reflect the heterogeneity of the parental tumor. Notwithstanding the foregoing distinctions, it has also been shown that various TProg populations can, on rare occasion, gain self-renewal capabilities normally attributed to stem cells and themselves become TPC (or CSC). In any event both types of tumor-initiating cells are likely represented in the typical tumor mass of a single patient and are subject to treatment with the modulators as disclosed herein. That is, the disclosed compositions are generally effective in reducing the frequency or altering the chemosensitivity of such CD324 positive tumor initiating cells regardless of the particular embodiment or mix represented in a tumor.

In the context of the instant invention, TPC are more tumorigenic, relatively more quiescent and often more chemoresistant than the TProg (both ETP and LTP), NTG cells and the tumor-infiltrating non-TPC derived cells (e.g., fibroblasts/stroma, endothelial & hematopoietic cells) that comprise the bulk of a tumor. Given that conventional therapies and regimens have, in large part, been designed to both debulk tumors and attack rapidly proliferating cells, TPC are likely to be more resistant to conventional therapies and regimens than the faster proliferating TProg and other bulk tumor cell populations. Further, TPC often express other characteristics that make them relatively chemoresistant to conventional therapies, such as increased expression of multi-drug resistance transporters, enhanced DNA repair mechanisms and anti-apoptotic proteins. These properties, each of which contribute to drug tolerance by TPC, constitute a key reason for the failure of standard oncology treatment regimens to ensure long-term benefit for most patients with advanced stage neoplasia; i.e. the failure to adequately target and eradicate those cells that fuel continued tumor growth and recurrence (i.e. TPC or CSC).

Unlike many prior art treatments, the novel compositions of the present invention preferably reduce the frequency of tumor initiating cells upon administration to a subject regardless of the form or specific target (e.g., genetic material, CD324 antibody or ligand fusion construct) of the selected modulator. As noted above, the reduction in tumor initiating cell frequency may occur as a result of a) elimination, depletion, sensitization, silencing or inhibition of tumor initiating cells; b) controlling the growth, expansion or recurrence of tumor initiating cells; c) interrupting the initiation, propagation, maintenance, or proliferation of tumor initiating cells; or d) by otherwise hindering the survival, regeneration and/or metastasis of the tumorigenic cells. In some embodiments, the reduction in the frequency of tumor initiating cells occurs as a result of a change in one or more physiological pathways. The change in the pathway, whether by reduction or elimination of the tumor initiating cells or by modifying their potential (e.g., induced differentiation, niche disruption) or otherwise interfering with their ability to exert affects on the tumor environment or other cells, in turn allows for the more effective treatment of CD324 associated disorders by inhibiting tumorigenesis, tumor maintenance and/or metastasis and recurrence.

Among art-recognized methods that can be used to assess such a reduction in the frequency of tumor initiating cells is limiting dilution analysis either in vitro or in vivo, preferably followed by enumeration using Poisson distribution statistics or assessing the frequency of predefined definitive events such as the ability to generate tumors in vivo or not. While such limiting dilution analysis comprise preferred methods of calculating reduction of tumor initiating cell frequency other, less demanding methods, may also be used to effectively determine the desired values, albeit slightly less accurately, and are entirely compatible with the teachings herein. Thus, as will be appreciated by those skilled in the art, it is also possible to determine reduction of frequency values through well-known flow cytometric or immunohistochemical means. As to all the aforementioned methods see, for example, Dylla et al. 2008, PMID: 18560594 & Hoey et al. 2009, PMID: 19664991; each of which is incorporated herein by reference in its entirety.

With respect to limiting dilution analysis, in vitro enumeration of tumor initiating cell frequency may be accomplished by depositing either fractionated or unfractionated human tumor cells (e.g. from treated and untreated tumors, respectively) into in vitro growth conditions that foster colony formation. In this manner, colony forming cells might be enumerated by simple counting and characterization of colonies, or by analysis consisting of, for example, the deposition of human tumor cells into plates in serial dilutions and scoring each well as either positive or negative for colony formation at least 10 days after plating. In vivo limiting dilution experiments or analyses, which are generally more accurate in their ability to determine tumor initiating cell frequency encompass the transplantation of human tumor cells, from either untreated control or treated populations, for example, into immunocompromised mice in serial dilutions and subsequently scoring each mouse as either positive or negative for tumor formation at least 60 days after transplant. The derivation of cell frequency values by limiting dilution analysis in vitro or in vivo is preferably done by applying Poisson distribution statistics to the known frequency of positive and negative events, thereby providing a frequency for events fulfilling the definition of a positive event; in this case, colony or tumor formation, respectively.

As to other methods compatible with the instant invention that may be used to calculate tumor initiating cell frequency, the most common comprise quantifiable flow cytometric techniques and immunohistochemical staining procedures. Though not as precise as the limiting dilution analysis techniques described immediately above, these procedures are much less labor intensive and provide reasonable values in a relatively short time frame. Thus, it will be appreciated that a skilled artisan may use flow cytometric cell surface marker profile determination employing one or more antibodies or reagents that bind art recognized cell surface proteins known to enrich for tumor initiating cells (see Example 1 below and PCT application 2012/031280, which is incorporated herein in its entirety) and thereby measure TIC levels from various samples. In still another compatible method one skilled in the art might enumerate TIC frequency in situ (e.g., in a tissue section) by immunohistochemistry using one or more antibodies or reagents that are able to bind cell surface proteins thought to demarcate these cells.

Those skilled in the art will recognize that numerous markers (or their absence) have been associated with various populations of cancer stem cells and used to isolate or characterize tumor cell subpopulations. In this respect exemplary cancer stem cell markers comprise OCT4, Nanog, STAT3, EPCAM, CD24, CD34, NB84, TrkA, GD2, CD133, CD20, CD56, CD29, B7H3, CD46, transferrin receptor, JAM3, carboxypeptidase M, oncostatin M, Lgr5, Lgr6, CD325, nestin, Sox1, Bmi-1, eed, easyh1, easyh2, mf2, yy1, smarcA3, smarckA5, smarcD3, smarcE1, mllt3, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4) SLC7A8, IL1RAP, TEM8, TMPRSS4, MUC16, GPRC5B, SLC6A14, SLC4A11, PPAP2C, CAV1, CAV2, PTPN3, EPHA1, EPHA2, SLC1A1, CX3CL1, ADORA2A, MPZL1, FLJ10052, C4.4A, EDG3, RARRES1, TMEPAI, PTS, CEACAM6, NID2, STEAP, ABCA3, CRIM1, IL1R1, OPN3, DAF, MUC1, CPD, NMA, ADAM9, GJA1, SLC19A2, ABCA1, PCDH7, ADCY9, SLC39A1, NPC1, ENPP1, N33, GPNMB, LY6E, CELSR1, LRP3, C20orf52, TMEPAI, FLVCR, PCDHA10, GPR54, TGFBR3, SEMA4B, PCDHB2, ABCG2, CD166, AFP, BMP-4, β-catenin, CD2, CD3, CD9, CD14, CD31, CD38, CD44, CD45, CD74, CD90, CXCR4, decorin, EGFR, CD105, CD64, CD16, CD16a, CD16b, GLI1, GLI2, CD49b, and CD49f. See, for example, Schulenburg et al., 2010, PMID: 20185329, U.S. Pat. No. 7,632,678 and U.S.P.Ns. 2007/0292414, 2008/0175870, 2010/0275280, 2010/0162416 and 2011/0020221 each of which is incorporated herein by reference. It will further be appreciated that each of the aforementioned markers may also be used as a secondary target antigen in the context of the bispecific or multispecific antibodies of the instant invention.

Similarly, non-limiting examples of cell surface phenotypes associated with cancer stem cells of certain tumor types include $CD44^{hi}CD24^{low}$, $ALDH^+$, $CD133^+$, $CD123^+$, $CD34^+CD38^-$, $CD44^+CD24^-$, $CD46^{hi}CD324^+CD66c^-$, $CD133^+CD34^+CD10^-CD19^-$, $CD138^-CD34^-CD19^+$, $CD133^+RC2^+$, $CD44^+\alpha_2, \beta_1{}^{hi}CD133+$, $CD44^+CD24^+ESA^+$, $CD271^+$, $ABCB5^+$ as well as other cancer stem cell surface phenotypes that are known in the art. See, for example, Schulenburg et al., 2010, supra, Visvader et al., 2008, PMID: 18784658 and U.S.P.N. 2008/0138313, each of which is incorporated herein in its entirety by reference. Those skilled in the art will appreciate that marker phenotypes such as those exemplified immediately above may be used in conjunction with standard flow cytometric analysis and cell sorting techniques to characterize, isolate, purify or enrich TIC and/or TPC cells or cell populations for further analysis. Of interest with regard to the instant invention CD46, CD324 and, optionally, CD66c are either highly or heterogeneously expressed on the surface of many human colorectal ("CR"), breast ("BR"), non-small cell lung (NSCLC), small cell lung (SCLC), pancreatic ("PA"), melanoma ("Mel"), ovarian ("OV"), and head and neck cancer ("HN") tumor cells, regardless of whether the tumor specimens being analyzed were primary patient tumor specimens or patient-derived NTX tumors.

Using any of the above-referenced methods it is then possible to quantify the reduction in frequency of TIC (or the TPC therein) provided by the disclosed CD324 modulators (including those conjugated to cytotoxic agents) in accordance with the teachings herein. In some instances, the compounds of the instant invention may reduce the frequency of TIC (by a variety of mechanisms noted above, including elimination, induced differentiation, niche disruption, silencing, etc.) by 10%, 15%, 20%, 25%, 30% or even by 35%. In other embodiments, the reduction in frequency of TIC may be on the order of 40%, 45%, 50%, 55%, 60% or 65%. In certain embodiments, the disclosed compounds my reduce the frequency of TIC by 70%, 75%, 80%, 85%, 90% or even 95%. Of course it will be appreciated that any reduction of the frequency of the TIC likely results in a corresponding reduction in the tumorigenicity, persistence, recurrence and aggressiveness of the neoplasia.

IV. CD324 Modulators

In any event, the present invention is directed to the use of CD324 modulators, including CD324 antagonists, for the diagnosis, theragnosis, treatment and/or prophylaxis of various disorders including any one of a number of CD324 associated malignancies. The disclosed modulators may be used alone or in conjunction with a wide variety of anti-cancer compounds such as chemotherapeutic or immunotherapeutic agents (e.g., therapeutic antibodies) or biological response modifiers. In other selected embodiments, two or more discrete CD324 modulators may be used in combination to provide enhanced anti-neoplastic effects or may be used to fabricate multispecific constructs.

In certain embodiments, the CD324 modulators of the present invention will comprise nucleotides, oligonucleotides, polynucleotides, peptides or polypeptides. More particularly, exemplary modulators of the invention may comprise antibodies and antigen-binding fragments or derivatives thereof, multispecific antibodies, proteins, peptides, glycoproteins, glycopeptides, glycolipids, polysaccharides, oligosaccharides, nucleic acids, antisense constructs, siRNA, miRNA, bioorganic molecules, peptidomimetics, pharmacological agents and their metabolites, transcriptional and translation control sequences, and the like. In certain embodiments the modulators will comprise soluble CD324 (sCD324) or a form, variant, derivative or fragment thereof including, for example, CD324 fusion constructs (e.g., CD324-Fc, CD324-targeting moiety, etc.) or CD324-conjugates (e.g., CD324-PEG, CD324-cytotoxic agent, CD324-brm, etc.). It will also be appreciated that, in other embodiments, the CD324 modulators comprise antibodies or immunoreactive fragments or derivatives thereof. In particularly preferred embodiments the modulators of the instant invention will comprise neutralizing antibodies or derivatives or fragments thereof. In other embodiments the CD324 modulators may comprise internalizing antibodies or fragments thereof. In still other embodiments the CD324 modulators may comprise depleting antibodies or fragments thereof. Moreover, as with the aforementioned fusion constructs, these antibody modulators may be conjugated, linked or otherwise associated with selected cytotoxic agents, polymers, biological response modifiers (BRMs) or the like to provide directed immunotherapies with various (and optionally multiple) mechanisms of action. In yet other embodiments the modulators may operate on the genetic level and may comprise compounds as antisense constructs, siRNA, miRNA and the like that interact or associate with the genotypic component of a CD324 determinant.

It will further be appreciated that the disclosed CD324 modulators may deplete, silence, neutralize, eliminate or inhibit growth, propagation or survival of tumor cells, including TPC, and/or associated neoplasia through a variety of mechanisms, including agonizing or antagonizing selected pathways, interfering with cell interactions or eliminating specific cells depending, for example, on the form of CD324 modulator, any associated payload or dosing and method of delivery. Accordingly, while preferred embodiments disclosed herein are directed to the depletion, inhibition or silencing of specific tumor cell subpopulations such as tumor perpetuating cells, it must be emphasized that such embodiments are merely illustrative and not limiting in any sense. Rather, as set forth in the appended claims, the present invention is broadly directed to CD324 modulators or to modulators that interact with a specific epitope or domain, and their use in the treatment, management or prophylaxis of various CD324 associated hyperproliferative disorders irrespective of any particular mechanism or target tumor cell population.

Regardless of the form of the modulator selected it will be appreciated that the chosen compound may be antagonistic in nature. As used herein an "antagonist" refers to a molecule capable of neutralizing, blocking, inhibiting, abrogating, reducing or interfering with the activities of a particular or specified target (e.g., CD324), including the binding of receptors to ligands or the interactions of enzymes with substrates. In this respect it will be appreciated that CD324 antagonists of the instant invention may comprise any ligand, polypeptide, peptide, fusion protein, antibody or immunologically active fragment or derivative thereof that recognizes, reacts, binds, combines, competes, associates or otherwise interacts with the CD324 protein or fragment thereof and eliminates, silences, reduces, inhibits, hinders, restrains or controls the growth of tumor initiating cells or other neoplastic cells including bulk tumor or NTG cells. Compatible antagonists may further include small molecule inhibitors, aptamers, antisense constructs, siRNA, miRNA and the like, receptor or ligand molecules and derivatives thereof which recognize or associate with a CD324 genotypic or phenotypic determinant thereby altering expression patterns or sequestering its binding or interaction with a substrate, receptor or ligand.

As used herein and applied to two or more molecules or compounds, the terms "recognizes" or "associates" shall be held to mean the reaction, binding, specific binding, combination, interaction, connection, linkage, uniting, coalescence, merger or joining, covalently or non-covalently, of the molecules whereby one molecule exerts an effect on the other molecule.

Moreover, as demonstrated in the examples herein, some modulators of human CD324 may, in certain cases, cross-react with CD324 from a species other than human (e.g., murine or cyno). In other cases exemplary modulators may be specific for human CD324 and will not exhibit cross-reactivity with CD324 orthologs.

In any event, and as will be discussed in more detail below, those skilled in the art will appreciate that the disclosed modulators may be used in a conjugated or unconjugated form. That is, the modulator may be associated with or conjugated to (e.g. covalently or non-covalently) pharmaceutically active compounds, biological response modifiers, anti-cancer agents, cytotoxic or cytostatic agents, diagnostic moieties or biocompatible modifiers. In this respect it will be understood that such conjugates may comprise peptides, polypeptides, proteins, fusion proteins, nucleic acid molecules, small molecules, mimetic agents, synthetic drugs, inorganic molecules, organic molecules and radioisotopes. Moreover, as indicated herein the selected conjugate may be covalently or non-covalently linked to the CD324 modulator in various molar ratios depending, at least in part, on the method used to effect the conjugation.

V. Modulator Fabrication and Supply
  A. Antibody Modulators
    a. Overview

As previously alluded to particularly preferred embodiments of the instant invention comprise CD324 modulators in the form of antibodies that preferentially associate with CD324 or fragments thereof. Those of ordinary skill in the art will appreciate the well developed knowledge base on antibodies such as set forth, for example, in Abbas et al., Cellular and Molecular Immunology, 6$^{th}$ ed., W.B. Saunders Company (2010) or Murphey et al., Janeway's Immunobiology, 8$^{th}$ ed., Garland Science (2011), each of which is incorporated herein by reference in its entirety.

The term "antibody" is intended to cover polyclonal antibodies, multiclonal antibodies, monoclonal antibodies, chimeric antibodies, humanized and primatized antibodies, human antibodies, recombinantly produced antibodies, intrabodies, multispecific antibodies, bispecific antibodies, monovalent antibodies, multivalent antibodies, anti-idiotypic antibodies, synthetic antibodies, including muteins and variants thereof; antibody fragments such as Fab fragments, F(ab') fragments, single-chain FvFcs, single-chain Fvs; and derivatives thereof including Fc fusions and other modifications, and any other immunologically active molecule so long as they exhibit the desired biological activity (i.e., antigen association or binding). Moreover, the term further comprises all classes of antibodies (i.e. IgA, IgD, IgE, IgG, and IgM) and all isotypes (i.e., IgG1, IgG2, IgG3, IgG4, IgA1, and IgA2), as well as variations thereof unless otherwise dictated by context. Heavy-chain constant domains that correspond to the different classes of antibodies are denoted by the corresponding lower case Greek letter $\alpha$, $\delta$, $\epsilon$, $\gamma$, and $\mu$, respectively. Light chains of the antibodies from any vertebrate species can be assigned to one of two clearly distinct types, called kappa ($\kappa$) and lambda ($\lambda$), based on the amino acid sequences of their constant domains.

While all such antibodies are within the scope of the present invention, preferred embodiments comprising the IgG class of immunoglobulin will be discussed in some detail herein solely for the purposes of illustration. It will be understood that such disclosure is, however, merely demonstrative of exemplary compositions and methods of practicing the present invention and not in any way limiting of the scope of the invention or the claims appended hereto.

As is well known, the variable domains of both the light ($V_L$) and heavy ($V_H$) chain portions determine antigen recognition and specificity and the constant domains of the light chain ($C_L$) and the heavy chain ($C_H1$, $C_H2$ or $C_H3$) confer and regulate important biological properties such as secretion, transplacental mobility, circulation half-life, complement binding, and the like.

The "variable" region includes hypervariable sites that manifest themselves in three segments commonly termed complementarity determining regions (CDRs), in both the light-chain and the heavy-chain variable domains. The more highly conserved portions of variable domains flanking the CDRs are termed framework regions (FRs). For example, in naturally occurring monomeric immunoglobulin G (IgG) antibodies, the six CDRs present on each arm of the "Y" are short, non-contiguous sequences of amino acids that are specifically positioned to form the antigen binding site as the antibody assumes its three dimensional configuration in an aqueous environment. Thus, each naturally occurring IgG antibody comprises two identical binding sites proximal to the amino-terminus of each arm of the Y.

It will be appreciated that the position of CDRs can be readily identified by one of ordinary skill in the art using standard techniques. Also familiar to those in the art is the numbering system described in Kabat et al. (1991, NIH Publication 91-3242, National Technical Information Service, Springfield, Va.). In this regard Kabat et al. defined a numbering system for variable domain sequences that is applicable to any antibody. One of ordinary skill in the art can unambiguously assign this system of "Kabat numbering" to any variable domain sequence, without reliance on any experimental data beyond the sequence itself. Unless otherwise specified, references to the numbering of specific amino acid residue positions in an antibody are according to the Kabat numbering system.

Thus, according to Kabat, in the $V_H$, residues 31-35 comprise CDR1, residues 50-65 make up CDR2, and 95-102 comprise CDR3, while in the $V_L$, residues 24-34 are CDR1, 50-56 comprise CDR2, and 89-97 make up CDR3. For context, in a $V_H$, FR1 corresponds to the domain of the variable region encompassing amino acids 1-30; FR2 corresponds to the domain of the variable region encompassing amino acids 36-49; FR3 corresponds to the domain of the variable region encompassing amino acids 66-94, and FR4 corresponds to the domain of the variable region from amino acids 103 to the end of the variable region. The FRs for the light chain are similarly separated by each of the light chain variable region CDRs.

Note that CDRs vary considerably from antibody to antibody (and by definition will not exhibit homology with the Kabat consensus sequences). In addition, the identity of certain individual residues at any given Kabat site number may vary from antibody chain to antibody chain due to interspecies or allelic divergence. Alternative numbering is set forth in Chothia et al., *J. Mol. Biol.* 196:901-917 (1987) and MacCallum et al., *J. Mol. Biol.* 262:732-745 (1996), although as in Kabat, the FR boundaries are separated by the respective CDR termini as described above. See also Chothia et al., Nature 342, pp. 877-883 (1989) and S. Dubel, ed., *Handbook of Therapeutic Antibodies*, 3$^{rd}$ ed., WILEY-VCH Verlag GmbH and Co. (2007), where the definitions include overlapping or subsets of amino acid residues when compared against each other. Each of the aforementioned references is incorporated herein by reference in its entirety and the amino acid residues which comprise binding regions or CDRs as defined by each of the above cited references and are set forth for comparison below.

CDR Definitions

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 50-58 | 47-58 |
| $V_H$ CDR3 | 95-102 | 95-102 | 93-101 |
| $V_L$ CDR1 | 24-34 | 23-34 | 30-36 |
| $V_L$ CDR2 | 50-56 | 50-56 | 46-55 |
| $V_L$ CDR3 | 89-97 | 89-97 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra In the context of the instant invention it will be appreciated that any of the disclosed light and heavy chain CDRs derived from the murine variable region amino acid sequences set forth in FIG. 11A or FIG. 11B may be combined or rearranged to provide optimized anti-CD324 (e.g. anti-hCD324) antibodies in accordance with the instant teachings. That is, one or more of the CDRs derived from the contiguous light chain variable region amino acid sequences set forth in FIG. 11A (SEQ ID NOS: 20-70, even numbers) or the contiguous heavy chain variable region amino acid sequences set forth in FIG. 11B (SEQ ED NOS: 21-71, odd numbers) may be incorporated in a CD324 modulator and, in particularly preferred embodiments, in a CDR grafted or humanized antibody that immunospecifically associates with one or more CD324 isoforms. An example of light (SEQ ID NO: 72) and heavy (SEQ ID NO: 73) chain variable region amino acid sequences of such a humanized modulator is also set forth in FIGS. 11A and 11B. Taken together these novel amino acid sequences depict twenty-six murine exemplary modulators and a single humanized construct in accordance with the instant invention. Moreover, corresponding nucleic acid sequences of each of the twenty six murine modulators and the exemplary humanized construct set forth in FIGS. 11A and 11B are included in FIG. 19 appended to the instant application (SEQ ID NOS: 120-173).

As discussed herein and demonstrated in the Examples below, one skilled in the art could readily define, identify derive and/or enumerate the CDRs as defined by Kabat et al., Chothia et al. or MacCallum et al. for each respective heavy and light chain sequence set forth in FIG. 11A or FIG. 11B. Accordingly, each of the subject CDRs and antibodies comprising CDRs defined by all such nomenclature are expressly included within the scope of the instant invention. More broadly, the term "variable region CDR amino acid residue" or more simply "CDR" includes amino acids in a CDR as identified using any sequence or structure based method as set forth above.

2. Antibody Modulator Generation a. Polyclonal Antibodies

The production of polyclonal antibodies in various host animals, including rabbits, mice, rats, etc. is well known in the art. In some embodiments, polyclonal anti-CD324 antibody-containing serum is obtained by bleeding or sacrificing the animal. The serum may be used for research purposes in the form obtained from the animal or, in the alternative, the anti-CD324 antibodies may be partially or fully purified to provide immunoglobulin fractions or homogeneous antibody preparations Briefly the selected animal is immunized with a CD324 immunogen (e.g., soluble CD324 or sCD324) which may, for example, comprise selected isoforms, domains and/or peptides, or live cells or cell preparations expressing CD324 or immunoreactive fragments thereof. Art known adjuvants that may be used to increase the immunological response, depending on the inoculated species include, but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants may protect the antigen from rapid dispersal by sequestering it in a local deposit, or they may contain substances that stimulate the host to secrete factors that are chemotactic for macrophages and other components of the immune system. Preferably the immunization schedule will involve two or more administrations of the selected immunogen spread out over a predetermined period of time.

The amino acid sequence of a CD324 protein as shown in FIG. 1C or 1D can be analyzed to select specific regions of the CD324 protein for generating antibodies. For example, hydrophobicity and hydrophilicity analyses of a CD324 amino acid sequence are used to identify hydrophilic regions in the CD324 structure. Regions of a CD324 protein that show immunogenic structure, as well as other regions and domains, can readily be identified using various other methods known in the art, such as Chou-Fasman, Garnier-Robson, Kyte-Doolittle, Eisenberg, Karplus-Schultz or Jameson-Wolf analysis. Average Flexibility profiles can be generated using the method of Bhaskaran R., Ponnuswamy P. K., 1988, Int. J. Pept. Protein Res. 32:242-255. Beta-turn profiles can be generated using the method of Deleage, G., Roux B., 1987, Protein Engineering 1:289-294. Thus, each CD324 region, domain or motif identified by any of these programs or methods is within the scope of the present invention and may be isolated or engineered to provide immunogens giving rise to modulators comprising desired properties. Preferred methods for the generation of CD324 antibodies are further illustrated by way of the Examples provided herein. Methods for preparing a protein or polypeptide for use as an immunogen are well known in the art. Also well known in the art are methods for preparing immunogenic conjugates of a protein with a carrier, such as BSA, KLH or other carrier protein. In some circumstances, direct conjugation using, for example, carbodiimide reagents are used; in other instances linking reagents are effective. Administration of a CD324 immunogen is often conducted by injection over a suitable time period and with use of a suitable adjuvant, as is understood in the art. During the immunization schedule, titers of antibodies can be taken as described in the Examples below to determine adequacy of antibody formation.

b. Monoclonal Antibodies

In addition, the invention contemplates use of monoclonal antibodies. As known in the art, the term "monoclonal antibody" (or mAb) refers to an antibody obtained from a population of substantially homogeneous antibodies, i.e., the individual antibodies comprising the population are identical except for possible mutations (e.g., naturally occurring mutations), that may be present in minor amounts. In certain embodiments, such a monoclonal antibody includes an antibody comprising a polypeptide sequence that binds or associates with an antigen wherein the antigen-binding polypeptide sequence was obtained by a process that includes the selection of a single target binding polypeptide sequence from a plurality of polypeptide sequences.

More generally, and as exemplified in Example 3 herein, monoclonal antibodies can be prepared using a wide variety of techniques known in the art including hybridoma, recombinant techniques, phage display technologies, transgenic animals (e.g., a XenoMouse®) or some combination thereof. For example, monoclonal antibodies can be produced using hybridoma and art-recognized biochemical and genetic engineering techniques such as described in more detail in Al-Rubeai, *Antibody Expression and Production (Cell Engineering)* Springer Science+Business Media LLC, 1$^{st}$ ed. 2011; An, Zhigiang (ed.) *Therapeutic Monoclonal Antibodies: From Bench to Clinic*, John Wiley and Sons, 1$^{st}$ ed. 2009; Shire et. Al. (eds.) *Current Trends in Monoclonal Antibody Development and Manufacturing*, Springer Science Business Media LLC, 1$^{st}$ ed. 2010; Harlow et al., *Antibodies: A Laboratory Manual*, Cold Spring Harbor Laboratory Press, 2nd ed. 1988; Hammerling, et al., in: *Monoclonal Antibodies and T-Cell Hybridomas* 563-681 (Elsevier, N.Y., 1981) each of which is incorporated herein in its entirety by reference. It should be understood that a selected binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also an antibody of this invention.

c. Chimeric Antibodies

In another embodiment, the antibody of the invention may comprise chimeric antibodies derived from covalently joined protein segments from at least two different species or types of antibodies. As known in the art, the term "chimeric" antibodies is directed to constructs in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81:6851-6855 (1984)).

In one embodiment, a chimeric antibody in accordance with the teachings herein may comprise murine $V_H$ and $V_L$ amino acid sequences and constant regions derived from human sources. In other compatible embodiments a chimeric antibody of the present invention may comprise a humanized antibody as described below. In another embodiment, the so-called "CDR-grafted" antibody, the antibody comprises one or more CDRs from a particular species or belonging to a particular antibody class or subclass, while the remainder of the antibody chain(s) is/are identical with or homologous to a corresponding sequence in antibodies derived from another species or belonging to another antibody class or subclass. For use in humans, selected rodent CDRs may be grafted into a human antibody, replacing one or more of the naturally occurring variable regions or CDRs of the human antibody. These constructs generally have the advantages of providing full strength modulator functions (e.g., CDC (complement dependent cytotoxicity), ADCC (antibody-dependent cell-mediated cytotoxicity), etc.) while reducing unwanted immune responses to the antibody by the subject.

d. Humanized Antibodies

Similar to the CDR-grafted antibody is a "humanized" antibody. As used herein, "humanized" forms of non-human (e.g., murine) antibodies are chimeric antibodies that contain a minimal sequence derived from one or more non-human immunoglobulins. In one embodiment, a humanized antibody is a human immunoglobulin (recipient or acceptor antibody) in which residues from a CDR of the recipient are replaced by residues from a CDR of a non-human species (donor antibody) such as mouse, rat, rabbit, or nonhuman primate having the desired specificity, affinity, and/or capacity. In certain preferred embodiments, residues in one or more FRs in the variable domain of the human immunoglobulin are replaced by corresponding non-human residues from the donor antibody to help maintain the appropriate three-dimensional configuration of the grafted CDR(s) and thereby improve affinity. Furthermore, humanized antibodies may comprise residues that are not found in the recipient antibody or in the donor antibody to, for example, further refine antibody performance.

CDR grafting and humanized antibodies are described, for example, in U.S. Pat. Nos. 6,180,370 and 5,693,762. The humanized antibody optionally may also comprise at least a portion of an immunoglobulin Fe, typically that of a human immunoglobulin. For further details, see, e.g., Jones et al., *Nature* 321:522-525 (1986); and U.S. Pat. Nos. 6,982,321 and 7,087,409. Still another method is termed "humaneering" which is described, for example, in U.S.P.N. 2005/0008625. Additionally, a non-human antibody may also be modified by specific deletion of human T-cell epitopes or "deimmunization" by the methods disclosed in WO 98/52976 and WO 00/34317. Each of the aforementioned references are incorporated herein in their entirety.

Humanized antibodies may also be bioengineered using common molecular biology techniques, such as isolating, manipulating, and expressing nucleic acid sequences that encode all or part of immunoglobulin variable regions from at least one of a heavy or light chain. In addition to the sources of such nucleic acid noted above, human germline sequences are available as disclosed, for example, in Tomlinson, L A. et al. (1992) *J. Mol. Biol.* 227:776-798; Cook, G. P. et al. (1995) *Immunol. Today* 16: 237-242; Chothia, D. et al. (1992) *J. Mol. Biol.* 227:799-817; and Tomlinson et al. (1995) *EMBO J* 14:4628-4638. The V-BASE directory (VBASE2 Retter et al., Nucleic Acid Res. 33; 671-674, 2005) provides a comprehensive directory of human immunoglobulin variable region sequences (compiled by Tomlinson, I. A. et al. MRC Centre for Protein Engineering, Cambridge, UK). Consensus human Fits can also be used, e.g., as described in U.S. Pat. No. 6,300,064.

In selected embodiments, and as detailed in Example 8 below, at least 60%, 65%, 70%, 75%, or 80% of the humanized antibody heavy or light chain variable region amino acid residues will correspond to those of the recipient FR and CDR sequences. In other embodiments at least 85% or 90% of the humanized antibody variable region residues will correspond to those of the recipient FR and CDR sequences. In a further preferred embodiment, greater than 95% of the humanized antibody variable region residues will correspond to those of the recipient FR and CDR sequences.

e. Human Antibodies

In another embodiment, the antibodies may comprise fully human antibodies. The term "human antibody" refers to an antibody which possesses an amino acid sequence that corresponds to that of an antibody produced by a human and/or has been made using any of the techniques for making human antibodies.

Human antibodies can be produced using various techniques known in the art. One technique is phage display in which a library of (preferably human) antibodies is synthesized on phages, the library is screened with the antigen of interest or an antibody-binding portion thereof, and the phage that binds the antigen is isolated, from which one may obtain the immunoreactive fragments. Methods for preparing and screening such libraries are well known in the art and kits for generating phage display libraries are commercially available (e.g., the Pharmacia Recombinant Phage Antibody System, catalog no. 27-9400-01; and the Stratagene SurfZAP™ phage display kit, catalog no. 240612). There also are other methods and reagents that can be used in generating and screening antibody display libraries (see, e.g., U.S. Pat. No. 5,223,409; PCT Publication Nos. WO 92/18619, WO 91/17271, WO 92/20791, WO 92/15679, WO 93/01288, WO 92/01047, WO 92/09690; and Barbas et al., *Proc. Natl. Acad. Sci. USA* 88:7978-7982 (1991)).

In one embodiment, recombinant human antibodies may be isolated by screening a recombinant combinatorial antibody library prepared as above. In one embodiment, the library is a scFv phage display library, generated using human $V_L$ and $V_H$ cDNAs prepared from mRNA isolated from B-cells.

The antibodies produced by naive libraries (either natural or synthetic) can be of moderate affinity ($K_a$ of about $10^6$ to $10^7$ $M^{-1}$), but affinity maturation can also be mimicked in vitro by constructing and reselecting from secondary libraries as described in the art. For example, mutation can be introduced at random in vitro by using error-prone polymerase (reported in Leung et al., *Technique,* 1: 11-15 (1989)), Additionally, affinity maturation can be performed by randomly mutating one or more CDRs, e.g. using PCR with primers carrying random sequence spanning the CDR of interest, in selected individual Fv clones and screening for higher-affinity clones. WO 9607754 described a method for inducing mutagenesis in a CDR of an immunoglobulin light chain to create a library of light chain genes. Another effective approach is to recombine the $V_H$ or $V_L$ domains selected by phage display with repertoires of naturally occurring V domain variants obtained from unimmunized donors and to screen for higher affinity in several rounds of chain reshuffling as described in Marks et al., *Biotechnol.,* 10: 779-783 (1992). This technique allows the production of antibodies and antibody fragments with a dissociation constant $K_D$ ($k_{off}/k_{on}$) of about $10^{-9}$ M or less.

In other embodiments, similar procedures may be employed using libraries comprising eukaryotic cells (e.g., yeast) that express binding pairs on their surface. See, for example, U.S. Pat. No. 7,700,302 and U.S. Ser. No. 12/404, 059. In one embodiment, the human antibody is selected from a phage library, where that phage library expresses human antibodies (Vaughan et al. *Nature Biotechnology* 14:309-314 (1996): Sheets et al. *Proc. Natl. Acad. Sci. USA* 95:6157-6162 (1998)). In other embodiments, human binding pairs may be isolated from combinatorial antibody libraries generated in eukaryotic cells such as yeast. See e.g., U.S. Pat. No. 7,700,302. Such techniques advantageously allow for the screening of large numbers of candidate modulators and provide for relatively easy manipulation of candidate sequences (e.g., by affinity maturation or recombinant shuffling).

Human antibodies can also be made by introducing human immunoglobulin loci into transgenic animals, e.g., mice in which the endogenous immunoglobulin genes have been partially or completely inactivated and human immunoglobulin genes have been introduced. Upon challenge, human antibody production is observed, which closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; 5,661, 016, and 6,075,181 and 6,150,584 regarding XenoMouse® technology; and Lonberg and Huszar, *Intern. Rev. Immunol.* 13:65-93 (1995). Alternatively, the human antibody may be prepared via immortalization of human B lymphocytes producing an antibody directed against a target antigen (such B lymphocytes may be recovered from an individual suffering from a neoplastic disorder or may have been immunized in vitro). See, e.g., Cole et al., *Monoclonal Antibodies and Cancer Therapy*, Alan R. Liss, p. 77 (1985); Boemer et al., *J. Immunol,* 147 (1):86-95 (1991); and U.S. Pat. No. 5,750,373.

3. Further Processing

No matter how obtained, modulator-producing cells (e.g., hybridomas, yeast colonies, etc.) may be selected, cloned and further screened for desirable characteristics including, for example, robust growth, high antibody production and, as discussed in more detail below, desirable antibody characteristics. Hybridomas can be expanded in vivo in syngeneic animals, in animals that lack an immune system, e.g., nude mice, or in cell culture in vitro. Methods of selecting, cloning and expanding hybridomas and/or colonies, each of which produces a discrete antibody species, are well known to those of ordinary skill in the art.

B. Recombinant Modulator Production

1. Overview

Once the source is perfected DNA encoding the desired CD324 modulators may be readily isolated and sequenced using conventional procedures (e.g., by using oligonucleotide probes that are capable of binding specifically to genes encoding antibody heavy and light chains). Isolated and subcloned hybridoma cells (or phage or yeast derived colonies) may serve as a preferred source of such DNA if the modulator is an antibody. If desired, the nucleic acid can further be manipulated as described herein to create agents including fusion proteins, or chimeric, humanized or fully human antibodies. More particularly, isolated DNA (which may be modified) can be used to clone constant and variable region sequences for the manufacture antibodies.

Accordingly, in exemplary embodiments antibodies may be produced recombinantly, using conventional procedures (such as those set forth in Al-Rubeai; An, and Shire et. al. all supra, and Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002)) in which the isolated and subcloned hybridoma cells (or phage or yeast derived colonies) serve as a preferred source of nucleic acid molecules.

The term "nucleic acid molecule", as used herein, is intended to include DNA molecules and RNA molecules and artificial variants thereof (e.g., peptide nucleic acids), whether single-stranded or double-stranded. The nucleic acids may encode one or both chains of an antibody of the invention, or a fragment or derivative thereof. The nucleic acid molecules of the invention also include polynucleotides sufficient for use as hybridization probes, PCR primers or sequencing primers for identifying, analyzing, mutating or amplifying a polynucleotide encoding a polypeptide; antisense nucleic acids for inhibiting expression of a polynucleotide, and as well as complementary sequences. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector.

It will be appreciated that such nucleic acid sequences can further be manipulated to create modulators including chimeric, humanized or fully human antibodies. More particularly, isolated nucleic acid molecules (which may be modified) can be used to clone constant and variable region sequences for the manufacture antibodies as described in U.S. Pat. No. 7,709,611.

The term "isolated nucleic acid" means a that the nucleic acid was (i) amplified in vitro, for example by polymerase chain reaction (PCR), (ii) recombinantly produced by cloning, (iii) purified, for example by cleavage and gel-electrophoretic fractionation, or (iv) synthesized, for example by chemical synthesis. An isolated nucleic acid is a nucleic acid that is available for manipulation by recombinant DNA techniques.

Whether the source of the nucleic acid encoding the desired immunoreactive portion of the antibody is obtained or derived from phage display technology, yeast libraries, hybridoma-based technology or synthetically, it is to be understood that the present invention encompasses the nucleic acid molecules and sequences encoding the antibodies or antigen-binding fragments or derivatives thereof. Further, the instant invention is directed to vectors and host cells comprising such nucleic acid molecules.

2. Hybridization and Sequence Identity

As indicated, the invention further provides nucleic acids that hybridize to other nucleic acids under particular hybridization conditions. More specifically the invention encompasses nucleic acids molecules that hybridize under moderate or high stringency hybridization conditions (e.g., as defined below), to the nucleic acid molecules of the invention. Methods for hybridizing nucleic acids are well-known in the art. As is well known, a moderately stringent hybridization conditions comprise a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. By way of comparison hybridization under highly stringent hybridization conditions comprise washing with 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65%, 70%, 75%, 80%, 85%, 90%, 95%, 98% or 99% identical to each other typically remain hybridized to each other.

The invention also includes nucleic acid molecules that are "substantially identical" to the described nucleic acid molecules. In one embodiment, the term substantially identical with regard to a nucleic acid sequence means may be construed as a sequence of nucleic acid molecules exhibiting at least about 65%, 70%, 75%, 80%, 85%, or 90% sequence identity. In other embodiments, the nucleic acid molecules exhibit 95% or 98% sequence identity to the reference nucleic acid sequence.

The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the nucleic acid.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, the sequence analysis tool GCG (Accelrys Software Inc.) contains programs such as "GAP" and "BEST-FIT" which can be used with default parameters to determine sequence homology or sequence identity between closely related polypeptides, such as homologous polypeptides from different species of organisms or between a wild type protein and a mutein thereof. (See, e.g., GCG Version 6.1 or Durbin et. Al., *Biological Sequence Analysis: Probabilistic models of proteins and nucleic acids.*, Cambridge Press (1998)).

Polypeptide sequences can also be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially blastp or tblastn, using default parameters. See, e.g., Altschul et al. (1990) J. Mol. Biol. 215: 403 410 and Altschul et al. (1997) Nucleic Acids Res. 25:3389 402, each of which is herein incorporated by reference.

In this regard the invention also includes nucleic acid molecules that encode polypeptides that are "substantially identical" with respect to an antibody variable region polypeptide sequence (e.g., either the donor light or heavy chain variable region or the acceptor light or heavy chain variable region. As applied to such polypeptides, the term "substantial identity" or "substantially identical" means that two peptide sequences, when optimally aligned, such as by the programs GAP or BEST-FIT using default gap weights, share at least 65% sequence identity, preferably at least 70%, 75%, 80%, 85%, or 90% sequence identity, even more preferably at least 93%, 95%, 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution.

3. Expression

The varied processes of recombinant expression, i.e., the production of RNA or of RNA and protein/peptide, are well known as set forth, for example, in Berger and Kimmel, Guide to Molecular Cloning Techniques, *Methods in Enzymology* volume 152 Academic Press, Inc., San Diego, Calif.; Sambrook et al., *Molecular Cloning-A Laboratory Manual* (3rd Ed.), Vol. 1-3, Cold Spring Harbor Laboratory, Cold Spring Harbor, N.Y., (2000); and *Current Protocols in Molecular Biology*, F. M. Ausubel et al., eds., Current Protocols, a joint venture between Greene Publishing Associates, Inc. and John Wiley & Sons, Inc., (supplemented through 2006).

Certain terms of interest include "expression control sequence" which comprises promoters, ribosome binding sites, enhancers and other control elements which regulate transcription of a gene or translation of mRNA. As is well known, a "promoter" or "promoter region" relates to a nucleic acid sequence which generally is located upstream (5') to the nucleic acid sequence being expressed and controls expression of the sequence by providing a recognition and binding site for RNA-polymerase.

Exemplary promoters which are compatible according to the invention include promoters for SP6, T3 and T7 polymerase, human U6 RNA promoter, CMV promoter, and artificial hybrid promoters thereof (e.g. CMV) where a part or parts are fused to a part or parts of promoters of genes of other cellular proteins such as e.g. human GAPDH (glyceraldehyde-3-phosphate dehydrogenase), and including or not including (an) additional intron(s).

In certain embodiments, the nucleic acid molecule may be present in a vector, where appropriate with a promoter, which controls expression of the nucleic acid. The well known term "vector" comprises any intermediary vehicle for a nucleic acid which enables said nucleic acid, for example, to be introduced into prokaryotic and/or eukaryotic cells and, where appropriate, to be integrated into a genome. Methods of transforming mammalian cells are well known in the art. See, for example, U.S. Pat. Nos. 4,399,216, 4,912,040, 4,740,461, and 4,959,455. The vectors may include a nucleotide sequence encoding an antibody of the invention (e.g., a whole antibody, a heavy or light chain of an antibody, a $V_H$ or $V_L$ of an antibody, or a portion thereof, or a heavy- or light-chain CDR, a single chain Fv, or fragments or variants thereof), operably linked to a promoter (see, e.g., PCT Publication WO 86/05807; PCT Publication WO 89/01036; and U.S. Pat. No. 5,122,464).

A variety of host-expression vector systems are commercially available, and many are compatible with the teachings herein and may be used to express the modulators of the invention. Such systems include, but are not limited to, microorganisms such as bacteria (e.g., *E. coli, B. subtilis, streptomyces*) transformed with recombinant bacteriophage DNA, plasmid DNA or cosmid DNA expression vectors containing modulator coding sequences; yeast (e.g., *Saccharomyces, Pichia*) transfected with recombinant yeast expression vectors containing modulator coding sequences; insect cell systems infected with recombinant virus expression vectors (e.g., baculovirus) containing modulator coding sequences; plant cell systems (e.g., *Nicotiana, Arabidopsis*, duckweed, corn, wheat, potato, etc.) infected with recombinant viral expression vectors (e.g., cauliflower mosaic virus; tobacco mosaic virus) or transfected with recombinant plasmid expression vectors (e.g., Ti plasmid) containing modulator coding sequences; or mammalian cell systems (e.g., COS, CHO, BHK, 293, 3T3 cells, etc.) harboring recombinant expression constructs containing promoters derived from the genome of mammalian cells (e.g., metallothionein promoter) or from mammalian viruses (e.g., the adenovirus late promoter; the vaccinia virus 7.5K promoter).

As used herein, the term "host cell" covers any kind of cellular system which can be engineered to generate the polypeptides and antigen-binding molecules of the present invention. In one embodiment, the host cell is engineered to allow the production of an antigen binding molecule with modified glycoforms. In a preferred embodiment, the antigen binding molecule, or variant antigen binding molecule, is an antibody, antibody fragment, or fusion protein. In certain embodiments, the host cells have been further manipulated to express increased levels of one or more polypeptides having N-acetylglucosaminyltransferase III (GnTIII) activity. Compatible host cells include cultured cells, e.g., mammalian cultured cells, such as CHO cells, BHK cells, NSO cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

For long-term, high-yield production of recombinant proteins stable expression is preferred. Accordingly, cell lines that stably express the selected modulator may be engineered using standard art recognized techniques. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Any of the selection systems well known in the art may be used, including the glutamine synthetase gene expression system (the GS system) which provides an efficient approach for enhancing expression under certain conditions. The GS system is discussed in whole or part in connection with EP patents 0 216 846, 0 256 055, 0 323 997 and 0 338 841 and U.S. Pat. Nos. 5,591,639 and 5,879,936 each of which is incorporated herein by reference. Another preferred expression system, the Freedom™ CHO-S Kit is commercially provided by Life Technologies (Catalog Number A13696-01) also allows for the development of stable cell lines that may be used for modulator production.

Such host-expression systems represent vehicles by which the coding sequences of interest may be produced and subsequently purified, but also represent cells which may, when transformed or transfected with the appropriate nucleotide coding sequences, express a molecule of the invention in situ. The host cell may be co-transfected with two expression vectors of the invention, for example, the first vector encoding a heavy chain derived polypeptide and the second vector encoding a light chain derived polypeptide.

Thus, in certain embodiments, the present invention provides recombinant host cells allowing for the expression of antibodies or portions thereof. Antibodies produced by expression in such recombinant host cells are referred to herein as recombinant antibodies. The present invention also provides progeny cells of such host cells, and antibodies produced by the same.

C. Chemical Synthesis

In addition, the modulators may be chemically synthesized using techniques known in the art (e.g., see Creighton, 1983, Proteins: Structures and Molecular Principles, W.H. Freeman & Co., N.Y., and Hunkapiller, M., et al., 1984, Nature 310:105-111). Furthermore, if desired, nonclassical amino acids or chemical amino acid analogs (such as D-isomers of the common amino acids, 2,4-diaminobutyric acid, a-amino isobutyric acid, 4-aminobutyric acid, and the like) can be introduced as a substitution or addition into a polypeptide sequence.

D. Transgenic Systems

In other embodiments modulators may be produced transgenically through the generation of a mammal or plant that is transgenic for recombinant molecules such as the immunoglobulin heavy and light chain sequences and that produces the desired compounds in a recoverable form. This includes, for example, the production of protein modulators (e.g., antibodies) in, and recovery from, the milk of goats, cows, or other mammals. See, e.g., U.S. Pat. Nos. 5,827,690, 5,756,687, 5,750,172, and 5,741,957. In some embodiments, non-human transgenic animals that comprise human immunoglobulin loci are immunized to produce antibodies.

Other transgenic techniques are set forth in Hogan et al., Manipulating the Mouse Embryo: A Laboratory Manual 2nd ed., Cold Spring Harbor Press (1999); Jackson et al., Mouse Genetics and Transgenics: A Practical Approach, Oxford University Press (2000); and Pinkert, Transgenic Animal Technology: A Laboratory Handbook, Academic Press (1999) and U.S. Pat. No. 6,417,429. In some embodiments, the non-human animals are mice, rats, sheep, pigs, goats, cattle or horses, and the desired product is produced in blood, milk, urine, saliva, tears, mucus and other bodily fluids from which it is readily obtainable using art recognized purification techniques.

Other compatible production systems include methods for making antibodies in plants such as described, for example, in U.S. Pat. Nos. 6,046,037 and 5,959,177 which are incorporated herein with respect to such techniques.

E. Isolation/Purification

Once a modulator of the invention has been produced by recombinant expression or any other of the disclosed techniques, it may be purified by any method known in the art for purification of immunoglobulins or proteins. In this respect the modulator may be "isolated" which means that it has been identified and separated and/or recovered from a component of its natural environment. Contaminant components of its natural environment are materials that would interfere with diagnostic or therapeutic uses for the polypeptide and may include enzymes, hormones, and other proteinaceous or nonproteinaceous solutes. Isolated modulators include a modulator in situ within recombinant cells because at least one component of the polypeptide's natural environment will not be present.

If the desired molecule is produced intracellularly, as a first step, the particulate debris, either host cells or lysed fragments, may be removed, for example, by centrifugation or ultrafiltration. Where the modulator is secreted into the medium, supernatants from such expression systems are generally first concentrated using a commercially available protein concentration filter, for example, an Amicon or Pellicon ultrafiltration unit (Millipore Corp.). Once the insoluble contaminants are removed the modulator preparation may be further purified using standard techniques such as, for example, hydroxylapatite chromatography, gel electrophoresis, dialysis, and affinity chromatography, with affinity chromatography of particular interest. In this regard protein A can be used to purify antibodies that are based on human IgG1, IgG2 or IgG4 heavy chains (Lindmark, et al., J Immunol Meth 62:1 (1983)) while protein G is recommended for all mouse isotypes and for human IgG3 (Guss, et al., EMBO J 5:1567 (1986)). Other techniques for protein purification such as fractionation on an ion-exchange column, ethanol precipitation, reverse phase HPLC, chromatography on silica, chromatography on heparin, sepharose chromatography on an anion or cation exchange resin (such as a polyaspartic acid column), chromatofocusing, SDS-PAGE and ammonium sulfate precipitation are also available depending on the antibody to be recovered. In particularly preferred embodiments the modulators of the instant invention will be purified, at least in part, using Protein A or Protein G affinity chromatography.

VI. CD324 Modulator Fragments and Derivatives

Whatever generation and production methodology is selected, modulators of the instant invention will recognize, react, bind, combine, complex, connect, attach, join, interact or otherwise associate with a target determinant (e.g., an epitope on an antigen) and thereby provide the desired results. Where the modulator comprises an antibody or fragment, construct or derivative thereof such associations may be through one or more "antigen-binding sites," "binding sites" or "binding components" comprising the CDRs and expressed on the antibody, where a binding site comprises a region of a polypeptide that is responsible for selectively binding to a target molecule or antigen epitope of interest. Binding domains comprise at least one binding site (e.g., an intact IgG antibody will have two binding domains and two binding sites). Exemplary binding domains include an antibody variable domain, a receptor-binding domain of a ligand, a ligand-binding domain of a receptor or an enzymatic domain.

A. Antibodies

As noted above, the term "antibody" is intended to cover polyclonal antibodies, multiclonal antibodies, chimeric antibodies, CDR grafted antibodies, humanized and primatized antibodies, human antibodies, recombinantly produced antibodies, intrabodies, antibody fragments, multispecific antibodies, bispecific antibodies, monovalent antibodies, multivalent antibodies, anti-idiotypic antibodies, as well as synthetic antibodies.

The terms "antigen-binding site," "binding site" or "binding component" when used herein refer to the amino acid residues of an antibody which are responsible for epitope recognition and antigen-binding. As discussed above the antigen-binding site of an antibody comprises amino acid residues from the complementary determining regions or CDRs.

B. Fragments

Regardless of which form of the modulator (e.g. chimeric, humanized, etc.) is selected to practice the invention it will be appreciated that immunoreactive fragments of the same may be used in accordance with the teachings herein. An "antibody fragment" comprises at least a portion of an intact antibody. As used herein, the term "fragment" of an antibody molecule includes antigen-binding fragments of antibodies, and the term "antigen-binding fragment" refers to a polypeptide fragment of an immunoglobulin or antibody that immunospecifically binds or reacts with a selected antigen or immunogenic determinant thereof or competes with the intact antibody from which the fragments were derived for specific antigen binding.

Exemplary fragments include: $V_L$, $V_H$, scFv, F(ab')2 fragment, Fab fragment, Fd fragment, Fv fragment, single domain antibody fragments, diabodies, linear antibodies, single-chain antibody molecules and multispecific antibodies formed from antibody fragments. In addition, an active fragment comprises a portion of the antibody that retains its ability to interact with the antigen/substrates or receptors and modify them in a manner similar to that of an intact antibody (though maybe with somewhat less efficiency).

In other embodiments, an antibody fragment is one that comprises the Fc region and that retains at least one of the biological functions normally associated with the Fc region when present in an intact antibody, such as FcRn binding, antibody half-life modulation, ADCC function and complement binding. In one embodiment, an antibody fragment is a monovalent antibody that has an in vivo half-life substantially similar to an intact antibody. For example, such an antibody fragment may comprise an antigen binding arm linked to an Fc sequence capable of conferring in vivo stability to the fragment.

As would be well recognized by those skilled in the art, fragments can be obtained via chemical or enzymatic treatment (such as papain or pepsin) of an intact or complete antibody or antibody chain or by recombinant means. See, e.g., Fundamental Immunology, W. E. Paul, ed., Raven Press, N.Y. (1999), for a more detailed description of antibody fragments. In this regard, while various antibody fragments are defined in terms of the digestion of an intact antibody, one of skill will appreciate that such fragments may be synthesized de novo either chemically or by using recombinant DNA methodology.

C. Derivatives

The invention further includes immunoreactive modulator derivatives and antigen binding molecules comprising one or more modifications.

1. Multivalent Antibodies

In one embodiment, the modulators of the invention may comprise monovalent or multivalent (e.g., bivalent, trivalent, etc.) antibodies. As used herein, the term "valency" refers to the number of potential antigen binding sites associated with an antibody. Each antigen binding site or binding component specifically binds one target molecule or specific position or locus on a target molecule. When an antibody is monovalent, each binding site of the molecule will specifically bind to a single antigen position or epitope. When an antibody comprises more than one antigen-binding site (multivalent), each antigen-binding site may specifically bind the same or different molecules (e.g., may bind to different ligands or different antigens, or different epitopes or positions on the same antigen).

As discussed the term "antibody" herein is used in the broadest sense and specifically covers monoclonal antibodies, polyclonal antibodies, multispecific antibodies, and antibody fragments so long as they exhibit the desired biological activity. Further, the term "multispecific antibody" is used in the broadest sense and specifically covers an antibody comprising an antigen-binding domain that has polyepitopic specificity (i.e., is capable of specifically binding to two, or more, different epitopes on one biological molecule or is capable of specifically binding to epitopes on two, or more, different biological molecules). One specific example of an antigen-binding domain is a $V_H V_L$ unit comprised of a heavy chain variable domain ($V_H$) and a light chain variable domain ($V_L$). Such multispecific antibodies include, but are not limited to, full length antibodies, antibodies having two or more VL and VH domains, antibody fragments such as Fab, Fv, dsFv, scFv, diabodies, bispecific diabodies and triabodies, antibody fragments that have been linked covalently or non-covalently. A "bispecific antibody" is a multispecific antibody comprising antigen-binding domains that are capable of specifically recognizing or binding to two different epitopes on one molecule or is capable of specifically recognizing or binding to epitopes on two different molecules. The bispecific antibody is also referred to herein as having "dual specificity" or as being "dual specific". See, for example, U.S.P.Ns. 2009/0130105 and 2012/0121596, In each case at least one of the binding sites will comprise an epitope, motif or domain associated with CD324 or an immunoreactive fragment thereof. Other compatible constructs may be found in U.S.P.N.s 2013/0017200, 2013/0004416 and 2012/0316324 as well as U.S. Pat. Nos. 8,349,332 and 7,521,056 as well as WO 2012/162583 and WO 2013/005194 each of which is incorporated herein by reference.

That is, for the purposes of the instant invention, the subject antibodies will preferably have at least one binding site specific for an epitope presented by human CD324. In one embodiment the antibodies of the instant invention will be monovalent in that each binding site of the molecule will specifically bind to a single CD324 position or epitope. In other embodiments, the antibodies will be multivalent in that they comprise more than one binding site and the different binding sites specifically associate with more than a single position or epitope. In such cases the multiple epitopes may be present on the selected CD324 polypeptide or variant or a single epitope may be present on CD324 while a second, different epitope may be present on another molecule or surface. In either case the multispecific antibodies recognize at least two distinct epitopes that are not equivalent as defined by competitive binding assays. That is, epitopes will be held to be distinct and not equivalent if the binding sites of the multispecific are able to recognize each respective epitope without interference or competition from one of the other binding sites. Such interference or competition (or lack thereof) may be determined using the same art-recognized competitive assays employed to define antibody bins.

In the context of the instant invention any art-recognized bispecific or multispecific construct comprising a binding site recognizing a first epitope present on CD324 and at least a second binding site that recognizes a second epitope which is distinct from the first epitope is compatible and may be used in conjunction with the teachings herein. In preferred embodiments the invention provides for bispecific antibodies in which two different antigen-binding sites are incorporated into a single molecule. Bispecific antibodies may be prepared by chemical cross-linking (Brennan, et al., Science 229, 81 (1985); Raso, et al., J. Biol. Chem. 272, 27623 (1997)), disulfide exchange, production of hybrid-hybridomas (quadromas), by transcription and translation to produce a single polypeptide chain embodying a bispecific antibody, or by transcription and translation to produce more than one polypeptide chain that can associate covalently to produce a bispecific antibody. The contemplated bispecific antibody can also be made entirely by chemical synthesis. The bispecific antibody may comprise two different variable regions, two different constant regions, a variable region and a constant region, or other variations.

In one selected embodiment, the modulators are bispecific antibodies in which the two chains have different specificities, as described in Millstein et al., 1983, *Nature*, 305:537-539. Other embodiments include antibodies with additional specificities such as trispecific antibodies. Other compatible multispecific constructs and methods of their fabrication are set forth in U.S.P.Ns. 2009/0155255 and 2011/0301331, WO 94/04690 and WO 96/27011; Suresh et al., 1986, *Methods in Enzymology*, 121:210; Coloma, M. J., et al., Nature Biotech 15 (1997) 159-163; WO 2001/077342; and Morrison, S. L., Nature Biotech 25 (2007) 1233-1234) each of which is incorporated herein by reference.

In yet other embodiments, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and/or $C_H3$ regions. In one example, the first heavy-chain constant region ($C_H1$) containing the site necessary for light chain binding is present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm (e.g., CD324), and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., 1986, Methods in Enzymology, 121:210. According to another approach described in WO96/27011, a pair of antibody molecules can be engineered to maximize the percentage of heterodimers that are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory cavities of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Yet other compatible constructs are set forth in Example 13 below where selected amino acids in the human IgG1 and kappa light chain were mutated to alter the charge distribution of the chains and improve assembly and stability of the multispecific modulators. More particularly several IgG-like anti-CD324/Nectin-4 bispecific antibody variants were constructed with human constant regions using the human IgG1 and kappa light chain background (Table 1). Mutations to the constant regions of each of the variants were introduced for the purpose of either: (i) preferentially pairing heavy chains of different specificity in heteromeric rather than homomeric fashion (asymmetric heavy chain pairing) or (ii) preferentially pairing each heavy chain with the corresponding light chain (heavy chain/light chain pairing). As seen in the Examples below these constructs are particularly effective in mediating cell killing.

Whatever multispecific framework or structure is selected to fabricate the construct it will be appreciated that the non-CD324 antigen-binding site may be chosen to bind or associate with any one of numerous target antigens and may be derived from available (commercially or otherwise) antibodies. That is, using standard molecular engineering techniques the constructs may be fabricated to incorporate the antigen-binding regions or CDRs from any antibody or reactive fragment for which the sequence is known. In this regard the non-CD324 antigen-binding site may, in preferred embodiments, be obtained or derived from an antibody selected from the group consisting of abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. Given that the constituent amino acid sequences are known for each of these antibodies it is well within the skill of the art to select one of the variable regions and incorporate them in compatible multispecific constructs.

In addition to incorporating known antibody binding domains it is well within the art to generate antibodies to a known antigen and engineer the resulting antigen-binding sites or derivatives thereof into compatible multispecific sequences. Particularly preferred embodiments will comprise an antigen-binding site that recognizes (e.g., binds or associates with) an antigen selected from the group consisting of OCT4, Nanog, STAT3, EPCAM, CD24, CD34, NB84, TrkA, GD2, CD133, CD20, CD56, CD29, B7113, CD46, transferrin receptor, JAM3, carboxypeptidase M, oncostatin M, Lgr5, Lgr6, CD325, nectin-4, nestin, Sox1, Bmi-1, eed, easyh1, easyh2, mf2, yy1, smarcA3, smarckA5, smarcD3, smarcE1, mllt3, DLL1, DLL4, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4) SLC7A8, SLC44A4, IL1RAP, TEM8, TMPRSS4, MUC16, GPRC5B, SLC6A14, SLC4A11, PPAP2C, CAV1, CAV2, PTPN3, EPHA1 EPHA2, EPHA3, EPHA4, EPHA5, EPHA6, EPHA7, EPHA8, EPHA9, EPHB1, EPHB2, EPHB3, EPHB4, EPHB5, EPHB6, EFNA1, EFNA2, EFNA3, EFNA5, EFNA6, EFNB1, EFNB2, EFNB3, SLC1A1, CX3CL1, ADORA2A, MPZL1, FLJ10052, C4.4A, EDG3, RARRES1, TMEPAI, PTS, CEACAM5, CEACAM6, NID2, STEAP, ABCA3, CRIM1, IL1R1, OPN3, DAF, MUC1, CPD, NMA, ADAM9, GJA1, SLC19A2, ABCA1, PCDH7, ADCY9, SLC39A1, NPC1, ENPP1, N33, GPNMB, LY6E, CELSR1, LRP3, C20orf52, TMEPAI, FLVCR, PCDHA10, GPR54, TGFBR3, SEMA4B, PCDHB2, ABCG2, CD166, AFP, BMP-4, β-catenin, CD2, CD3, CD9, CD14, CD31, CD38, CD44, CD45, CD74, CD90, CXCR4, decorin, APCDD1, PTK7, EGFR, CD105, CD64, CD16, CD16a, CD16b, GLI1, GLI2, CD49b, CD49e and CD49f. While the aforementioned antigens may comprise selected target embodiments of the instant invention it will be appreciated that one skilled in the art could readily incorporate any antigen-binding region from an antibody made to any particular antigen.

In accordance with the teachings herein it will further be appreciated that the disclosed bispecific and multispecific constructs may be used in a conjugated (e.g., with a cytotoxic agent) or unconjugated state.

2. Fc Region Modifications

In addition to the various modifications, substitutions, additions or deletions to the variable or binding region of the disclosed modulators (e.g., Fc-CD324 or anti-CD324 antibodies) set forth above, those skilled in the art will appreciate that selected embodiments of the present invention may also comprise substitutions or modifications of the constant region (i.e. the Fc region). More particularly, it is contemplated that the CD324 modulators of the invention may contain inter alia one or more additional amino acid residue substitutions, mutations and/or modifications which result in a compound with preferred characteristics including, but not limited to: altered pharmacokinetics, increased serum half life, increase binding affinity, reduced immunogenicity, increased production, altered Fc ligand binding to an Fc receptor (FcR), enhanced or reduced "ADCC" (antibody-dependent cell mediated cytotoxicity) or "CDC" (complement-dependent cytotoxicity) activity, altered glycosylation and/or disulfide bonds and modified binding specificity. In this regard it will be appreciated that these Fc variants may advantageously be used to enhance the effective anti-neoplastic properties of the disclosed modulators.

To this end certain embodiments of the invention may comprise substitutions or modifications of the Fc region, for example the addition of one or more amino acid residue, substitutions, mutations and/or modifications to produce a compound with enhanced or preferred Fc effector functions. For example, changes in amino acid residues involved in the interaction between the Fc domain and an Fc receptor (e.g., FcγRI, FcγRIIA and B, FcγRIII and FcRn) may lead to increased cytotoxicity and/or altered pharmacokinetics, such as increased serum half-life (see, for example, Ravetch and Kinet, Annu. Rev. Immunol 9:457-92 (1991); Capel et al., Immunomethods 4:25-34 (1994); and de Haas et al., J. Lab. Clin. Med. 126:330-41 (1995) each of which is incorporated herein by reference).

In selected embodiments, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S.P.N. 2003/0190311. With regard to such embodiments, Fc variants may provide half-lives in a mammal, preferably a human, of greater than 5 days, greater than 10 days, greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-life results in a higher serum titer which thus reduces the frequency of the administration of the antibodies and/or reduces the concentration of the antibodies to be administered. Binding to human FcRn in vivo and serum half life of human FcRn high affinity binding polypeptides can be assayed, e.g., in transgenic mice or transfected human cell lines expressing human FcRn, or in primates to which the polypeptides with a variant Fc region are administered. WO 2000/42072 describes antibody variants with improved or diminished binding to FcRns. See also, e.g., Shields et al. J. Biol. Chem. 9(2):6591-6604 (2001).

In other embodiments, Fc alterations may lead to enhanced or reduced ADCC or CDC activity. As in known in the art, CDC refers to the lysing of a target cell in the presence of complement, and ADCC refers to a form of cytotoxicity in which secreted Ig bound onto FcRs present on certain cytotoxic cells (e.g., Natural Killer cells, neutrophils, and macrophages) enables these cytotoxic effector cells to bind specifically to an antigen-bearing target cell and subsequently kill the target cell with cytotoxins. In the context of the instant invention antibody variants are provided with "altered" FcR binding affinity, which is either enhanced or diminished binding as compared to a parent or unmodified antibody or to an antibody comprising a native sequence FcR. Such variants which display decreased binding may possess little or no appreciable binding, e.g., 0-20% binding to the FcR compared to a native sequence, e.g. as determined by techniques well known in the art. In other embodiments the variant will exhibit enhanced binding as compared to the native immunoglobulin Fc domain. It will be appreciated that these types of Fc variants may advantageously be used to enhance the effective anti-neoplastic properties of the disclosed antibodies. In yet other embodiments, such alterations lead to increased binding affinity, reduced immunogenicity, increased production, altered glycosylation and/or disulfide bonds (e.g., for conjugation sites), modified binding specificity, increased phagocytosis; and/or down regulation of cell surface receptors (e.g. B cell receptor; BCR), etc.

3. Altered Glycosylation

Still other embodiments comprise one or more engineered glycoforms, i.e., a CD324 modulator comprising an altered glycosylation pattern or altered carbohydrate composition that is covalently attached to the protein (e.g., in the Fc domain). See, for example, Shields, R. L. et al. (2002) J. Biol. Chem. 277:26733-26740. Engineered glycoforms may be useful for a variety of purposes, including but not limited to enhancing or reducing effector function, increasing the affinity of the modulator for a target or facilitating production of the modulator. In certain embodiments where reduced effector function is desired, the molecule may be engineered to express an aglycosylated form. Substitutions that may result in elimination of one or more variable region framework glycosylation sites to thereby eliminate glycosylation at that site are well known (see e.g. U.S. Pat. Nos. 5,714,350 and 6,350,861). Conversely, enhanced effector functions or improved binding may be imparted to the Fc containing molecule by engineering in one or more additional glycosylation sites.

Other embodiments include an Fc variant that has an altered glycosylation composition, such as a hypofucosylated antibody having reduced amounts of fucosyl residues or an antibody having increased bisecting GlcNAc structures. Such altered glycosylation patterns have been demonstrated to increase the ADCC ability of antibodies. Engineered glycoforms may be generated by any method known to one skilled in the art, for example by using engineered or variant expression strains, by co-expression with one or more enzymes (for example N-acetylglucosaminyltransferase III (GnTI11)), by expressing a molecule comprising an Fc region in various organisms or cell lines from various organisms or by modifying carbohydrate(s) after the molecule comprising Fc region has been expressed (see, for example, WO 2012/117002).

4. Additional Processing

The modulators may be differentially modified during or after production, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, NaBH$_4$, acetylation, formylation, oxidation, reduction, metabolic synthesis in the presence of tunicamycin, etc.

Various post-translational modifications also encompassed by the invention include, for example, N-linked or O-linked carbohydrate chains, processing of N-terminal or C-terminal ends, attachment of chemical moieties to the amino acid backbone, chemical modifications of N-linked or O-linked carbohydrate chains, and addition or deletion of an N-terminal methionine residue as a result of prokaryotic host cell expression. Moreover, the modulators may also be modified with a detectable label, such as an enzymatic, fluorescent, radioisotopic or affinity label to allow for detection and isolation of the modulator.

VII. Modulator Characteristics

No matter how obtained or which of the aforementioned forms the modulator takes, various embodiments of the disclosed modulators may exhibit certain characteristics. In selected embodiments, antibody-producing cells (e.g., hybridomas or yeast colonies) may be selected, cloned and further screened for favorable properties including, for example, robust growth, high modulator production and, as discussed in more detail below, desirable modulator characteristics. In other cases characteristics of the modulator may be imparted or influenced by selecting a particular antigen (e.g., a specific CD324 isoform) or immunoreactive fragment of the target antigen for inoculation of the animal. In still other embodiments the selected modulators may be engineered as described above to enhance or refine immunochemical characteristics such as affinity or pharmacokinetics.

A. Neutralizing Modulators

In certain embodiments, the modulators will comprise "neutralizing" antibodies or derivatives or fragments thereof. That is, the present invention may comprise antibody molecules that bind specific domains, motifs or epitopes and are capable of blocking or inhibiting the biological activity of CD324. More generally, the term "neutralizing antibody" refers to an antibody that binds to or interacts with a target molecule or ligand and prevents binding or association of the target antigen to a binding partner such as a receptor or substrate, thereby interrupting the biological response that otherwise would result from the interaction of the molecules. In the case of the instant invention the neutralizing modulator would associate with CD324 and preferably interfere or reduce homotypic or heterotypic association of the molecule thereby interrupting biological processes such as cell-cell adhesion that otherwise would result from the interaction of the molecules.

It will be appreciated that competitive binding assays known in the art may be used to assess the binding and specificity of an antibody or immunologically functional fragment or derivative thereof. With regard to the instant invention an antibody or fragment will be held to inhibit or reduce binding of CD324 to a binding partner or substrate (e.g., CD324, EGFR, αEβ7) when an excess of antibody reduces the quantity of binding partner bound to CD324 by at least about 20%, 30%, 40%, 50%, 60%, 70%, 80%, 85%, 90%, 95%, 97%, 99% or more as measured, for example, by disruption of the homotypic cell-cell contacts leading to cell death (e.g., apoptosis or anoikis) or, more directly, in art-recognized in vitro competitive binding assays such as the one described in Example 10 below. Similarly, inhibition of heterotypic binding may be readily assessed using analogous assays comprising a binding partner other than CD324. In the case of antibodies to CD324 for example, a neutralizing antibody or antagonist will preferably diminish CD324 homotypic or heterotypic binding by at least about 20%, 30%, 40%, 50%, 60%, 70%, 80%, 85%, 90%, 95%, 97%, 99% or more.

B. Internalizing Modulators

There is evidence that a substantial portion of expressed CD324 protein remains associated with the tumorigenic cell surface, thereby allowing for localization and internalization of the disclosed modulators. In preferred embodiments such modulators may be associated with, or conjugated to, anti-cancer agents such as cytotoxic moieties that kill the cell upon internalization. In particularly preferred embodiments the modulator will comprise an internalizing antibody drug conjugate.

As used herein, a modulator that "internalizes" is one that is taken up (along with any payload) by the cell upon binding to an associated antigen or receptor. As will be appreciated, the internalizing modulator may, in preferred embodiments, comprise an antibody including antibody fragments and derivatives thereof, as well as antibody conjugates. Internalization may occur in vitro or in vivo. For therapeutic applications, internalization will preferably occur in vivo in a subject in need thereof. The number of antibody molecules internalized may be sufficient or adequate to kill an antigen-expressing cell, especially an antigen-expressing cancer stem cell. Depending on the potency of the antibody or antibody conjugate, in some instances, the uptake of a single antibody molecule into the cell is sufficient to kill the target cell to which the antibody binds. For example, certain toxins are so highly potent that the internalization of a few molecules of the toxin conjugated to the antibody is sufficient to kill the tumor cell. Whether an antibody internalizes upon binding to a mammalian cell can be determined by various assays including those described in the Examples below. Methods of detecting whether an antibody internalizes into a cell are also described in U.S. Pat. No. 7,619,068 which is incorporated herein by reference in its entirety.

C. Depleting Modulators

In other embodiments the antibodies will comprise depleting antibodies or derivatives or fragments thereof. The term "depleting" antibody refers to an antibody that preferably binds to or associates with an antigen on or near the cell surface and induces, promotes or causes the death or elimination of the cell (e.g., by CDC, ADCC or introduction of a cytotoxic agent). In some embodiments, the selected depleting antibodies will be associated or conjugated to a cytotoxic agent.

Preferably a depleting antibody will be able to remove, incapacitate, eliminate or kill at least 20%, 30%, 40%, 50%, 60%, 70%, 80%, 85%, 90%, 95%, 97%, or 99% of CD324 tumorigenic cells in a defined cell population. In some embodiments the cell population may comprise enriched, sectioned, purified or isolated tumor perpetuating cells. In other embodiments the cell population may comprise whole tumor samples or heterogeneous tumor extracts that comprise tumor perpetuating cells. Those skilled in the art will appreciate that standard biochemical techniques as described in the Examples below may be used to monitor and quantify the depletion of tumorigenic cells or tumor perpetuating cells in accordance with the teachings herein.

D. Binning and Epitope Binding

It will further be appreciated the disclosed anti-CD324 antibody modulators will associate with, or bind to, discrete epitopes or immunogenic determinants presented by the selected target or fragment thereof. In certain embodiments, epitope or immunogenic determinants include chemically active surface groupings of molecules such as amino acids, sugar side chains, phosphoryl groups, or sulfonyl groups, and, in certain embodiments, may have specific three-dimensional structural characteristics, and/or specific charge characteristics. Thus, as used herein the term "epitope" includes any protein determinant capable of specific binding to an immunoglobulin or T-cell receptor or otherwise interacting with a molecule. In certain embodiments, an antibody is said to specifically bind (or immunospecifically bind or react) an antigen when it preferentially recognizes its target antigen in a complex mixture of proteins and/or macromolecules. In selected embodiments, an antibody is said to recognize or specifically bind an antigen (i.e., an epitope) when the equilibrium dissociation constant ($K_D$) is less than or equal to $10^{-6}$M or more preferably when it is less than or equal to $10^{-7}$M. In particularly preferred aspects the antibody will recognize or specifically bind an epitope when the equilibrium dissociation constant is less than or equal to $10^{-9}$M, and most preferably when the dissociation constant is less than or equal to $10^{-10}$M.

For the instant disclosure the term "epitope" refers to that portion of the target antigen capable of being recognized and specifically bound by a particular antibody modulator. When the antigen is a polypeptide such as CD324, epitopes may generally be formed from both contiguous amino acids and noncontiguous amino acids juxtaposed by tertiary folding of a protein ("conformational epitopes"). In such conformational epitopes the points of interaction occur across amino acid residues on the protein that are linearly separated from one another. Epitopes formed from contiguous amino acids (sometimes referred to as "linear" or "continuous" epitopes) are typically retained upon protein denaturing, whereas epitopes formed by tertiary folding are typically lost upon protein denaturing. In any event an epitope typically includes at least 3, and more usually, at least 5 or 8-10 amino acids in a unique spatial conformation.

In this respect it will be appreciated that, in certain embodiments, an epitope may be associated with, or reside in, one or more regions, domains or motifs of the CD324 protein. As discussed in more detail herein the extracellular region of the CD324 protein comprises a series of generally recognized domains including five ECA domains. For the purposes of the instant disclosure the term "domain" will be used in accordance with its generally accepted meaning and will be held to refer to an identifiable or definable conserved structural entity within a protein that exhibits a distinctive secondary structure content. In many cases homologous domains with common functions will usually show sequence similarities and be found in a number of disparate proteins. Similarly, the art recognized term "motif" will be used in accordance with its common meaning and shall generally refer to a short, conserved region of a protein that is typically ten to twenty contiguous amino acid residues. As discussed throughout, selected embodiments comprise modulators that associate with or bind to an epitope within specific regions, domains or motifs of CD324.

In any event once a desired epitope on an antigen is determined, it is possible to generate antibodies to that epitope, e.g., by immunizing with a peptide comprising the epitope using techniques described in the present invention. Alternatively, during the discovery process, the generation and characterization of antibodies may elucidate information about desirable epitopes located in specific domains or motifs. From this information, it is then possible to competitively screen antibodies for binding to the same epitope. An approach to achieve this is to conduct competition studies to find antibodies that competitively bind with one another, i.e. the antibodies compete for binding to the antigen. A high throughput process for binning antibodies based upon their cross-competition is described in WO 03/48731. Other methods of binning or domain level or epitope mapping comprising modulator competition or antigen fragment expression on yeast.

As used herein, the term "binning" refers to methods used to group or classify antibodies based on their antigen binding characteristics and competition. While the techniques are useful for defining and categorizing modulators of the instant invention, the bins do not always directly correlate with epitopes and such initial determinations of epitope binding may be further refined and confirmed by other art recognized methodology as described herein. However, as discussed and shown in the Examples below (e.g., Example 7), empirical assignment of antibody modulators to individual bins provides information that may be indicative of the therapeutic potential of the disclosed modulators.

More specifically, one can determine whether a selected reference antibody (or fragment thereof) binds to the same epitope or cross competes for binding with a second test antibody (i.e., is in the same bin) by using methods known in the art and set forth in the Examples herein. In one embodiment, a reference antibody modulator is associated with CD324 antigen under saturating conditions and then the ability of a secondary or test antibody modulator to bind to CD324 is determined using standard immunochemical techniques. If the test antibody is able to substantially bind to CD324 at the same time as the reference anti-CD324 antibody, then the secondary or test antibody binds to a different epitope than the primary or reference antibody. However, if the test antibody is not able to substantially bind to CD324 at the same time, then the test antibody binds to the same epitope, an overlapping epitope, or an epitope that is in close proximity (at least sterically) to the epitope bound by the primary antibody. That is, the test antibody competes for antigen binding and is in the same bin as the reference antibody.

The term "compete" or "competing antibody" when used in the context of the disclosed modulators means competition between antibodies as determined by an assay in which a test antibody or immunologically functional fragment under test prevents or inhibits specific binding of a reference antibody to a common antigen. Typically, such an assay involves the use of purified antigen (e.g., CD324 or a domain or fragment thereof) bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Additional details regarding methods for determining competitive binding are provided in the Examples herein. Usually, when a competing antibody is present in excess, it will inhibit specific binding of a reference antibody to a common antigen by at least 40%, 45%, 50%, 55%, 60%, 65%, 70% or 75%. In some instance, binding is inhibited by at least 80%, 85%, 90%, 95%, or 97% or more.

With regard to the instant invention, and as set forth in the Example 7 below, it has been determined that the extracellular domain of CD324 defines at least five bins termed "bin A" to "bin E" herein.

More generally, and as known in the art and detailed in the Examples below, the desired binning or competitive binding data can be obtained using solid phase direct or indirect radioimmunoassay (RIA), solid phase direct or indirect enzyme immunoassay (EIA or ELISA), sandwich competition assay, a Biacore™ 2000 system (i.e., surface plasmon resonance—GE Healthcare), a ForteBio® Analyzer (i.e., bio-layer interferometry ForteBio, Inc.) or flow cytometric methodology. The term "surface plasmon resonance," as used herein, refers to an optical phenomenon that allows for the analysis of real-time specific interactions by detection of alterations in protein concentrations within a biosensor matrix. The term "bio-layer interferometry" refers to an optical analytical technique that analyzes the interference pattern of white light reflected from two surfaces: a layer of immobilized protein on a biosensor tip, and an internal reference layer. Any change in the number of molecules bound to the biosensor tip causes a shift in the interference pattern that can be measured in real-time. In particularly preferred embodiments the analysis (whether surface plasmon resonance, bio-layer interferometry or flow cytometry) is performed using a Biacore or ForteBio instrument or a flow cytometer (e.g., FACSAria II) as demonstrated in the Examples below.

In order to further characterize the epitopes that the disclosed CD324 antibody modulators associate with or bind to, domain-level epitope mapping could be performed using a modification of the protocol described by Cochran et al. (J Immunol Methods. 287 (1-2):147-158 (2004) which is incorporated herein by reference). Briefly, individual domains of CD324 comprising specific amino acid sequences could be expressed on the surface of yeast and binding by each CD324 antibody could be determined through flow cytometry.

Other compatible epitope mapping techniques include alanine scanning mutants, peptide blots (Reineke (2004) Methods Mol Biol 248:443-63) (herein specifically incorporated by reference in its entirety), or peptide cleavage analysis. In addition, methods such as epitope excision, epitope extraction and chemical modification of antigens can be employed (Tomer (2000) Protein Science 9: 487-496) (herein specifically incorporated by reference in its entirety). In other embodiments Modification-Assisted Profiling (MAP), also known as Antigen Structure-based Antibody Profiling (ASAP) provides a method that categorizes large numbers of monoclonal antibodies (mAbs) directed against the same antigen according to the similarities of the binding profile of each antibody to chemically or enzymatically modified antigen surfaces (U.S.P.N. 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. It will be appreciated that MAP may be used to sort the hCD324 antibody modulators of the invention into groups of antibodies binding different epitopes Agents useful for altering the structure of the immobilized antigen include enzymes such as proteolytic enzymes (e.g., trypsin, endoproteinase Glu-C, endoproteinase Asp-N, chymotrypsin, etc.). Agents useful for altering the structure of the immobilized antigen may also be chemical agents, such as, succinimidyl esters and their derivatives, primary amine-containing compounds, hydrazines and carbohydrazines, free amino acids, etc.

The antigen protein may be immobilized on either biosensor chip surfaces or polystyrene beads. The latter can be processed with, for example, an assay such as multiplex LUMINEX™ detection assay (Luminex Corp.). Because of the capacity of LUMINEX to handle multiplex analysis with up to 100 different types of beads, LUMINEX provides almost unlimited antigen surfaces with various modifications, resulting in improved resolution in antibody epitope profiling over a biosensor assay.

E. Modulator Binding Characteristics

Besides epitope specificity the disclosed antibodies may be characterized using physical characteristics such as, for example, binding affinities. In this regard the present invention further encompasses the use of antibodies that have a high binding affinity for one or more CD324 variants or immunoreactive fragments thereof.

The term "$K_D$", as used herein, is intended to refer to the dissociation constant of a particular antibody-antigen interaction. An antibody of the invention is said to immunospecifically bind or recognize its target antigen when the dissociation constant $K_D$ ($k_{off}/k_{on}$) is $\leq 10^{-6}$M. The antibody specifically binds antigen with high affinity when the $K_D$ is $\leq 5 \times 10^{-9}$M, and with very high affinity when the $K_D$ is $\leq 5 \times 10^{-10}$M. In one embodiment of the invention, the antibody has a $K_D$ of $\leq 10^{-9}$M and an off-rate of about $1 \times 10^{-4}$/sec. In one embodiment of the invention, the off-rate is $<1 \times 10^{-5}$/sec. In other embodiments of the invention, the antibodies will bind to CD324 with a $K_D$ of between about $10^{-7}$M and $10^{-10}$M, and in yet another embodiment it will bind with a $K_D \leq 2 \times 10^{-10}$M. Still other selected embodiments of the present invention comprise antibodies that have a disassociation constant or $K_D$ ($k_{off}/k_{on}$) of less than $10^{-2}$M, less than $5 \times 10^{-2}$M, less than $10^{-3}$M, less than $5 \times 10^{-3}$M, less than $10^{-4}$M, less than $5 \times 10^{-4}$M, less than $10^{-5}$M, less than $5 \times 10^{-5}$M, less than $10^{-6}$M, less than $5 \times 10^{-6}$M, less than $10^{-7}$M, less than $5 \times 10^{-7}$M, less than $10^{-8}$M, less than $5 \times 10^{-8}$M, less than $10^{-9}$M, less than $5 \times 10^{-9}$M, less than $10^{-10}$M, less than $5 \times 10^{-10}$M, less than $10^{-11}$M, less than $5 \times 10^{-11}$M, less than $10^{-12}$M, less than $5 \times 10^{-12}$M, less than $10^{-13}$M, less than $5 \times 10^{-13}$M, less than $10^{-14}$M, less than $5 \times 10^{-14}$M, less than $10^{-15}$M or less than $5 \times 10^{-15}$M.

In specific embodiments, an antibody of the invention that immunospecifically binds to CD324 has an association rate constant or $k_{on}$ (or $k_a$) rate (CD324 (Ab)+antigen (Ag)$^{k_{on}}$←Ab-Ag) of at least $10^5 M^{-1} s^{-1}$, at least $2 \times 10^5 M^{-1} s^{-1}$, at least $5 \times 10^5 M^{-1} s^{-1}$, at least $10^6 M^{-1} s^{-1}$, at least $5 \times 10^6 M^{-1} s^{-1}$, at least $10^7 M^{-1} s^{-1}$, at least $5 \times 10^7 M^{-1} s^{-1}$, or at least $10^8 M^{-1} s^{-1}$.

In another embodiment, an antibody of the invention that immunospecifically binds to CD324 has a disassociation rate constant or $k_{off}$ (or $k_d$) rate (CD324 (Ab)+antigen (Ag)$^{k_{off}}$←Ab-Ag) of less than $10^{-1} s^{-1}$, less than $5 \times 10^{-1} s^{-1}$, less than $10^{-2} s^{-1}$, less than $5 \times 10^{-2} s^{-1}$, less than $10^{-3} s^{-1}$, less than $5 \times 10^{-3} s^{-1}$, less than $10^{-4} s^{-1}$, less than $5 \times 10^{-4} s^{-1}$, less than $10^{-5} s^{-1}$, less than $5 \times 10^{-5} s^{-1}$, less than $10^{-6} s^{-1}$, less than $5 \times 10^{-6} s^{-1}$ less than $10^{-7} s^{-1}$, less than $5 \times 10^{-7} s^{-1}$, less than $10^{-8} s^{-1}$, less than $5 \times 10^{-8} s^{-1}$, less than $10^{-9} s^{-1}$, less than $5 \times 10^{-9} s^{-1}$ or less than $10^{-10} s^{-1}$.

In other selected embodiments of the present invention anti-CD324 antibodies will have an affinity constant or $K_a$ ($k_{on}/k_{off}$) of at least $10^2 M^{-1}$, at least $5 \times 10^2 M^{-1}$, at least $10^3 M^{-1}$, at least $5 \times 10^3 M^{-1}$, at least $10^4 M^{-1}$, at least $5 \times 10^4 M^{-1}$, at least $10^5 M^{-1}$, at least $5 \times 10^5 M^{-1}$, at least $10^6 M^{-1}$, at least $5 \times 10^6 M^{-1}$, at least $10^7 M^{-1}$, at least $5 \times 10^7 M^{-1}$, at least $10^8 M^{-1}$, at least $5 \times 10^8 M^{-1}$, at least $10^9 M^{-1}$, at least $5 \times 10^9 M^{-1}$, at least $10^{10} M^{-1}$, at least $5 \times 10^{10} M^{-1}$, at least $10^{11} M^{-1}$, at least $5 \times 10^{11} M^{-1}$, at least $10^{12}M^{-1}$, at least $5\times10^{12}M^{-1}$, at least $10^{13}M^{-1}$, at least $5\times10^{13}M^{-1}$, at least $10^{14}M^{-1}$, at least $5\times10^{14}M^{-1}$, at least $10^{15}M^{-1}$ or at least $5\times10^{15}M^{-1}$.

Besides the aforementioned modulator characteristics antibodies of the instant invention may further be characterized using additional physical characteristics including, for example, thermal stability (i.e, melting temperature; Tm), and isoelectric points. (See, e.g., Bjellqvist et al., 1993, Electrophoresis 14:1023; Vermeer et al., 2000, Biophys. J. 78:394-404; Vermeer et al., 2000, Biophys. J. 79: 2150-2154 each of which is incorporated herein by reference).

VIII. Conjugated Modulators

A. Overview

Once the modulators of the invention have been generated and/or fabricated and selected according to the teachings herein they may be linked with, fused to, conjugated to (e.g., covalently or non-covalently) or otherwise associated with pharmaceutically active or diagnostic moieties or biocompatible modifiers. As used herein the term "conjugate" or "modulator conjugate" or "antibody conjugate" will be used broadly and held to mean any biologically active or detectable molecule or drug associated with the disclosed modulators regardless of the method of association. In this respect it will be understood that such conjugates may, in addition to the disclosed modulators, comprise peptides, polypeptides, proteins, prodrugs which are metabolized to an active agent in vivo, polymers, nucleic acid molecules, small molecules, binding agents, mimetic agents, synthetic drugs, inorganic molecules, organic molecules and radioisotopes. Moreover, as indicated above the selected conjugate may be covalently or non-covalently associated with, or linked to, the modulator and exhibit various stoichiometric molar ratios depending, at least in part, on the method used to effect the conjugation.

Particularly preferred aspects of the instant invention will comprise antibody modulator conjugates or antibody-drug conjugates that may be used for the diagnosis and/or treatment of proliferative disorders. It will be appreciated that, unless otherwise dictated by context, the term "antibody-drug conjugate" or "ADC" or the formula M-[L-D]n shall be held to encompass conjugates comprising both therapeutic and diagnostic moieties. In such embodiments antibody-drug conjugate compounds will comprise a CD324 modulator (typically an anti-CD324 antibody) as the modulator or binding unit (M), a therapeutic or diagnostic moiety (D), and optionally a linker (L) that joins the drug and the antigen binding agent. For the purposes of the instant disclosure "n" shall be held to mean an integer from 1 to 20. In a preferred embodiment, the modulator is a CD324 mAb comprising at least one CDR from the heavy and light chain variable regions as described above.

Those skilled in the art will appreciate that a number of different reactions are available for the attachment or association of therapeutic or diagnostic moieties and/or linkers to binding agents. In selected embodiments this may be accomplished by reaction of the amino acid residues of the binding agent, e.g., antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates and azlactones can also be used as coupling agents for covalently attaching drugs to binding agents.

In other embodiments the disclosed modulators of the invention may be conjugated or associated with proteins, polypeptides or peptides that impart selected characteristics (e.g., biotoxins, biomarkers, purification tags, etc.). In certain preferred embodiments the present invention encompasses the use of modulators or fragments thereof recombinantly fused or chemically conjugated (including both covalent and non-covalent conjugations) to a heterologous protein or peptide wherein the protein or peptide comprises at least 10, at least 20, at least 30, at least 40, at least 50, at least 60, at least 70, at least 80, at least 90 or at least 100 amino acids. The construct does not necessarily need to be directly linked, but may occur through amino acid linker sequences. For example, antibodies may be used to target heterologous polypeptides to particular cell types expressing CD324, either in vitro or in vivo, by fusing or conjugating the modulators of the present invention to antibodies specific for particular cell surface receptors to provide bispecific constructs. Moreover, modulators fused or conjugated to heterologous polypeptides may also be used in in vitro immunoassays and may be particularly compatible with purification methodology (e.g., his-tags) as is known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452.

B. Linkers

Besides the aforementioned peptide linkers or spacers, it will be appreciated that several other varieties or types of linker may be used to associate the disclosed modulators with pharmaceutically active or diagnostic moieties or biocompatible modifiers. In some embodiments, the linker is cleavable under intracellular conditions, such that cleavage of the linker releases the drug unit from the antibody in the intracellular environment. In yet other embodiments, the linker unit is not cleavable and the drug is released, for example, by antibody degradation.

To this end certain embodiments of the invention comprise the use a linker that is cleavable by a cleaving agent that is present in the intracellular environment (e.g., within a lysosome or endosome or caveolae). The linker can be, for example, a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, each of which is known to hydrolyze dipeptide drug derivatives resulting in the release of active drug inside target cells. Exemplary peptidyl linkers that are cleavable by the thiol-dependent protease Cathepsin-B are peptides comprising Phe-Leu since Cathepsin-B has been found to be highly expressed in cancerous tissue. Other examples of such linkers are described, for example, in U.S. Pat. No. 6,214,345 and U.S.P.N. 2012/0078028 each of which incorporated herein by reference in its entirety. In a specific preferred embodiment, the peptidyl linker cleavable by an intracellular protease is a Val-Cit linker, an Ala-Val linker or a Phe-Lys linker such as is described in U.S. Pat. No. 6,214,345. One advantage of using intracellular proteolytic release of the therapeutic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker hydrolyzable under acidic conditions. For example, an acid-labile linker that is hydrolyzable in the lysosome (e.g., a hydrazone, oxime, semicarbazone, thiosemicarbazone, cis-aconitic amide, orthoester, acetal, ketal, or the like) can be used (See, e.g., U.S. Pat. Nos. 5,122,368; 5,824,805; 5,622,929). Such linkers are relatively stable under neutral pH conditions, such as those in the blood, but are unstable at below pH 5.5 or 5.0, the approximate pH of the lysosome.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio) butyrate) and SMPT (N-succinimidyl-oxycarbonyl-alpha-methyl-alpha-(2-pyridyldithio)toluene). In yet other specific embodiments, the linker is a malonate linker (Johnson et al., 1995, Anticancer Res. 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem,* 3(10):1305-12). In yet other embodiments, the linker unit is not cleavable and the drug is released by antibody degradation. (See U.S. Publication No. 2005/0238649 incorporated by reference herein in its entirety and for all purposes).

In another preferred embodiment the modulators of the instant, invention may be associated with biocompatible polymers comprising drug linker units. In this respect one such type of compatible polymer comprises Fleximer® polymers (Mersana Therapeutics). Such polymers are reportedly biodegradable, well tolerated and have been clinically validated. Moreover, such polymers are compatible with a number of customizable linker technologies and chemistries allowing for control of pharmacokinetics, localization of drug release and improved biodistribution.

The selected modulators can also be directly conjugated radioisotopes or may comprise macrocyclic chelators useful for conjugating radiometal ions (as described herein). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4:2483; Peterson et al., 1999, Bioconjug. Chem. 10:553; and Zimmerman et. al., 1999, Nucl. Med. Biol. 26:943.

More generally, techniques for conjugating therapeutic moieties or cytotoxic agents to modulators are well known. As discussed above moieties can be conjugated to modulators by any art-recognized method, including, but not limited to aldehyde/Schiff linkage, sulphydryl linkage, acid-labile linkage, cis-aconityl linkage, hydrazone linkage, enzymatically degradable linkage (see generally Garnett, 2002, Adv Drug Deliv Rev 53:171). Also see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119. In preferred embodiments a CD324 modulator that is conjugated to a therapeutic moiety or cytotoxic agent may be internalized by a cell upon binding to a CD324 molecule associated with the cell surface thereby delivering the therapeutic payload.

C. Biocompatible Modifiers

In selected embodiments the modulators of the invention may be conjugated or otherwise associated with biocompatible modifiers that may be used to adjust, alter, improve or moderate modulator characteristics as desired. For example, antibodies or fusion constructs with increased in vivo half-lives can be generated by attaching relatively high molecular weight polymer molecules such as commercially available polyethylene glycol (PEG) or similar biocompatible polymers. Those skilled in the art will appreciate that PEG may be obtained in many different molecular weight and molecular configurations that can be selected to impart specific properties to the antibody (e.g. the half-life may be tailored). PEG can be attached to modulators or antibody fragments or derivatives with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity may be used. The degree of conjugation can be closely monitored by SDS-PAGE and mass spectrometry to ensure optimal conjugation of PEG molecules to antibody molecules. Unreacted PEG can be separated from antibody-PEG conjugates by, e.g., size exclusion or ion-exchange chromatography. In a similar manner, the disclosed modulators can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. 0 413, 622. Other biocompatible conjugates are evident to those of ordinary skill and may readily be identified in accordance with the teachings herein.

D. Diagnostic or Detection Agents

In other preferred embodiments, modulators of the present invention, or fragments or derivatives thereof, are conjugated to a diagnostic or detectable agent, marker or reporter which may be, for example, a biological molecule (e.g., a peptide or nucleotide), a small molecule, fluorophore, or radioisotope. Labeled modulators can be useful for monitoring the development or progression of a hyperproliferative disorder or as part of a clinical testing procedure to determine the efficacy of a particular therapy including the disclosed modulators (i.e. theragnostics) or to determine a future course of treatment. Such markers or reporters may also be useful in purifying the selected modulator, modulator analytics (e.g., epitope binding or antibody binning), separating or isolating TIC or in preclinical procedures or toxicology studies.

Such diagnosis analysis and/or detection can be accomplished by coupling the modulator to detectable substances including, but not limited to, various enzymes comprising for example horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In, $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, noradioactive paramagnetic metal ions, and molecules that are radiolabeled or conjugated to specific radioisotopes. In such embodiments appropriate detection methodology is well known in the art and readily available from numerous commercial sources.

As indicated above, in other embodiments the modulators or fragments thereof can be fused or conjugated to marker sequences or compounds, such as a peptide or fluorophore to facilitate purification or diagnostic or analytic procedures such as immunohistochemistry, bio-layer interferometry, surface plasmon resonance, flow cytometry, competitive ELISA, FACs, etc. In preferred embodiments, the marker comprises a his-tag such as that provided by the pQE vector (Qiagen GmbH), among others, many of which are commercially available. Other peptide tags useful for purification include, but are not limited to, the hemagglutinin "HA" tag, which corresponds to an epitope derived from the influenza hemagglutinin protein (Wilson et al., 1984, Cell 37:767) and the "flag" tag (U.S. Pat. No. 4,703,004).

E. Therapeutic Moieties

As previously alluded to the modulators or fragments or derivatives thereof may also be conjugated, linked or fused to or otherwise associated with a "therapeutic moiety" or "drug" such as an anti-proliferative or anti-cancer agent including, but not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents.

Preferred exemplary anti-cancer agents include cytochalasin B, gramicidin D, ethidium bromide, emetine, mitomycin, etoposide, tenoposide, vincristine, vinblastine, colchicin, doxorubicin, daunorubicin, dihydroxy anthracin, maytansinoids such as DM-1 and DM-4 (Immunogen, Inc.), dione, mitoxantrone, mithramycin, actinomycin D, 1-dehydrotestosterone, glucocorticoids, procaine, tetracaine, lidocaine, propranolol, puromycin, epirubicin, and cyclophosphamide and analogs or homologs thereof. Additional compatible cytotoxins comprise dolastatins and auristatins, including monomethyl auristatin E (MMAE) and monomethyl auristatin F (MMAF) (Seattle Genetics, Inc.), amanitins such as alpha-amanitin, beta-amanitin, gamma-amanitin or epsilon-amanitin (Heidelberg Pharma AG), DNA minor groove binding agents such as duocarmycin derivatives (Syntarga, B.V.) and modified pyrrolobenzodiazepine dimers (Spirogen, Ltd.), splicing inhibitors such as meayamycin analogs or derivatives (e.g., FR901464 as set forth in U.S. Pat. No. 7,825,267), tubular binding agents such as epothilone analogs and paclitaxel and DNA damaging agents such as calicheamicins and esperamicins. Furthermore, in certain embodiments the CD324 modulators of the instant invention may be associated with anti-CD3 binding molecules to recruit cytotoxic T-cells and have them target the tumor initiating cells (BiTE technology; see e.g., Fuhrmann, S. et. al. Annual Meeting of AACR Abstract No. 5625 (2010) which is incorporated herein by reference).

As indicated above selected embodiments of the instant invention are directed to conjugated CD324 modulators such as anti-CD324 antibody drug conjugates that comprise pyrrolobenzodiazepine (PBD) as a cytotoxic agent. It will be appreciated that PBDs are alkylating agents that exert antitumor activity by covalently binding to DNA in the minor groove and inhibiting nucleic acid synthesis. In this respect PBDs have been shown to have potent antitumor properties while exhibiting minimal bone marrow depression. PBDs compatible with the present invention may be linked to the CD324 modulator using any one of several types of linker (e.g., a peptidyl linker comprising a maleimido moiety with a free sulfhydryl) and, in certain embodiments are dimeric in faint (i.e., PBD dimers). Compatible PBDs (and optional linkers) that may be conjugated to the disclosed modulators are described, for example, in U.S. Pat. Nos. 6,362,331, 7,049,311, 7,189,710, 7,429,658, 7,407,951, 7,741,319, 7,557,099, 8,034,808, 8,163,736 U.S.P.N. 2011/0256157 and PCT filings WO2011/130613, WO2011/128650 and WO2011/130616 each of which is incorporated herein by reference. Accordingly, in particularly preferred embodiments the modulator will comprise an anti CD324 antibody conjugated or associated with one or more PBD dimers (i.e., a CD324-PBD ADC).

Still additional compatible anti-cancer agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BCNU) and lomustine (CCNU), busulfan, dibromomannitol, streptozotocin, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, and anthramycin (AMC)), and anti-mitotic agents (e.g., vincristine and vinblastine). A more extensive list of therapeutic moieties can be found in PCT publication WO 03/075957 and U.S.P.N. 2009/0155255 each of which is incorporated herein by reference.

Another aspect of the invention includes ADCs comprising radioisotopes. Exemplary radioisotopes that may be compatible with such embodiments include, but are not limited to, iodine ($^{131}$I, $^{125}$I, $^{123}$I, $^{121}$I), carbon ($^{14}$C), copper ($^{62}$Cu, $^{64}$Cu, $^{67}$Cu), sulfur ($^{35}$S), tritium ($^{3}$H), indium ($^{115}$In, $^{113}$In, $^{112}$In, $^{111}$In), bismuth ($^{212}$Bi, $^{213}$Bi), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn, $^{225}$Ac, $^{76}$Br, and $^{211}$At. Other radionuclides are also available as diagnostic and therapeutic agents, especially those in the energy range of 60 to 4,000 keV. Depending on the condition to be treated and the desired therapeutic profile, those skilled in the art may readily select the appropriate radioisotope for use with the disclosed modulators.

CD324 modulators of the present invention may also be conjugated to a therapeutic moiety or drug that modifies a given biological response (e.g., biological response modifiers or BRMs). That is, therapeutic agents or moieties compatible with the instant invention are not to be construed as limited to classical chemical therapeutic agents. For example, in particularly preferred embodiments the drug moiety may be a protein or polypeptide or fragment thereof possessing a desired biological activity. Such proteins may include, for example, a toxin such as abrin, ricin A, Onconase (or another cytotoxic RNase), *pseudomonas* exotoxin, cholera toxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, J. Immunol., 6:1567), and VEGI (see, International Publication No. WO 99/23105), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")). As set forth above, methods for fusing or conjugating modulators to polypeptide moieties are known in the art. In addition to the previously disclosed subject references see, e.g., U.S. Pat. Nos. 5,336,603; 5,622,929; 5,359,046; 5,349,053; 5,447,851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vii et al., 1992, PNAS USA 89:11337 each of which is incorporated herein by reference. Moreover, as set forth above the association of a modulator with such moieties does not necessarily need to be direct, but may occur through linker sequences. As previously alluded to, such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171 each of which is incorporated herein.

IX. Diagnostics and Screening

A. Diagnostics

In yet other embodiments, the invention provides in vitro or in vivo methods for detecting, diagnosing or monitoring proliferative disorders and methods of screening cells from a patient to identify tumorigenic cells including CSCs. Such methods include identifying an individual having cancer for treatment or monitoring progression of a cancer comprising contacting the patient or a sample obtained from a patient (i.e. either in vivo or in vitro) with a modulator as described herein and detecting presence or absence, or level of association, of the modulator to bound or free target molecules in the sample. In particularly preferred embodiments the modulator will comprise a detectable label or reporter molecule as described herein.

In some embodiments, the association of the modulator, such as an antibody, with particular cells in the sample likely denotes that the sample may contain CSCs, thereby indicating that the individual having cancer may be effectively treated with a modulator as described herein. The methods may further comprise a step of comparing the level of binding to a control. Conversely, when the modulator is a Fc-construct, the binding properties may be exploited and monitored (directly or indirectly, in vivo or in vitro) when in contact with the sample to provide the desired information.

Exemplary compatible assay methods include radioimmunoassays, enzyme immunoassays, competitive-binding assays, fluorescent immunoassay, immunoblot assays, Western Blot analysis, flow cytometry assays, and ELISA assays. Compatible in vivo theragnostics or diagnostics may comprise art recognized imaging or monitoring techniques such as magnetic resonance imaging, computerized tomography (e.g. CAT scan), positron tomography (e.g., PET scan) radiography, ultrasound, etc., as would be known by those skilled in the art.

In another embodiment, the invention provides a method of analyzing cancer progression and/or pathogenesis in vivo. In another embodiment, analysis of cancer progression and/or pathogenesis in vivo comprises determining the extent of tumor progression. In another embodiment, analysis comprises the identification of the tumor. In another embodiment, analysis of tumor progression is performed on the primary tumor. In another embodiment, analysis is performed over time depending on the type of cancer as known to one skilled in the art. In another embodiment, further analysis of secondary tumors originating from metastasizing cells of the primary tumor is analyzed in-vivo. In another embodiment, the size and shape of secondary tumors are analyzed. In some embodiments, further ex vivo analysis is performed.

In another embodiment, the invention provides a method of analyzing cancer progression and/or pathogenesis in vivo including determining cell metastasis or detecting and quantifying the level of circulating tumor cells. In yet another embodiment, analysis of cell metastasis comprises determination of progressive growth of cells at a site that is discontinuous from the primary tumor. In another embodiment, the site of cell metastasis analysis comprises the route of neoplastic spread. In some embodiment, cells can disperse via blood vasculature, lymphatics, within body cavities or combinations thereof. In another embodiment, cell metastasis analysis is performed in view of cell migration, dissemination, extravasation, proliferation or combinations thereof.

Accordingly, in a particularly preferred embodiment the modulators of the instant invention may be used to detect and quantify CD324 levels in a patient sample (e.g., plasma or blood) which may, in turn, be used to detect, diagnose or monitor CD324 associated disorders including proliferative disorders. In related embodiments the modulators of the instant invention may be used to detect, monitor and/or quantify circulating tumor cells either in vivo or in vitro (see, for example, WO 2012/0128801 which is incorporated herein by reference). In still other preferred embodiments the circulating tumor cells may comprise cancer stem cells.

In certain examples, the tumorigenic cells in a subject or a sample from a subject may be assessed or characterized using the disclosed modulators prior to therapy or regimen to establish a baseline. In other examples the sample is derived from a subject that was treated. In some examples the sample is taken from the subject at least about 1, 2, 4, 6, 7, 8, 10, 12, 14, 15, 16, 18, 20, 30, 60, 90 days, 6 months, 9 months, 12 months, or >12 months after the subject begins or terminates treatment. In certain examples, the tumorigenic cells are assessed or characterized after a certain number of doses (e.g., after 2, 5, 10, 20, 30 or more doses of a therapy). In other examples, the tumorigenic cells are characterized or assessed after 1 week, 2 weeks, 1 month, 2 months, 1 year, 2 years, 3 years, 4 years or more after receiving one or more therapies.

In another aspect, and as discussed in more detail below, the present invention provides kits for detecting, monitoring or diagnosing a hyperproliferative disorder, identifying individual having such a disorder for possible treatment or monitoring progression (or regression) of the disorder in a patient, wherein the kit comprises a modulator as described herein, and reagents for detecting the impact of the modulator on a sample.

Yet another aspect of the instant invention comprises the use of labeled CD324 for immunohistochemistry (IHC). In this respect CD324 IHC may be used as a diagnostic tool to aid in the diagnosis of various proliferative disorders and to monitor the potential response to treatments including CD324 modulator therapy. Compatible diagnostic assays may be performed on tissues that have been chemically fixed (including but not limited to: formaldehyde, gluteraldehyde, osmium tetroxide, potassium dichromate, acetic acid, alcohols, zinc salts, mercuric chloride, chromium tetroxide and picric acid) and embedded (including but not limited to: glycol methacrylate, paraffin and resins) or preserved via freezing. As discussed in more detail below such assays could be used to guide treatment decisions and determine dosing regimens and timing.

B. Screening

In certain embodiments, the modulators can also be used to screen for or identify compounds or agents (e.g., drugs) that alter a function or activity of tumorigenic cells or progeny thereof by interacting with an antigen (e.g., genotypic or phenotypic components thereof). Such compounds and agents can be drug candidates that are screened for the treatment of a proliferative disorder, for example. In one embodiment, a system or method includes tumorigenic cells comprising CD324 and a compound or agent (e.g., drug), wherein the cells and compound or agent are in contact with each other. In such embodiments the subject cells may have been identified, monitored and/or enriched using the disclosed modulators.

In yet another embodiment, a method includes contacting, directly or indirectly, tumorigenic cells or progeny thereof with a test agent or compound and determining if the test agent or compound modulates an activity or function of the antigen-associated tumorigenic cells. One example of a direct interaction is physical interaction, while an indirect interaction includes the action of a composition upon an intermediary molecule that, in turn, acts upon the referenced entity (e.g., cell or cell culture). Exemplary activities or functions that can be modulated include changes in cell morphology or viability, expression of a marker, differentiation or de-differentiation, cell respiration, mitochondrial activity, membrane integrity, maturation, proliferation, viability, apoptosis or cell death.

Methods of screening and identifying agents and compounds include those suitable for high throughput screening, which include arrays of cells (e.g., microarrays) positioned or placed, optionally at pre-determined locations or addresses. For example, cells can be positioned or placed (pre-seeded) on a culture dish, tube, flask, roller bottle or plate (e.g., a single multi-well plate or dish such as an 8, 16, 32, 64, 96, 384 and 1536 multi-well plate or dish). High-throughput robotic or manual handling methods can probe chemical interactions and determine levels of expression of many genes in a short period of time. Techniques have been developed that utilize molecular signals (e.g., via fluorophores) and automated analyses that process information at a very rapid rate (see, e.g., Pinhasov et al., Comb. Chem. High Throughput Screen. 7:133 (2004)). For example, microarray technology has been extensively used to probe the interactions of thousands of genes at once, while providing information for specific genes (see, e.g., Mocellin and Rossi, Adv. Exp. Med. Biol. 593:19 (2007)).

Libraries that can be screened include, for example, small molecule libraries, phage display libraries, fully human antibody yeast display libraries (Adimab, LLC), siRNA libraries, and adenoviral transfection vectors.

X. Pharmaceutical Preparations and Therapeutic Uses

A. Formulations and Routes of Administration

Depending on the form of the modulator along with any optional conjugate, the mode of intended delivery, the disease being treated or monitored and numerous other variables, compositions of the invention may be formulated as desired using art recognized techniques. In some embodiments, the therapeutic compositions of the invention may be administered neat or with a minimum of additional components while others may optionally be formulated to contain suitable pharmaceutically acceptable carriers comprising excipients and auxiliaries that are well known in the art (see, e.g., Gennaro, *Remington: The Science and Practice of Pharmacy with Facts and Comparisons: Drug/acts Plus,* 20th ed. (2003); Ansel et al., *Pharmaceutical Dosage Forms and Drug Delivery Systems,* $7^{th}$ ed., Lippencott Williams and Wilkins (2004); Kibbe et al., *Handbook of Pharmaceutical Excipients,* $3^{rd}$ ed., Pharmaceutical Press (2000)). Various pharmaceutically acceptable carriers, which include vehicles, adjuvants, and diluents, are readily available from numerous commercial sources. Moreover, an assortment of pharmaceutically acceptable auxiliary substances, such as pH adjusting and buffering agents, tonicity adjusting agents, stabilizers, wetting agents and the like, are also available. Certain non-limiting exemplary carriers include saline, buffered saline, dextrose, water, glycerol, ethanol, and combinations thereof.

More particularly it will be appreciated that, in some embodiments, the therapeutic compositions of the invention may be administered neat or with a minimum of additional components. Conversely the CD324 modulators of the present invention may optionally be formulated to contain suitable pharmaceutically acceptable carriers comprising excipients and auxiliaries that are well known in the art and are relatively inert substances that facilitate administration of the modulator or which aid processing of the active compounds into preparations that are pharmaceutically optimized for delivery to the site of action. For example, an excipient can give form or consistency or act as a diluent to improve the pharmacokinetics or stability of the modulator. Suitable excipients or additives include, but are not limited to, stabilizing agents, wetting and emulsifying agents, salts for varying osmolarity, encapsulating agents, buffers, and skin penetration enhancers. In certain preferred embodiments the pharmaceutical compositions may be provided in a lyophilized form and reconstituted in, for example, buffered saline prior to administration.

Disclosed modulators for systemic administration may be formulated for enteral, parenteral or topical administration. Indeed, all three types of formulation may be used simultaneously to achieve systemic administration of the active ingredient. Excipients as well as formulations for parenteral and nonparenteral drug delivery are set forth in Remington, The Science and Practice of Pharmacy 20th Ed. Mack Publishing (2000). Suitable formulations for parenteral administration include aqueous solutions of the active compounds in water-soluble form, for example, water-soluble salts. In addition, suspensions of the active compounds as appropriate for oily injection suspensions may be administered. Suitable lipophilic solvents or vehicles include fatty oils, for example, hexylsubstituted poly(lactide), sesame oil, or synthetic fatty acid esters, for example, ethyl oleate or triglycerides. Aqueous injection suspensions may contain substances that increase the viscosity of the suspension and include, for example, sodium carboxymethyl cellulose, sorbitol, and/or dextran. Optionally, the suspension may also contain stabilizers. Liposomes can also be used to encapsulate the agent for delivery into the cell.

Suitable formulations for enteral administration include hard or soft gelatin capsules, pills, tablets, including coated tablets, elixirs, suspensions, syrups or inhalations and controlled release forms thereof.

In general the compounds and compositions of the invention, comprising CD324 modulators may be administered in vivo, to a subject in need thereof, by various routes, including, but not limited to, oral, intravenous, intra-arterial, subcutaneous, parenteral, intranasal, intramuscular, intracranial, intracardiac, intraventricular, intratracheal, buccal, rectal, intraperitoneal, intradermal, topical, transdermal, and intrathecal, or otherwise by implantation or inhalation. The subject compositions may be formulated into preparations in solid, semi-solid, liquid, or gaseous forms; including, but not limited to, tablets, capsules, powders, granules, ointments, solutions, suppositories, enemas, injections, inhalants, and aerosols. The appropriate formulation and route of administration may be selected according to the intended application and therapeutic regimen.

B. Dosages

Similarly, the particular dosage regimen, i.e., dose, timing and repetition, will depend on the particular individual and that individual's medical history, as well as empirical considerations such as pharmacokinetics (e.g., half-life, clearance rate, etc.). Frequency of administration may be determined and adjusted over the course of therapy, and is based on reducing the number of proliferative or tumorigenic cells, maintaining the reduction of such neoplastic cells, reducing the proliferation of neoplastic cells, or delaying the development of metastasis. In other embodiments the dosage administered may be adjusted or attenuated to manage potential side effects and/or toxicity. Alternatively, sustained continuous release formulations of a subject therapeutic composition may be appropriate.

In general, the modulators of the invention may be administered in various ranges. These include about 10 µg/kg body weight to about 100 mg/kg body weight per dose; about 50 µg/kg body weight to about 5 mg/kg body weight per dose; about 100 µg/kg body weight to about 10 mg/kg body weight per dose. Other ranges include about 100 µg/kg body weight to about 20 mg/kg body weight per dose and about 0.5 mg/kg body weight to about 20 mg/kg body weight per dose. In certain embodiments, the dosage is at least about 100 µg/kg body weight, at least about 250 µg/kg body weight, at least about 750 µg/kg body weight, at least about 3 mg/kg body weight, at least about 5 mg/kg body weight, at least about 10 mg/kg body weight.

Other dosing regimens may be predicated on Body Surface Area (BSA) calculations as disclosed in U.S. Pat. No. 7,744,877. As is well known, the BSA is calculated using the patient's height and weight and provides a measure of a subject's size as represented by the surface area of his or her body. In certain embodiments, the modulators may be administered in dosages from 10 mg/m$^2$ to 800 mg/m$^2$, from 50 mg/m$^2$ to 500 mg/m$^2$ and at dosages of 100 mg/m$^2$, 150 mg/m$^2$, 200 mg/m$^2$, 250 mg/m$^2$, 300 mg/m$^2$, 350 mg/m$^2$, 400 mg/m$^2$ or 450 mg/m$^2$.

In any event, CD324 modulators are preferably administered as needed to subjects in need thereof. Determination of the frequency of administration may be made by persons skilled in the art, such as an attending physician based on considerations of the condition being treated, age of the subject being treated, severity of the condition being treated, general state of health of the subject being treated and the like. Generally, an effective dose of the CD324 modulator is administered to a subject one or more times. More particularly, an effective dose of the modulator is administered to the subject once a month, more than once a month, or less than once a month. In certain embodiments, the effective dose of the CD324 modulator may be administered multiple times, including for periods of at least a month, at least six months, at least a year, at least two years or a period of several years. In yet other embodiments, several days (2, 3, 4, 5, 6 or 7), several weeks (1, 2, 3, 4, 5, 6, 7 or 8) or several months (1, 2, 3, 4, 5, 6, 7 or 8) or even a year or several years may lapse between administration of the disclosed modulators.

Dosages and regimens may also be determined empirically for the disclosed therapeutic compositions in individuals who have been given one or more administration(s). For example, individuals may be given incremental dosages of a therapeutic composition produced as described herein. In selected embodiments the dosage may be gradually increased or reduced or attenuated based respectively on empirically determined or observed side effects or toxicity. To assess efficacy of the selected composition, a marker of the specific disease, disorder or condition can be followed as described previously. In embodiments where the individual has cancer, these include direct measurements of tumor size via palpation or visual observation, indirect measurement of tumor size by x-ray or other imaging techniques; an improvement as assessed by direct tumor biopsy and microscopic examination of the tumor sample; the measurement of an indirect tumor marker (e.g., PSA for prostate cancer) or an antigen identified according to the methods described herein, a decrease in pain or paralysis; improved speech, vision, breathing or other disability associated with the tumor; increased appetite; or an increase in quality of life as measured by accepted tests or prolongation of survival. It will be apparent to one of skill in the art that the dosage will vary depending on the individual, the type of neoplastic condition, the stage of neoplastic condition, whether the neoplastic condition has begun to metastasize to other location in the individual, and the past and concurrent treatments being used.

In addition to the aforementioned dosing regimens it will be appreciated that the present invention comprise the administration of an amount of a CD324 modulator in an amount necessary to reduce or eliminate any modulator "sink" prior to administering a therapeutic dose of the disclosed modulator. As discussed above the first administered CD324 modulator will preferably be non-internalizing and/or non-depleting. In other preferred embodiments the subsequently administered CD324 modulator will be internalizing and/or depleting and will optionally be conjugated to a cytotoxic agent. Preferably the pre-administration of the modulator will take place long enough before the administration of the therapeutic modulator dose to allow partial or complete saturation of the antigen present in normal tissue. In this regard one skilled in the art could readily determine the amount of modulator necessary to effectively reduce the modulator sink through empirical observation or standard clinical methodology. Preferably the sink reduction dose will be 1, 2, 3, 4, 5, 6, 7, 8, 9 or 10 times the subsequent therapeutic dose. In other embodiments the sink reduction dose will be 12, 14, 16, 18 or 20 times the therapeutic dose. Similarly, the timing of the pre-dosing could readily be determined by a clinician skilled in the art and, in preferred embodiments, will be 1, 2, 3, 4, 5, 6, 7, 8, 9 or 10 days prior to the administration of a therapeutic dose. Again, the results of the initial dosing may readily be monitored and subsequent doses administered as determined to optimize the effectiveness of the treatment.

C. Combination Therapies

Combination therapies may be particularly useful in decreasing or inhibiting unwanted neoplastic cell proliferation, decreasing the occurrence of cancer, decreasing or preventing the recurrence of cancer, or decreasing or preventing the spread or metastasis of cancer. In such cases the modulators of the instant invention may function as sensitizing or chemosensitizing agents by removing the CSCs that would otherwise prop up and perpetuate the tumor mass and thereby allow for more effective use of current standard of care debulking or anti-cancer agents. That is, the disclosed modulators may, in certain embodiments provide an enhanced effect (e.g., additive or synergistic in nature) that potentiate the mode of action of another administered therapeutic agent. In the context of the instant invention "combination therapy" shall be interpreted broadly and merely refers to the administration of a modulator and one or more anti-cancer agents that include, but are not limited to, cytotoxic agents, cytostatic agents, anti-angiogenic agents, debulking agents, chemotherapeutic agents, radiotherapy and radiotherapeutic agents, targeted anti-cancer agents (including both monoclonal antibodies and small molecule entities), BRMs, therapeutic antibodies, cancer vaccines, cytokines, hormone therapies, radiation therapy and antimetastatic agents and immunotherapeutic agents, including both specific and non-specific approaches.

There is no requirement for the combined results to be additive of the effects observed when each treatment (e.g., antibody and anti-cancer agent) is conducted separately. Although at least additive effects are generally desirable, any increased anti-tumor effect above one of the single therapies is beneficial. Furthermore, the invention does not require the combined treatment to exhibit synergistic effects. However, those skilled in the art will appreciate that with certain selected combinations that comprise preferred embodiments, synergism may be observed.

In practicing combination therapy, the modulator and anti-cancer agent may be administered to the subject simultaneously, either in a single composition, or as two or more distinct compositions using the same or different administration routes. Alternatively, the modulator may precede, or follow, the anti-cancer agent treatment by, e.g., intervals ranging from minutes to weeks. The time period between each delivery is such that the anti-cancer agent and modulator are able to exert a combined effect on the tumor. In at least one embodiment, both the anti-cancer agent and the modulator are administered within about 5 minutes to about two weeks of each other. In yet other embodiments, several days (2, 3, 4, 5, 6 or 7), several weeks (1, 2, 3, 4, 5, 6, 7 or 8) or several months (1, 2, 3, 4, 5, 6, 7 or 8) may lapse between administration of the modulator and the anti-cancer agent.

The combination therapy may be administered once, twice or at least for a period of time until the condition is treated, palliated or cured. In some embodiments, the combination therapy is administered multiple times, for example, from three times daily to once every six months. The administering may be on a schedule such as three tunes daily, twice daily, once daily, once every two days, once every three days, once weekly, once every two weeks, once every month, once every two months, once every three months, once every six months or may be administered continuously via a minipump. The combination therapy may be administered via any route, as noted previously. The combination therapy may be administered at a site distant from the site of the tumor.

In one embodiment a modulator is administered in combination with one or more anti-cancer agents for a short treatment cycle to a subject in need thereof. The invention also contemplates discontinuous administration or daily doses divided into several partial administrations. The modulator and anti-cancer agent may be administered interchangeably, on alternate days or weeks; or a sequence of antibody treatments may be given, followed by one or more treatments of anti-cancer agent therapy. In any event, as will be understood by those of ordinary skill in the art, the appropriate doses of chemotherapeutic agents will be generally around those already employed in clinical therapies wherein the chemotherapeutics are administered alone or in combination with other chemotherapeutics.

In another preferred embodiment the CD324 modulators of the instant invention may be used in maintenance therapy to reduce or eliminate the chance of tumor recurrence following the initial presentation of the disease. Preferably the disorder will have been treated and the initial tumor mass eliminated, reduced or otherwise ameliorated so the patient is asymptomatic or in remission. At such time the subject may be administered pharmaceutically effective amounts of the disclosed modulators one or more times even though there is little or no indication of disease using standard diagnostic procedures. In some embodiments, the modulators will be administered on a regular schedule over a period of time, such as weekly, every two weeks, monthly, every six weeks, every two months, every three months every six months or annually. Given the teachings herein, one skilled in the art could readily determine favorable dosages and dosing regimens to reduce the potential of disease recurrence. Moreover such treatments could be continued for a period of weeks, months, years or even indefinitely depending on the patient response and clinical and diagnostic parameters.

In yet another preferred embodiment the modulators of the present invention may be used to prophylactically or as an adjuvant therapy to prevent or reduce the possibility of tumor metastasis following a debulking procedure. As used in the instant disclosure a "debulking procedure" is defined broadly and shall mean any procedure, technique or method that eliminates, reduces, treats or ameliorates a tumor or tumor proliferation. Exemplary debulking procedures include, but are not limited to, surgery, radiation treatments (i.e., beam radiation), chemotherapy, immunotherapy or ablation. At appropriate times readily determined by one skilled in the art in view of the instant disclosure the disclosed modulators may be administered as suggested by clinical, diagnostic or theragnostic procedures to reduce tumor metastasis. The modulators may be administered one or more times at pharmaceutically effective dosages as determined using standard techniques. Preferably the dosing regimen will be accompanied by appropriate diagnostic or monitoring techniques that allow it to be modified.

Yet other embodiments of the invention comprise administering the disclosed modulators to subjects that are asymptomatic but at risk of developing a proliferative disorder. That is, the modulators of the instant invention may be used in a truly preventative sense and given to patients that have been examined or tested and have one or more noted risk factors (e.g., genomic indications, family history, in vivo or in vitro test results, etc.) but have not developed neoplasia. In such cases those skilled in the art would be able to D. Anti-Cancer Agents The term "anti-cancer agent" or "anti-proliferative agent" means any agent that can be used to treat a cell proliferative disorder such as cancer, and includes, but not limited to, cytotoxic agents, cytostatic agents, anti-angiogenic agents, debulking agents, chemotherapeutic agents, radiotherapy and radiotherapeutic agents, targeted anti-cancer agents, BRMs, therapeutic antibodies, cancer vaccines, cytokines, hormone therapies, radiation therapy and anti-metastatic agents and immunotherapeutic agents. It will be appreciated that, in selected embodiments as discussed above, such anti-cancer agents may comprise conjugates and may be associated with modulators prior to administration. In certain embodiments the disclosed anti-cancer agent will be linked to a CD324 modulator to provide an ADC as set forth herein.

As used herein the term "cytotoxic agent" means a substance that is toxic to the cells and decreases or inhibits the function of cells and/or causes destruction of cells. Typically, the substance is a naturally occurring molecule derived from a living organism. Examples of cytotoxic agents include, but are not limited to, small molecule toxins or enzymatically active toxins of bacteria (e.g., Diptheria toxin, *Pseudomonas* endotoxin and exotoxin, Staphylococcal enterotoxin A), fungal (e.g., α-sarcin, restrictocin), plants (e.g., abrin, ricin, modeccin, viscumin, pokeweed anti-viral protein, saporin, gelonin, momoridin, trichosanthin, barley toxin, *Aleurites fordii* proteins, dianthin proteins, *Phytolacca mericana* proteins (PAPI, PAPII, and PAP-S), *Momordica charantia* inhibitor, curcin, crotin, *saponaria officinalis* inhibitor, gelonin, mitegellin, restrictocin, phenomycin, neomycin, and the tricothecenes) or animals, (e.g., cytotoxic RNases, such as extracellular pancreatic RNases; DNase I, including fragments and/or variants thereof).

For the purposes of the instant invention a "chemotherapeutic agent" comprises a chemical compound that non-specifically decreases or inhibits the growth, proliferation, and/or survival of cancer cells (e.g., cytotoxic or cytostatic agents). Such chemical agents are often directed to intracellular processes necessary for cell growth or division, and are thus particularly effective against cancerous cells, which generally grow and divide rapidly. For example, vincristine depolymerizes microtubules, and thus inhibits cells from entering mitosis. In general, chemotherapeutic agents can include any chemical agent that inhibits, or is designed to inhibit, a cancerous cell or a cell likely to become cancerous or generate tumorigenic progeny (e.g., TIC). Such agents are often administered, and are often most effective, in combination, e.g., in regimens such as CHOP or FOLFIRI. Again, in selected embodiments such chemotherapeutic agents may be conjugated to the disclosed modulators.

Examples of anti-cancer agents that may be used in combination with (or conjugated to) the modulators of the present invention include, but are not limited to, alkylating agents, alkyl sulfonates, aziridines, ethylenimines and methylamelamines, acetogenins, a camptothecin, bryostatin, callystatin, CC-1065, cryptophycins, dolastatin, duocarmycin, eleutherobin, pancratistatin, a sarcodictyin, spongistatin, nitrogen mustards, antibiotics, enediyne antibiotics, dynemicin, bisphosphonates, esperamicin, chromoprotein enediyne antiobiotic chromophores, aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine. ADRIAMYCIN® doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites, folic acid analogues, purine analogs, androgens, anti-adrenals, folic acid replenisher such as frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, an epothilone, etoglucid, gallium nitrate, hydroxyurea, lentinan, lonidainine, maytansinoids, mitoguazone, mitoxantrone, mopidanmol, nitraerine, pentostatin, phenamet, pirarubicin, losoxantrone, podophyllinic acid, 2-ethylhydrazide, procarbazine, PSK® polysaccharide complex (JHS Natural Products, Eugene, Oreg.), razoxane; rhizoxin; sizofiran; spirogermanium; tenuazonic acid; triaziquone; 2,2',2"-trichlorotriethyl amine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, chloranbucil; GEMZAR® gemcitabine; 6-thioguanine; mercaptopurine; methotrexate; platinum analogs, vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11), topoisomerase inhibitor RFS 2000; difluorometlhylornithine; retinoids; capecitabine; combretastatin; leucovorin; oxaliplatin; inhibitors of PKC-alpha, Raf, H-Ras, EGFR and VEGF-A that reduce cell proliferation and pharmaceutically acceptable salts, acids or derivatives of any of the above. Also included in this definition are anti-hormonal agents that act to regulate or inhibit hormone action on tumors such as anti-estrogens and selective estrogen receptor modulators, aromatase inhibitors that inhibit the enzyme aromatase, which regulates estrogen production in the adrenal glands, and anti-androgens; as well as troxacitabine (a 1,3-dioxolane nucleoside cytosine analog); antisense oligonucleotides, ribozymes such as a VEGF expression inhibitor and a HER2 expression inhibitor; vaccines, PROLEUKIN® rIL-2; LUR-TOTECAN® topoisomerase 1 inhibitor; ABARELIX® rmRH; Vinorelbine and Esperamicins and pharmaceutically acceptable salts, acids or derivatives of any of the above.

In yet other embodiments the modulators of the instant invention may be used in conjunction with antibodies in clinical development. To that end the disclosed 324 modulators may be used in conjunction with one or more antibodies selected from the group consisting of abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8. In particularly preferred embodiments the invention will comprise the use of CD324 modulators with antibodies approved for cancer therapy including, but not limited to, rituximab, trastuzumab, gemtuzumab ozogamcin, alemtuzumab, ibritumomab tiuxetan, tositumomab, bevacizumab, cetuximab, panitumumab, ofatumumab, ipilimumab and brentuximab vedotin. Those skilled in the art will be able to readily identify additional anti-cancer agents that are compatible with the teachings herein.

E. Radiotherapy

The present invention also provides for the combination of modulators with radiotherapy (i.e., any mechanism for inducing DNA damage locally within tumor cells such as gamma-irradiation, X-rays, UV-irradiation, microwaves, electronic emissions and the like). Combination therapy using the directed delivery of radioisotopes to tumor cells is also contemplated, and may be used in connection with a targeted anti-cancer agent or other targeting means. Typically, radiation therapy is administered in pulses over a period of time from about 1 to about 2 weeks. The radiation therapy may be administered to subjects having head and neck cancer for about 6 to 7 weeks. Optionally, the radiation therapy may be administered as a single dose or as multiple, sequential doses.

XI. Indications

It will be appreciated that the modulators of the instant invention may be used to diagnose, treat or inhibit the occurrence or recurrence of any CD324 associated disorder. Accordingly, whether administered alone or in combination with an anti-cancer agent or radiotherapy, the modulators of the invention are particularly useful for generally treating neoplastic conditions in patients or subjects which may include benign or malignant tumors (e.g., adrenal, liver, kidney, bladder, breast, gastric, ovarian, colorectal, prostate, pancreatic, lung, thyroid, hepatic, cervical, endometrial, esophageal and uterine carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic, immunologic disorders and disorders caused by pathogens. Particularly, key targets for treatment are neoplastic conditions comprising solid tumors, although hematologic malignancies are within the scope of the invention. Preferably the "subject" or "patient" to be treated will be human although, as used herein, the terms are expressly held to comprise any mammalian species.

More specifically, neoplastic conditions subject to treatment in accordance with the instant invention may be selected from the group including, but not limited to, adrenal gland tumors, AIDS-associated cancers, alveolar soft part sarcoma, astrocytic tumors, bladder cancer (squamous cell carcinoma and transitional cell carcinoma), bone cancer (adamantinoma, aneurismal bone cysts, osteochondroma, osteosarcoma), brain and spinal cord cancers, metastatic brain tumors, breast cancer, carotid body tumors, cervical cancer, chondrosarcoma, chordoma, chromophobe renal cell carcinoma, clear cell carcinoma, colon cancer, colorectal cancer, cutaneous benign fibrous histiocytomas, desmoplastic small round cell tumors, ependymomas, Ewing's tumors, extraskeletal myxoid chondrosarcoma, fibrogenesis imperfecta ossium, fibrous dysplasia of the bone, gallbladder and bile duct cancers, gestational trophoblastic disease, germ cell tumors, head and neck cancers, islet cell tumors, Kaposi's Sarcoma, kidney cancer (nephroblastoma, papillary renal cell carcinoma), leukemias, lipoma/benign lipomatous tumors, liposarcoma/malignant lipomatous tumors, liver cancer (hepatoblastoma, hepatocellular carcinoma), lymphomas, lung cancers (small cell carcinoma, adenocarcinoma, squamous cell carcinoma, large cell carcinoma etc.), medulloblastoma, melanoma, meningiomas, multiple endocrine neoplasia, multiple myeloma, myelodysplastic syndrome, neuroblastoma, neuroendocrine tumors, ovarian cancer, pancreatic cancers, papillary thyroid carcinomas, parathyroid tumors, pediatric cancers, peripheral nerve sheath tumors, phaeochromocytoma, pituitary tumors, prostate cancer, posterious unveal melanoma, rare hematologic disorders, renal metastatic cancer, rhabdoid tumor, rhabdomysarcoma, sarcomas, skin cancer, soft-tissue sarcomas, squamous cell cancer, stomach cancer, synovial sarcoma, testicular cancer, thymic carcinoma, thymoma, thyroid metastatic cancer, and uterine cancers (carcinoma of the cervix, endometrial carcinoma, and leiomyoma).

In certain preferred embodiments the proliferative disorder will comprise a solid tumor including, but not limited to, adrenal, liver, kidney, bladder, breast, gastric, ovarian, cervical, uterine, esophageal, colorectal, prostate, pancreatic, lung (both small cell and non-small cell), thyroid, carcinomas, sarcomas, glioblastomas and various head and neck tumors. In other preferred embodiments, and as shown in the Examples below, the disclosed modulators are especially effective at treating small cell lung cancer (SCLC) and non-small cell lung cancer (NSCLC) (e.g., squamous cell non-small cell lung cancer or squamous cell small cell lung cancer). In one embodiment, the lung cancer is refractory, relapsed or resistant to a platinum based agent (e.g., carboplatin, cisplatin, oxaliplatin) and/or a taxane (e.g., docetaxel, paclitaxel, larotaxel or cabazitaxel). Further, in particularly preferred embodiments the disclosed modulators may be used in a conjugated form to treat small cell lung cancer.

With regard to hematologic malignancies it will be further be appreciated that the compounds and methods of the present invention may be particularly effective in treating a variety of B-cell lymphomas, including low grade/NHL follicular cell lymphoma (FCC), mantle cell lymphoma (MCL), diffuse large cell lymphoma (DLCL), small lymphocytic (SL) NHL, intermediate grade/follicular NHL, intermediate grade diffuse NHL, high grade immunoblastic NHL, high grade lymphoblastic NHL, high grade small non-cleaved cell NHL, bulky disease NHL, Waldenstrom's Macroglobulinemia, lymphoplasmacytoid lymphoma (LPL), mantle cell lymphoma (MCL), follicular lymphoma (FL), diffuse large cell lymphoma (DLCL), Burkitt's lymphoma (BL), AIDS-related lymphomas, monocytic B cell lymphoma, angioimmunoblastic lymphoadenopathy, small lymphocytic, follicular, diffuse large cell, diffuse small cleaved cell, large cell immunoblastic lymphoblastoma, small, non-cleaved, Burkitt's and non-Burkitt's, follicular, predominantly large cell; follicular, predominantly small cleaved cell; and follicular, mixed small cleaved and large cell lymphomas. See, Gaidono et al., "Lymphomas", IN CANCER: PRINCIPLES & PRACTICE OF ONCOLOGY, Vol. 2: 2131-2145 (DeVita et al., eds., 5.sup.th ed. 1997). It should be clear to those of skill in the art that these lymphomas will often have different names due to changing systems of classification, and that patients having lymphomas classified under different names may also benefit from the combined therapeutic regimens of the present invention.

The present invention also provides for a preventative or prophylactic treatment of subjects who present with benign or precancerous tumors. Beyond being a CD324 associated disorder It is not believed that any particular type of tumor or proliferative disorder should be excluded from treatment using the present invention. However, the type of tumor cells may be relevant to the use of the invention in combination with secondary therapeutic agents, particularly chemotherapeutic agents and targeted anti-cancer agents.

XII. Articles of Manufacture

Pharmaceutical packs and kits comprising one or more containers, comprising one or more doses of a CD324 modulator are also provided. In certain embodiments, a unit dosage is provided wherein the unit dosage contains a predetermined amount of a composition comprising, for example, an anti-CD324 antibody, with or without one or more additional agents. For other embodiments, such a unit dosage is supplied in single-use prefilled syringe for injection. In still other embodiments, the composition contained in the unit dosage may comprise saline, sucrose, or the like; a buffer, such as phosphate, or the like; and/or be formulated within a stable and effective pH range. Alternatively, in certain embodiments, the composition may be provided as a lyophilized powder that may be reconstituted upon addition of an appropriate liquid, for example, sterile water. In certain preferred embodiments, the composition comprises one or more substances that inhibit protein aggregation, including, but not limited to, sucrose and arginine. Any label on, or associated with, the container(s) indicates that the enclosed composition is used for diagnosing or treating the disease condition of choice.

The present invention also provides kits for producing single-dose or multi-dose administration units of a CD324 modulator and, optionally, one or more anti-cancer agents. The kit comprises a container and a label or package insert on or associated with the container. Suitable containers include, for example, bottles, vials, syringes, etc. The containers may be formed from a variety of materials such as glass or plastic and contain a pharmaceutically effective amount of the disclosed modulators in a conjugated or unconjugated form. In other preferred embodiments the container(s) comprise a sterile access port (for example the container may be an intravenous solution bag or a vial having a stopper pierceable by a hypodermic injection needle). Such kits will generally contain in a suitable container a pharmaceutically acceptable formulation of the CD324 modulator and, optionally, one or more anti-cancer agents in the same or different containers. The kits may also contain other pharmaceutically acceptable formulations, either for diagnosis or combined therapy. For example, in addition to the CD324 modulator of the invention such kits may contain any one or more of a range of anti-cancer agents such as chemotherapeutic or radiotherapeutic drugs; anti-angiogenic agents; anti-metastatic agents; targeted anti-cancer agents; cytotoxic agents; and/or other anti-cancer agents. Such kits may also provide appropriate reagents to conjugate the CD324 modulator with an anti-cancer agent or diagnostic agent (e.g., see U.S. Pat. No. 7,422,739 which is incorporated herein by reference in its entirety).

More specifically the kits may have a single container that contains the CD324 modulator, with or without additional components, or they may have distinct containers for each desired agent. Where combined therapeutics are provided for conjugation, a single solution may be pre-mixed, either in a molar equivalent combination, or with one component in excess of the other. Alternatively, the CD324 modulator and any optional anti-cancer agent of the kit may be maintained separately within distinct containers prior to administration to a patient. The kits may also comprise a second/third container means for containing a sterile, pharmaceutically acceptable buffer or other diluent such as bacteriostatic water for injection (BWFI), phosphate-buffered saline (PBS), Ringer's solution and dextrose solution.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent may also be provided in another container.

As indicated briefly above the kits may also contain a means by which to administer the antibody and any optional components to an animal or patient, e.g., one or more needles or syringes, or even an eye dropper, pipette, or other such like apparatus, from which the formulation may be injected or introduced into the animal or applied to a diseased area of the body. The kits of the present invention will also typically include a means for containing the vials, or such like, and other component in close confinement for commercial sale, such as, e.g., injection or blow-molded plastic containers into which the desired vials and other apparatus are placed and retained. Any label or package insert indicates that the CD324 modulator composition is used for treating cancer, for example small cell lung cancer.

In other preferred embodiments the modulators of the instant invention may be used in conjunction with, or comprise, diagnostic or therapeutic devices useful in the diagnosis or treatment of proliferative disorders. For example, in on preferred embodiment the compounds and compositions of the instant invention may be combined with certain diagnostic devices or instruments that may be used to detect, monitor, quantify or profile cells or marker compounds involved in the etiology or manifestation of proliferative disorders. For selected embodiments the marker compounds may comprise NSE, CD56, synaptophysin, chromogranin A, and PGP9.5.

In particularly preferred embodiments the devices may be used to detect, monitor and/or quantify circulating tumor cells either in vivo or in vitro (see, for example, WO 2012/0128801 which is incorporated herein by reference). In still other preferred embodiments, and as discussed above, the circulating tumor cells may comprise cancer stem cells.

XIII. Research Reagents

Other preferred embodiments of the invention also exploit the properties of the disclosed modulators as an instrument useful for identifying, monitoring, isolating, sectioning or enriching populations or subpopulations of tumor initiating cells through methods such as flow cytometry, fluorescent activated cell sorting (FACS), magnetic activated cell sorting (MACS) or laser mediated sectioning. Those skilled in the art will appreciate that the modulators may be used in several compatible techniques for the characterization and manipulation of TIC including cancer stem cells (e.g., see U.S. Ser. Nos. 12/686,359, 12/669,136 and 12/757,649 each of which is incorporated herein by reference in its entirety).

XIV. Miscellaneous

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. More specifically, as used in this specification and the appended claims, the singular forms "a," "an" and "the" include plural referents unless the context clearly dictates otherwise. Thus, for example, reference to "a protein" includes a plurality of proteins; reference to "a cell" includes mixtures of cells, and the like. In addition, ranges provided in the specification and appended claims include both end points and all points between the end points. Therefore, a range of 2.0 to 3.0 includes 2.0, 3.0, and all points between 2.0 and 3.0.

Generally, nomenclature used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Abbas et al., Cellular and Molecular Immunology, 6$^{th}$ ed., W.B. Saunders Company (2010); Sambrook J. & Russell D. *Molecular Cloning: A Laboratory Manual*, 3rd ed., Cold Spring Harbor Laboratory Press, Cold Spring Harbor, N.Y. (2000); Ausubel et al., *Short Protocols in Molecular Biology: A Compendium of Methods from Current Protocols in Molecular Biology*, Wiley, John & Sons, Inc. (2002); Harlow and Lane *Using Antibodies: A Laboratory Manual*, Cold Spring Harbor Laboratory Press, Cold Spring Harbor, N.Y. (1998); and Coligan et al., *Short Protocols in Protein Science*, Wiley, John & Sons, Inc. (2003). Enzymatic reactions and purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well known and commonly used in the art.

XV. CD324 References

All references or documents disclosed or cited within this specification are, without limitation, incorporated herein by reference in their entirety. Moreover, any section headings used herein are for organizational purposes only and are not to be construed as limiting the subject matter described.

1. Takeichi M. Cadherins: a molecular family important in selective cell-cell adhesion. Annu Rev Biochem. 59:237-52. (1990).
2. Takeichi M. Cadherin cell adhesion receptors as a morphogenetic regulator. Science 251: 1451-1455 (1991).
3. Gumbiner B M. Cell adhesion: the molecular basis of tissue architecture and morphogenesis. Cell. 84:345-57 (1996).
4. Nollet F, Kools P, van Roy F. Phylogenetic analysis of the cadherin superfamily allows identification of six major subfamilies besides several solitary members. J Mol Biol. 299:551-72 (2000).
5. Huntsman D G, Caldas C. Assignment of the E-cadherin gene (CDH1) to chromosome 16q22.1 by radiation hybrid mapping. Cytogenet Cell Genet. 83:82-3 (1998).
6. Shiozaki H, et al. E-Cadherin mediated adhesion system in cancer cells. Cancer 77: 1605-1613 (1996).
7. Niessen C M, Gottardi C J. Molecular components of the adherens junction. Biochim Biophys Acta. 1778: 562-71 (2008).
8. Nose, A., Nagafuchi, A., and Takeichi, M. Expressed recombinant cadherins mediate cell sorting in model systems. Cell 54: 993-1001 (1998).
9. Chen, C. P et al. Critical role for low-affinity dimerization through-strand swapping. Proc. Natl. Acad. Sci. 102: 8531-8536 (2005)
10. Patel, S. D. et al. Type H cadherin ectodomain structures: Implications for classical cadherin specificity. Cell 124: 1255-1268 (2006).
11. Mohamet L, Hawkins K, and Ward C M. Loss of function of e-cadherin in embryonic stem cells and the relevance to models of tumorigenesis. J Oncol. 2011: 352616 (2011).
12. Duguay D, Foty R A, and Steinberg M S. Cadherin-mediated cell adhesion and tissue segregation: qualitative and quantitative determinants. Dev Biol. 253(2): 309-23 (2003).
13, Perez-Moreno M, Jamora C, and Fuchs E. Sticky business: orchestrating cellular signals at adherens junctions. Cell 112: 535-548 (2003).
14. Haegel H, et al. Lack of beta-catenin affects mouse development at gastrulation. Development. 121(11): 3529-37 (1995).
15. Samavarchi-Tehrani P, et al. Functional genomics reveals a BMP-driven mesenchymal-to-epithelial transition in the initiation of somatic cell reprogramming. Cell Stem Cell. 7:64-77 (2010).
16. Li R et al. A Mesenchymal-to-Epithelial Transition Initiates and Is Required for the Nuclear Reprogramming of Mouse Fibroblasts. Cell Stem Cell 7: 51-63 (2010).
17. Redmer et al. E-cadherin is crucial for embryonic stem cell pluripotency and can replace OCT4 during somatic cell reprogramming. EMBO Reports 12:719 (2011).
18. Acloque H, Thiery J P, and Nieto M A. The physiology and pathology of the EMT. Meeting on the epithelial-mesenchymal transition. EMBO Rep. 9:322-6 (2008).

All references or documents disclosed or cited within this specification are, without limitation, incorporated herein by reference in their entirety. Moreover, any section headings used herein are for organizational purposes only and are not to be construed as limiting the subject matter described.

XVI. Selected Embodiments of the Invention

In addition to the disclosure and Examples herein, the present invention is directed to selected embodiments specifically set forth in this section.

Putative Claims

1. An isolated CD324 modulator.
2. The isolated CD324 modulator of claim 1, wherein the CD324 modulator comprises a CD324 antagonist.
3. The isolated CD324 modulator of claim 1, wherein the CD324 modulator comprises an antibody or immunoreactive fragment thereof.
4. The isolated CD324 modulator of claim 3 wherein the antibody or immunoreactive fragment thereof comprises a monoclonal antibody.
5. The isolated CD324 modulator of claim 4 wherein the monoclonal antibody is selected from the group consisting of chimeric antibodies, humanized antibodies and human antibodies.
6. The isolated CD324 modulator of claim 4 wherein said monoclonal antibody comprises a neutralizing antibody.
7. The isolated CD324 modulator of claim 4 wherein said monoclonal antibody comprises a depleting antibody.
8. The isolated CD324 modulator of claim 4 wherein said monoclonal antibody comprises an internalizing antibody.

9. The isolated CD324 modulator of claim 8 wherein said monoclonal antibody further comprises a cytotoxic agent.

10. The isolated CD324 modulator of claim 4 wherein said monoclonal antibody or immunoreactive fragment thereof comprises a light chain variable region having three complementarity determining regions and a heavy chain variable region having three complementarity determining regions wherein the heavy and light chain complementarity determining regions comprise at least one complementarity determining region set forth in FIG. 11A and FIG. 11B.

11. The isolated CD324 modulator of claim 4 wherein said monoclonal antibody or immunoreactive fragment thereof comprises a light chain variable region and a heavy chain variable region wherein said light chain variable region comprises an amino acid sequence having at least 60% identity to an amino acid sequence selected from the group consisting of amino acid sequences as set forth in SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68 and SEQ ID NO: 70 and wherein said heavy chain variable region comprises an amino acid sequence having at least 60% identity to an amino acid sequence selected from the group consisting of amino acid sequences as set forth in SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51 SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69 and SEQ ID NO: 71.

12. The isolated CD324 modulator of claim 10 or 11 further comprising a cytotoxic agent.

13. An isolated CD324 modulator comprising a competing antibody wherein said competing antibody inhibits the binding of an isolated CD324 modulator of claim 10 or 11 to CD324 by at least about 40%.

14. A nucleic acid encoding an amino acid heavy chain variable region or an amino acid light chain variable region of claim 11.

15. A vector comprising the nucleic acid of claim 14.

16. The isolated CD324 modulator of claim 1 wherein the modulator comprises a multispecific antibody.

17. The isolated CD324 modulator of claim 16 wherein the multispecific antibody comprises a bispecific antibody.

18. The isolated CD324 modulator of claim 1 wherein said modulator reduces the frequency of tumor initiating cells upon administration to a subject in need thereof.

19. The isolated CD324 modulator of claim 18 wherein the reduction in frequency is determined using flow cytometric analysis of tumor cell surface markers known to enrich for tumor initiating cells.

20. The isolated CD324 modulator of claim 18 wherein the reduction in frequency is determined using immunohistochemical detection of tumor cell surface markers known to enrich for tumor initiating cells.

21. The isolated CD324 modulator of claim 18 wherein said tumor initiating cells comprise tumor perpetuating cells.

22. The isolated CD324 modulator of claim 1 further comprising a cytotoxic agent.

23. A pharmaceutical composition comprising the isolated CD324 modulator of claim 1.

24. The pharmaceutical composition of claim 23 wherein said isolated CD324 modulator comprises a monoclonal antibody.

25. The pharmaceutical composition of claim 24 wherein said monoclonal antibody comprises a humanized antibody.

26. The pharmaceutical composition of claim 25 wherein said humanized antibody comprises a cytotoxic agent.

27. The isolated CD324 modulator of claim 26 wherein said cytotoxic agent comprises a pyrrolobenzodiazepine.

28. A method of treating a CD324 associated disorder comprising administering a therapeutically effective amount of a CD324 modulator to a subject in need thereof.

29. The method of claim 28 wherein said CD324 modulator comprises a CD324 antagonist.

30. The method of claim 28 wherein said CD324 modulator comprises an antibody or immunoreactive fragment thereof.

31. The method of claim 30 wherein the antibody or immunoreactive fragment thereof comprises a monoclonal antibody.

32. The method of claim 31 wherein the monoclonal antibody is selected from the group consisting of chimeric antibodies, humanized antibodies and human antibodies.

33. The method of claim 32 wherein said monoclonal antibody comprises a light chain variable region and a heavy chain variable region wherein said light chain variable region comprises an amino acid sequence having at least 60% identity to an amino acid sequence selected from the group consisting of amino acid sequences as set forth in SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, SEQ ID NO: 38, SEQ ID NO: 40, SEQ ID NO: 42, SEQ ID NO: 44, SEQ ID NO: 46, SEQ ID NO: 48, SEQ ID NO: 50, SEQ ID NO: 52, SEQ ID NO: 54, SEQ ID NO: 56, SEQ ID NO: 58, SEQ ID NO: 60, SEQ ID NO: 62, SEQ ID NO: 64, SEQ ID NO: 66, SEQ ID NO: 68 and SEQ ID NO: 70 and wherein said heavy chain variable region comprises an amino acid sequence having at least 60% identity to an amino acid sequence selected from the group consisting of amino acid sequences as set forth in SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35, SEQ ID NO: 37, SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, SEQ ID NO: 61, SEQ ID NO: 63, SEQ ID NO: 65, SEQ ID NO: 67, SEQ ID NO: 69 and SEQ ID NO: 71.

34. The method of claim 33 wherein said monoclonal antibody is a humanized antibody.

35. The method of claim 31 wherein said monoclonal antibody comprises a neutralizing antibody.

36. The method of claim 31 wherein said monoclonal antibody comprises an internalizing antibody.

37. The method of claim 36 wherein said internalizing antibody comprises a cytotoxic agent.

38. The method of claim 28 wherein said CD324 modulator comprises a multispecific antibody.

39. The method of claim 38 wherein said multispecific antibody comprises a bispecific antibody.

40. The method of claim 28 wherein said CD324 associated disorder comprises a neoplastic disorder.

41. The method of claim 40 wherein said neoplastic disorder comprises selected from the group consisting of adrenal cancer, bladder cancer, cervical cancer, endometrial cancer, kidney cancer, liver cancer, lung cancer, ovarian cancer, colorectal cancer, pancreatic cancer, prostate cancer and breast cancer.

42. The method of claim 40 wherein said solid tumor comprises a hematologic malignancy.

43. The method of claim 42 wherein said hematologic malignancy comprises leukemia or lymphoma.

44. The method of claim 40 wherein the subject suffering said neoplastic disorder exhibits tumors comprising tumor initiating cells.

45. The method of claim 44 further comprising the step of reducing the frequency of tumor initiating cells in said subject.

46. The method of claim 45 wherein the reduction in frequency is determined using flow cytometric analysis of tumor cell surface markers known to enrich for tumor initiating cells or immunohistochemical detection of tumor cell surface markers known to enrich for tumor initiating cells.

47. The method of claim 45 wherein the reduction in frequency is determined using in vitro or in vivo limiting dilution analysis.

48. The method of claim 47 wherein the reduction in frequency is determined using in vivo limiting dilution analysis comprising transplant of live human tumor cells into immunocompromised mice.

49. The method of claim 48 wherein the reduction of frequency determined using in vivo limiting dilution analysis comprises quantification of tumor initiating cell frequency using Poisson distribution statistics.

50. The method of claim 47 wherein the reduction of frequency is determined using in vitro limiting dilution analysis comprising limiting dilution deposition of live human tumor cells into in vitro colony supporting conditions.

51. The method of claim 50 wherein the reduction of frequency determined using in vitro limiting dilution analysis comprises quantification of tumor initiating cell frequency using Poisson distribution statistics.

52. The method of claim 28 further comprising the step of administering an anti-cancer agent.

53. The method of claim 28 further comprising the subsequent administration of a CD324 modulator.

54. The method of claim 53 wherein the subsequently administered CD324 modulator comprises an internalizing CD324 modulator.

55. A method of reducing the frequency of tumor initiating cells in a subject in need thereof comprising the step of administering a CD324 modulator to said subject.

56. The method of claim 55 wherein the tumor initiating cells comprise tumor perpetuating cells.

57. The method of claim 56 wherein said tumor perpetuating cells are $CD46^+$ cells.

58. The method of claim 55 wherein said CD324 modulator comprises an antibody.

59. The method of claim 58 wherein said antibody comprises a monoclonal antibody.

60. The method of claim 59 wherein said monoclonal antibody further comprises a cytotoxic agent.

61. The method of claim 55 wherein the subject is suffering from a neoplastic disorder selected from the group consisting of adrenal cancer, bladder cancer, cervical cancer, endometrial cancer, kidney cancer, liver cancer, lung cancer, ovarian cancer, colorectal cancer, pancreatic cancer, prostate cancer and breast cancer.

62. The method of claim 55 wherein the frequency of tumor initiating cells is reduced by at least 10%.

63. The method of claim 55 wherein the reduction in frequency is determined using flow cytometric analysis of tumor cell surface markers known to enrich for tumor initiating cells or immunohistochemical detection of tumor cell surface markers known to enrich for tumor initiating cells.

64. A method of treating a subject suffering from a hematologic malignancy comprising the step of administering a CD324 modulator to said subject.

65. The method of claim 64 wherein said CD324 modulator comprises a monoclonal antibody.

66. A method of sensitizing a tumor in a subject for treatment with an anti-cancer agent comprising the step of administering a CD324 modulator to said subject.

67. The method of claim 66 wherein said CD324 modulator comprises an antibody.

68. The method of claim 66 wherein said tumor is a solid tumor.

69. The method of claim 66 wherein said anti-cancer agent comprises a chemotherapeutic agent.

70. The method of claim 66 wherein said anti-cancer agent comprises an immunotherapeutic agent.

71. A method of diagnosing a proliferative disorder in a subject in need thereof comprising the steps of:
  a. obtaining a tissue sample from said subject;
  b. contacting the tissue sample with at least one CD324 modulator; and
  c. detecting or quantifying the CD324 modulator associated with the sample.

72. The method of claim 71 wherein the CD324 modulator comprises a monoclonal antibody.

73. The method of claim 72 wherein the antibody is operably associated with a reporter.

74. An article of manufacture useful for diagnosing or monitoring CD324 associated disorders comprising a receptacle comprising a CD324 modulator and instructional materials for using said CD324 modulator to diagnose or monitor the CD324 associated disorder.

75. The article of manufacture of claim 74 wherein said CD324 modulator is a monoclonal antibody.

76. The article of manufacture of claim 74 wherein the receptacle comprises a readable plate.

77. A method of treating a subject suffering from neoplastic disorder comprising the step of administering a therapeutically effective amount of at least one internalizing CD324 modulator.

78. The method of claim 77 wherein said CD324 modulator comprises an antibody.

79. The method of claim 78 wherein said antibody comprises a monoclonal antibody.

80. The method of claim 79 wherein the monoclonal antibody further comprises a cytotoxic agent.

81. The method of claim 80 further comprising the step of administering a non-internalizing CD324 modulator prior to administering the internalizing CD324 modulator.

82. A method of treating a subject suffering from neoplastic disorder comprising the step of administering a therapeutically effective amount of at least one neutralizing CD324 modulator.

83. The method of claim 82 wherein said CD324 modulator comprises an antibody.

84. The method of claim 83 wherein said antibody comprises a monoclonal antibody.

85. The method of claim 84 wherein said monoclonal antibody comprises a humanized antibody.

86. The method of claim 85 wherein said humanized antibody further comprises a cytotoxic agent.

87. The method of claim 82 wherein administration of the neutralizing CD324 modulator is followed by the administration of an internalizing CD324 modulator.

88. A method of identifying, isolating, sectioning or enriching a population of tumor initiating cells comprising the step of contacting said tumor initiating cells with a CD324 modulator.

89. The method of claim 88 wherein said CD324 modulator comprises an antibody.

90. A CD324 modulator comprising a humanized antibody wherein said humanized antibody comprises a light chain variable region and a heavy chain variable region wherein said light chain variable region comprises an amino acid sequence having at least 60% identity to the amino acid sequence set forth in SEQ ID NO: 72 and wherein said heavy chain variable region comprises an amino acid sequence having at least 60% identity to an amino acid sequence selected from the group consisting of amino acid sequences as set forth in SEQ ID NO: 73.

91. A method inhibiting or preventing metastasis in a subject in need thereof comprising the step of administering a pharmaceutically effective amount of a CD324 modulator.

92. The method of claim 91 wherein the subject undergoes a debulking procedure before or after the administration of the CD324 modulator.

93. The method of claim 92 wherein said debulking procedure comprises the administration of at least one anticancer agent.

94. A method of performing maintenance therapy on a subject in need thereof comprising the step of administering a pharmaceutically effective amount of a CD324 modulator.

95. The method of claim 94 wherein said subject is treated for a neoplastic disorder prior to the administration of the CD324 modulator.

96. A method of depleting tumor initiating cells in a subject suffering from a proliferative disorder comprising the step of administering a CD324 modulator.

97. A method of diagnosing, detecting or monitoring a CD324 associated disorder in vivo in a subject in need thereof comprising the step of administering a CD324 modulator.

98. A method of diagnosing, detecting or monitoring a CD324 associated disorder in a subject in need thereof comprising the step contacting circulating tumor cells with a CD324 modulator.

99. The method of claim 98 wherein said contacting step occurs in vivo.

100. The method of claim 98 wherein said contacting step occurs in vitro.

101. A method of treating a tumor in a patient in need thereof comprising the step of administering a therapeutically effective amount of a CD324 modulator conjugated to a cytotoxic agent.

102. The method of claim 101 wherein the conjugated CD324 modulator comprises an internalizing CD324 antibody.

103. A CD324 modulator derived from an antibody selected from the group consisting of SC10.6, SC10.15, SC10.17, SC10.19, SC10.35, SC10.36, SC10.38, SC10.75, SC10.111, SC10.112, SC10.115, SC10.118, SC10.123, SC10.124, SC10.125, SC10.126, SC10.127, SC10.128, SC10.129, SC10.130, SC10.132, SC10.133, SC10.134, SC10.163, SC10.168, and SC10.178.

104. An isolated CD324 modulator that binds to an epitope associated with the EC1 domain of CD324.

105. The CD324 modulator of claim 104 wherein said CD324 modulator comprises an antibody or immunoreactive fragment thereof.

106. The CD324 modulator of claim 105 wherein said antibody or immunoreactive fragment thereof comprises a monoclonal antibody.

107. The CD324 modulator of claim 106 wherein said CD324 modulator comprises an ADC.

108. The CD324 modulator of claim 106 wherein said CD324 modulator comprises a multispecific antibody.

109. The CD324 modulator of claim 108 wherein said multispecific antibody comprises a bispecific antibody.

110. An isolated CD324 modulator that binds to an epitope associated with the EC2 domain of CD324.

111. The CD324 modulator of claim 110 wherein said CD324 modulator comprises an antibody or immunoreactive fragment thereof.

112. The CD324 modulator of claim 111 wherein said antibody or immunoreactive fragment thereof comprises a monoclonal antibody.

113. The CD324 modulator of claim 112 wherein said CD324 modulator comprises an ADC.

114. The CD324 modulator of claim 112 wherein said CD324 modulator comprises a multispecific antibody.

115. The CD324 modulator of claim 114 wherein said multispecific antibody comprises a bispecific antibody.

116. An isolated CD324 modulator that binds to an epitope associated with the EC3 domain of CD324.

117. The CD324 modulator of claim 116 wherein said CD324 modulator comprises an antibody or immunoreactive fragment thereof.

118. The CD324 modulator of claim 117 wherein said antibody or immunoreactive fragment thereof comprises a monoclonal antibody.

119. The CD324 modulator of claim 118 wherein said CD324 modulator comprises an ADC.

120. The CD324 modulator of claim 118 wherein said CD324 modulator comprises a multispecific antibody.

121. The CD324 modulator of claim 120 wherein said multispecific antibody comprises a bispecific antibody.

122. An isolated CD324 modulator that binds to an epitope associated with the EC4 domain of CD324.

123. The CD324 modulator of claim 122 wherein said CD324 modulator comprises an antibody or immunoreactive fragment thereof.

124. The CD324 modulator of claim 123 wherein said antibody or immunoreactive fragment thereof comprises a monoclonal antibody.

125. The CD324 modulator of claim 124 wherein said CD324 modulator comprises an ADC.

126. The CD324 modulator of claim 124 wherein said CD324 modulator comprises a multispecific antibody.

127. The CD324 modulator of claim 126 wherein said multispecific antibody comprises a bispecific antibody.

128. An isolated CD324 modulator that binds to an epitope associated with the EC5 domain of CD324.

129. The CD324 modulator of claim 128 wherein said CD324 modulator comprises an antibody or immunoreactive fragment thereof.

130. The CD324 modulator of claim 129 wherein said antibody or immunoreactive fragment thereof comprises a monoclonal antibody.

131. The CD324 modulator of claim 130 wherein said CD324 modulator comprises an ADC.

132. The CD324 modulator of claim 130 wherein said CD324 modulator comprises a multispecific antibody.

133. The CD324 modulator of claim 132 wherein said multispecific antibody comprises a bispecific antibody.

134. An isolated CD324 modulator residing in a bin selected from the group consisting of bin A, bin B, bin C, bin D and bin E.

135. An isolated CD324 modulator residing in a bin defined by a reference antibody selected from the group consisting of SC10.6, SC10.15, SC10.17, SC10.19, SC10.35, SC10.36, SC10.38, SC10.75, SC10.111, SC10.112, SC10.115, SC10.118, SC10.123, SC10.124, SC10.125, SC10.126, SC10.127, SC10.128, SC10.129, SC10.130, SC10.132, SC10.133, SC10.134, SC10.163, SC10.168, and SC10.178.

136. An antibody drug conjugate of the formula:

M-[L-D]n or a pharmaceutically acceptable salt thereof wherein
a) M comprises a CD324 modulator;
b) L comprises an optional linker;
c) D is a anti-proliferative agent; and
d) n is an integer from about 1 to about 20.

137. The antibody drug conjugate of claim 136 wherein said CD324 modulator comprises an antibody or immunoreactive fragment thereof.

138. The antibody drug conjugate of claim 137 wherein said antibody comprises a monoclonal antibody.

139. The antibody drug conjugate of claim 138 wherein said antibody is derived from an antibody selected from the group consisting of SC10.6, SC10.15, SC10.17, SC10.19, SC10.35, SC10.36, SC10.38, SC10.75, SC10.111, SC10.112, SC10.115, SC10.118, SC10.123, SC10.124, SC10.125, SC10.126, SC10.127, SC10.128, SC10.129, SC10.130, SC10.132, SC10.133, SC10.134, SC10.163, SC10.168, and SC10.178.

140. The antibody drug conjugate of claim 138 wherein said antibody is humanized.

141. The antibody drug conjugate of claim 136 wherein the optional linker is present and the linker comprises a cleavable linker, 142. The antibody drug conjugate of claim 141 wherein said cleavable linker comprises a peptidyl linker.

143. The antibody drug conjugate of claim 136 wherein said anti-proliferative agent comprises a cytotoxic agent.

144. The antibody drug conjugate of claim 143 wherein said cytotoxic agent comprises a pyrrolobenzodiazepine.

145. The antibody drug conjugate of claim 144 wherein said pyrrolobenzodiazepine comprises a pyrrolobenzodiazepine dimer, 146. A multispecific CD324 modulator.

147. The multispecific CD324 modulator of claim 146 wherein said modulator comprises a first binding site recognizing a first epitope on CD324 and a second binding site recognizing a second epitope wherein said first and second epitopes are not equivalent.

148. The multispecific CD324 modulator of claim 147 wherein the second epitope is present on CD324.

149. The multispecific CD324 modulator of claim 147 wherein the second epitope is present on an antigen other than CD324.

150. The multispecific CD324 modulator of claim 149 wherein the second epitope is present on an antigen selected from the group consisting of OCT4, Nanog, STAT3, EPCAM, CD24, CD34, NB84, TrkA, GD2, CD133, CD20, CD56, CD29, B7H3, CD46, transferrin receptor, JAM3, carboxypeptidase M, oncostatin M, Lgr5, Lgr6, CD325, nectin-4, nestin, Sox1, Bmi-1, eed, easyh1, easyh2, mf2, yy1, smarcA3, smarckA5, smarcD3, smarcE1, mllt3, DLL1, DLL4, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4) SLC7A8, SLC44A4, IL1RAP, TEM8, TMPRSS4, MUC16, GPRC5B, SLC6A14, SLC4A11, PPAP2C, CAV1, CAV2, PTPN3, EPHA1, EPHA2, EPHA3, EPHA4, EPHA5, EPHA6, EPHA7, EPHA8, EPHA9, EPHB1, EPHB2, EPHB3, EPHB4, EPHB5, EPHB6, EFNA1 EFNA2, EFNA3, EFNA5, EFNA6, EFNB1, EFNB2, EFNB3, SLC1A1, CX3CL1, ADORA2A, MPZL1, FLJ10052, C4.4A, EDG3, RARRES1, TMEPAI, PTS, CEACAM5, CEACAM6, NID2, STEAP, ABCA3, CRIM1, ILIR1, OPN3, DAF, MUC1, CPD, NMA, ADAM9, GJA1, SLC19A2, ABCA1, PCD117, ADCY9, SLC39A1, NPC1, ENPP1, N33, GPNMB, LY6E, CELSR1, LRP3, C20orf52, TMEPAI, FLVCR, PCDHA10, GPR54, TGFBR3, SEMA4B, PCDHB2, ABCG2, CD166, AFP, BMP-4, β-catenin, CD2, CD3, CD9, CD14, CD31, CD38, CD44, CD45, CD74, CD90, CXCR4, decorin, APCDD1, PTK7, EGFR, CD105, CD64, CD16, CD16a, CD16b, GLI1, GLI2, CD49b, CD49e and CD49f.

151. The multispecific CD324 modulator of claim 147 wherein said modulator comprises a bispecific antibody.

152. A bispecific antibody comprising a first binding site recognizing a first epitope on CD324 and a second binding site recognizing a second epitope wherein said first and second epitopes are not equivalent.

153. The bispecific antibody of claim 152 wherein the second epitope is present on CD324.

154. The bispecific antibody of claim 152 wherein the second epitope is present on an antigen other than CD324.

155. A multispecific CD324 modulator comprising a first binding site derived from an antibody that recognizes a first epitope on CD324 and a second binding site derived from an antibody that recognizes a second epitope wherein said first and second epitopes are not equivalent.

156. The multispecific CD324 modulator of claim 155 wherein the first binding site is derived from an antibody selected from the group consisting of SC10.6, SC10.15, SC10.17, SC10.19, SC10.35, SC10.36, SC10.38, SC10.75, SC10.111, SC10.112, SC10.115, SC10.118, SC10.123, SC10.124, SC10.125, SC10.126, SC10.127, SC10.128, SC10.129, SC10.130, SC10.132, SC10.133, SC10.134, SC10.163, SC10.168, and SC10.178.

157. The multispecific CD324 modulator of claim 155 wherein the second binding site is derived from an antibody selected from the group consisting of abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8.

158. The multispecific CD324 modulator of claim 157 wherein the modulator comprises a bispecific antibody.
159. The multispecific CD324 modulator of claim 158 further comprising a conjugated anti-cancer agent.
160. A pharmaceutical composition comprising a multispecific CD324 modulator.
161. A method of treating a patient suffering from a CD324 associated disorder comprising the step of administering a multispecific CD324 modulator.
162. A method of treating a patient suffering from a CD324 associated disorder comprising the step of administering a neutralizing CD324 modulator and subsequently administering an internalizing CD324 modulator.
163. The method of claim 162 wherein said internalizing CD324 modulator is conjugated to a cytotoxic agent.

EXAMPLES

The present invention, thus generally described above, will be understood more readily by reference to the following examples, which are provided by way of illustration and are not intended to be limiting of the instant invention. The examples are not intended to represent that the experiments below are all or the only experiments performed. Unless indicated otherwise, parts are parts by weight, molecular weight is weight average molecular weight, temperature is in degrees Centigrade, and pressure is at or near atmospheric.

Example 1

Characterization of CD324 Expression on Human Solid Tumors

To characterize the cellular heterogeneity of solid tumors as they exist in cancer patients, elucidate the identity of tumor perpetuating cells (TPC; i.e. cancer stem cells: CSC) using particular phenotypic markers and identify clinically relevant therapeutic targets, a large non-traditional xenograft (NTX) tumor bank was developed and maintained using art recognized techniques. The NTX tumor bank, comprising a number of discrete tumor cell lines, was propagated in immunocompromised mice through multiple passages of heterogeneous tumor cells originally obtained from numerous cancer patients afflicted by a variety of solid tumor malignancies. The continued availability of a large number of discrete early passage NTX tumor cell lines having well defined lineages greatly facilitate the identification and isolation of TPC as they allow for the reproducible and repeated characterization of cells purified from the cell lines. More particularly, isolated or purified TPC are most accurately defined retrospectively according to their ability to generate phenotypically and morphologically heterogeneous tumors in mice that recapitulate the patient tumor sample from which the cells originated. Thus, the ability to use small populations of isolated cells to generate fully heterogeneous tumors in mice is strongly indicative of the fact that the isolated cells comprise TPC. In such work the use of minimally passaged NTX cell lines greatly simplifies in vivo experimentation and provides readily verifiable results. Moreover, early passage NTX tumors also respond to therapeutic agents such as irinotecan (i.e. Camptosar®), which provides clinically relevant insights into underlying mechanisms driving tumor growth, resistance to current therapies and tumor recurrence.

As the NTX tumor cell lines were established the constituent tumor cell phenotypes were analyzed using flow cytometry to identify discrete markers that might be used to characterize, isolate, purify or enrich tumor initiating cells (TIC) and separate or analyze TPC and TProg cells within such populations. In this regard the inventors employed a proprietary proteomic based platform (i.e. PhenoPrint™ Array) that provided for the rapid characterization of cells based on protein expression and the concomitant identification of potentially useful markers. The PhenoPrint Array is a proprietary proteomic platform comprising hundreds of discrete binding molecules, many obtained from commercial sources, arrayed in 96 well plates wherein each well contains a distinct antibody in the phycoerythrin fluorescent channel and multiple additional antibodies in different fluorochromes arrayed in every well across the plate. This allows for the determination of expression levels of the antigen of interest in a subpopulation of selected tumor cells through rapid inclusion of relevant cells or elimination of non-relevant cells via non-phycoerythrin channels. When the PhenoPrint Array was used in combination with tissue dissociation, transplantation and stem cell techniques well known in the art (Al-Hajj et al., 2004, Dalerba et al., 2007 and Dylla et al., 2008, all supra, each of which is incorporated herein by reference in its entirety), it was possible to effectively identify relevant markers and subsequently isolate and transplant specific human tumor cell subpopulations with great efficiency.

In the instant case various NTX tumor lines comprising human tumors were established in severely immunocompromised mice using art recognized techniques. Upon reaching 800-2,000 mm³, tumors were resected from mice and dissociated into single cell suspensions using art recognized mechanical and enzymatic dissociation techniques involving the use of collagenase, hyaluronidase and DNAse I (See for example U.S.P.N. 2007/0292414 which is incorporated herein). Data obtained from these suspensions using the PhenoPrint Array provided both absolute (per cell) and relative (vs. other cells in the population) surface protein expression on a cell-by-cell basis, leading to more complex characterization and stratification of cell populations. More specifically, use of the PhenoPrint Array allowed for the rapid identification of proteins or markers that prospectively distinguished TIC or TPC from NTG bulk tumor cells and tumor stroma and, when isolated from NTX tumor models, provided for the relatively rapid characterization of tumor cell subpopulations expressing differing levels of specific cell surface proteins. In particular, proteins with heterogeneous expression across the tumor cell population allow for the isolation and transplantation of distinct, and highly purified, tumor cell subpopulations expressing either high and low levels of a particular determinant or marker into immune-compromised mice, thereby facilitating the assessment of whether TPC were enriched in one subpopulation or another.

The term "enriching" is used synonymously with isolating cells and means that the yield (fraction) of cells of one type is increased over the fraction of other types of cells as compared to the starting or initial cell population. Preferably, enriching refers to increasing the percentage by about 10%, by about 20%, by about 30%, by about 40%, by about 50% or greater than 50% of one type of cell in a population of cells as compared to the starting population of cells.

As used herein a "marker", in the context of a cell or tissue, means any characteristic in the form of a chemical or biological entity that is identifiably associated with, or specifically found in or on a particular cell, cell population or tissue including those identified in or on a tissue or cell population affected by a disease or disorder. As manifested, markers may be morphological, functional or biochemical in nature. In preferred embodiments the marker is a cell surface antigen that is differentially or preferentially expressed by specific cell types (e.g., TPC) or by cells under certain conditions (e.g., during specific points of the cell life cycle or cells in a particular niche). Preferably, such markers are proteins, and more preferably, possess an epitope for antibodies, aptamers or other binding molecules as known in the art. However, a marker may consist of any molecule found on the surface or within a cell including, but not limited to, proteins (peptides and polypeptides), lipids, polysaccharides, nucleic acids and steroids. Examples of morphological marker characteristics or traits include, but are not limited to, shape, size, and nuclear to cytoplasmic ratio. Examples of functional marker characteristics or traits include, but are not limited to, the ability to adhere to particular substrates, ability to incorporate or exclude particular dyes, for example but not limited to exclusions of lipophilic dyes, ability to migrate under particular conditions and the ability to differentiate along particular lineages. Markers can also be a protein expressed from a reporter gene, for example a reporter gene expressed by the cell as a result of introduction of the nucleic acid sequence encoding the reporter gene into the cell and its transcription resulting in the production of the reporter protein that can be used as a marker. Such reporter genes that can be used as markers are, for example but not limited to fluorescent proteins enzymes, chromomeric proteins, resistance genes and the like.

In a related sense the term marker phenotype in the context of a tissue, cell or cell population (e.g., a stable TPC phenotype) means any marker or combination of markers that may be used to characterize, identify, separate, isolate or enrich a particular cell or cell population (e.g., by flow cytometry or FACS). In specific embodiments, the marker phenotype is a cell surface phenotype that may be determined by detecting or identifying the expression of a combination of cell surface markers.

In this regard it will be appreciated that, in addition to unexpectedly providing a therapeutic target, CD324 also comprises a marker that may be used to identify and characterize tumor perpetuating cells. More generally those skilled in the art will recognize that numerous markers (or their absence) have been associated with various populations of cancer stem cells and used to isolate or characterize selected tumor cell subpopulations. In this respect exemplary cancer stem cell markers comprise OCT4, Nanog, STAT3, EPCAM, CD24, CD34, NB84, TrkA, GD2, CD133, CD20, CD56, CD29, B7H3, CD46, transferrin receptor, JAM3, carboxypeptidase M, oncostatin M, Lgr5, Lgr6, CD325, nestin, Sox1, Bmi-1, eed, easyh1, easyh2, mf2, yy1, smarcA3, smarckA5, smarcD3, smarcE1, mllt3, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4) SLC7A8, IL1RAP, TEM8, TMPRSS4, MUC16, GPRC5B, SLC6A14, SLC4A11, PPAP2C, CAV1, CAV2, PTPN3, EPHA1, EPHA2, SLC1A1, CX3CL1, ADORA2A, MPZL1, FLJ10052, C4.4A, EDG3, RARRES1, TMEPAI, PTS, CEACAM6, NID2, STEAP, ABCA3, CRIM1, ILIR1, OPN3, DAF, MUC1, CPD, NMA, ADAM9, GJA1, SLC19A2, ABCA1, PCDH7, ADCY9, SLC39A1, NPC1, ENPP1, N33, GPNMB, LY6E, CELSR1, LRP3, C20orf52, TMEPAI, FLVCR, PCDHA10, GPR54, TGFBR3, SEMA4B, PCDHB2, ABCG2, CD166, AFP, BMP-4, β-catenin, CD2, CD3, CD9, CD14, CD31, CD38, CD44, CD45, CD74, CD90, CXCR4, decorin, EGFR, CD105, CD64, CD16, CD16a, CD16b, GLI1, GLI2, CD49b, and CD49f. See, for example, Schulenburg et al., 2010, PMID: 20185329, U.S. Pat. No. 7,632,678 and U.S.P.Ns. 2007/0292414, 2008/0175870, 2010/0275280, 2010/0162416 and 2011/0020221 each of which is incorporated herein by reference. It will be appreciated that a number of these markers were included in the PhenoPrint Array described above.

Similarly, non-limiting examples of cell surface phenotypes associated with cancer stem cells of certain tumor types include $CD44^{hi}CD24^{low}$, $ALDH^+$, $CD133^+$, $CD123^+$, $CD34^+CD38^-$, $CD44^+CD24^-$, $CD46^{hi}CD324^+CD66c^-$, $CD133^+CD34^+CD10^-CD19^-$, $CD138^-CD34^-CD19^+$, $CD133^+RC2^+$, $CD44^+\alpha_2\beta_1^{hi}CD133^+$, $CD44^+CD24^+ESA^+$, $CD271^+$, $ABCB5^+$ as well as other cancer stem cell surface phenotypes that are known in the art. See, for example, Schulenburg et al., 2010, supra, Visvader et al., 2008, PMID: 18784658 and U.S.P.N. 2008/0138313, each of which is incorporated herein in its entirety by reference. Those skilled in the art will appreciate that marker phenotypes such as those exemplified immediately above may be used in conjunction with standard flow cytometric analysis and cell sorting techniques to characterize, isolate, purify or enrich TIC and/or TPC cells or cell populations for further analysis. Of interest with regard to the instant invention CD46, CD324 and, optionally, CD66c are either highly or heterogeneously expressed on the surface of many human colorectal ("CR"), breast ("BR"), non-small cell lung (NSCLC), small cell lung (SCLC), pancreatic ("VA"), melanoma ("Mel"), ovarian ("OV"), and head and neck cancer ("FIN") tumor cells, regardless of whether the tumor specimens being analyzed were primary patient tumor specimens or patient-derived NTX tumors.

Cells with negative expression (i.e."−") are herein defined as those cells expressing less than, or equal to, the $95^{th}$ percentile of expression observed with an isotype control antibody in the channel of fluorescence in the presence of the complete antibody staining cocktail labeling for other proteins of interest in additional channels of fluorescence emission. Those skilled in the art will appreciate that this procedure for defining negative events is referred to as "fluorescence minus one", or "FMO", staining. Cells with expression greater than the $95^{th}$ percentile of expression observed with an isotype control antibody using the FMO staining procedure described above are herein defined as "positive" (i.e."+"). As defined herein there are various populations of cells broadly defined as "positive." First, cells with low expression (i.e. "lo") are generally defined as those cells with observed expression above the $95^{th}$ percentile determined using FMO staining with an isotype control antibody and within one standard deviation of the $95^{th}$ percentile of expression observed with an isotype control antibody using the FMO staining procedure described above. Cells with "high" expression (i.e. "hi") may be defined as those cells with observed expression above the $95^{th}$ percentile determined using FMO staining with an isotype control antibody and greater than one standard deviation above the 95th percentile of expression observed with an isotype control antibody using the FMO staining procedure described above. In other embodiments the 99th percentile may preferably be used as a demarcation point between negative and positive FMO staining and in particularly preferred embodiments the percentile may be greater than 99%.

Using techniques such as those described above to quickly identify and rank colorectal tumor antigens based on expression intensity and heterogeneity across several NTX tumors from colorectal cancer patients, candidate TPC antigens were further assessed by comparison of tumor versus normal adjacent tissue and then selected based, at least in part, on the up- or down-regulation of the particular antigen in malignant cells. Moreover, systematic analysis of a variety of cell surface markers for their ability to enrich for the ability to transplant fully heterogeneous tumors into mice (i.e. tumorigenic ability), and subsequent combination of these markers substantially improved the resolution of the method and improved the ability to tailor fluorescence activated cell sorting (FACS) techniques to identify and characterize distinct, highly enriched tumor cell subpopulations that exclusively contained all tumor generating ability upon transplantation (i.e. tumor initiating cells).

In the instant case, using standard flow cytometric techniques, individual tumor cells were characterized on a BD FACSCanto™ II flow cytometer (BD Biosciences) for the expression of hundreds of cell surface proteins. In contrast to most cell surface proteins that were uniformly expressed or absent, selected proteins including CD324 were, to a greater or lesser extent, positively and/or heterogeneously expressed on the surface of numerous primary human colorectal, pancreatic, breast, lung, and ovarian tumor cells. Such expression patterns are indicative of a marker that may be used to selectively isolate, enrich and/or target tumorigenic cell subpopulations.

Figure 2B:
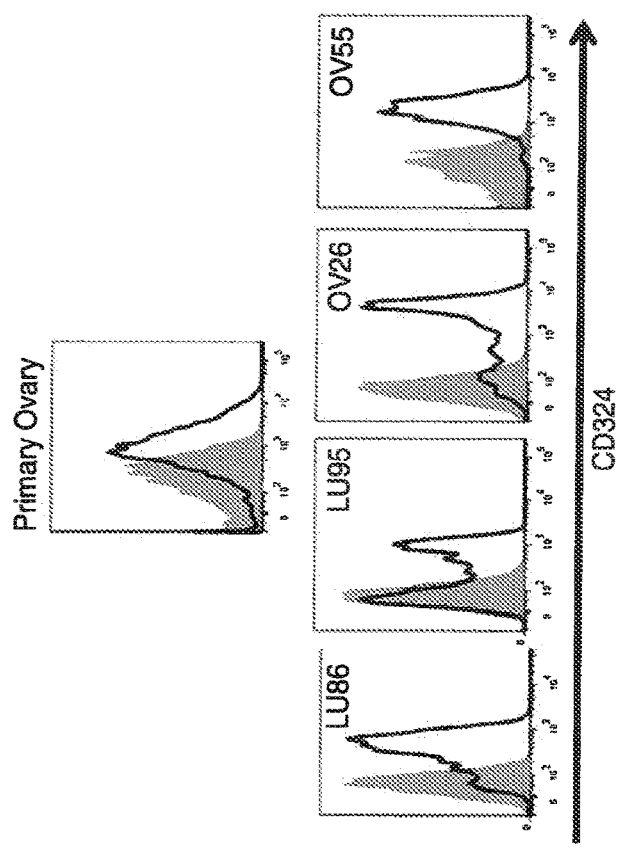
Figure 5A:
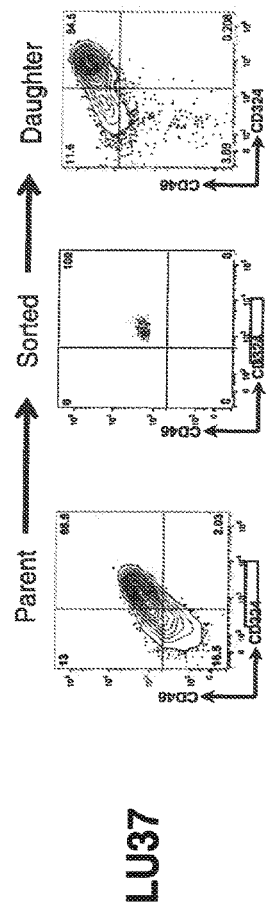
FIGS. 5A and 5B depict, respectively, a scatter plot demonstrating the CD46 CD324 phenotype of the parental tumor, an enriched $CD46^{hi}CD324^+$ subpopulation transplanted into a recipient animal, and the CD46 CD324 phenotype of the resultant daughter tumor (FIG. 5A) and a graphical representation of the tumorigenicity of the various sorted subpopulations (FIG. 5B) from a representative non-small cell lung cancer tumor (LU37)
Figure 5B:
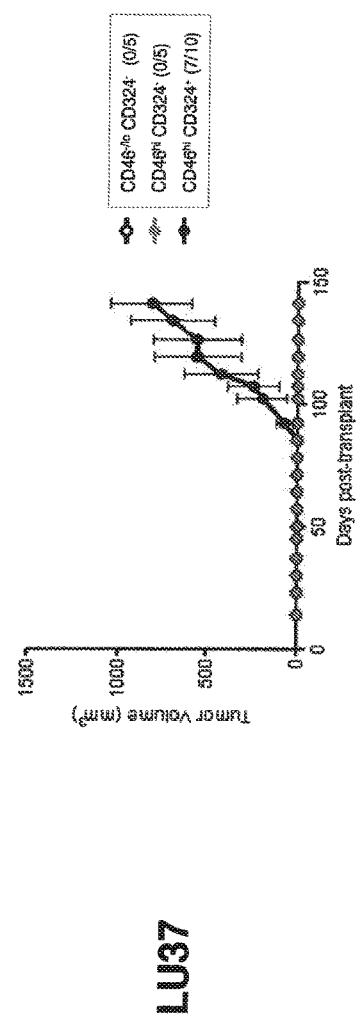
Figure 7A:
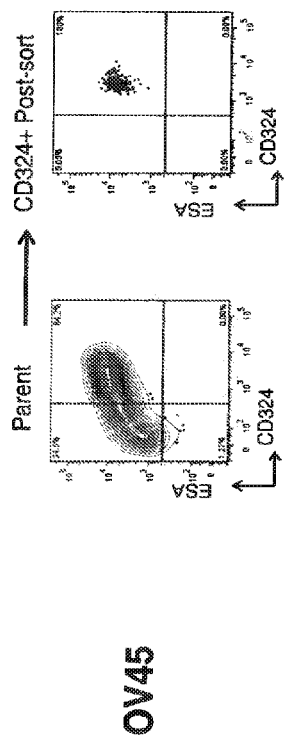
FIGS. 7A and 7B depict, respectively, a scatter plot demonstrating the ESA CD324 phenotype of the parental tumor and an enriched $ESA^+CD46^{hi}CD324^+$ subpopulation (FIG. 7A) and a graphical representation of the tumorigenicity of the various sorted subpopulations (FIG. 7B) from a representative ovarian tumor (OV45)
Figure 7B:
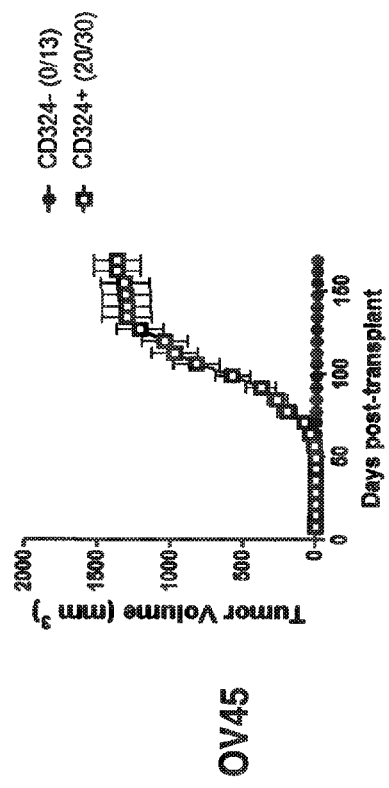

In this regard representative heterogeneous expression of CD324 is illustrated in FIGS. 2A and 2B for different NTX derived tumor types and one primary ovarian tumor (FIG. 2B). More particularly, FIGS. 2A and 2B depict flow cytometry-based protein expression data for individual tumor cells displayed as histogram plots wherein fluorescence minus one (FMO) staining using isotype control antibodies is shown in the gray, filled histograms and target antigen expression (i.e. CD324) as determined using commercially available antigen-specific, PE-conjugated antibodies (BioLegend Inc.), is displayed using bold, black lines.

As evidenced by FIGS. 2A and 2B, and in accordance with the instant invention, heterogeneous CD324 expression was generally observed in various types of solid tumors. Specifically, a review of the plots generated using tumor cells from freshly isolated tumors reveals that CD324 expression was heterogeneous in tumors derived from colorectal, pancreatic, lung, breast (FIG. 2A), and lung and ovarian cancer patients (FIG. 2B), indicative of various subpopulations demonstrating negative/b or positive expression. Moreover, cells positively expressing CD324 often had staining ranging from low levels to high levels as quantified using isotype control/FMO staining and standard flow cytometric methodology.

The combined use of NTX tumor models that accurately recapitulate tumor physiology with the PhenoPrint Array analysis of tumor cells as described above, demonstrate the possibility identifying putative therapeutic targets by characterizing cell surface expression levels of tumor antigens, including CD324. That is, unlike markers exhibiting homogeneous expression, the heterogeneous expression of CD324 indicates that it is likely associated with certain tumor cell subpopulations and may therefore be used to enrich cell populations for tumorigenic cells and provide an effective therapeutic target for anti-proliferative agents.

Example 2

Identification, Enrichment and Isolation of Tumor Initiating Cell Populations Using CD324 Modulators In tumors exhibiting heterogeneous expression of a particular protein or proteins of interest (e.g., CD324), cells were enriched or isolated based on such markers and then transplanted into immunocompromised mice. More particularly, to determine whether high or low levels of surface CD324 expression could be correlated with enhanced tumorigenicity, NTX tumor samples were disassociated using state of the art techniques as described above and isolated using a FACSAria™ Flow Cytometer (BD Biosciences) to provide distinct marker enriched subpopulations that were subsequently transplanted into immunocompromised mice. In this respect cells were injected subcutaneously into the mammary fat pad of recipient female immunocompromised NOD/SCID mice at doses typically ranging between 1,000 to 50 cells per mouse. When tumors arising from these transplants reached 800-2,000 $mm^3$, mice were euthanized and the tumors were removed and dissociated by enzymatic digestion to a single cell suspension for the purpose of phenotypic characterization to assess whether the constitution of cells was representative of the parental tumor from which the transplanted cells were originally isolated.

FIGS. 3-8 illustrate the results of such experiments conducted using representative NTX cell lines derived from colorectal (FIGS. 3A and 3B), pancreatic (FIGS. 4A and 4B), non-small cell lung (FIGS. 5A and 5B), breast (FIGS. 6A and 6B), ovarian (FIGS. 7A and 7B), and small cell lung cancer (FIGS. 8A and 8B) tumors obtained from patients. FIGS. 9A and 9B depict the results of a similar analysis performed on a primary melanoma tumor resected from a patient. In each respective set FIG. A comprises scatter plots (gated using CD324 and another putative marker) showing the distribution of the parent tumor, sorted putative tumorigenic cells and the resulting heterogeneous daughter tumor arising from implanting those sorted cells. Note that, in some instances, the second marker was uniformly high and therefore another property of the cells such as forward scatter (FSC) or marker (ESA) was used for display purposes. FIG. B in each set graphically shows the measured tumor volume arising from the implantation of sorted cell subpopulations gated on CD324 and CD46 into immunocompromised mice. Values in parenthesis indicate the number of tumors generated per mice implanted.

In a similar vein the results of numerous transplantation experiments to determine the tumorigenicity of cell subpopulations expressing differing combinations of CD46 and CD324 expression, as well as the efficiency of tumor formation with limiting numbers of transplanted cells, are presented in a tabular format in FIGS. 10A and 10B. Note that empty spaces in FIGS. 10A and 10B denote that the indicated experimental condition was not tested.

Significantly, the data from FIGS. 3-10 show that tumorigenicity was consistently associated with the subpopulation of cells expressing CD324 in combination with high levels of CD46, and the tumors generated by cells with the $CD46^{hi}CD324^+$ phenotype were analogous in composition to their parental tumors. As described above and repeated using NTX lines derived from many breast, colorectal, pancreatic, non-small cell lung, ovarian and small cell lung cancer patients, CD46$^{hi}$CD324$^+$ cells consistently generated heterogeneous tumors when transplanted into mice, thereby indicating that this isolated subpopulation of cells is significantly enriched for TICs. Conversely, these same data demonstrate that tumor cells expressing either no, or low levels of CD324 were much less tumorigenic than their high or positive counterparts, respectively. Based on the generated data it was surprisingly found that subpopulations of tumor cells expressing the CD46$^{hi}$ CD324$^+$ phenotype generally contain the vast majority of tumorigenic capability and suggest that CD324 may provide an effective therapeutic target for tumorigenic cell modulation.

Example 3

Generation of CD324 Modulators

CD324 modulators in the form of murine antibodies were produced in accordance with the teachings herein by inoculating mice with human CD324-His recombinant protein (Sino Biological, Inc.). In this respect three strains of female mice (3 each: Balb/c, CD-1, FVB) were immunized via the footpad route with 10 μg of CD324-His immunogen emulsified with an equal volume of Titermax™ or alum adjuvant.

Solid-phase ELISA assays were used to screen mouse sera for mouse IgG antibodies specific for human CD324. A positive signal above background was indicative of antibodies specific for CD324. Briefly, 96 well plates (VWR International, Cat. #610744) were coated with recombinant CD324-His at 0.5 g/ml in ELISA coating buffer overnight. After washing with PBS containing 0.02% (v/v) Tween 20, the wells were blocked with 3% (w/v) BSA in PBS, 200 μL/well for 1 hour at room temperature (RT). Mouse serum was titrated (1:100, 1:200, 1:400, and 1:800) and added to the CD324 coated plates at 50 μL/well and incubated at RT for 1 hour. The plates are washed and then incubated with 50 μL/well HRP-labeled goat anti-mouse IgG diluted 1:10,000 in 3% BSA-PBS or 2% FCS in PBS for 1 hour at RT. Again the plates were washed and 40 μL/well of a TMB substrate solution (Thermo Scientific 34028) was added for 15 minutes at RT. After developing, an equal volume of 2N H$_2$SO$_4$ was added to stop substrate development and the plates were analyzed by spectrophotometer at OD 450.

Sera-positive immunized mice were sacrificed and draining lymph nodes (popliteal and inguinal, and medial iliac if enlarged) were dissected out and used as a source for antibody producing cells. A single cell suspension of B cells (228.9×10$^6$ cells) was fused with non-secreting P3x63Ag8.653 myeloma cells (ATCC #CRL-1580) at a ratio of 1:1 by electrofusion. Electrofusion was performed using the BTX Hybrimmune™ System, (BTX Harvard Apparatus) as per the manufacturer's direction. After the fusion procedure the cells were resuspended in hybridoma selection medium supplemented with Azaserine (Sigma #A9666), high glucose DMEM medium with sodium pyruvate (Cellgro cat#15-017-CM) containing, 15% Fetal Clone I serum (Hyclone), 10% BM Condimed (Roche Applied Sciences), 4 mM L-glutamine, 100 IU Penicillin-Streptomycin and 50 μM 2-mercaptoethanol and then plated in three T225 flasks in 90 mL selection medium per flask. The flasks were then placed in a humidified 37° C. incubator containing 5% CO$_2$ and 95% air for 6-7 days. After six to seven days of growth the library consisting of the cells grown in bulk in the T225s was plated at 1 cell per well in Falcon 96 well U-bottom plates using the Aria I cell sorter. The selected hybridomas were then grown in 200 μL of culture medium containing 15% Fetal Clone I serum (Hyclone), 10% BM-Condimed (Roche Applied Sciences), 1 mM sodium pyruvate, 4 mM L-glutamine, 100 IU Penecillin-Streptamycin, 50 μM 2-mercaptoethanol, and 100 μM hypoxanthine. Any remaining unused hybridoma library cells were frozen for future library testing. After ten to eleven days of growth supernatants from each well of the plated cells were assayed for antibodies reactive for CD324 by ELISA and FACS assays.

For the ELISA assay, 96 well plates (VWR, 610744) were coated with 0.5 μg/mL CD324-His in sodium carbonate buffer overnight at 4° C. The plates were washed and blocked with 3% BSA in PBS/Tween for one hour at 37° C. and used immediately or kept at 4° C. Undiluted hybridoma supernatants were incubated on the plates for one hour at RT. The plates are washed and probed with HRP labeled goat anti-mouse IgG diluted 1:10,000 in 1% BSA-PBS for one hour at RT. Following incubation with substrate solution as described above the plates were read at OD 450. Wells containing immunoglobulin that bound the CD324 protein were transferred and expanded.

Growth positive hybridoma wells secreting murine immunoglobulin were also screened for human CD324 specificity using a flow cytometry based assay with BR22 CD324+ cells. Briefly 1×10$^5$ BR22 cells per well were incubated for 30 minutes with 25-100 μL hybridoma supernatant. Cells were washed PBS/2% FCS twice and then incubated with 50 μL per sample DyeLight 649 labeled goat-anti-mouse IgG, Fc fragment specific secondary diluted 1:200 in PBS/2% FCS. After a 15 minute incubation, cells were washed twice with PBS/2% FCS and re-suspended in PBS/2% FCS with DAPI (Life Technologies) and analyzed by flow cytometry using a FACSCanto II as per the manufacturer's instructions. Wells containing immunoglobulin that bound the BR22 with a similar profile to the commercial CD324-APC antibody (BioLegend Inc.) were transferred and expanded. The resulting hCD324 specific clonal hybridomas were cryopreserved in CS-10 freezing medium (Biolife Solutions) and stored in liquid nitrogen.

ELISA and flow cytometry analysis confirmed that purified antibody from most or all of these hybridomas bound CD324 in a concentration-dependent manner. Two fusions were performed and seeded in 48 plates (4608×2 wells at approximately 65% cloning efficiency) providing hundreds of hits. Selected clones provided on the order of 170 antibodies that were immunospecific for human CD324, a number of which also cross-reacted with murine CD324.

Example 4

Sequencing of CD324 Modulators

Based on the foregoing, a number of exemplary distinct monoclonal antibodies that bind immobilized human CD324 or BR22 cells with apparently high affinity were selected for sequencing and further analysis. As shown in a tabular fashion in FIGS. 11A and 11B, sequence analysis of the light chain variable regions (FIG. 11A) and heavy chain variable regions (FIG. 11B) from selected monoclonal antibodies generated in Example 3 confirmed that many had novel complementarity determining regions and often displayed novel VDJ arrangements. Note that the complementarity determining regions set forth in FIGS. 11A and 11B are defined as per Chothia et al., supra.

As a first step in sequencing exemplary modulators, the selected hybridoma cells were lysed in Trizol® reagent (Trizol Plus RNA Purification System, Life Technologies) to prepare the RNA. In this regard between $10^4$ and $10^5$ cells were resuspended in 1 mL Trizol and shaken vigorously after addition of 200 µL of chloroform. Samples were then centrifuged at 4° C. for 10 minutes and the aqueous phase was transferred to a fresh microfuge tube where an equal volume of isopropanol was added. The tubes were again shaken vigorously and allowed to incubate at RT for 10 minutes before being centrifuged at 4° C. for 10 minutes. The resulting RNA pellets were washed once with 1 mL of 70% ethanol and dried briefly at RT before being resuspended in 40 µL of DEPC-treated water. The quality of the RNA preparations was determined by fractionating 3 µL in a 1% agarose gel before being stored at −80° C. until used.

The variable region of the Ig heavy chain of each hybridoma was amplified using a 5' primer mix comprising thirty-two mouse specific leader sequence primers, designed to target the complete mouse $V_H$ repertoire, in combination with a 3° mouse Cγ primer specific for all mouse Ig isotypes. A 400 bp PCR fragment of the $V_H$ was sequenced from both ends using the same PCR primers. Similarly a mix of thirty-two 5' $V_\kappa$ leader sequence primers designed to amplify each of the $V_\kappa$ mouse families combined with a single reverse primer specific to the mouse kappa constant region were used to amplify and sequence the kappa light chain. The $V_H$ and $V_L$ transcripts were amplified from 100 ng total RNA using reverse transcriptase polymerase chain reaction (RT-PCR).

A total of eight RT-PCR reactions were run for each hybridoma: four for the $V_\kappa$ light chain and four for the V gamma heavy chain (γ1). The One Step RT-PCR kit was used for amplification (Qiagen GmbH). This kit provides a blend of Sensiscript and Omniscript Reverse Transcriptases, HotStarTaq DNA Polymerase, dNTP mix, buffer and Q-Solution, a novel additive that enables efficient amplification of "difficult" (e.g., GC-rich) templates. Reaction mixtures were prepared that included 3 µL of RNA, 0.5 of 100 µM of either heavy chain or kappa light chain primers (custom synthesized by IDT), 5 µL of 5×RT-PCR buffer, 1 µL dNTPs, 1 µL of enzyme mix containing reverse transcriptase and DNA polymerase, and 0.4 µL of ribonuclease inhibitor RNasin (1 unit). The reaction mixture contains all of the reagents required for both reverse transcription and PCR. The thermal cycler program was set for an RT step 50° C. for 30 minutes, 95° C. for 15 minutes, followed by 30 cycles of PCR (95° C. for 30 seconds, 48° C. for 30 seconds, 72° C. for one minute). There was then a final incubation at 72° C. for 10 minutes.

To prepare the PCR products for direct DNA sequencing, they were purified using the QIAquick™ PCR Purification Kit (Qiagen GmbH) according to the manufacturer's protocol. The DNA was eluted from the spin column using 50 µL of sterile water and then sequenced directly from both strands. The extracted PCR products were directly sequenced using specific V region primers. Nucleotide sequences were analyzed using IMGT to identify germline V, D and J gene members with the highest sequence homology. The derived sequences were compared to known germline DNA sequences of the Ig V- and J-regions using V-BASE2 (Retter et al., supra) and by alignment of $V_H$ and $V_L$, genes to the mouse germline database to provide the annotated sequences set forth in FIGS. 11A and 11B.

More specifically, FIG. 11A depicts the contiguous amino acid sequences of twenty-six novel murine light chain variable regions from anti-CD324 antibodies (SEQ ID NOS: 20-70, even numbers) and a humanized light chain variable region (SEQ ID NO: 72) derived from representative murine light chains. Similarly, FIG. 11B depicts the contiguous amino acid sequences of twenty-six novel murine heavy chain variable regions (SEQ ID NOS: 21-71, odd numbers) from the same anti-CD324 antibodies and a humanized heavy chain variable region (SEQ ID NO: 73) from the same murine antibody providing the humanized light chain. Thus, taken together FIGS. 11A and 11B provide the annotated sequences of twenty-six murine anti-CD324 antibodies (termed SC10.6, SC10.1.5, SC10.17, SC10.19, SC10.35, SC10.36, SC10.38, SC10.75, SC10.111, SC10.112, SC10A15, SC10.118, SC10.123, SC10.124, SC10.125, SC10.126, SC10.127, SC10.128, SC10.129, SC10.130, SC10.132, SC10.133, SC10.134, SC10.163, SC10.168, and SC10.178.) and a humanized antibody (termed hSC10.17).

For the purposes of the instant application the SEQ ID NOS of each particular antibody are sequential. Thus mAb SC10.6 comprises SEQ ID NOS: 20 and 21 for the heavy and light chain variable regions respectively. In this regard SC10.15 comprises SEQ ID NOS: 22 and 23, SC10.17 comprises SEQ ID NOS: 24 and 25, and so on. Moreover, corresponding nucleic acid sequences for each antibody amino acid sequence in FIGS. 11A and 11B are included in the instant application as set forth in FIG. 19. In FIG. 19 the included nucleic acid sequences comprise SEQ ID NOS that are one hundred greater than the corresponding amino acid sequence (heavy or light chain). Thus, nucleic acid sequences encoding the heavy and light chain variable region amino acid sequences of mAb SC10.6 (i.e., SEQ ID NOS: 20 and 21) comprise SEQ ID NOS: 120 and 121 in FIG. 19. The other antibody nucleic acid sequences, including those encoding the humanized construct, are numbered similarly.

Example 5

Humanization of CD324 Modulators

An exemplary murine antibody from Example 4 was humanized using complementarity determining region (CDR) grafting. Human frameworks for heavy and light chains were selected based on sequence and structure similarity with respect to functional human germline genes. In this regard structural similarity was evaluated by comparing the mouse canonical CDR structure to human candidates with the same canonical structures as described in Chothia et al. (supra).

More particularly murine antibody SC10.17 was humanized using a computer-aided CDR-grafting method (Abysis Database, UCL Business Plc.) and standard molecular engineering techniques to provide the hSC10.17 modulator. The human framework regions of the variable regions were selected based on their highest sequence homology to the mouse framework sequence and its canonical structure. For the purposes of the analysis the assignment of amino acids to each of the CDR domains is in accordance with the Kabat et al. numbering. A single humanized antibody was made in order to demonstrate that relatively non-immunogenic constructs could be fabricated comprising the antigen-binding complementarity-determining regions (CDRs) from the mouse hybridoma in association with human framework regions. Ultimately it was found that the humanized SC10.17 mAb binds to CD324 antigen with similar affinity to the murine counterpart with a similar affinity as measured using the Biacore system (e.g., as per Example 6).

Molecular engineering procedures were conducted using art-recognized techniques. Using the protocol for determining the sequences of the CD324 modulators as detailed in Example 4 above, the nucleotide sequence information for the V. D and J gene segments of the heavy and light chains of SC10.17 were obtained. Based on these sequence data, new primer sets specific to the leader sequence of the Ig VH and VK chains of SC10.17 were designed for cloning of the recombinant monoclonal antibody. Subsequently the V-(D)-J sequences were aligned with mouse Ig germline sequences, with the heavy chain gene of SC10.17 identified as IGHV5-17 (V), DQ52a.1 (D) and JH4 (J) and the kappa light chain genes were identified as IGKV1-117, JK1. The obtained heavy and light chain sequences for hSC10.17 were aligned to the functional human variable region sequences and reviewed for homology and canonical structure. Following analysis the hSC10.17 was generated using human VH3-48 (V), IGHD7-27 (D) and JH4 (J) for the heavy chain and human kappa light chain genes A17 and JK1. The resulting humanized heavy chain exhibited 93% homology to the human germline sequence and 88% homology to the parent mouse sequence. Similarly, the humanized light chain exhibited 92% homology to the human germline sequence and 90% homology to the parent mouse sequence.

The amino acid sequences of the humanized heavy variable region chain and the humanized kappa light chain for hSC10.17 are shown in FIGS. 11A and 11B (SEQ ID NOS: 72 and 73), and the corresponding nucleic acid sequences (SEQ ID NOS: 172 and 173) are set forth in FIG. 19.

In any event the disclosed modulators were expressed and isolated using art recognized techniques. To that end synthetic humanized variable DNA fragments (Integrated DNA Technologies) of the heavy chain was cloned into human IgG1 expression vector. The variable light chain fragment was cloned into human C-kappa expression vector. The humanized antibody was expressed by co-transfection of the heavy and the light chain into CHO cells.

More particularly, for antibody production directional cloning of the murine and humanized variable gene PCR products into human immunoglobulin expression vectors was undertaken. All primers used in Ig gene-specific PCRs included restriction sites (AgeI and XhoI for IgH, XmaI and DraIII for IgK, which allowed direct cloning into expression vectors containing the human IgG1, and IGK constant regions, respectively. In brief, PCR products were purified with Qiaquick PCR purification kit (Qiagen, Inc.) followed by digestion with AgeI and XhoI (IgH), XmaI and DraIII (IgK), respectively. Digested PCR products were purified prior to ligation into expression vectors. Ligation reactions were performed in a total volume of 10 µL with 200 U T4-DNA Ligase (New England Biolabs), 7.5 µL of digested and purified gene-specific PCR product and 25 ng linearized vector DNA. Competent E. coli DH10B bacteria (Life Technologies) were transformed via heat shock at 42° C. with 3 µL ligation product and plated onto ampicillin plates (100 µg/mL) The AgeI-EcoRI fragment of the VH region was than inserted into the same sites of pEE6.4HuIgG1 expression vector while the synthetic XmaI-DraIII VK insert was cloned into the XmaI-DraIII sites of -the respective pEE12.4Hu-Kappa expression vector.

Cells producing humanized antibody were generated by transfection of HEK 293 cells with the appropriate plasmids using 293fectin. In this respect plasmid DNA was purified with QIAprep Spin columns (Qiagen Inc.). Human embryonic kidney (HEK) 293T (ATCC No CRL-11268) cells were cultured in 150 mm plates (Falcon, Becton Dickinson) under standard conditions in Dulbecco's Modified Eagle's Medium (DMEM) supplemented with 10% heat inactivated FCS, 100 µg/mL streptomycin, 100 U/mL penicillin G (all from Life Technologies).

For transient transfections cells were grown to 80% confluency. Equal amounts of IgH and corresponding IgL chain vector DNA (12.5 µg of each vector DNA) was added to 1.5 mL Opti-MEM mixed with 50 HEK 293 transfection reagent in 1.5 mL opti-MEM. The mix was incubated for 30 min at room temperature and distributed evenly to the culture plate. Supernatants were harvested three days after transfection, replaced by 20 mL of fresh DMEM supplemented with 10% FBS and harvested again at day 6 after transfection. Culture supernatants were cleared from cell debris by centrifugation at 800×g for 10 min and stored at 4° C. Recombinant chimeric and humanized antibodies were purified with Protein G beads (GE Healthcare).

Example 6

Characteristics of CD324 Modulators

Various methods were used to analyze the binding characteristics of selected CD324 modulators generated as set forth above. Specifically, a number of these murine antibodies were characterized as to epitope recognition under reducing conditions, cross reactivity with regard to mouse CD324 by ForteBio and bin determination (each as per Example 7) and the ability to kill cells using an in vitro cytotoxicity assay (as per Example 8). The results of each of these assays for exemplary modulators are presented in a tabular form in FIG. 12.

With regard to epitope recognition the modulators were tested to determine if they react with reduced CD324 using an ELISA assay. More specifically purified, soluble, His-Tagged CD324 was reduced at 95° C. with DTT in the presence of SDS to denature the protein. This preparation was then cooled, combined with 2.5-fold higher molar ratio of iodoacetamide compared to the initial DTT concentration and incubated 15 minutes at 50° C. This procedure effectively blocked the free cysteine residues and allowed for stability during ELISA screening where excess DTT would interfere with antibody structure and binding. As seen in FIG. 12 a number of the tested modulators did react with the reduced protein indicating that they recognized a linear epitope.

Besides the aforementioned assays the humanized construct hSC10.17 was analyzed to determine its binding characteristics. Moreover, humanized antibody binding was directly compared with the parent murine antibody to identify any subtle changes in rate constants brought about by the humanization process.

Figure 13:
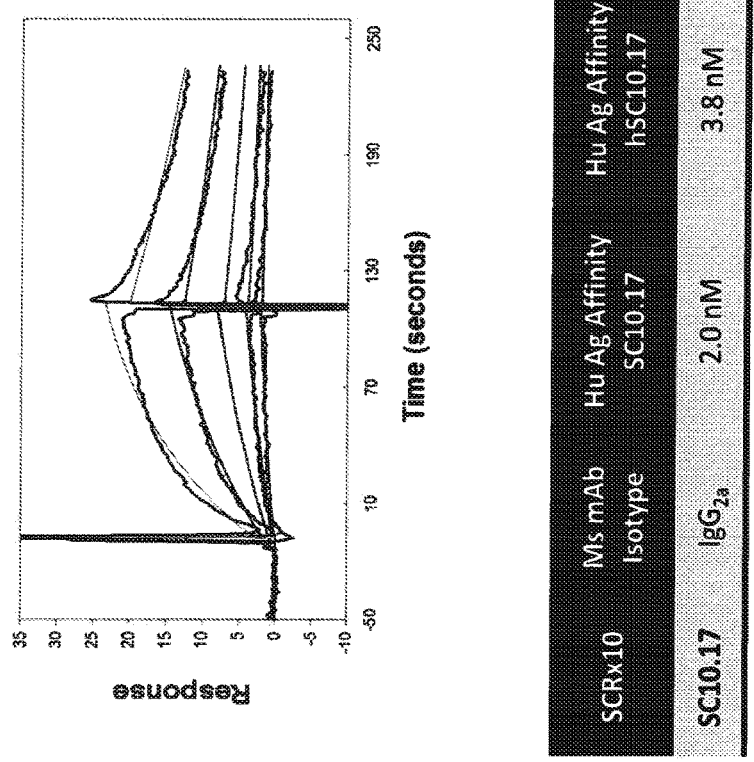
FIG. 13 shows comparative binding affinities of a selected murine modulator and its humanized counterpart.

More specifically, the affinity of murine SC10.17 was measured by a Biacore using surface plasmon resonance (SPR) to provide the results set forth in FIG. 13. Based on a concentration series of 25, 12.5, and 6.25 nM (generating the curves from top to bottom in FIG. 13) and using a 1:1 Langmuir binding model, the $K_d$ of the SC10.17 antibody binding to human CD324 antigen was estimated to be 2.0 nM. Similar experiments then run with the humanized hSC10.17 antibody with a Kd estimated to be 3.8 nM. Such results indicated that the humanization process had not materially impacted the affinity of the modulator.

Example 7 hCD324 Modulator Cross-Reactivity and Bin Determination

In light of the fact that the extracellular domains of human and mouse CD324 proteins share 82% sequence identity, the disclosed modulators to human CD324 were tested to see if they associated with the mouse homolog. More specifically, a direct ELISA was used to determine the level of cross-reactivity of hCD324-specific monoclonal antibodies with its mouse homolog. In addition selected modulators were examined through competitive binding to define associated bins as previously discussed.

To test cross-reactivity a high protein binding 96-well assay plate was coated with 0.5 µg/ml of a mouse CD324 purchased from Sino Biologics. The protein coating of the plate occurred in 100 µl volume per well using a 50 mM Sodium Carbonate buffer (pH9.6) during a 16 hour incubation at 4° C. After washing the coated plate in PBS buffer containing 0.05% Tween20 (PBST) the plate was then clocked washed with PBST and 100 µL/well PBSA containing 10% spent hybridoma supernatant or 1 µg/ml purified monoclonal antibody (as positive control) was added to the plate for the duration of 1 hour at ambient temperature. After washing the plate with PBST, 100 µL per well of PBSA containing a 1:10,000 dilution of goat anti-mouse IgG polyclonal antibody, specific for the Fc portion of Mouse IgG and conjugated to horseradish peroxidase (Jackson Immuno Research), was added to the plate for 30 minutes at ambient temperature. After washing the plate extensively with PBST, 100 µL per well TMB substrate (Thermo Fisher) was added to the wells for 15 minutes. The enzymatic reaction was stopped by adding 100 µL/well 2M sulfuric acid. The absorbance of this colorimetric assay was measured at 450 nm using a Victor plate reader (Perkin Elmer). In this assay a signal above background was indicative of cross-reactivity.

FIG. 12 shows that, while the majority of tested modulators did not react with the murine ortholog, monoclonal antibodies SC10.60 and SC10.178 recognize both human and mouse CD324 in this assay.

As to antibody binning, a ForteBio RED was used per manufacturer's instructions to identify competing antibodies that bound to the same or different bins. Briefly, a reference antibody (Ab1) was captured onto an anti-mouse capture chip, a high concentration of non-binding antibody was then used to block the chip and a baseline was collected. Monomeric, recombinant human hCD324-His was then captured by the specific antibody (Ab1) and the tip was dipped into a well with either the same antibody (Ab1) as a control or into a well with a different test antibody (Ab2). If additional binding was observed with a new antibody, then Ab1 and Ab2 were determined to be in a different bin. If no further binding occurred, as determined by comparing binding levels with the control Ab1, then Ab2 was determined to be in the same bin. As known in the art this process can be expanded to screen large libraries of unique antibodies using a full row of antibodies representing unique bins in a 96-well plate. In the instant case this binning process showed the screened antibodies bound to at least five different and distinct bins (designated as bins A though E in FIG. 12) on the CD324 protein. In addition selected antibodies were found not to be in bins A-E but rather bound to other epitopes and were not cross-competitive with each other. Such modulators were placed in an undefined bin (bin U) as seen in FIG. 12. N.D. in FIG. 12 indicates that bins for the designated modulators were not determined.

Example 8

CD324 Modulators Facilitate Delivery of Cytotoxic Agents

Targeting of a cytotoxic drug stably linked to an antibody represents an approach that might have great therapeutic benefit for patients with solid tumors through reduced toxicity and improved efficacy. To determine whether the disclosed CD324 modulators are able to mediate the delivery of a cytotoxic agent to live cells, an in vitro cell killing assay was performed wherein anti-mouse IgG Fab fragment covalently linked to saporin was combined with unlabeled CD324 antibodies, and the ability of these saporin complexes to internalize and kill cells was measured 5 days later by measuring cell viability.

Figure 14A:
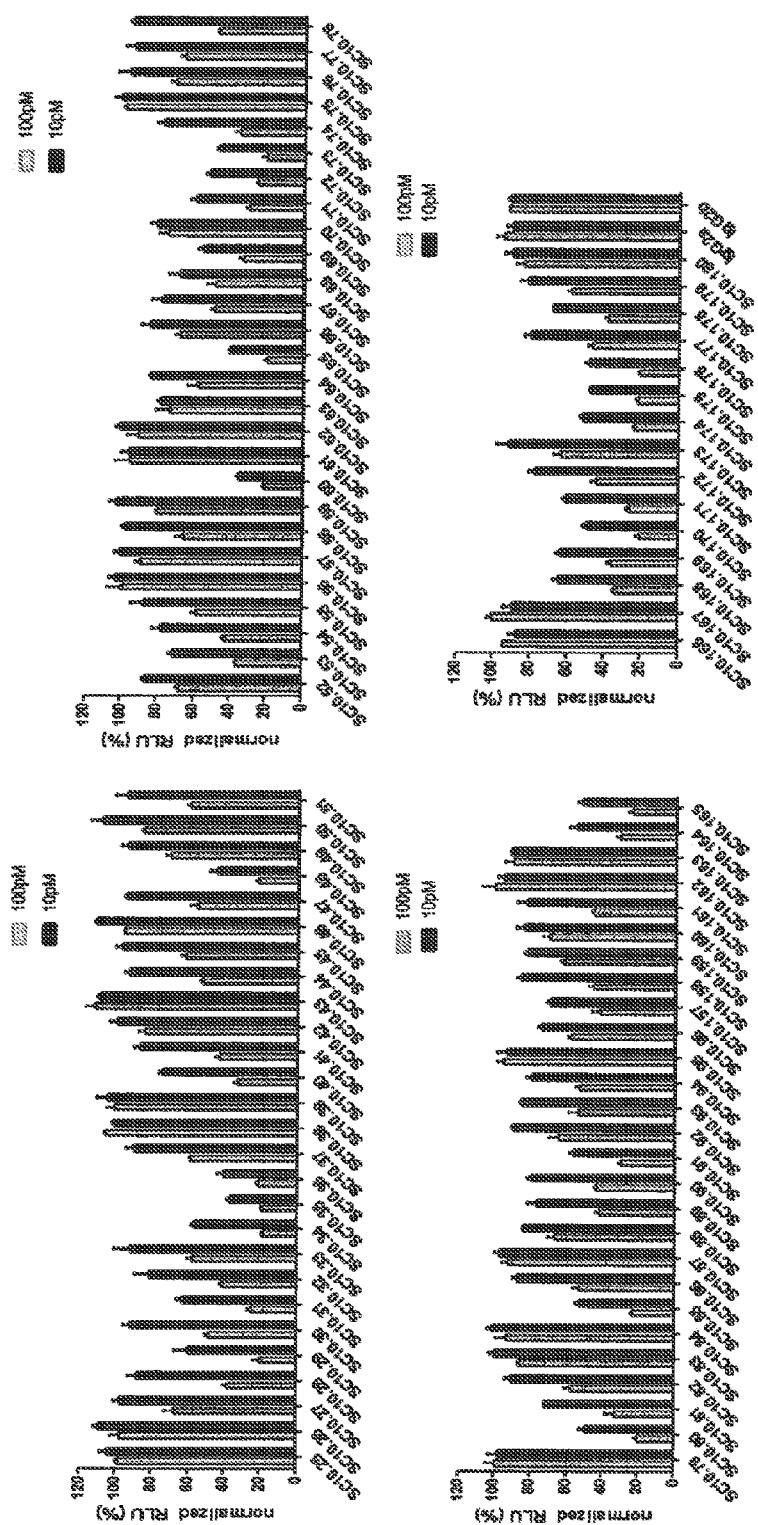

Specifically 500 cells/well of MCF7 cells, a breast cancer cell line purchased from ATCC which endogenously express CD324, were plated into 96 well tissue culture plates in their ATCC recommended culture media one day before the addition of antibodies and toxin. Purified ('naked') murine CD324 modulator at 100 pM and 10 pM and a fixed concentration of 2 nM anti-mouse IgG Fab fragment covalently linked to saporin (Advanced Targeting Systems, #IT-48) were added to the cultures for 5 days. Viable cell numbers were enumerated using CellTiter Glo® (Promega Corp.) as per manufacturer's instructions. Raw luminescence counts using cultures containing cells with the saporin Fab fragment were set as 100% reference values and all other counts calculated accordingly (referred to as "Normalized RLU"). Using this assay it was demonstrated that anti-CD324 antibodies, but not isotype control antibodies, are able to kill CD324 expressing cells (FIG. 14A with corresponding tabular data in FIG. 14B and FIG. 12).

Figures 14C, 14D:
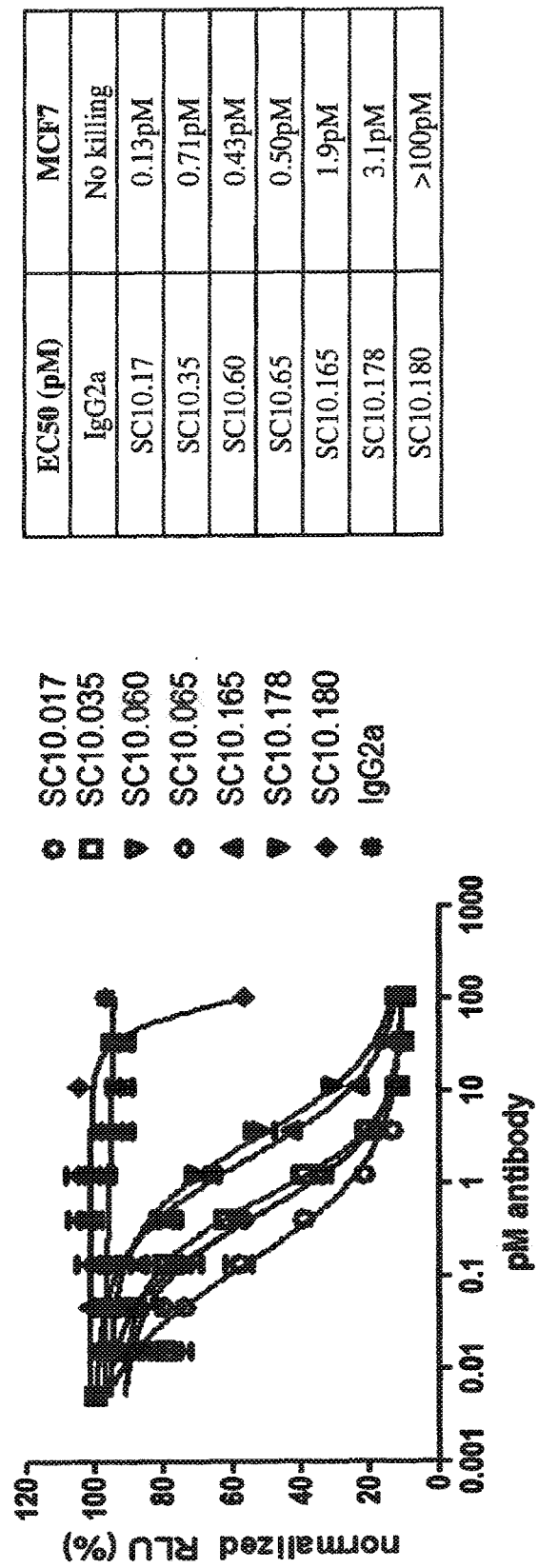

In addition to the aforementioned assay, a subset of CD324 antibodies, selected to represent modulators with varying affinity, mouse-cross reactivity and differing cytotoxic activity in this screen were tested to more accurately determine their ability to kill cells in vitro. Using the same general techniques set forth immediately above dilution assays were performed provide killing curves and to determine EC50 values for the selected modulators (FIG. 14C with corresponding tabular data in FIG. 14D). These data further demonstrate that the exemplary antibodies described above are specific to CD324, are able to bind CD324 antigen on the cell surface, and thereby mediate the delivery of a cytotoxic payload that results in cell death.

Example 9

CD324 Effectors can Mediate Cytotoxicity in Lung, Ovarian, Colon, Kidney, Liver and Pancreatic Tumor Cells To corroborate the results of Example 8 and determine whether CD324 modulators can mediate toxin internalization and cell killing of primary human tumor cells, mouse lineage-depleted NTX cells (i.e. human tumor cells propagated as low-passage xenografts in immunocompromised mice) were plated and subsequently exposed to anti-CD324 antibodies and FAB saporin. Specifically, NTX tumors were dissociated into a single cell suspension and plated on Primaria™ plates (BD Biosciences) in growth factor supplemented serum free media as is known in the art. After 3-5 days of culture at 37° C./5% CO2/5% O2, cells were contacted with a control (IgG2b) or a murine CD324 modulator and Fab saporin as described in Example 8. Modulator-mediated saporin cytotoxicity was then assessed by quantifying the remaining number of cells using CellTiter Glo 5-7 days later.

Figure 15:
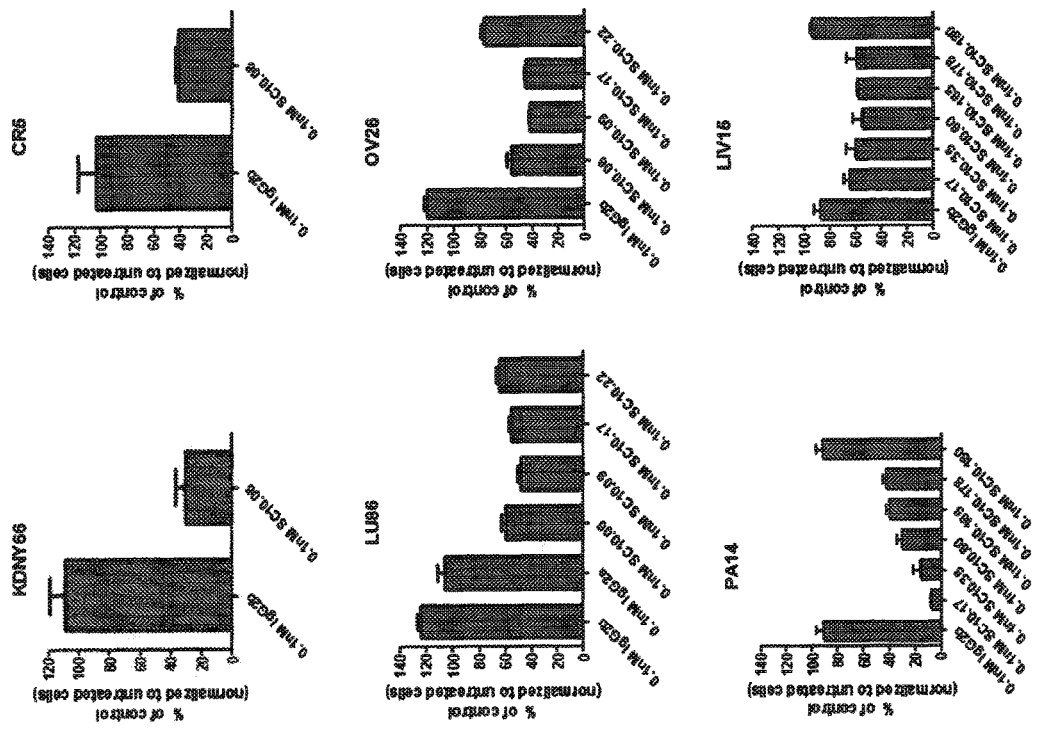
FIG. 15 is a graphical representation demonstrating that the disclosed CD324 modulators may effectively be used as targeting moieties to direct cytotoxic payloads to various patient-derived non-traditional xenograft cells expressing CD324 wherein the decrease in normalized RLU value is indicative of cell killing through internalized toxin.

As seen in FIG. 15, exposure to almost all of the CD324 modulators resulted in reduced cell numbers for each of the six different tumor cell lines (including kidney, colorectal, lung, ovarian, pancreatic and liver), whereas the IgG2b isotype control antibody did not impact the number of live cells after treatment. Not only does this data demonstrate that exemplary antibodies described herein are specific to CD324, are able to bind CD324 antigen on the cell surface and facilitate the delivery of a cytotoxic payload resulting in cell death, but the above data also demonstrated that multiple anti-CD324 antibodies can mediate killing of multiple NTX tumor cells.

Example 10

CD324 Modulators Can Block CD324 Mediated Homotypic Binding

As previously discussed CD324 protein is known to bind other CD324 proteins, otherwise known as homotypic binding, in a calcium dependent manner. CD324 present on normal tissues may be sequestered in tight junctions where homotypic binding domains are inaccessible. In tumors, CD324 is often disregulated and these homotypic-binding domains may now be accessible to modulators. Using antibodies (e.g., antagonistic or neutralizing modulators) that disrupt this function may target cancer cells with disregulated CD324 while sparing the normal cells where the binding domain is masked.

To determine if the disclosed CD324 modulators can block homotypic binding, MCF7 cells endogenously expressing CD324 were added to a plate coated with recombinant CD324 protein, and the ability of CD324 modulators to block the homotypic interactions between the recombinant protein and the cells assessed. Specifically, a high binding 96 well plate was coated 1.5 µg/ml of recombinant CD324-Fc (RnD Systems) in PBS overnight. The following day, the plate was incubated in assay buffer (PBS with 2% bovine serum albumin and 2 mM calcium chloride) and subsequently incubated with or without CD324 modulators in assay buffer for 30 minutes. Simultaneously, MCF7 cells were harvested and resuspended in assay buffer with or without CD324 modulators for 30 minutes. Finally the coated plate was washed and the MCF7 cell/modulator solution is added to the plate and incubated for 2 hours. To measure the ability of MCF7 cells to bind to the plate, the plate was washed three times and then remaining cell count was measured using CellTiter Glo as per manufacturer's instructions.

Figure 16:
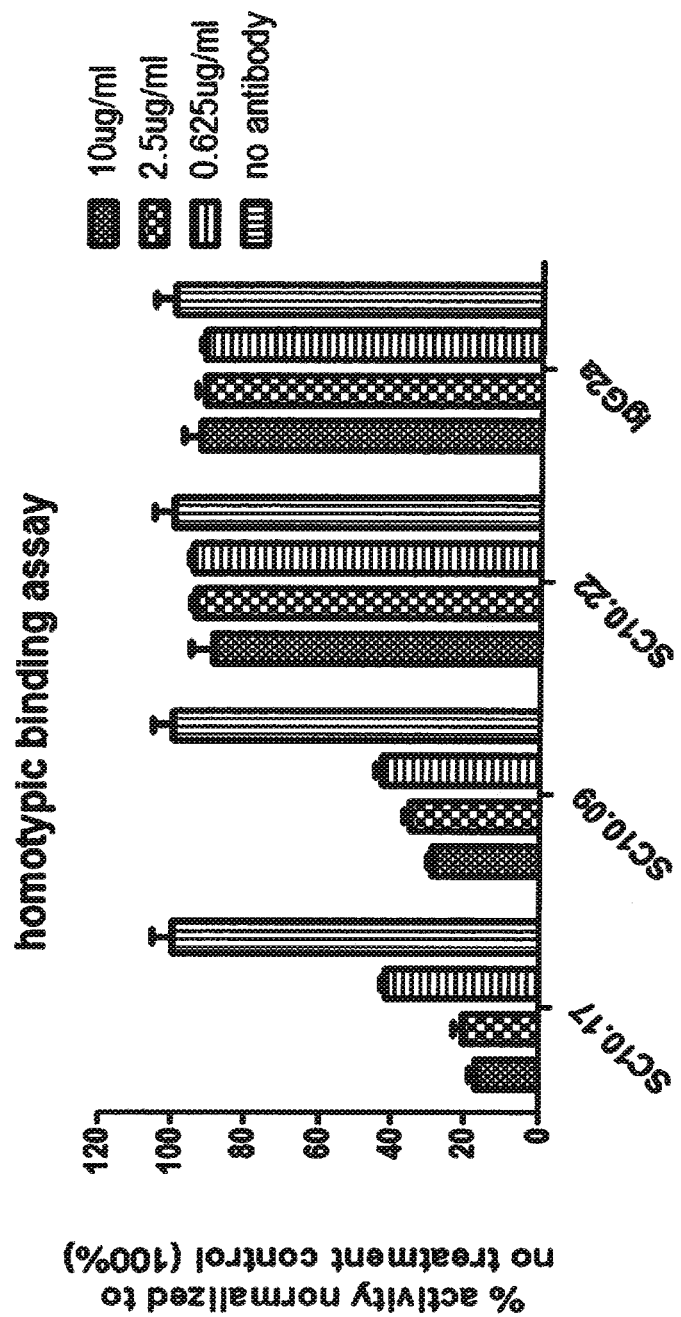
FIG. 16 illustrates the ability of the disclosed modulators to inhibit CD324 homotypic binding.

As seen in FIG. 16 SC10.9 and SC10.17, but not SC10.22 or IgG2a, block homotypic binding. These data demonstrate that SC10.17 and SC10.9 specifically inhibit CD324 homotypic binding and may be used to selectively target tumorigenic cells expressing disregulated CD324.

Example 11

Humanized CD324 Modulators Facilitate Delivery of Cytotoxic Agents

As preferred embodiments of the present invention will likely employ humanized CD324 modulators in a therapeutic setting, work was performed to demonstrate that humanized anti-CD324 antibodies (fabricated as set forth in Example 5) function as effective mediators of cell killing through delivery of cytotoxic agents.

Generally, using the saporin assay as set forth for the murine anti-CD324 antibodies in Example 8, a humanized construct was tested to demonstrate the ability of humanized modulators to selectively eliminate CD324 positive cells. More particularly, hSC10.17 was employed to mediate the introduction of a cytotoxic payload in accordance with the teachings herein. In this respect MCF7 cells expressing CD324 were exposed to different concentrations of the selected modulators and saporin linked to an anti-human Fab (Fab-ZAP human, Advanced Targeting Systems). Following incubation the cells were washed and directed saporin cytotoxicity was then assessed by quantifying the remaining number of cells using CellTiter Glo as per the manufacturer's instructions 5-7 days later. The results were normalized to untreated cells and are graphically presented in FIG. 17.

Figure 17:
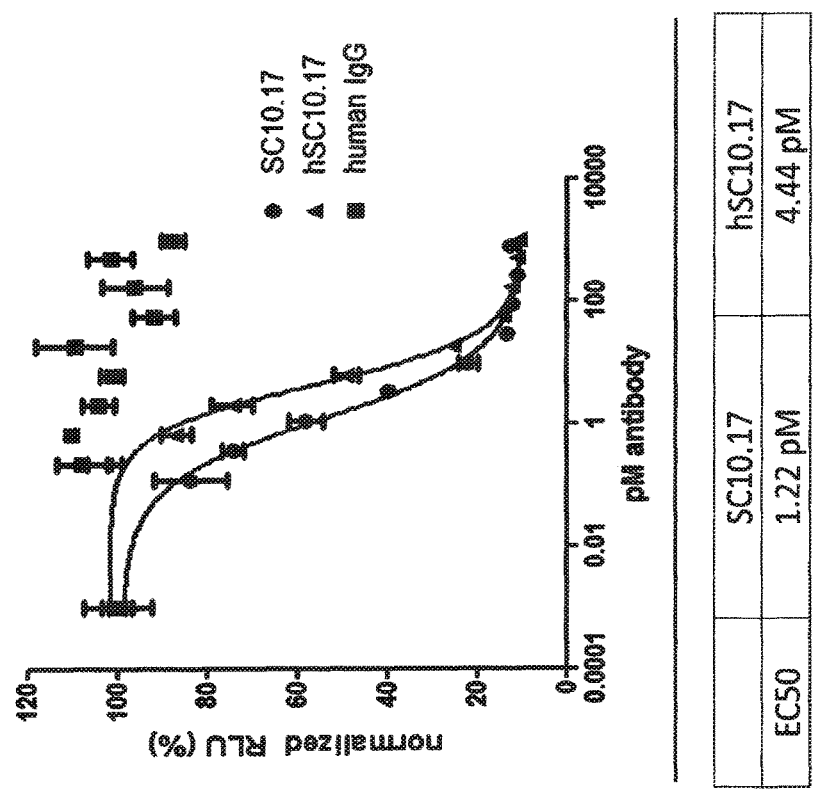
FIG. 17 demonstrates that humanized CD324 modulators may effectively be used as targeting moieties to direct cytotoxic payloads to cells expressing CD324, wherein the decrease in normalized RLU value is indicative of cell killing through internalized toxin and where the determined EC50 (e.g., half-maximal effective concentration) values are indicative of efficient cell killing.

Examination of the curves set forth in FIG. 17 shows that the humanized CD324 modulator, hSC10.17, kills CD324-expressing cells with an EC50 of 4.4 pM. This apparent EC50 is in good agreement with that measured for the murine anti-CD324 modulator SC10.17, which showed an EC50 of 1.2 pM, indicating that the humanization process has not materially impacted the functional activity of the SC10.17 modulator.

Example 12

CD324 Modulators Inhibit Tumorigenic Cells In Vivo

To determine the impact of CD324 modulators on tumor growth, immunocompromised mice implanted with pancreatic NTX tumor cells grew xenograft tumors and were subsequently treated with SC10.17. Briefly, in independent studies, immunocompromised mice were injected with 50,000 cells of pancreatic non-traditional patient-derived xenograft tumor lines known to express CD324 (refer to previous example). Mice were randomized at 180-200 mm3, and treated twice weekly with a dose of 10 mg/kg antibody (n=5 mice/group). Tumor weights were measured at least one per week.

As evidenced by FIGS. 18A and 18B pancreatic tumor growth in two discrete NTX cell lines was inhibited by an unconjugated murine CD324 modulator of the instant invention. More particularly SC10.17 (empty circles) substantially eliminated any tumor growth when compared to a control IgG1 (filled triangles) in either tumor cell line PA14 (FIG. 18A) or PA3 (FIG. 18B). In conjunction with the teachings of the instant application these data suggest that the disclosed CD324 modulators can effectively inhibit the growth of tumors expressing CD324 and that such inhibition is sustained for greater than three weeks after initial treatment.

Example 13

Fabrication of Bispecific Antibodies Comprising Antigen Binding Sites Specific for CD324 and Nectin-4

In order to improve the ability of the disclosed modulators to kill tumorigenic cells bispecific constructs were generated comprising antigen binding sites for CD324 and Nectin-4. It will be appreciated that such bispecific antibody constructs may be particularly useful in patients with moderate serum concentrations of soluble CD324. Moreover, in accordance with the teachings herein such constructs may be used in a conjugated or unconjugated state.

Variable regions were used from anti-CD324 antibody hSC10.17 (see FIGS. 11 and 19 for amino acid and nucleic acid sequences, respectively) and anti-Nectin-4 antibody Ha22-2(2,4)6.1 (as set forth in U.S.P.N. 2012/0078028 which is incorporated herein by reference). Several IgG-like anti-CD324/Nectin-4 bispecific antibody variants were constructed with human constant regions using the human IgG1 and a kappa light chain (Table 1). Mutations to the constant regions of each of the variants were introduced for the purpose of either: (i) preferentially pairing heavy chains of different specificity in heteromeric rather than homomeric fashion (asymmetric heavy chain pairing) or (ii) preferentially pairing each heavy chain with the corresponding light chain (heavy chain/light chain pairing). Mutations were incorporated on the human IgG1 constant region using the Quikchange mutagenesis kit according to the manufacturer's instructions (Agilent Technologies). pEE6.4HuIgG1 and pEE12.4Hu-kappa expression vectors (Lonza AG) were used for transient transfection of the bispecific antibodies.

The bispecific antibodies were generated in transient transfections using art-recognized techniques of suspension or adherent cultures of HEK-293T cells, or suspension CHO-S cells. Polyethylenimine polymer was used as the transfecting reagent, and equal mass ratios of four expression vectors for each of the two heavy chains and two light chains were used for co-transfections. Seven to ten days after transfection, the bispecific antibodies were purified from clarified cell-supernatants using MabSelect SuRe™ Protein A (GE Healthcare Life Sciences).

TABLE 1

Anti-CD324/Nectin-4 Bispecific Antibody Variants

| Construct | Chain | Variable Region Specificity | Mutations for Asymmetric Heavy Chain Pairing | Mutations for Heavy Chain/Light Chain Pairing. |
|---|---|---|---|---|
| hSC10.17/N4 KiH-CM | Heavy 1 | CD324 | T366W S354C* | Crossmab CH1-CL† |
|  | Heavy 2 | Nectin 4 | T366S, L368A, Y407A, Y349C* |  |
|  | Light 1 | CD324 |  | Crossmab CH1-CL† |
|  | Light 2 | Nectin 4 |  |  |
| hSC10.17/N4 Elec-CM | Heav 1 | CD324 | K392D K409D†† | Crossmab CH1-CL† |
|  | Heavy 2 | Nectin 4 | D356K D399K†† |  |
|  | Light 1 | CD324 |  | Crossmab CH1-CL† |
|  | Light 2 | Nectin 4 |  |  |
| hSC10.17/N4 KiH-KK | Heavy 1 | CD324 | T366W S354C* | S188D, 192D |
|  | Heavy 2 | Nectin 4 | T366S, L368A, Y407A, Y349C* | S188K, 192K |
|  | Light 1 | CD324 |  | S176K, 137K |
|  | Light 2 | Nectin 4 |  | S176D, 137D |
| hSC10.17/N4 KiH-KR | Heavy 1 | CD324 | T366W S354C* | S188D, T192D |
|  | Heavy 2 | Nectin 4 | T366S, L368A, Y407A, Y349C* | S188K, T192K |
|  | Light 1 | CD324 |  | S176K, N137R |
|  | Light 2 | Nectin 4 |  | S176D, N137D |

*Merchant A, et al. An efficient route to human bispecific IgG. Nat Biotechnol 16: 677-681 (1998).
†Schaefer W., et al. Immunoglobulin domain crossover as a generic approach for the production of bispecific IgG antibodies. Procl Nati Acad Sci USA. 108(27): 11187-11192 (2011).
††Gunasekaran K, et al. Enhancing antibody Fc heterodimer formation through electrostatic steering effects. J Biol Chem. 285(25): 19637-19646 (2010).

Example 14

Characterization of Anti-CD324/Nectin-4 Bispecific Antibodies

The bispecific antibodies generated in Example 13 were characterized using (i) a bridging ELISA assay to confirm that the antibodies were able to bind specifically to both CD324 and Nectin-4 and; (ii) an in vitro killing assay to demonstrate the ability of the bispecific antibodies to internalize and mediate the delivery of a cytotoxin to live cells.

The bridging ELISA assay was performed by coating Nectin-4 protein (R&D Systems) onto an ELISA plate, which was then blocked with PBS+0.1% Tween and 3% BSA. The plate was incubated with either anti-CD324/Nectin-4 bispecific antibody; monospecific anti-Nectin-4 Ha22-2(2,4)6.1 antibody; or monospecific anti-CD324 hSC10.17 antibody. After three washes with PBS+0.1% Tween, the plate was incubated with biotinylated CD324 W2A followed by three additional washes and incubation with horseradish peroxidase conjugated streptavidin. After three washes, the plates were developed using the 1-step Turbo TMB reagent (Pierce), and quenched with 2 M sulfuric acid. ELISA analysis indicated that all four bispecific constructs, shown in Table 1 above, were capable of bridging Nectin-4 and CD324, whereas each of the monospecific antibodies individually was not. These results confirm that all the tested bispecific constructs were assembled correctly and exhibited specificity to both Nectin-4 and CD324.

Table 2 immediately below shows the results of an in vitro killing assay performed using three cell lines: MCF-7, which express both Nectin-4 and CD324; SKBR3, which express Nectin-4 only and 293-hCD324, an engineered 293T cell line that overexpress CD324 and is negative in Nectin-4 expression The 293-hCD324 cell line was made by transduction of 293T cells using a bicistronic lentiviral vector expressing both human CD324 and GFP, and expansion of the CD324$^+$ FACS-sorted subset. 500 cells/well of MCF-7, SKBR3, or 293-hCD324 in DMEM supplemented with 10% fetal bovine serum were plated into 96 well tissue culture treated plates. After incubation for 24 hours, 2 nM Anti-Human IgG Fab fragment covalently linked to saporin (Advanced Targeting Systems, #IT-48) was combined with unlabeled anti-CD324/Nectin-4 bispecific antibodies or anti-CD324 or anti-Nectin-4 monospecific antibodies at concentrations varying between 0.01 pM and 1000 pM, The Fab-saporin-antibody complexes were added to the cells. The ability of the complexes to internalize and kill the cells was measured after 96, 72 or 144 hours by measuring cell viability of MCF-7, 293-hCD324 or SKBR3 cells, respectively, using Cell Titer Glo® (Promega) as per manufacturer's instructions. Raw luminescence counts using cultures containing cells exposed to the Fab-saporin fragment were set as 100% reference values and all other counts calculated accordingly (referred to as "Normalized RLU").

TABLE 2

Anti-CD324/Nectin-4 Bispecific Antibody in vitro Efficacy

| Modulator | IC50 on MCF-7 (PM) | IC50 on SKBR3 (PM) | IC50 on 293-hCD324 (PM) |
|---|---|---|---|
| Ha22-2(2,4)6.1 IgG | 9.94 | 0.95 | >1000 |
| hSC10.17 IgG | 3.10 | >1000 | 0.27 |
| hSC10.17/N4 KiH-CM | 3.09 | 17.45 | 3.79 |
| hSC10.17/N4 Elec-CM | 2.77 | 10.39 | 5.14 |
| hSC10.17/N4 KiH-KK | 5.98 | 144.1 | 12.25 |
| hSC10.17/N4 KiH-KR | 5.21 | 77.8 | 5.66 |
| Human IgG1 | >1000 | >1000 | >1000 |

The results demonstrated that anti-CD324/Nectin-4 bispecific antibodies were equally or more effective at delivering toxin as monospecific anti-CD324 or anti-Nectin-4 antibodies in the CD324$^+$Nectin-4$^+$ cell line, MCF-7. The results also demonstrated that anti-CD324/Nectin-4 bispecific antibodies were able to deliver toxin in both the CD324⁻Nectin-4⁺ cell line, SKBR3, and the CD324⁺Nectin-4⁻ cell line, 293-hCD324, but were less effective at delivering toxin than either monospecific anti-Nectin-4 or anti-CD324 antibodies, respectively. These data support the finding that the bispecific antibodies generated in Example 13 were able to internalize and kill cells in vitro, with increased specificity to cell lines expressing both antigens, and with decreased off-target toxicity on single positive cells compared to monospecific antibodies.

The complete disclosure of all patents, patent applications, and publications, and electronically available material (including, for example, nucleotide sequence submissions in, e.g., GenBank and RefSeq, and amino acid sequence submissions in, e.g., SwissProt, PIR, PRF, PBD, and translations from annotated coding regions in GenBank and RefSeq cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

The invention claimed is:

1. An isolated anti-CD324 antibody or an antigen binding fragment thereof, wherein the antibody or antigen binding fragment thereof is selected from the group consisting of:
 a) an antibody comprising a light chain variable region set forth as SEQ ID NO: 20, and comprising a heavy chain variable region set forth as SEQ ID NO: 21;
 b) an antibody comprising a light chain variable region set forth as SEQ ID NO: 22, and comprising a heavy chain variable region set forth as SEQ ID NO: 23;
 c) an antibody comprising a light chain variable region set forth as SEQ ID NO: 24, and comprising a heavy chain variable region set forth as SEQ ID NO: 25;
 d) an antibody comprising a light chain variable region set forth as SEQ ID NO: 26, and comprising a heavy chain variable region set forth as SEQ ID NO: 27;
 e) an antibody comprising a light chain variable region set forth as SEQ ID NO: 28, and comprising a heavy chain variable region set forth as SEQ ID NO: 29;
 f) an antibody comprising a light chain variable region set forth as SEQ ID NO: 30, and comprising a heavy chain variable region set forth as SEQ ID NO: 31;
 g) an antibody comprising a light chain variable region set forth as SEQ ID NO: 32, and comprising a heavy chain variable region set forth as SEQ ID NO: 33;
 h) an antibody comprising a light chain variable region set forth as SEQ ID NO: 34, and comprising a heavy chain variable region set forth as SEQ ID NO: 35;
 i) an antibody comprising a light chain variable region set forth as SEQ ID NO: 36, and comprising a heavy chain variable region set forth as SEQ ID NO: 37;
 j) an antibody comprising a light chain variable region set forth as SEQ ID NO: 38, and comprising a heavy chain variable region set forth as SEQ ID NO: 39;
 k) an antibody comprising a light chain variable region set forth as SEQ ID NO: 40, and comprising a heavy chain variable region set forth as SEQ ID NO: 41;
 l) an antibody comprising a light chain variable region set forth as SEQ ID NO: 42, and comprising a heavy chain variable region set forth as SEQ ID NO: 43;
 m) an antibody comprising a light chain variable region set forth as SEQ ID NO: 44, and comprising a heavy chain variable region set forth as SEQ ID NO: 45;
 n) an antibody comprising a light chain variable region set forth as SEQ ID NO: 46, and comprising a heavy chain variable region set forth as SEQ ID NO: 47;
 o) an antibody comprising a light chain variable region set forth as SEQ ID NO: 48, and comprising a heavy chain variable region set forth as SEQ ID NO: 49;
 p) an antibody comprising a light chain variable region set forth as SEQ ID NO: 50, and comprising a heavy chain variable region set forth as SEQ ID NO: 51;
 q) an antibody comprising a light chain variable region set forth as SEQ ID NO: 52, and comprising a heavy chain variable region set forth as SEQ ID NO: 53;
 r) an antibody comprising a light chain variable region set forth as SEQ ID NO: 54, and comprising a heavy chain variable region set forth as SEQ ID NO: 55;
 s) an antibody comprising a light chain variable region set forth as SEQ ID NO: 56, and comprising a heavy chain variable region set forth as SEQ ID NO: 57;
 t) an antibody comprising a light chain variable region set forth as SEQ ID NO: 58, and comprising a heavy chain variable region set forth as SEQ ID NO: 59;
 u) an antibody comprising a light chain variable region set forth as SEQ ID NO: 60, and comprising a heavy chain variable region set forth as SEQ ID NO: 61;
 v) an antibody comprising a light chain variable region set forth as SEQ ID NO: 62, and comprising a heavy chain variable region set forth as SEQ ID NO: 63;
 w) an antibody comprising a light chain variable region set forth as SEQ ID NO: 64, and comprising a heavy chain variable region set forth as SEQ ID NO: 65;
 x) an antibody comprising a light chain variable region set forth as SEQ ID NO: 66, and comprising a heavy chain variable region set forth as SEQ ID NO: 67;
 y) an antibody comprising a light chain variable region set forth as SEQ ID NO: 68, and comprising a heavy chain variable region set forth as SEQ ID NO: 69; and
 z) an antibody comprising a light chain variable region set forth as SEQ ID NO: 70, and comprising a heavy chain variable region set forth as SEQ ID NO: 71.

2. The isolated anti-CD324 antibody or antigen binding fragment thereof according to claim 1, wherein the antibody or antigen binding fragment thereof is selected from the group consisting of:
 a) an antibody comprising three light chain complementarity determining regions set forth as residues 24-34 of SEQ ID NO: 20 for CDR-L1, residues 50-56 of SEQ ID NO: 20 for CDR-L2, and residues 89-97 of SEQ ID NO: 20 for CDR-L3, and comprising three heavy chain complementarity determining regions set forth as residues 31-35 of SEQ ID NO: 21 for CDR-H1, residues 50-65 of SEQ ID NO: 21 for CDR-H2 and residues 95-102 of SEQ ID NO: 21 for CDR-H3, wherein the residues are numbered according to Kabat;
 b) an antibody comprising three light chain complementarity determining regions set forth as residues 24-34 of SEQ ID NO: 22 for CDR-L1, residues 50-56 of SEQ ID NO: 22 for CDR-L2, and residues 89-97 of SEQ ID NO: 22 for CDR-L3, and comprising three heavy chain complementarity determining regions set forth as residues 31-35 of SEQ ID NO: 23 for CDR-H1, residues 50-65 of SEQ ID NO: 23 for CDR-H2 and residues 95-102 of SEQ ID NO: 23 for CDR-H3, wherein the residues are numbered according to Kabat;

c) an antibody comprising three light chain complementarity determining regions set forth as residues 24-34 of SEQ ID NO: 24 for CDR-L1, residues 50-56 of SEQ ID NO: 24 for CDR-L2, and residues 89-97 of SEQ ID NO: 24 for CDR-L3, and comprising three heavy chain complementarity determining regions set forth as residues 31-35 of SEQ ID NO: 25 for CDR-H1, residues 50-65 of SEQ ID NO: 25 or SEQ ID NO. 73 for CDR-H2 and residues 95-102 of SEQ ID NO: 25 for CDR-H3, wherein the residues are numbered according to Kabat;

d) an antibody comprising three light chain complementarity determining regions set forth as residues 24-34 of SEQ ID NO: 26 for CDR-L1, residues 50-56 of SEQ ID NO: 26 for CDR-L2, and residues 89-97 of SEQ ID NO: 26 for CDR-L3, and comprising three heavy chain complementarity determining regions set forth as residues 31-35 of SEQ ID NO: 27 for CDR-H1, residues 50-65 of SEQ ID NO: 27 for CDR-H2 and residues 95-102 of SEQ ID NO: 27 for CDR-H3, wherein the residues are numbered according to Kabat;

e) an antibody comprising three light chain complementarity determining regions set forth as residues 24-34 of SEQ ID NO: 28 for CDR-L1, residues 50-56 of SEQ ID NO: 28 for CDR-L2, and residues 89-97 of SEQ ID NO: 28 for CDR-L3, and comprising three heavy chain complementarity determining regions set forth as residues 31-35 of SEQ ID NO: 29 for CDR-H1, residues 50-65 of SEQ ID NO: 29 for CDR-H2 and residues 95-102 of SEQ ID NO: 29 for CDR-H3, wherein the residues are numbered according to Kabat;

f) an antibody comprising three light chain complementarity determining regions set forth as residues 24-34 of SEQ ID NO: 30 for CDR-L1, residues 50-56 of SEQ ID NO: 30 for CDR-L2, and residues 89-97 of SEQ ID NO: 30 for CDR-L3, and comprising three heavy chain complementarity determining regions set forth as residues 31-35 of SEQ ID NO: 31 for CDR-H1, residues 50-56 of SEQ ID NO: 31 for CDR-H2 and residues 95-102 of SEQ ID NO: 31 for CDR-H3, wherein the residues are numbered according to Kabat;

g) an antibody comprising three light chain complementarity determining regions set forth as residues 24-34 of SEQ ID NO: 32 for CDR-L1, residues 50-56 of SEQ ID NO: 32 for CDR-L2, and residues 89-97 of SEQ ID NO: 32 for CDR-L3, and comprising three heavy chain complementarity determining regions set forth as residues 31-35 of SEQ ID NO: 33 for CDR-H1, residues 50-56of SEQ ID NO: 33 for CDR-H2 and residues 95-102 of SEQ ID NO: 33 for CDR-H3, wherein the residues are numbered according to Kabat;

h) an antibody comprising three light chain complementarity determining regions set forth as residues 24-34 of SEQ ID NO: 34 for CDR-L1, residues 50-56 of SEQ ID NO: 34 for CDR-L2, and residues 89-97 of SEQ ID NO: 34 for CDR-L3, and comprising three heavy chain complementarity determining regions set forth as residues 31-35 of SEQ ID NO: 35 for CDR-H1, residues 50-65 of SEQ ID NO: 35 for CDR-H2 and residues 95-102 of SEQ ID NO: 35 for CDR-H3, wherein the residues are numbered according to Kabat;

i) an antibody comprising three light chain complementarity determining regions set forth as residues 24-34 of SEQ ID NO: 36 for CDR-L1, residues 50-56 of SEQ ID NO: 36 for CDR-L2, and residues 89-97 of SEQ ID NO: 36 for CDR-L3, and comprising three heavy chain complementarity determining regions set forth as residues 31-34 of SEQ ID NO: 37 for CDR-H1, residues 50-65 of SEQ ID NO: 37 for CDR-H2 and residues 95-102 of SEQ ID NO: 37 for CDR-H3, wherein the residues are numbered according to Kabat;

j) an antibody comprising three light chain complementarity determining regions set forth as residues 24-34 of SEQ ID NO: 38 for CDR-L1, residues 50-56 of SEQ ID NO: 38 for CDR-L2, and residues 89-97 of SEQ ID NO: 38 for CDR-L3, and comprising three heavy chain complementarity determining regions set forth as residues 31-35 of SEQ ID NO: 39 for CDR-H1, residues 50-65 of SEQ ID NO: 39 for CDR-H2 and residues 95-102 of SEQ ID NO: 39 for CDR-H3, wherein the residues are numbered according to Kabat;

k) an antibody comprising three light chain complementarity determining regions set forth as residues 24-34 of SEQ ID NO: 40 for CDR-L1, residues 50-56 of SEQ ID NO: 40 for CDR-L2, and residues 89-97 of SEQ ID NO: 40 for CDR-L3, and comprising three heavy chain complementarity determining regions set forth as residues 31-35 of SEQ ID NO: 41 for CDR-H1, residues 50-65 of SEQ ID NO: 41 for CDR-H2 and residues 95-102 of SEQ ID NO: 41 for CDR-H3, wherein the residues are numbered according to Kabat;

l) an antibody comprising three light chain complementarity determining regions set forth as residues 24-34 of SEQ ID NO: 42 for CDR-L1, residues 50-56 of SEQ ID NO: 42 for CDR-L2, and residues 89-97 of SEQ ID NO: 42 for CDR-L3, and comprising three heavy chain complementarity determining regions set forth as residues 31-35 of SEQ ID NO: 43 for CDR-H1, residues 50-65 of SEQ ID NO: 43 for CDR-H2 and residues 95-102 of SEQ ID NO: 43 for CDR-H3, wherein the residues are numbered according to Kabat;

m) an antibody comprising three light chain complementarity determining regions set forth as residues 24-34 of SEQ ID NO: 44 for CDR-L1, residues 50-56 of SEQ ID NO: 44 for CDR-L2, and residues 89-97 of SEQ ID NO: 44 for CDR-L3, and comprising three heavy chain complementarity determining regions set forth as residues 31-35 of SEQ ID NO: 45 for CDR-H1, residues 50-65 of SEQ ID NO: 45 for CDR-H2 and residues 95-102 of SEQ ID NO: 45 for CDR-H3, wherein the residues are numbered according to Kabat;

n) an antibody comprising three light chain complementarity determining regions set forth as residues 24-34 of SEQ ID NO: 46 for CDR-L1, residues 50-56 of SEQ ID NO: 46 for CDR-L2, and residues 89-97 of SEQ ID NO: 46 for CDR-L3, and comprising three heavy chain complementarity determining regions set forth as residues 31-35 of SEQ ID NO: 47 for CDR-H1, residues 50-65 of SEQ ID NO: 47 for CDR-H2 and residues 95-102 of SEQ ID NO: 47 for CDR-H3, wherein the residues are numbered according to Kabat;

o) an antibody comprising three light chain complementarity determining regions set forth as residues 24-34 of SEQ ID NO: 48 for CDR-L1, residues 50-56 of SEQ ID NO: 48 for CDR-L2, and residues 89-97 of SEQ ID NO: 48 for CDR-L3, and comprising three heavy chain complementarity determining regions set forth as residues 31-35 of SEQ ID NO: 49 for CDR-H1, residues 50-65 of SEQ ID NO: 49 for CDR-H2 and residues 95-102 of SEQ ID NO: 49 for CDR-H3, wherein the residues are numbered according to Kabat;

p) an antibody comprising three light chain complementarity determining regions set forth as residues 24-34 of SEQ ID NO: 50 for CDR-L1, residues 50-56 of SEQ ID NO: 50 for CDR-L2, and residues 89-97 of SEQ ID NO: 50 for CDR-L3, and comprising three heavy chain complementarity determining regions set forth as residues 31-35 of SEQ ID NO: 51 for CDR-H1, residues 50-65 of SEQ ID NO: 51 for CDR-H2 and residues 95-102 of SEQ ID NO: 51 for CDR-H3, wherein the residues are numbered according to Kabat;

q) an antibody comprising three light chain complementarity determining regions set forth as residues 24-34 of SEQ ID NO: 52 for CDR-L1, residues 50-56 of SEQ ID NO: 52 for CDR-L2, and residues 89-97 of SEQ ID NO: 52 for CDR-L3, and comprising three heavy chain complementarity determining regions set forth as residues 31-35 of SEQ ID NO: 53 for CDR-H1, residues 50-65 of SEQ ID NO: 53 for CDR-H2 and residues 95-102 of SEQ ID NO: 53 for CDR-H3, wherein the residues are numbered according to Kabat;

r) an antibody comprising three light chain complementarity determining regions set forth as residues 24-34 of SEQ ID NO: 54 for CDR-L1, residues 50-56 of SEQ ID NO: 54 for CDR-L2, and residues 89-97 of SEQ ID NO: 54 for CDR-L3, and comprising three heavy chain complementarity determining regions set forth as residues 31-35 of SEQ ID NO: 55 for CDR-H1, residues 50-65 of SEQ ID NO: 55 for CDR-H2 and residues 95-102 of SEQ ID NO: 55 for CDR-H3, wherein the residues are numbered according to Kabat;

s) an antibody comprising three light chain complementarity determining regions set forth as residues 24-34 of SEQ ID NO: 56 for CDR-L1, residues 50-56 of SEQ ID NO: 56 for CDR-L2, and residues 89-97 of SEQ ID NO: 56 for CDR-L3, and comprising three heavy chain complementarity determining regions set forth as residues 31-35 of SEQ ID NO: 57 for CDR-H1, residues 50-65 of SEQ ID NO: 57 for CDR-H2 and residues 95-102 of SEQ ID NO: 57 for CDR-H3, wherein the residues are numbered according to Kabat;

t) an antibody comprising three light chain complementarity determining regions set forth as residues 24-34 of SEQ ID NO: 58 for CDR-L1, residues 50-56 of SEQ ID NO: 58 for CDR-L2, and residues 89-97 of SEQ ID NO: 58 for CDR-L3, and comprising three heavy chain complementarity determining regions set forth as residues 31-35 of SEQ ID NO: 59 for CDR-H1, residues 50-65 of SEQ ID NO: 59 for CDR-H2 and residues 95-102 of SEQ ID NO: 59 for CDR-H3, wherein the residues are numbered according to Kabat;

u) an antibody comprising three light chain complementarity determining regions set forth as residues 24-34 of SEQ ID NO: 60 for CDR-L1, residues 50-56 of SEQ ID NO: 60 for CDR-L2, and residues 89-97 of SEQ ID NO: 60 for CDR-L3, and comprising three heavy chain complementarity determining regions set forth as residues 31-35 of SEQ ID NO: 61 for CDR-H1, residues 50-65 of SEQ ID NO: 61 for CDR-H2 and residues 95-102 of SEQ ID NO: 61 for CDR-H3, wherein the residues are numbered according to Kabat;

v) an antibody comprising three light chain complementarity determining regions set forth as residues 24-34 of SEQ ID NO: 62 for CDR-L1, residues 50-56 of SEQ ID NO: 62 for CDR-L2, and residues 89-97 of SEQ ID NO: 62 for CDR-L3, and comprising three heavy chain complementarity determining regions set forth as residues 31-35 of SEQ ID NO: 63 for CDR-H1, residues 50-65 of SEQ ID NO: 63 for CDR-H2 and residues 95-102 of SEQ ID NO: 63 for CDR-H3, wherein the residues are numbered according to Kabat;

w) an antibody comprising three light chain complementarity determining regions set forth as residues 24-34 of SEQ ID NO: 64 for CDR-L1, residues 50-56 of SEQ ID NO: 64 for CDR-L2, and residues 89-97 of SEQ ID NO: 64 for CDR-L3, and comprising three heavy chain complementarity determining regions set forth as residues 31-35 of SEQ ID NO: 65 for CDR-H1, residues 50-65 of SEQ ID NO: 65 for CDR-H2 and residues 95-102 of SEQ ID NO: 65 for CDR-H3, wherein the residues are numbered according to Kabat;

x) an antibody comprising three light chain complementarity determining regions set forth as residues 24-34 of SEQ ID NO: 66 for CDR-L1, residues 50-56 of SEQ ID NO: 66 for CDR-L2, and residues 89-97 of SEQ ID NO: 66 for CDR-L3, and comprising three heavy chain complementarity determining regions set forth as residues 31-35 of SEQ ID NO: 67 for CDR-H1, residues 50-65 of SEQ ID NO: 67 for CDR-H2 and residues 95-102 of SEQ ID NO: 67 for CDR-H3, wherein the residues are numbered according to Kabat;

y) an antibody comprising three light chain complementarity determining regions set forth as residues 24-34 of SEQ ID NO: 68 for CDR-L1, residues 50-56 of SEQ ID NO: 68 for CDR-L2, and residues 89-97 of SEQ ID NO: 68 for CDR-L3, and comprising three heavy chain complementarity determining regions set forth as residues 31-35 of SEQ ID NO: 69 for CDR-H1, residues 50-65 of SEQ ID NO: 69 for CDR-H2 and residues 95-102 of SEQ ID NO: 69 for CDR-H3, wherein the residues are numbered according to Kabat; and z) an antibody comprising three light chain complementarity determining regions set forth as residues 24-34 of SEQ ID NO: 70 for CDR-L1, residues 50-56 of SEQ ID NO: 70 for CDR-L2, and residues 89-97 of SEQ ID NO: 70 for CDR-L3, and comprising three heavy chain complementarity determining regions set forth as residues 31-35 of SEQ ID NO: 71 for CDR-H1, residues 50-65 of SEQ ID NO: 71 for CDR-H2 and residues 95-102 of SEQ ID NO: 71 for CDR-H3, wherein the residues are numbered according to Kabat.

3. The isolated anti-CD324 antibody or antigen binding fragment thereof according to claim 2, wherein the antibody or antigen binding fragment thereof is selected from the group consisting of:

a) an antibody comprising a light chain variable region set forth as SEQ ID NO: 20, and comprising a heavy chain variable region set forth as SEQ ID NO: 21;

b) an antibody comprising a light chain variable region set forth as SEQ ID NO: 22, and comprising a heavy chain variable region set forth as SEQ ID NO: 23;

c) an antibody comprising a light chain variable region set forth as SEQ ID NO: 24, and comprising a heavy chain variable region set forth as SEQ ID NO: 25;

d) an antibody comprising a light chain variable region set forth as SEQ ID NO: 26, and comprising a heavy chain variable region set forth as SEQ ID NO: 27;

e) an antibody comprising a light chain variable region set forth as SEQ ID NO: 28, and comprising a heavy chain variable region set forth as SEQ ID NO: 29;

f) an antibody comprising a light chain variable region set forth as SEQ ID NO: 30, and comprising a heavy chain variable region set forth as SEQ ID NO: 31;

g) an antibody comprising a light chain variable region set forth as SEQ ID NO: 32, and comprising a heavy chain variable region set forth as SEQ ID NO: 33;
h) an antibody comprising a light chain variable region set forth as SEQ ID NO: 34, and comprising a heavy chain variable region set forth as SEQ ID NO: 35;
i) an antibody comprising a light chain variable region set forth as SEQ ID NO: 36, and comprising a heavy chain variable region set forth as SEQ ID NO: 37;
j) an antibody comprising a light chain variable region set forth as SEQ ID NO: 38, and comprising a heavy chain variable region set forth as SEQ ID NO: 39;
k) an antibody comprising a light chain variable region set forth as SEQ ID NO: 40, and comprising a heavy chain variable region set forth as SEQ ID NO: 41;
l) an antibody comprising a light chain variable region set forth as SEQ ID NO: 42, and comprising a heavy chain variable region set forth as SEQ ID NO: 43;
m) an antibody comprising a light chain variable region set forth as SEQ ID NO: 44, and comprising a heavy chain variable region set forth as SEQ ID NO: 45;
n) an antibody comprising a light chain variable region set forth as SEQ ID NO: 46, and comprising a heavy chain variable region set forth as SEQ ID NO: 47;
o) an antibody comprising a light chain variable region set forth as SEQ ID NO: 48, and comprising a heavy chain variable region set forth as SEQ ID NO: 49;
p) an antibody comprising a light chain variable region set forth as SEQ ID NO: 50, and comprising a heavy chain variable region set forth as SEQ ID NO: 51;
q) an antibody comprising a light chain variable region set forth as SEQ ID NO: 52, and comprising a heavy chain variable region set forth as SEQ ID NO: 53;
r) an antibody comprising a light chain variable region set forth as SEQ ID NO: 54, and comprising a heavy chain variable region set forth as SEQ ID NO: 55;
s) an antibody comprising a light chain variable region set forth as SEQ ID NO: 56, and comprising a heavy chain variable region set forth as SEQ ID NO: 57;
t) an antibody comprising a light chain variable region set forth as SEQ ID NO: 58, and comprising a heavy chain variable region set forth as SEQ ID NO: 59;
u) an antibody comprising a light chain variable region set forth as SEQ ID NO: 60, and comprising a heavy chain variable region set forth as SEQ ID NO: 61;
v) an antibody comprising a light chain variable region set forth as SEQ ID NO: 62, and comprising a heavy chain variable region set forth as SEQ ID NO: 63;
w) an antibody comprising a light chain variable region set forth as SEQ ID NO: 64, and comprising a heavy chain variable region set forth as SEQ ID NO: 65;
x) an antibody comprising a light chain variable region set forth as SEQ ID NO: 66, and comprising a heavy chain variable region set forth as SEQ ID NO: 67;
y) an antibody comprising a light chain variable region set forth as SEQ ID NO: 68, and comprising a heavy chain variable region set forth as SEQ ID NO: 69; and
z) an antibody comprising a light chain variable region set forth as SEQ ID NO: 70, and comprising a heavy chain variable region set forth as SEQ ID NO: 71.

4. The isolated anti-CD324 antibody or antigen binding fragment thereof according to claim 1, wherein the isolated anti-CD324 antibody or antigen binding fragment thereof is selected from the group consisting of monoclonal antibodies, chimeric antibodies, and humanized antibodies.

5. The isolated anti-CD324 antibody or antigen binding fragment thereof according to claim 2, comprising a light chain variable region set forth as SEQ ID NO: 72, and comprising a light chain variable region set forth as SEQ ID NO: 73.

6. The isolated anti-CD324 antibody or antigen binding fragment thereof according to claim 1, wherein the isolated anti-CD324 antibody or antigen binding fragment thereof is conjugated to a cytotoxic agent.

7. The isolated anti-CD324 antibody or antigen binding fragment thereof according to claim 5, wherein the isolated anti-CD324 antibody or antigen binding fragment thereof is conjugated to a cytotoxic agent.

8. A bispecific antibody comprising the antibody of claim 1 and an antibody that recognizes an epitope present on an antigen selected from the group consisting of OCT4, Nanog, STAT3, EPCAM, CD24, CD34, NB84, TrkA, GD2, CD133, CD20, CD56, CD29, B7H3, CD46, transferrin receptor, JAM3, carboxypeptidase M, oncostatin M, Lgr5, Lgr6, CD325, nectin-4, nestin, Soxl, Bmi-1, eed, easyhl, easyh2, mf2, yyl, smarckA3, smarckA5, smarcD3, smarcE1, m1lt3, DLL1, DLL4, FZD1, FZD2, FZD3, FZD4, FZD6, FZD7, FZD8, FZD9, FZD10, WNT2, WNT2B, WNT3, WNT5A, WNT10B, WNT16, AXIN1, BCL9, MYC, (TCF4) SLC7A8, SLC44A4, IL1RAP, TEM8, TMPRSS4, MUC16, GPRC5B, SLC6A14, SLC4A11, PPAP2C, CAV1, CAV2, PTPN3, EPHA1, EPHA2, EPHA3, EPHA4, EPHA5, EPHA6, EPHA7, EPHA8, EPHA9, EPHB1, EPHB2, EPHB3, EPHB4, EPH5, EPHB6, EFNA1, EFNA2, EFNA3, EFNA5, EFNA6, EFNB1, EFNB2, EFNB3, SLC1A1, CX3CL1, ADORA2A, MPZL1, F1110052, C4.4A, EDG3, RARRES1, TMEPAI, PTS, CEACAM5, CEACAM6, NID2, STEAP, ABCA3, CRIM1, IL1R1, OPN3, DAF, MUC1, CPD, NMA, ADAMS, GJA1, SLC19A2, ABCA1, PCDH7, ADCY9, SLC39A1, NPC1, ENPP1, N33, GPNMB, LY6E, CELSR1, LRP3, C20orf52, TMEPAI, FLVCR, PCDHA10, GPR54, TGFBR3, SEMA4B, PCDHB2, ABCG2, CD166, AFP, BMP-4, β-catenin, CD2, CD3, CD9, CD14, CD31, CD38, CD44, CD45, CD74, CD90, CXCR4, decorin, APCDD1, PTK7, EGFR, CD105, CD64, CD16, CD16a, CD16b, GLI1, GLI2, CD49b, CD49e and CD49f.

9. The bispecific antibody of claim 8, comprising the antibody of claim 1 and an antibody selected from the group consisting of abagovomab, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, cetuximab, citatuzumab, cixutumumab, clivatuzumab, conatumumab, daratumumab, drozitumab, duligotumab, dusigitumab, detumomab, dacetuzumab, dalotuzumab, ecromeximab, elotuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab, iratumumab, labetuzumab, lexatumumab, lintuzumab, lorvotuzumab, lucatumumab, mapatumumab, matuzumab, milatuzumab, minretumomab, mitumomab, moxetumomab, narnatumab, naptumomab, necitumumab, nimotuzumab, nofetumomabn, ocaratuzumab, ofatumumab, olaratumab, onartuzumab, oportuzumab, oregovomab, panitumumab, parsatuzumab, patritumab, pemtumomab, pertuzumab, pintumomab, pritumumab, racotumomab, radretumab, rilotumumab, rituximab, robatumumab, satumomab, sibrotuzumab, siltuximab, simtuzumab, solitomab, tacatuzumab, taplitumomab, tenatumomab, teprotumumab, tigatuzumab, tositumomab, trastuzumab, tucotuzumab, ublituximab, veltuzumab, vorsetuzumab, votumumab, zalutumumab, CC49 and 3F8.

10. A vector comprising a polynucleotide, wherein the polynucleotide encodes a polypeptide comprising a light chain variable region or a heavy chain variable region of an antibody according to claim 3.

* * * * *

UNITED STATES PATENT AND TRADEMARK OFFICE
CERTIFICATE OF CORRECTION

PATENT NO. : 9,534,058 B2  
APPLICATION NO. : 14/377343  
DATED : January 3, 2017  
INVENTOR(S) : Stull et al.

Page 1 of 1

It is certified that error appears in the above-identified patent and that said Letters Patent is hereby corrected as shown below:

In the Claims

At Column 190, Claim 2, Line 46, the text "The isolated anti-CD324 antibody" should be changed to -- An isolated anti-CD324 antibody --

At Column 190, Line 47, the text "according to claim 1," should be deleted

At Column 192, Claim 2, Lines 2-3, the text "residues 31-34 of SEQ ID NO:37 for CDR-H1," should be changed to -- residues 31-35 of SEQ ID NO:37 for CDR-H1, --

At Column 195, Claim 4, Line 62, the text "fragment thereof according to claim 1," should be changed to -- fragment thereof according to claim 2, --

At Column 196, Claim 6, Line 5, the text "fragment thereof according to claim 1," should be changed to -- fragment thereof according to claim 2, --

At Column 196, Claim 8, Lines 12-13, the text "claim 1 and an antibody" should be changed to -- claim 2 and an antibody --

At Column 196, Claim 8, Line 30, the text "F1110052" should be changed to -- FLJ10052 --

At Column 196, Claim 8, Line 33, the text "ADAMS" should be changed to -- ADAM9 --

At Column 196, Claim 9, Line 43, the text "antibody of claim 1" should be changed to -- antibody of claim 2 --

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*